(12) United States Patent
Sharma et al.

(10) Patent No.: US 12,594,069 B2
(45) Date of Patent: Apr. 7, 2026

(54) HANDLE ASSEMBLY PROVIDING UNLIMITED ROLL

(71) Applicant: LivsMed, Inc., Seongnam-si (KR)

(72) Inventors: Deepak Sharma, Ann Arbor, MI (US); Gregory Brian Bowles, Fenton, MI (US); James Michael Licht, Boyne Falls, MI (US); Zachary Zimmerman, Northville, MI (US); Shorya Awtar, Ann Arbor, MI (US); James Duncan Geiger, Ottawa Hills, OH (US)

(73) Assignee: LivsMed, Inc., Seongnam-si (KR)

( * ) Notice: Subject to any disclaimer, the term of this patent is extended or adjusted under 35 U.S.C. 154(b) by 1422 days.

(21) Appl. No.: 16/926,928

(22) Filed: Jul. 13, 2020

(65) Prior Publication Data

US 2021/0038865 A1 Feb. 11, 2021

Related U.S. Application Data

(63) Continuation-in-part of application No. 15/943,689, filed on Apr. 2, 2018, now abandoned, which is a
(Continued)

(51) Int. Cl.
*A61B 17/062* (2006.01)
*A61B 17/00* (2006.01)
(Continued)

(52) U.S. Cl.
CPC ...... *A61B 17/062* (2013.01); *A61B 17/00234* (2013.01); *A61M 25/0136* (2013.01);
(Continued)

(58) Field of Classification Search
CPC .......... A61B 17/2909; A61B 2017/003; A61B 2017/00318; A61B 2017/00323;
(Continued)

(56) References Cited

U.S. PATENT DOCUMENTS 331,598 A 12/1885 White
3,028,126 A 4/1962 Holleman
(Continued)

FOREIGN PATENT DOCUMENTS

CN 111789662 A 10/2020
CN 113925569 A 1/2022
(Continued)

OTHER PUBLICATIONS

International Search Report and Written Opinion for International Application No. PCT/US2021/050843 dated Dec. 28, 2021 (11 pages).
(Continued)

*Primary Examiner* — Thomas Mcevoy
(74) *Attorney, Agent, or Firm* — REISING ETHINGTON, P.C.

(57) ABSTRACT

An example roll handle assembly includes a handle body, a roll body, a closure body, and a shuttle body. The roll body is coupled to the handle body and has a rotational degree of freedom about a roll axis relative to the handle body. The roll body is translationally constrained along the roll axis relative to the handle body. The closure body is coupled to the handle body and has one or more degrees of freedom of motion relative to the handle body. The shuttle body is coupled to the roll body and the closure body, and has a translational degree of freedom along the roll axis relative to the roll body. The shuttle body is rotationally constrained about the roll axis relative to the roll body, and has a rotational degree of freedom about the roll axis relative to the closure body.

20 Claims, 80 Drawing Sheets

Related U.S. Application Data continuation of application No. PCT/US2016/055105, filed on Oct. 3, 2016.

(60) Provisional application No. 62/236,835, filed on Oct. 2, 2015.

(51) Int. Cl.
| | | |
|---|---|---|
| *A61M 25/01* | (2006.01) | |
| *A61B 1/00* | (2006.01) | |
| *A61B 1/005* | (2006.01) | |

(52) U.S. Cl.
CPC ......... *A61B 1/00147* (2013.01); *A61B 1/0052* (2013.01); *A61B 2017/00314* (2013.01); *A61B 2017/00323* (2013.01); *A61B 2017/00424* (2013.01); *A61B 2017/00438* (2013.01); *A61B 2017/00442* (2013.01)

(58) Field of Classification Search
CPC ........... A61B 2017/00424; A61B 2017/00442; A61B 2017/291; A61B 2017/00464; A61B 2017/2939; A61B 34/70; A61B 2017/2927; A61B 2017/2929
See application file for complete search history.

(56) References Cited

U.S. PATENT DOCUMENTS

| | | | |
|---|---|---|---|
| 3,350,956 | A | 11/1967 | Monge |
| 3,497,083 | A | 2/1970 | Anderson et al. |
| 4,328,839 | A | 5/1982 | Lyons et al. |
| 4,466,649 | A | 8/1984 | Ozawa |
| 4,491,325 | A | 1/1985 | Bersheim |
| 4,568,311 | A | 2/1986 | Miyake |
| 4,712,545 | A | 12/1987 | Honkanen |
| 4,740,126 | A | 4/1988 | Richter |
| 4,750,475 | A | 6/1988 | Yoshihashi |
| 4,754,909 | A | 7/1988 | Barker et al. |
| 4,950,273 | A | 8/1990 | Briggs |
| 5,021,969 | A | 6/1991 | Okamura et al. |
| 5,069,596 | A | 12/1991 | Mueller et al. |
| 5,147,357 | A | 9/1992 | Rose et al. |
| 5,209,747 | A | 5/1993 | Knoepfler |
| 5,297,443 | A | 3/1994 | Wentz |
| 5,317,952 | A | 6/1994 | Immega |
| 5,323,570 | A | 6/1994 | Kuhlman et al. |
| 5,330,502 | A | 7/1994 | Hassler et al. |
| 5,350,391 | A | 9/1994 | Iacovelli |
| 5,368,600 | A | 11/1994 | Failla et al. |
| 5,374,277 | A | 12/1994 | Hassler |
| 5,379,663 | A | 1/1995 | Hara |
| 5,379,758 | A | 1/1995 | Snyder |
| 5,454,827 | A | 10/1995 | Aust et al. |
| 5,456,695 | A | 10/1995 | Herve Dallemagne |
| 5,549,637 | A | 8/1996 | Crainich |
| 5,560,532 | A | 10/1996 | Defonzo et al. |
| 5,599,151 | A | 2/1997 | Daum et al. |
| 5,620,415 | A | 4/1997 | Lucey et al. |
| 5,626,608 | A | 5/1997 | Cuny et al. |
| 5,683,412 | A | 11/1997 | Scarfone |
| 5,713,505 | A | 2/1998 | Huitema |
| 5,716,352 | A | 2/1998 | Viola et al. |
| 5,735,874 | A | 4/1998 | Measamer et al. |
| 5,782,748 | A | 7/1998 | Palmer et al. |
| 5,807,376 | A | 9/1998 | Viola et al. |
| 5,810,880 | A | 9/1998 | Jensen et al. |
| 5,813,813 | A | 9/1998 | Daum et al. |
| 5,816,770 | A | 10/1998 | Itagaki |
| 5,817,084 | A | 10/1998 | Jensen |
| 5,820,009 | A | 10/1998 | Melling et al. |
| 5,853,412 | A | 12/1998 | Mayenberger |
| 5,860,995 | A | 1/1999 | Berkelaar |
| 5,908,436 | A | 6/1999 | Cuschieri et al. |
| 6,042,555 | A | 3/2000 | Kramer et al. |
| 6,088,020 | A | 7/2000 | Mor |
| 6,104,379 | A | 8/2000 | Petrich et al. |
| 6,270,453 | B1 | 8/2001 | Sakai |
| 6,309,403 | B1 | 10/2001 | Minor et al. |
| 6,312,435 | B1 | 11/2001 | Wallace et al. |
| 6,330,837 | B1 | 12/2001 | Charles et al. |
| 6,413,229 | B1 | 7/2002 | Kramer et al. |
| 6,607,475 | B2 | 8/2003 | Doyle et al. |
| 6,707,447 | B1 | 3/2004 | Goranowski |
| 6,714,839 | B2 | 3/2004 | Salisbury, Jr. et al. |
| 6,746,443 | B1 | 6/2004 | Morley et al. |
| 6,853,879 | B2 | 2/2005 | Sunaoshi |
| 6,858,005 | B2 | 2/2005 | Ohline et al. |
| 6,889,116 | B2 | 5/2005 | Jinno |
| 6,994,716 | B2 | 2/2006 | Jinno et al. |
| 7,101,363 | B2 | 9/2006 | Nishizawa et al. |
| 7,147,650 | B2 | 12/2006 | Lee |
| 7,338,513 | B2 | 3/2008 | Lee et al. |
| 7,410,338 | B2 | 8/2008 | Schiele et al. |
| 7,470,268 | B2 | 12/2008 | Doyle et al. |
| 7,553,275 | B2 | 6/2009 | Padget et al. |
| 7,608,083 | B2 | 10/2009 | Lee et al. |
| 7,708,756 | B2 | 5/2010 | Nobis et al. |
| 7,736,254 | B2 | 6/2010 | Schena |
| 7,862,554 | B2 | 1/2011 | Hegeman et al. |
| 7,866,527 | B2 | 1/2011 | Hall et al. |
| 7,947,035 | B2 | 5/2011 | Miyamoto et al. |
| 7,963,913 | B2 | 6/2011 | Devengenzo et al. |
| 8,029,531 | B2 | 10/2011 | Lee et al. |
| 8,057,487 | B2 | 11/2011 | Chu et al. |
| 8,105,319 | B2 | 1/2012 | Doyle et al. |
| 8,105,350 | B2 | 1/2012 | Lee et al. |
| 8,365,633 | B2 | 2/2013 | Simaan et al. |
| 8,398,587 | B2 | 3/2013 | Dewaele et al. |
| 8,425,408 | B2 | 4/2013 | Boulais et al. |
| 8,465,475 | B2 | 6/2013 | Isbell, Jr. |
| 8,528,440 | B2 | 9/2013 | Morley et al. |
| 8,540,748 | B2 | 9/2013 | Murphy et al. |
| 8,551,076 | B2 | 10/2013 | Duval et al. |
| 8,603,135 | B2 | 12/2013 | Mueller |
| 8,668,702 | B2 | 3/2014 | Awtar et al. |
| 8,672,206 | B2 | 3/2014 | Aranyi et al. |
| 8,734,312 | B2 | 5/2014 | Conner et al. |
| 8,764,448 | B2 | 7/2014 | Yang et al. |
| 8,777,898 | B2 | 7/2014 | Suon et al. |
| 8,821,512 | B2 | 9/2014 | Barrier et al. |
| 8,828,046 | B2 | 9/2014 | Stefanchik et al. |
| 8,870,867 | B2 | 10/2014 | Walberg et al. |
| 8,881,616 | B2 | 11/2014 | Dize et al. |
| 8,968,355 | B2 | 3/2015 | Malkowski et al. |
| 8,992,422 | B2 | 3/2015 | Spivey et al. |
| 9,050,121 | B2 | 6/2015 | Doyle |
| 9,060,796 | B2 | 6/2015 | Seo |
| 9,084,621 | B2 | 7/2015 | Weitzner et al. |
| 9,161,771 | B2 | 10/2015 | Steger |
| 9,220,398 | B2 | 12/2015 | Woodley et al. |
| 9,522,014 | B2 | 12/2016 | Nishizawa et al. |
| 9,532,839 | B2 | 1/2017 | Seo |
| 9,575,504 | B2 | 2/2017 | Dize et al. |
| 9,579,013 | B2 | 2/2017 | Dewaele et al. |
| 9,622,729 | B2 | 4/2017 | Dewaele et al. |
| 9,629,682 | B2 | 4/2017 | Wallace et al. |
| 9,629,689 | B2 | 4/2017 | Bowles et al. |
| 9,649,096 | B2 | 5/2017 | Sholev |
| 9,675,370 | B2 | 6/2017 | Awtar et al. |
| 9,695,916 | B2 | 7/2017 | Lee |
| 9,696,700 | B2 | 7/2017 | Beira et al. |
| 9,770,300 | B2 | 9/2017 | Kwon et al. |
| 9,814,451 | B2 | 11/2017 | Sharma et al. |
| 9,869,339 | B2 | 1/2018 | Zimmerman et al. |
| 9,889,874 | B1 | 2/2018 | Clause |
| 9,901,412 | B2 | 2/2018 | Lathrop et al. |
| 9,955,988 | B2 | 5/2018 | Stefanchik et al. |
| 10,005,181 | B2 | 6/2018 | Hasegawa et al. |
| 10,085,624 | B2 | 10/2018 | Isoda et al. |
| 10,198,086 | B2 | 2/2019 | Parazynski et al. |
| 10,265,129 | B2 | 4/2019 | Beira |
| 10,271,913 | B2 | 4/2019 | Yoshii et al. |
| 10,325,072 | B2 | 6/2019 | Beira et al. |

(56) References Cited

U.S. PATENT DOCUMENTS

| | | | |
|---|---|---|---|
| 10,363,055 B2 | 7/2019 | Beira et al. |
| 10,426,471 B2 | 10/2019 | Shelton, IV et al. |
| 10,449,010 B2 | 10/2019 | Dewaele et al. |
| 10,617,413 B2 | 4/2020 | Shelton, IV et al. |
| 10,660,719 B2 | 5/2020 | De Mathelin et al. |
| 10,660,721 B2 | 5/2020 | Bonny et al. |
| 10,664,002 B2 | 5/2020 | Parazynski et al. |
| 10,695,141 B2 | 6/2020 | Lee |
| 10,709,467 B2 | 7/2020 | Lee et al. |
| 10,722,315 B2 | 7/2020 | Lee et al. |
| 10,758,230 B2 | 9/2020 | Shelton, IV et al. |
| 11,241,247 B2 | 2/2022 | Yuan et al. |
| 11,344,381 B2 | 5/2022 | Lee et al. |
| 11,490,980 B2 | 11/2022 | Lee et al. |
| 11,510,746 B2 | 11/2022 | Lee et al. |
| 11,523,840 B2 | 12/2022 | Yuan et al. |
| 2001/0031983 A1 | 10/2001 | Brock et al. |
| 2003/0036748 A1 | 2/2003 | Cooper et al. |
| 2003/0083673 A1 | 5/2003 | Tierney et al. |
| 2003/0135203 A1 | 7/2003 | Wang et al. |
| 2003/0135204 A1 | 7/2003 | Lee et al. |
| 2003/0153902 A1 | 8/2003 | Doyle et al. |
| 2003/0176880 A1 | 9/2003 | Long et al. |
| 2003/0176948 A1 | 9/2003 | Green |
| 2004/0023616 A1 | 2/2004 | Straub et al. |
| 2004/0049205 A1 | 3/2004 | Lee et al. |
| 2004/0138700 A1 | 7/2004 | Cooper et al. |
| 2004/0236316 A1 | 11/2004 | Danitz et al. |
| 2004/0253079 A1 | 12/2004 | Sanchez |
| 2005/0004431 A1 | 1/2005 | Kogasaka et al. |
| 2005/0038469 A1 | 2/2005 | Lang |
| 2005/0090811 A1 | 4/2005 | Doyle et al. |
| 2005/0107667 A1 | 5/2005 | Danitz et al. |
| 2006/0074415 A1 | 4/2006 | Scott et al. |
| 2006/0111210 A1 | 5/2006 | Hinman |
| 2006/0111616 A1 | 5/2006 | Danitz |
| 2006/0156848 A1 | 7/2006 | Gosselin et al. |
| 2006/0199999 A1 | 9/2006 | Ikeda et al. |
| 2006/0259073 A1 | 11/2006 | Miyamoto et al. |
| 2006/0282063 A1 | 12/2006 | Gotani |
| 2007/0021738 A1 | 1/2007 | Hasser et al. |
| 2007/0072466 A1 | 3/2007 | Miyamoto et al. |
| 2007/0078565 A1 | 4/2007 | Ghodoussi et al. |
| 2007/0093790 A1 | 4/2007 | Downey et al. |
| 2008/0004493 A1 | 1/2008 | Schiemann |
| 2008/0039256 A1 | 2/2008 | Jinno et al. |
| 2008/0065098 A1 | 3/2008 | Larkin |
| 2008/0177285 A1 | 7/2008 | Brock et al. |
| 2008/0193260 A1 | 8/2008 | Yokokohji et al. |
| 2008/0243176 A1 | 10/2008 | Weitzner et al. |
| 2009/0118044 A1 | 5/2009 | Kuo et al. |
| 2009/0171147 A1 | 7/2009 | Lee et al. |
| 2009/0192511 A1 | 7/2009 | Haffenreffer |
| 2010/0004606 A1 | 1/2010 | Hansen et al. |
| 2010/0016853 A1 | 1/2010 | Burbank |
| 2010/0030018 A1* | 2/2010 | Fortier .............. A61B 18/1445 |
| | | 600/104 |
| 2010/0056863 A1 | 3/2010 | Dejima et al. |
| 2010/0111645 A1 | 5/2010 | Al-Mouhamed et al. |
| 2010/0191278 A1 | 7/2010 | Lee et al. |
| 2010/0234831 A1 | 9/2010 | Hinman et al. |
| 2010/0249497 A1 | 9/2010 | Peine et al. |
| 2011/0024145 A1 | 2/2011 | Click et al. |
| 2011/0106145 A1 | 5/2011 | Jeong |
| 2011/0118707 A1 | 5/2011 | Burbank |
| 2011/0152881 A1 | 6/2011 | Conner et al. |
| 2011/0152922 A1 | 6/2011 | Jeong |
| 2011/0178531 A1 | 7/2011 | Caputo et al. |
| 2011/0319911 A1 | 12/2011 | Conner et al. |
| 2012/0083799 A1 | 4/2012 | Chen et al. |
| 2012/0095298 A1 | 4/2012 | Stefanchik et al. |
| 2012/0118097 A1 | 5/2012 | Ilch |
| 2012/0186383 A1 | 7/2012 | Schvalb et al. |
| 2012/0271283 A1 | 10/2012 | Doyle |
| 2012/0277762 A1 | 11/2012 | Lathrop et al. |
| 2012/0289973 A1 | 11/2012 | Prisco et al. |
| 2013/0012958 A1 | 1/2013 | Marczyk et al. |
| 2013/0023868 A1 | 1/2013 | Worrell et al. |
| 2013/0023974 A1 | 1/2013 | Amrani |
| 2013/0066334 A1 | 3/2013 | Schoepp |
| 2013/0172860 A1 | 7/2013 | Szewczyk et al. |
| 2013/0224710 A1 | 8/2013 | Yang et al. |
| 2013/0239734 A1 | 9/2013 | Hinman |
| 2014/0135805 A1 | 5/2014 | Windgassen et al. |
| 2014/0142595 A1 | 5/2014 | Awtar et al. |
| 2014/0246471 A1 | 9/2014 | Jaworek et al. |
| 2014/0331798 A1 | 11/2014 | Shim et al. |
| 2014/0371532 A1 | 12/2014 | Trovato |
| 2015/0021068 A1 | 1/2015 | Bernhardt et al. |
| 2015/0053455 A1 | 2/2015 | Hagi |
| 2015/0164601 A1 | 6/2015 | Sholev |
| 2015/0209059 A1 | 7/2015 | Trees et al. |
| 2015/0230697 A1 | 8/2015 | Phee et al. |
| 2016/0135830 A1 | 5/2016 | Volkmer et al. |
| 2016/0256232 A1 | 9/2016 | Awtar et al. |
| 2016/0291383 A1 | 10/2016 | Han et al. |
| 2016/0303734 A1 | 10/2016 | Bowles et al. |
| 2017/0095922 A1 | 4/2017 | Licht et al. |
| 2017/0245954 A1 | 8/2017 | Beira |
| 2017/0360522 A1 | 12/2017 | Beira |
| 2018/0000318 A9 | 1/2018 | Rogers et al. |
| 2018/0049842 A1 | 2/2018 | Bowles et al. |
| 2018/0125519 A1 | 5/2018 | Beira et al. |
| 2018/0125592 A1 | 5/2018 | Beira |
| 2018/0221045 A1 | 8/2018 | Zimmerman et al. |
| 2018/0289384 A1 | 10/2018 | Bowles et al. |
| 2018/0368839 A1 | 12/2018 | Shelton, IV et al. |
| 2019/0133698 A1 | 5/2019 | Beira et al. |
| 2019/0336230 A1 | 11/2019 | Awtar et al. |
| 2020/0121406 A1 | 4/2020 | Lee |
| 2020/0146766 A1 | 5/2020 | Lee |
| 2020/0222137 A1 | 7/2020 | Lee et al. |
| 2020/0229835 A1 | 7/2020 | Lee et al. |
| 2020/0237466 A1 | 7/2020 | Lee et al. |
| 2020/0289141 A1 | 9/2020 | Yuan et al. |
| 2021/0045825 A1 | 2/2021 | Lee et al. |
| 2021/0145470 A1 | 5/2021 | Holsten |
| 2021/0282797 A1 | 9/2021 | Bhowmick et al. |
| 2021/0386428 A1 | 12/2021 | Larsen et al. |
| 2022/0079611 A1 | 3/2022 | Lee et al. |
| 2022/0273381 A1 | 9/2022 | Lee et al. |
| 2023/0034145 A1 | 2/2023 | Awtar et al. |

FOREIGN PATENT DOCUMENTS

| | | | |
|---|---|---|---|
| EP | 3232951 A2 | 10/2017 |
| EP | 3232952 A1 | 10/2017 |
| EP | 3232973 A1 | 10/2017 |
| EP | 3232974 A2 | 10/2017 |
| EP | 3232977 A1 | 10/2017 |
| EP | 3340897 A1 | 7/2018 |
| EP | 3566664 B1 | 3/2022 |
| GB | 937587 A | 9/1963 |
| GB | 973587 A | 10/1964 |
| GB | 2513326 A | 10/2014 |
| GB | 2552540 A | 1/2018 |
| GB | 2552541 A | 1/2018 |
| JP | H0884702 A | 4/1996 |
| JP | H0996146 A | 4/1997 |
| JP | 2002102248 A | 4/2002 |
| JP | 3292879 B2 | 6/2002 |
| JP | 2003061969 A | 3/2003 |
| JP | 2007130485 A | 5/2007 |
| JP | 2009127289 A | 6/2009 |
| JP | 6220085 B2 | 10/2017 |
| WO | WO2006036067 A2 | 4/2006 |
| WO | WO2007137304 A2 | 11/2007 |
| WO | WO2007146894 A2 | 12/2007 |
| WO | WO2008020964 A2 | 2/2008 |
| WO | WO2013027203 A1 | 2/2013 |
| WO | WO2014033717 A1 | 3/2014 |
| WO | WO2015125140 A1 | 8/2015 |

(56)                    References Cited

FOREIGN PATENT DOCUMENTS

| WO | WO2016063213 A1 | 4/2016 |
| WO | WO2016161449 A1 | 10/2016 |
| WO | WO2020141702 A1 | 7/2020 |

OTHER PUBLICATIONS

International Preliminary Report on Patentability for International Application No. PCT/US2021/035469 dated Dec. 6, 2022 (8 pages).
International Search Report and Written Opinion for PCT/US21/41365 dated Dec. 16, 2021 (12 pages).
Kuta et al.; Shape Memory Alloy Servo Actuator System With Electric Resistance Feedback and Application for Active Endoscope (conf. paper); 1988 IEEE Int'l Conf. on Robotics and Automation; pp. 427-430; Apr. 24-29, 1988.
Clement et al.; Design of a Snake-Like Manipulator; Robotics and Autonomous Systems; 6(3); pp. 265-282; Jul. 1990.
Jug et al.; The JPL Sepentine Robot: a 12 DOF System for Inspection (Conference Paper); Proceedings—IEEE International Conference on Robotics and Automation 3: 5 pgs.; Jun. 1995.
Walker et al.; Novel 'Elephant's Trunk' Robot; IEEE/ASME International Conference on Advanced Intelligent Mechatronics, AIM; Piscataway, NJ, United States; pp. 410-415; Sep. 19-23, 1999.
Peirs et al.; A flexible distal tip with two degrees of freedom for enhanced dexterity in endoscopic robot surgery; MME'02; The 13th Micromechanics Europe Workshop; Sinaia, Romania; pp. 271-274; Oct. 6-8, 2002.
Simaan et al.; A dexterous system for laryngeal surgery; Proceedings of the 2004 IEEE International Conference on Robotics and Automation; New Orleans, LA.; pp. 351-357; Apr. 2004.
Awtar et al.; A minimally invasive surgical tool with enhanced dexterity and intuitive actuation; J. Med. Devices; 4(3); 8 pages; (Author's Draft; 12 pages); Sep. 10, 2010.
Do et al.; Adaptive control of position compensation for cable-conduit mechanisms used in flexible surgical robots; Proceedings of the 11th International Conference on Informatics in Control, Automation and Robotics (ICINCO-2014); IEEE; pp. 110-117; Sep. 1, 2014.
Licht et al.; U.S. Appl. No. 15/286,489 entitled "Medical devices having smoothly articulating multi-cluster joints," filed Oct. 5, 2016.
Zimmerman et al.; U.S. Appl. No. 15/286,547 entitled "End-effector jaw closure transmission system for remote access tools," filed Oct. 5, 2016.
Wikipedia; Constant Velocity Joint; 6 pgs.; retrieved from the Internet (https://en.wikipedia.org/wiki/Constant -velocity_joint) on Dec. 22, 2016.
Awtar; U.S. Appl. No. 15/564,112 entitled "Tension management apparatus for cable-driven transmission," filed Oct. 3, 2017.
Zimmerman et al.; U.S. Appl. No. 15/946,612 entitled "End-effector jaw closure transmission systems for remote access tools," filed Apr. 5, 2018.
Wikipedia; Six-bar linkage; 2 pages; retrieved from the internet (https://en.wikipedia.org/w/index.php?title=Six-par_linkage&oldid=670945266) on Apr. 26, 2019.
Partial Supplementary European Search Report for EP Application No. 21842968.6 dated Jul. 1, 2024 (13 pages).
European Search Report for European Application No. 21842968.6 dated Sep. 23, 2024 (12 pages).

* cited by examiner 101, 301
H.Body A

105', 105"

Axis 1
111, 311

H.Body C
103, 303

101, 301
H.Body A

105', 105"

320
Keying
Interface

H.Body C
(D-Shaft)
103, 303

Axis 1
111, 311

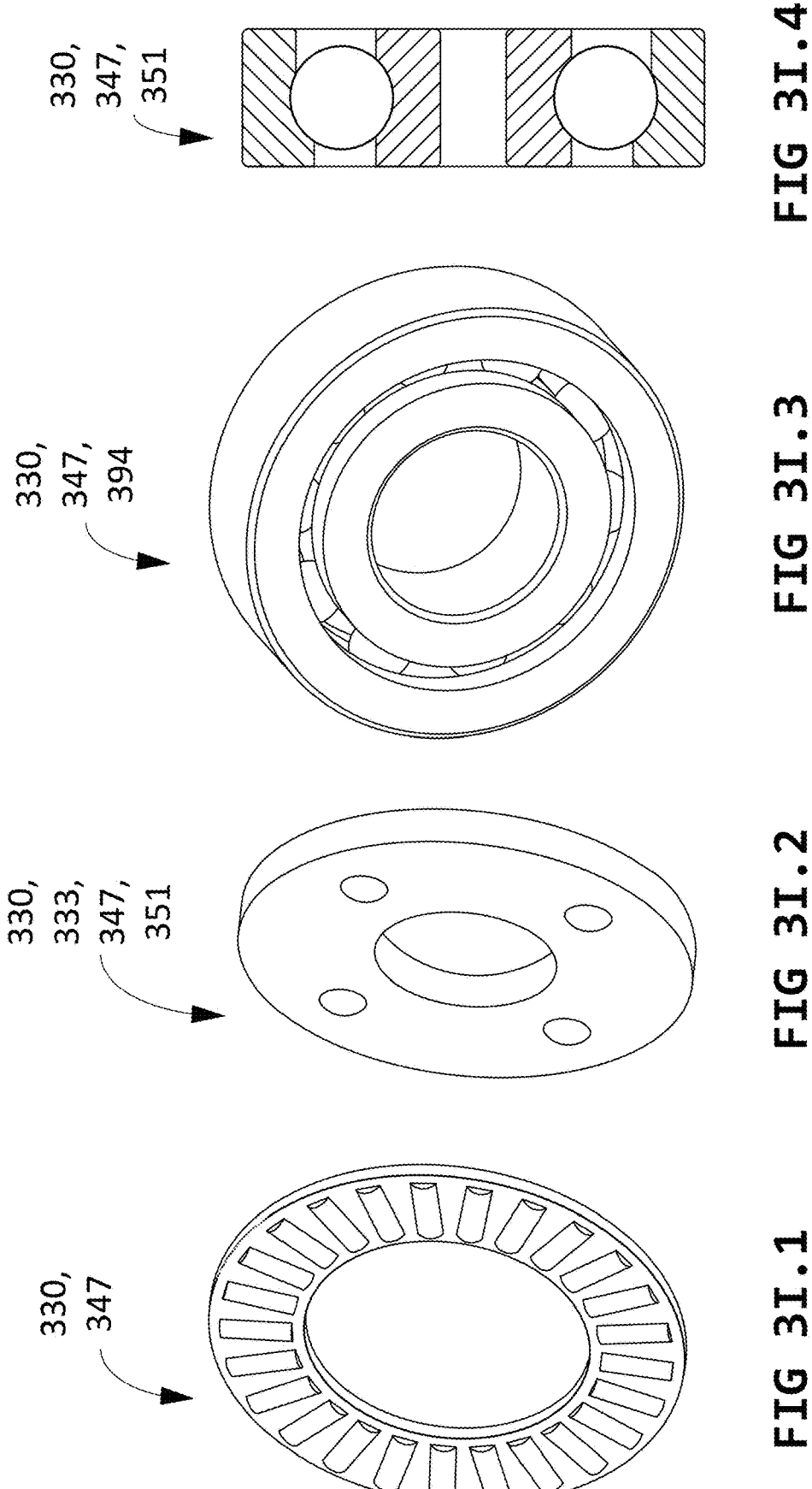
330,
347,
351
FIG 3I.4
330,
347,
394
FIG 3I.3
330,
333,
347,
351
FIG 3I.2
330,
347
FIG 3I.1

400

101, 401
Shell (H. BodyA)

104, 404
Shuttle (H.Body D)

335
Washer between
H.Body B and
bearing 102, 402
Rotation Dial Left
part (H.Body B)

330, 333, 347
Thrust Bearing 103, 403
Pull Rod
(H.Body C)

Thrust Bearing
between H.Body
C and H.Body D
455

Rotation Dial-Right
part (H.Body B)
102, 402

Handle Lever
(Extension of H.Body C)
413

Washer between
H.Body A and
bearing
334

Ergonomic Handle Shell
(H.Body A)
101, 501

400

Tool Frame
525

Rotation Dial (H.Body B)
102, 502

529

533
Transmission Strip 1

111, 511
Axis 1

534
Transmission Strip 2

566
Cable (Jaw Closure
Transmission Member) and
Conduit (outer jacket to
cable)

526
Tool Shaft

568
EE.Moving Jaw

515
Axis 3

513
Axis 2

EE Articulation
Output Joint
583

569
EE.Fixed Jaw

913
Axis 2

969
EE. Fixed Jaw

965

EE Articulation
Output Joint
928

EE. Moving Jaw
968

927

926
Tool Shaft

950
EE Rotation Transmission
Member. May house Jaw Closure
Actuation Transmission Member
471

915
Axis 3

925
Tool Frame 111, 911
Axis 1

101, 901
Ergonomic Handle
Shell (H.Body A)

102, 902
Rotation Dial
(H.Body B)

Handle Lever
(Extension
of H.Body C)
949

Transmission Strip
533, 933

1000

Ergonomic Handle Shell
(H.Body A)
1001, 101

1002, 102
Rotation Dial (H.Body B)

1011, 111
Axis 1

1065
End Effector

1068

1015
Axis 3

1013
Axis 2

Handle Lever
(Extension of H.Body C)
1049

Tool Shaft
1026

1067

1069

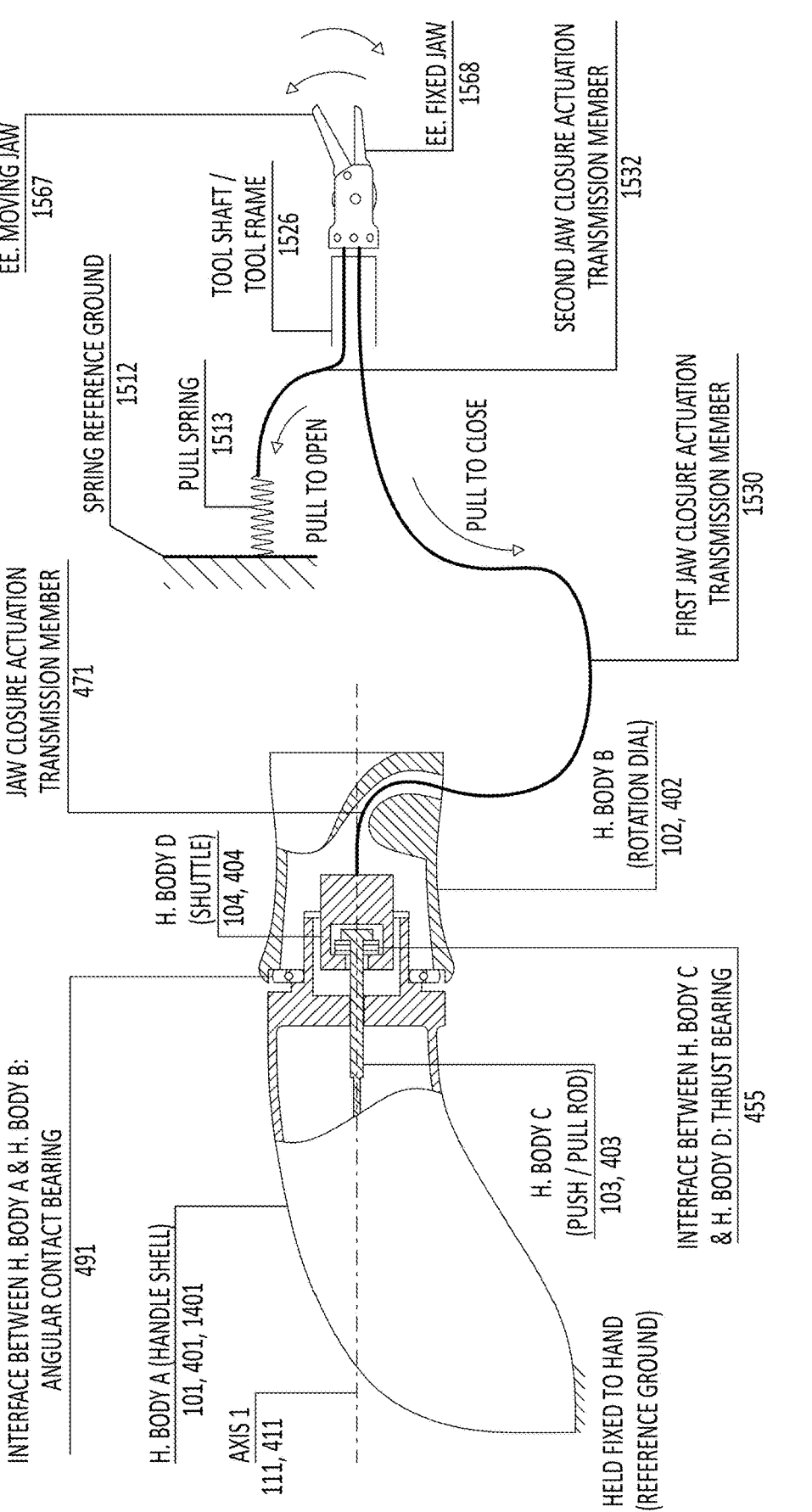

EE. MOVING JAW 1567

EE. FIXED JAW 1568

SECOND JAW CLOSURE ACTUATION TRANSMISSION MEMBER 1532

TOOL SHAFT / TOOL FRAME 1526

SPRING REFERENCE GROUND 1512

PULL SPRING 1513

PULL TO OPEN

PULL TO CLOSE

FIRST JAW CLOSURE ACTUATION TRANSMISSION MEMBER 1530

JAW CLOSURE ACTUATION TRANSMISSION MEMBER 471

H. BODY D (SHUTTLE) 104, 404

H. BODY B (ROTATION DIAL) 102, 402

INTERFACE BETWEEN H. BODY A & H. BODY B: ANGULAR CONTACT BEARING 491

H. BODY A (HANDLE SHELL) 101, 401, 1401

AXIS 1 111, 411

H. BODY C (PUSH / PULL ROD) 103, 403

INTERFACE BETWEEN H. BODY C & H. BODY D: THRUST BEARING 455

HELD FIXED TO HAND (REFERENCE GROUND)

FIG. 15

Virtual Center 1721

Transmission Strip 2 534

533 Transmission Strip 1

525 Tool Frame

Ergonomic Handle Shell (H.Body A) 101, 501

Handle Lever (Extension of H.Body C) 549

Rotation Dial (H.Body B) 102, 502

526 Tool shaft

515 Axis 3

Jaw Closure Actuation Transmission Member and Conduit (outer jacket) 566

End Effector Assembly 1765

1700

1800

525
Tool Frame

526
Tool Shaft 102, 502
Handle
Dial

400

101, 501
Handle
Shell

1807
Forearm
Attachment
Joint

Roll Axis
111, 1835

600

566

533

1833
Pitch Axis

1805
Pulley Block/
Outer Ring

Tool Input Joint:
VC mechanism
1801, 1801'

549

Transmission
Strip
534

Transmission
Pulley
1813.1

Yaw Axis
1831

Wrist Cuff
1803

Virtual Center
1821

Transmission
Pulley
1813.2

Transmission
Pulley Rotation Axis
1831.2

Transmission
Pulley Rotation Axis
1833.2

Shaft 2011

Output Articulation Joint 2020

EE Frame 2016

Moving Jaw Pivot Pin 2018

Moving Jaw Pivot Axis / Axis 4

Moving Jaw 2012

End-Effector Assembly 2010

EE Roll Axis / Axis 2

Fixed Jaw 2014 (distal end)

Shaft
2011

Output Articulation
Joint 2020

EE Base
(proximal end)

Thrust Bearing
2030

EE Frame
2016

Moving Jaw Pivot
Pin 2018

Moving Jaw
Pivot Axis /
Axis 4

Moving Jaw
2012

EE Roll Axis / Axis 2

Fixed Jaw
2014

End-Effector Assembly 2010

Rack & pinion gearset 2056, 2060

Handle Body 2026

Closure Input Pivot Axis

Closure Input (pinion gear) 2048

2052 Interface between Dial and Handle Body: Plain bearing

2046 Shuttle

2062 Interface between Shuttle and Dial: Prismatic Joint

Dial 2024

Push Rod (rack) 2044

Interface between Push Rod and Handle Body: Prismatic Joint 2058

Interface between Push Rod and Shuttle: Thrust bearing 2054

Axis 1

2022

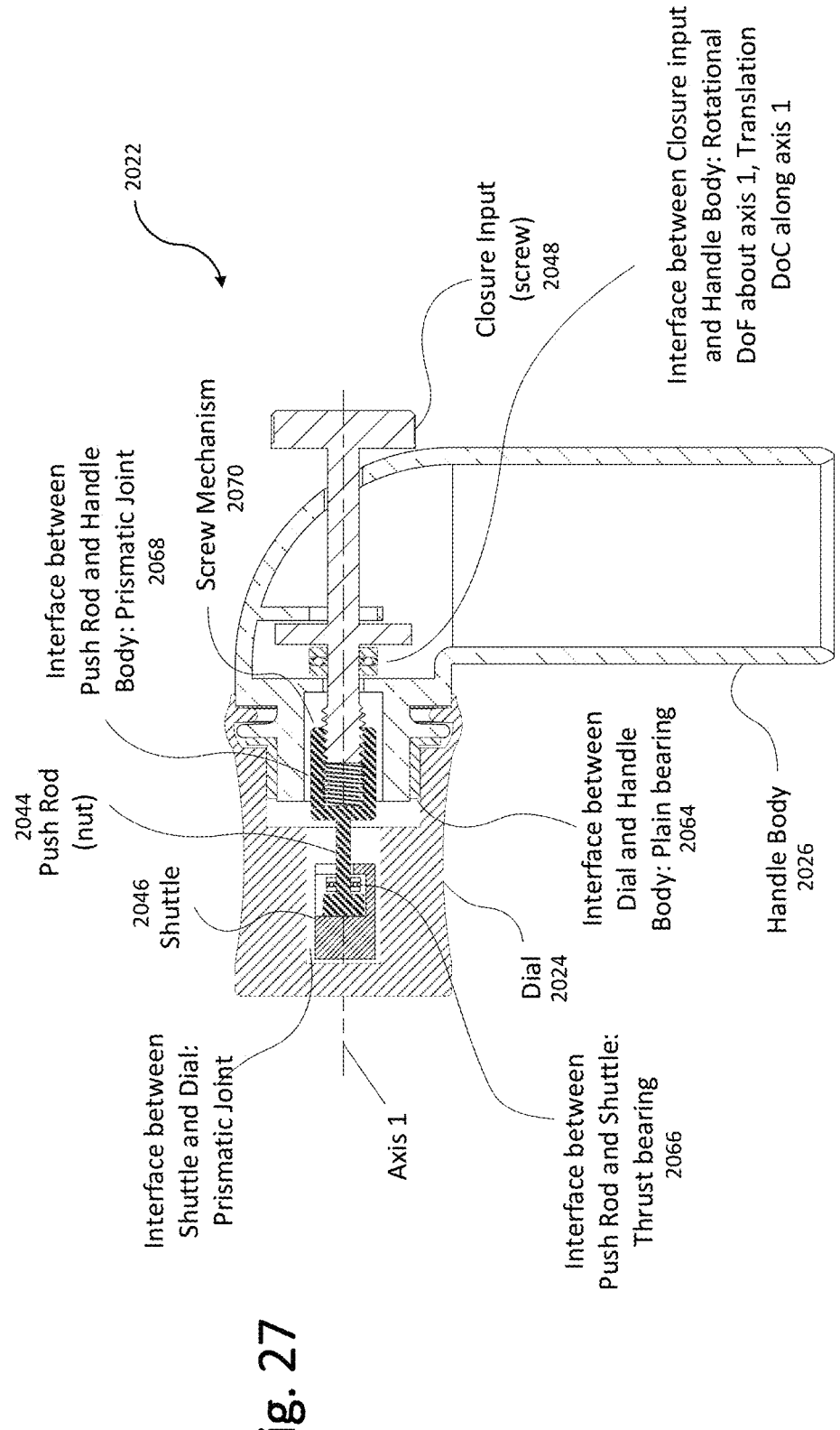

2022

Closure Input (screw) 2048

Interface between Closure input and Handle Body: Rotational DoF about axis 1, Translation DoC along axis 1

Interface between Push Rod and Handle Body: Prismatic Joint 2068

Screw Mechanism 2070

2044 Push Rod (nut)

2046 Shuttle

Interface between Dial and Handle Body: Plain bearing 2064

Handle Body 2026

Interface between Shuttle and Dial: Prismatic Joint

Axis 1

Dial 2024

Interface between Push Rod and Shuttle: Thrust bearing 2066

Interface between Push Rod and Handle Body: Prismatic Joint

Interface between Handle Body and Dial: Ball bearing 2080

Push Rod 2044

2026 Handle Body

Interface between Roll Input and Handle Body: Ball bearing

Interface between Shuttle and Push Rod: Thrust Bearing 2082

Axis 1'

Roll Input 2050

Axis 1

Bevel Gear Interface 2084

Dial 2024

Shuttle 2046

2022

2024
Dial

Shuttle
2046

Interface between
Shuttle and Dial:
Compliant beams-
based prismatic joint
2086

Interface between
Shuttle and Push Rod:
Ball Bearing

Interface between Dial and
Handle Body: Ball Bearing

2026
Handle Body

Interface between Handle
Body and Push Rod:
Compliant beams-based
prismatic joint 2088

Push Rod
2044

Axis 1

2022

2024
Dial

2026
Handle Body

2044
Push Rod

Shuttle
2046

Axis 1

Interface between
Shuttle and Dial:
Compliant beams-
based prismatic joint
2086

Interface between
Shuttle and Push Rod:
Ball Bearing

Interface between Dial and
Handle Body: Ball Bearing

Interface between Handle
Body and Push Rod:
Compliant beams-based
prismatic joint
2088

Shuttle
2046

Flexure Bearing providing
Shuttle 1 DoF translation
relative to Dial along
direction 1
2090

2024
Dial

Flexure Bearing providing
Shuttle 1 DoF translation
relative to Dial along
direction 1
2090

Axis 1

2024
Dial

Compliant features providing
translation of Shuttle w.r.t. Dial
along Direction 1
2092

2046
Shuttle

Axis 1

2024
Dial (local
ground)

Shuttle
2046

Force
application

Deflected
compliant
beams

2022

Interface between
Roll Body and
Handle Body: Plain
bearing

Interface between
Shuttle and Closure
Body: Ball end and
Prongs

Handle Body
2026

Closure Body
2044

2096
Interface between
Shuttle and Roll Body:
Prismatic Joint

Axis 1

Shuttle
2046

Roll Body
2024

Closure Body
Pivot Axis

3012 Diaphragm Spring

Section 1-1 Location

Section 2-2 Location

Axis 1

Counter Clockwise Ratchet interface between Dial and Shuttle

Dial 2024

Clockwise Ratchet interface between Dial and Shuttle

Shuttle 2046

Handle Body
2026

Axis 1

Discrete or continuous dial
rotation switch/push-push button

Dial
2024

HANDLE ASSEMBLY PROVIDING UNLIMITED ROLL

CROSS REFERENCE TO RELATED APPLICATIONS

This application is a continuation-in-part of U.S. patent application Ser. No. 15/943,689, entitled "HANDLE MECHANISM PROVIDING UNLIMITED ROLL", and filed on Apr. 2, 2018, the contents of which are hereby incorporated herein in their entirety by reference. U.S. patent application Ser. No. 15/943,689 is a continuation of International application Ser. No. PCT/US2016/055195, entitled "HANDLE MECHANISM PROVIDING UNLIMITED ROLL", filed on Oct. 3, 2016, the contents of which are hereby incorporated herein in their entirety by reference. International application Ser. No. PCT/US2016/055195 claims priority to U.S. provisional patent application No. 62/236,835, filed on Oct. 2, 2015, the contents of which are hereby incorporated herein in their entirety by reference.

This application may also be related to U.S. patent application Ser. No. 15/130,915, titled "ATTACHMENT APPARATUS FOR REMOTE ACCESS TOOLS" filed on Apr. 15, 2016, which claimed priority to U.S. provisional patent application No. 62/147,998, titled "FOREARM ATTACHMENT APPARATUS FOR REMOTE ACCESS TOOLS" filed on Apr. 15, 2015, and U.S. provisional patent application No. 62/236,805, titled "FOREARM ATTACHMENT APPARATUS FOR REMOTE ACCESS TOOLS" filed on Oct. 2, 2015. This application may also be related to U.S. patent application Ser. No. 15/054,068, titled "PARALLEL KINEMATIC MECHANISMS WITH DECOUPLED ROTATIONAL MOTIONS" filed on Feb. 25, 2016, which claims priority as a continuation-in-part to U.S. patent application Ser. No. 14/166,503, titled "MINIMAL ACCESS TOOL" filed on Jan. 28, 2014, Publication No. US-2014-0142595-A1, which is a continuation of U.S. patent application Ser. No. 12/937,523, titled "MINIMUM ACCESS TOOL" filed on Apr. 13, 2009, now U.S. Pat. No. 8,668,702, which claimed priority to U.S. provisional patent application No. 61/044,168, titled "MINIMALLY INVASIVE SURGICAL TOOL" filed on Apr. 11, 2008. Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are handle assemblies, and apparatuses and applications using them. For example, described herein are handle assemblies with a mechanism that enables unlimited rotation ("unlimited-roll handle assemblies") and apparatuses for minimally invasive surgical tools and remote access tools using them.

BACKGROUND

A number of remote access tools and minimally invasive surgical tools which incorporate handle assemblies with unlimited (or infinite) rotation functionality are known, for example, as described in International Patent Application Publication WO 2007/146894 A2. This application describes laparoscopy tools primarily consisting of a proximal handle, a tool frame/tool shaft, and a distal end-effector (EE). In some of these laparoscopic devices, to rotate the end-effector about the tool shaft axis (i.e., to provide a roll rotation of the end-effector), the user may have to rotate the handle about the tool shaft axis. While the handle may fit or conform in the user's hand, palm, and/or fingers in the nominal condition (i.e., prior to any roll rotation), it may no longer continue to fit/conform with the user's hand during and after the roll rotation. In fact, during such rotation, the handle may start to collide with areas of the hand that are holding the device, typically limiting the amount of roll rotation and/or requiring repositioning of the handle within the surgeon's hand to achieve maximum roll rotation at the end-effector. Thus, many of these devices may require more than one hand to operate or may require repositioning of the device during operation within a user's hand in order to continue to roll in a single direction beyond a limited amount of roll. In addition, a device that is repositioned to continue roll rotation is usually not ergonomic and more difficult to operate due to loss of access to the input joint/mechanism between the tool frame/tool shaft. Attempts have been made to address the challenge of limited rotation and reduced ergonomics by providing a rotational joint in the handle assembly between the stationary portion of the handle that is held generally by a user's hand and palm (and possibly by finger(s) and/or thumb) in the nominal condition and the roll portion (e.g. a dial, handle dial, rotation dial or the like) that is rotated with respect to the stationary portion about its center axis generally by the user's finger(s) and/or thumb; these attempts have met this challenge with only limited success, in part because rolling the device in this manner may result in winding of internal transmission members when rolling the roll portion (e.g., dial, handle dial, rotation dial or the like) relative to the stationary portion. The stationary portion of the handle is defined stationary as far as roll rotation motion is concerned. Generally, this stationary portion is "stationary" with respect to the user's palm. This stationary portion may move along with the user's hand to provide other degrees of freedom (e.g., pitch and yaw rotations in articulating laparoscopic devices).

These devices that incorporate the stationary portion and roll portion in the handle assembly may be articulating or non-articulating. In some non-articulating devices, the handle assembly and tool shaft can be rigidly connected and rotation of the entire handle assembly may drive rotation of the tool shaft and end-effector. In other non-articulating devices, the handle assembly and tool shaft can be rigidly connected and the handle may be equipped with a dial, wherein the dial is connected to the end-effector and drives the rotation of the end-effector via a roll transmission member routed through the tool shaft. Furthermore, laparoscopic devices are becoming more complex and catering to challenging laparoscopic procedures. Laparoscopic tools may now include articulating end-effectors that can be actuated by an input articulation joint between the tool shaft and the handle assembly. Articulating end-effectors enable the surgeon to alter the axis of roll rotation of the end-effector by articulating the handle assembly about an input articulation joint (also referred to as the input joint or the articulation input joint here) with respect to the tool shaft. The handle assembly in such device is not rigidly connected to the tool shaft but is instead connected via an input joint that generally allows two articulation degrees of freedom (e.g., yaw rotation and pitch rotation) and constrains, and therefore transmits, roll rotation. In some articulating devices, rotation of the end-effector may be driven by the rotation of the dial portion of the handle assembly, which further transmits roll to the end-effector via rotation of tool shaft. Here, the tool shaft is connected to the handle assembly via an input articulation joint providing yaw and pitch degrees of freedom but transmitting roll rotation from the handle assembly to the tool shaft. Similarly, the roll rotation of the tool shaft is transmitted to the end-effector via an output articulation joint. An example of such device configuration is an articulating device by Novare™ (International Patent Application Publication WO2007/146894 A2). In other articulating devices, articulation transmission and roll transmission are decoupled such that roll is directly transmitted from the rotation of the dial portion of handle assembly to the end-effector via a separate roll transmission member and not via the roll degree of constraint (DoC) with respect to the input articulation joint, tool shaft, and output articulation joint (also referred to as output joint or the articulation output joint here). This roll transmission member should be adequately stiff in torsion to transmit roll rotation. This roll transmission member may or may not be routed through the input articulation joint or the tool frame/tool shaft. An example of such device configuration is an articulation device sold by Covidien™ (U.S. Pat. No. 8,603, 135).

Typically, the enhanced dexterity that these articulating tools offer comes with the tradeoff of increased resistance to roll rotation of the roll portion of the handle assembly. This resistance to roll rotation is further increased when the end-effector is articulated. This resistance may increase further when a handle input (e.g., lever within the handle assembly) is engaged, which leads to the end-effector actuation (e.g., opening and closing of a moving portion of the end-effector relative to a reference portion of the end-effector). The resistance to roll can be considerable while simultaneously performing end-effector articulation and end-effector actuation. Engagement of a handle input (e.g., handle input lever) to actuate the opening/closing of an end-effector having a jaw at the end of the tool shaft typically results in high loads generated between the stationary portion of the handle assembly held by the user and the rotatable portion of the handle assembly (e.g., dial) that interface with each other to allow rotation. The result of the high load between these independent bodies is typically an increase in frictional resistance to roll rotation which limits the surgeon's ability to use fine rotation input at the handle assembly to precisely control the end-effector roll rotation. The high jaw (open/close) actuation loads are typically transmitted from the handle input by a transmission member such as a steel cable, steel wire, a monofilament steel, a Nitinol rod, or a tungsten cable, etc. These types of transmission members function well to transfer loads from an input location to an output or remote portion of an instrument. Due to the complexity in simultaneously transmitting and providing roll, articulation, and actuation functionality to the end-effector in such devices, as well as the limitation of working within a tight volume to incorporate features to meet these functionalities, it is challenging to incorporate assemblies, mechanisms, joints, and bodies that meet the structural and interface requirements to be able to provide the aforementioned functionalities.

Described herein are apparatuses (e.g., mechanisms, devices, tools, machines, systems, etc.) including handle assemblies with an unlimited-roll mechanism which may address these problems.

SUMMARY OF THE DISCLOSURE

Described herein are apparatuses (including mechanisms, instruments, devices, tools, systems, etc.) that may include handle assemblies that provide unlimited (e.g., "infinite") roll of a portion of the handle assembly relative to another portion of the handle assembly, and may transmit this roll to an end-effector in an advantageous manner. The unlimited-roll mechanisms described herein may be part of an apparatus that includes the handle assembly, a tool frame (which may be a tool shaft or may include a tool shaft), and an end-effector assembly. In some variations, the apparatus may include an end-effector assembly (or simply, end-effector) that can be articulated with respect to the tool frame via an end-effector articulation joint at the distal end of the device; articulation of the end-effector may be controlled by an input articulation joint (input joint) at the proximal end of the device, including between the handle assembly and the tool frame. In any of these apparatuses, the tool frame may be interfaced with a user's arm (e.g., wrist, forearm, etc.) via an arm attachment (e.g., forearm attachment), while the user's hand (palm, fingers, thumb, etc.) is interfaced with the handle assembly. The arm attachment may be connected to the tool frame by a joint (e.g., a bearing) that allows one or more degrees of freedom (e.g., pitch, yaw, roll) between the user's arm and the tool frame. In any of these apparatuses, the end-effector may have at least one moving portion (e.g., a moving jaw) that can be actuated (e.g., opened/closed) by an input control on the handle assembly that causes an output actuation of the end-effector via an end-effector jaw actuation member. In some of these apparatuses, the jaw actuation transmission member may be a tension/compression member which may be pulled by the input control in the handle assembly to cause end-effector actuation (say, jaw closure actuation). The same or a different jaw actuation transmission member, either tension/compression member may be used to cause the end-effector actuation (say, jaw opening actuation), undoing the previous actuation. This may lead to a pull (first actuation)-pull (second actuation) operation as part of end-effector actuation or a pull (first actuation)-push (second actuation) operation or a push (first actuation)-pull (second actuation) operation.

In general, the unlimited-roll handle assemblies described herein may also be referred to as unlimited rotation handle assemblies, or as unlimited rotation handle apparatuses, or as unlimited-roll handle apparatuses, or the like. In general, the stationary portion of the handle assembly may also be referred to as a handle shell, or as an ergonomic handle shell or as a handle body or as a first portion of the handle assembly or the like. In general, the rotational portion of the handle assembly may also be referred to as a rotation portion, or as a rotation dial, or as a rotating portion, or as a dial or as a second portion of the handle assembly or the like. In general, the input control in the handle assembly may also be referred to as a control, or as an input lever, or as an end-effector control, or as an input lever control or the like.

These unlimited-roll handle assemblies may allow actuation of a distal end-effector (e.g., open and close of end-effector jaws) by an input control on a first portion of the handle assembly (e.g., a handle body) using an end-effector actuation transmission member comprising a cable (steel, tungsten, etc.), steel wire, etc. or a monofilament steel or Nitinol rod, etc. to transmit actuation from the handle assembly without binding up or disruption of the end-effector actuation. This actuation may happen independently, or in parallel, or regardless of the other motions such as end-effector articulation and end-effector roll rotation.

For example, when end-effector is a jaw assembly, it may include one or two moving jaws that are movable with respect to a base end-effector portion (a first end-effector portion). These one or more moving jaws refer to the second, third, and so on end-effector portions. In some variations, one of the jaws of the jaw assembly may be part of (or rigidly attached to) the base end-effector portion. The one or more movable jaws may be moved by a jaw actuation transmission member that is connected to the shuttle portion of the handle assembly. This open/close action of the jaws in the end-effector assembly may be controlled by an end-effector control that may be a moving body (such as a lever, button, slider, etc.) in the handle assembly. Thus, disclosed herein are unlimited-roll handle assemblies that may be part of an apparatus that includes a corresponding rotation of an end-effector assembly, while being able to transmit a control input from the handle assembly to an actuation of the end-effector (e.g., open/close motion).

The apparatuses described herein may be configured for use in any application, including, but not limited to, medical devices (e.g., surgical devices including minimally invasive devices such as laparoscopes, endoscopes, etc.) and the like. For example, an articulated unlimited-roll handle assembly as described herein may be used as part of a remote access tool that require finesse rotation about a tool-shaft axis and manipulation or articulation of a tool shaft and/or end-effector. In general, the apparatuses described herein may be useful for a variety of purposes.

As will be described in greater detail herein, any of these apparatuses may include a handle assembly having multiple portions or bodies or components that are coupled together to provide specific rotational and/or translational degrees of freedom relative to each other to provide a reference or ground portion (also referred to herein as a palm grip, palm grip portion, handle body, handle shell, or the like) that may be held within a user's hand and to provide a rotating portion (referred to herein as a knob, dial, finger dial, rotation dial etc.) that may be operated by the fingers (including the thumb) of the same hand holding the palm grip In some variations, the handle assembly may be referred to as a handle, a handle mechanism, an unlimited-roll handle assembly, an infinite roll handle, or the like. In some variations the handle assembly includes four interconnected components (or bodies) and an end-effector control input (also sometimes referred to as closure input), such as a lever, button, dial or other control, to actuate (e.g., open/close) the end-effector. The four interconnected bodies that are part of the handle assembly may include a first handle portion (e.g., palm grip), a second handle portion (e.g., finger dial), a push rod (typically internal to the first handle portion), and a shuttle body (typically internal to the second handle portion). The push rod is typically a rigid member and may alternatively be referred to as a pull rod. The shuttle body typically connects to (or includes) a portion of an end-effector actuation transmission member, such as a transmission cable, for transmitting actuation of the end-effector control input to the end-effector. As used to describe degrees of freedom here, axis refers to a specific line in space. A body may rotate with respect to (w.r.t.) another body about a certain axis. A body may translate w.r.t. another body along a certain direction. A direction is not defined by a particular axis and is instead commonly defined by multiple parallel axes. Thus, X axis is a specific axis defined and shown in a figure, while X direction refers to the direction of this X axis. Multiple different but parallel X axes have the same X direction. Direction only has an orientation and not a location in space.

For example, a handle assembly configured as an unlimited-roll handle assembly may include a first handle portion that is an outer proximal body configured as a palm grip. Generically, this body may be referred to as handle body A ("H.Body A"), also referred to as "handle shell". The handle assembly may also include a second handle portion configured as an outer distal body, which may be generically referred to as handle body B ("H.Body B"). These two bodies may be considered independent bodies with an established joint where additional features may exist. Within the joint between these two bodies, there may exist specific geometric features such as ribs, surfaces, edges, washers, bushings, bearings, lubricants, etc. which may function to offer some degrees of freedom while constraining others. This joint between the outer bodies may also be internally traversed by a secondary pair of bodies. These secondary bodies may have a portion of them proximal or distal to the joint between H.Body A and H.Body B. One of the secondary bodies may be generically referred to herein as handle body C ("H.Body C") and may be, e.g., a proximal push rod having a portion of it connecting to H.Body A. The other secondary body may be generically referred to herein as handle body D ("H.Body D") and may be, e.g., a distal shuttle having a portion of it connecting to H.Body B. Likewise, the joints between either of the inner secondary bodies with respect to each other and with respect to the outer two bodies may also comprise specific geometric features such as ribs, surfaces, edges, washers, bushings, bearings, lubricants, etc. which may function to offer some degrees of freedom while constraining others. A generic description of this four-body structure showing the degrees of constraint and degrees of freedom is illustrated in FIG. 1. A four-body unlimited-roll handle assembly such as the one shown generically in FIG. 1 may be incorporated as part of an articulating laparoscopic instrument, for example. A user (such as a physician, doctor, surgeon, etc.) may hold the handle assembly and apply articulation input (causing pitch/yaw motion) through a joint distal or proximal to the handle assembly. This articulation input joint (pitch/yaw) may connect the handle assembly to the tool frame/tool shaft. This articulation input may be transmitted to an articulation output joint (pitch/yaw) at the distal end of the instrument via one or more articulation transmission members. This articulation output joint may connect the tool shaft/tool frame to the end-effector assembly. This transmission member(s) connects to the articulation input joint and an articulation output joint (proximal to the end-effector assembly). The surgeon may then rotate the end-effector about its center/roll axis (Axis 2) by rotation of the second portion or dial body (H.Body B) relative to first portion of the handle assembly or proximal outer body (H.Body A) about its center axis (Axis 1). While holding (grounding) the proximal outer body (H.Body A, e.g., a palm grip) in his/her palm, the user may rotate the distal outer body (e.g., H.Body B, e.g., a rotation dial) to drive rotation with a finesse twirling motion between the thumb and forefinger. A rotation joint between H.Body A (first portion) and H.Body B (second portion) presented in FIG. 1 may function to reduce friction and relieve the user of strenuous resistances which can otherwise be generated when the user also chooses to activate the jaw closure, for example, by transferring translation along a first axis direction (e.g., Axis 1 in FIG. 2) from H.Body C to H.Body D and generating a force in the tension/compression (jaw close/open) transmission member of the handle assembly. As will be described and illustrated in greater detail below, when the user activates the end-effector input control at the handle assembly, this motion is transmitted to the translation of H.Body C along a first axis direction with respect to H.Body A via a transmission mechanism in the handle assembly. The translation of H.Body C is further transmitted to the translation of H.Body D, which is transmitted to an end-effector via an end-effector actuation transmission member. While the transmission happens, the surgeon can also infinitely rotate the rotation dial (H.Body B) on the handle assembly clockwise or counterclockwise without twisting the end-effector actuation transmission member due to keying or constrained joints between H.Body B and H.Body D.

In variations in which the handle assembly is used with an articulating joint, such as the joint between the handle assembly and the tool shaft, the articulation input joint may be a parallel kinematic (P-K) joint (e.g., per U.S. Patent Application Publication 2013/0012958 or U.S. Pat. No. 8,668,702), or a virtual center (VC) joint (e.g., per U.S. Pat. No. 5,908,436), or a parallel kinematic virtual center joint (e.g., per U.S. Pat. No. 8,668,702), or a serial kinematic (S-K) joint (e.g., per U.S. Pat. Nos. 8,465,475 or 5,713,505), or a combination of a serial kinematic and a parallel kinematic joint. The unlimited-roll handle assemblies described herein may be particularly useful with apparatuses that are articulating, e.g., having an articulation input joint between the handle assembly and the tool frame (e.g., tool shaft). Here, transmission cables (that are compliant in compression, torsion, and bending, such as a rope, braided cable, etc.) may be the effective end-effector actuation transmission member and/or end-effector articulation member. These highly compliant transmission members may be able to bend through tight bend radii and provide effective transmission. Wire that is torsionally stiff but compliant in bending may also be used for either of the two aforementioned transmissions and/or for end-effector rotation transmission. Articulation transmission members, roll transmission members, and end-effector actuation transmission members may be distinct bodies, or they may be combined into one body in a pair or triplet to perform intended transmission. The transmission members may route through different paths to link their respective joints. For example, an articulation transmission member may be routed through the body of the tool frame (e.g., tool shaft), or it may be routed externally to the body of the tool shaft.

As mentioned above, any of the apparatuses described herein may include an unlimited-roll handle assembly and an arm attachment (e.g., forearm attachment) so that a proximal end region of the apparatus may be connected to the user's arm/forearm. These apparatuses may permit improved control of the apparatus when the apparatus is rigidly coupled to the user's arm (e.g., having no degrees of freedom between the apparatus and the user's arm), but may be particularly helpful where the arm attachment permits one or more degrees of freedom between the tool frame and the user's arm, such as one or more of roll, pitch, and/or yaw degrees of freedom.

For example, described herein are apparatuses, including medical devices, comprising: an elongate tool frame having a forearm attachment portion at a proximal end, the elongate frame having a tool axis; an end-effector at a distal end of the elongate tool frame; a handle assembly that provides unlimited roll to the end-effector, wherein the handle assembly includes: a first handle portion; a second handle portion coupled to the first handle portion so that the second handle portion has one rotational degree of freedom in a first axis relative to the first handle portion but is translationally constrained relative to the first handle portion along the first axis direction; a push rod completely or partially within the first handle portion and coupled to the first handle portion so that it has one translational degree of freedom along the first axis direction relative to the first handle portion but is rotationally constrained about the first axis relative to the first handle portion; a shuttle body completely or partially within the second handle portion, wherein the shuttle body is coupled to the push rod so that it has one rotational degree of freedom about the first axis relative to the push rod but is translationally constrained along the first axis direction relative to the push rod, further wherein the shuttle body is coupled to the second handle portion so that it has one translational degree of freedom along the first axis direction relative to the second handle portion; and an end-effector control input on the first handle portion coupled to the push rod via a mechanism or other transmission system and configured to translate the push rod along the first axis direction, wherein the rotation of the second handle portion about the first axis is transmitted to the end-effector so that the end-effector rotates about its center axis in consequence of the rotation of second handle portion; and a cuff having a passage therethrough that is configured to hold a wrist or forearm of a user, wherein the cuff is configured to couple to the forearm attachment portion of the tool frame. In some instances, the shuttle body may be completely outside the second handle portion.

The forearm attachment portion and/or the cuff may be configured to permit one or more degrees of freedom between the cuff (which is typically rigidly attached to the user's arm) and the forearm attachment portion. For example, the device may include a joint between the forearm attachment portion of the tool frame and the cuff, wherein the joint is configured to provide one or more rotational degrees of freedom between the cuff and the forearm attachment portion of the tool frame. The joint may be a bearing (e.g., a machine element that constrains the relative motion to one or more desired motions such as pitch, roll, or yaw, and may reduce friction between the moving parts). For example, the device may include one or more joints between the forearm attachment portion of the tool frame and the cuff, wherein the one or more joints are configured to provide one or more of the following degrees of freedom: a roll degree of freedom with respect to the tool axis, a pitch degree of freedom between the cuff and the forearm attachment portion of the tool frame, or a yaw degree of freedom between the cuff and the forearm attachment portion of the tool frame.

In general, the cuff may include a strap and/or securement so that it may be attached securely to the user's arm (e.g., forearm), and may be removable from the forearm attachment portion of the tool frame so that it can be attached to the user's forearm, then snapped or otherwise attached to the forearm attachment portion of the tool frame.

In general, the unlimited roll between the second handle portion and the first handle portion may be transmitted to the end-effector. As mentioned, the roll between the second handle portion and the first handle portion may be transmitted by a transmission member that is separate from the tool frame and may be routed around or through the tool frame. For example, the rotation of the second handle portion may be transmitted to the end-effector through a rotation transmission extending between the second handle portion and the end-effector. Alternatively, in some variations, the tool shaft transmits the roll between the second handle portion and the first handle portion; for example, either the second handle portion or the first handle portion may be rigidly connected to the tool shaft so that roll between the second handle portion and the first handle portion is transmitted by the tool frame to the end-effector at the distal end of the apparatus. In general, because the unlimited roll between the second handle portion and the first handle portion is relative between the two, the transmission member for this roll may be connected to either the second handle portion or the first handle portion, although it is illustrated herein primarily as coupled to the second handle portion (e.g., the knob or dial at a distal region of the handle). For example, the rotation of the second handle portion (e.g., the knob or dial) may be transmitted to the end-effector because the elongate tool frame is coupled to the second handle portion so that the elongate tool frame is rotationally constrained relative to the second handle portion and the end-effector is coupled to the elongate tool frame so that the end-effector is rotationally constrained relative to the elongate tool frame.

As mentioned, any of the apparatuses described herein may include an input joint between the handle assembly and the tool frame. For example, any of these apparatuses may include an input joint wherein the input joint provides a pitch degree of freedom between the handle assembly and the tool about a pitch axis of rotation and a yaw degree of freedom between the handle assembly and the tool about a yaw axis of rotation. This input joint may be a parallel kinematic input joint or a serial kinematic input joint or a combination of parallel and serial kinematic input joint. For example, any of these devices may include an input joint between the handle assembly and the tool frame and an output joint (i.e., the articulation output joint) between the tool frame and the end-effector, wherein the input joint comprises a pitch motion path and a yaw motion path, further wherein the pitch motion path and the yaw motion path are independent and coupled in parallel (forming a parallel kinematic input joint) between the handle and the tool frame, wherein the pitch motion path captures pitch motion of the handle assembly relative to the tool frame for transmission to the output joint but does not capture yaw motion of the handle assembly relative to the tool frame for transmission to the output joint, and wherein the yaw motion path captures yaw motion of the handle assembly relative to the tool frame for transmission to the output joint but does not capture pitch motion of the handle assembly relative to the tool frame for transmission to the output joint. Alternatively, the pitch motion path and the yaw motion path may be arranged in series (as a serial kinematic input joint). However, as will be described herein, any of the devices including an input joint having more than one degree of freedom axis of rotation (e.g., pitch and yaw, pitch and roll, yaw and roll, etc.) may be configured so that the two or more axes of rotation intersect at a center of rotation (e.g., a virtual center of rotation) that is positioned behind (proximal to) the handle assembly, including at a virtual center of rotation that would be located within the user's wrist when the device is operated by the user. For example, the pitch axis of rotation and the yaw axis of rotation may intersect in a center of rotation that is proximal to the handle assembly.

In any of the variations including an input joint having multiple degrees of freedom (e.g., pitch and yaw), one or more transmission members may be included to transmit the motion (e.g., pitch motion, yaw motion) to the output joint and therefore the end-effector. For example, a device may include a pitch transmission member and a yaw transmission member extending from the input joint to the output joint, wherein the pitch transmission member transmits pitch rotations and the yaw transmission member transmits yaw rotations of the input joint to corresponding rotations of the output joint.

As mentioned, any appropriate end-effector may be used. The end-effector may or may not have grasping jaws (or simply jaws) that may or may not move. For example, the end-effector may have a soft end to spread delicate tissues (e.g., dissector) or a camera or a laser pointer. Therefore, an end-effector assembly may also be referred to as an end-effector or the like. The end-effector may also have one or more moving jaws, one or more stationary jaws (stationary with respect to moving jaws), or other bodies required for end-effector actuation. In some examples, an end-effector may be configured as a jaw assembly that include jaws that open and close. The end-effector control input on the handle assembly may be actuated, e.g., by a user's finger or fingers, including the user's thumb, of the same hand holding the handle assembly. For example, any of these devices may include an end-effector assembly that is configured as a jaw assembly so that the actuation of the end-effector control input opens or closes the jaw assembly. The end-effector control input may be operated to hold the jaws open or closed (e.g., by continuing to actuate the end-effector control input). For example, when the end-effector control input is a trigger or lever on the handle assembly, holding the trigger or lever down may hold the jaws closed, whereas releasing the trigger or lever may release/open the jaws.

The end-effector may generally be configured as an assembly having multiple portions that are coupled together to allow relative motion between the parts. For example, the end-effector may include a second end-effector portion that is movably coupled to a first end-effector portion; and the apparatus (e.g., device) may further include a transmission cable connecting the shuttle body to the second end-effector portion so that actuation of the end-effector control input on the handle assembly moves the second end-effector portion relative to the first end-effector portion when the second handle portion is in any rotational position about the first axis relative to the first handle portion. As mentioned, the transmission cable may be a rope or braided material that is compliant in compression, torsion and bending.

The end-effector control input may be any appropriate control, including but not limited to a trigger, lever, or button, which is typically positioned on the first handle portion and configured for actuation by one or more of a user's fingers or thumb. This end-effector control input may be connected to the push rod (H.Body C) via an input transmission mechanism which takes input from the end-effector control input and outputs a translation of the push rod (H.Body C) along a first axis direction.

For example, a medical device having an unlimited-roll handle assembly may include: an elongate tool frame having a forearm attachment portion at a proximal end, the elongate frame having a tool axis; an end-effector at a distal end of the elongate tool frame; a handle assembly that provides unlimited roll to the end-effector, wherein the handle assembly includes: a first handle portion, a second handle portion coupled to the first handle portion so that the second handle portion has one rotational degree of freedom about a first axis relative to the first handle portion but is translationally constrained relative to the first handle portion along the first axis direction, a push rod within the first handle portion and coupled to the first handle portion so that it has one translational degree of freedom along the first axis direction relative to the first handle portion but is rotationally constrained about the first axis relative to the first handle portion, a shuttle body within the second handle portion, wherein the shuttle body is coupled to the push rod so that it has one rotational degree of freedom about the first axis relative to the push rod but is translationally constrained along the first axis direction relative to the push rod, further wherein the shuttle body is coupled to the second handle portion so that it has one translational degree of freedom along the first axis direction relative to the second handle portion but is rotationally constrained about the first axis relative to the second handle portion, wherein rotation of the second handle portion is transmitted to the end-effector so that the end-effector rotates with the second handle portion, and an end-effector control input on the first handle portion coupled to the push rod and configured to translate the push rod along the first axis direction,; and a cuff having a passage therethrough that is configured to hold a user's wrist or forearm; and a joint between the forearm attachment portion of the tool frame and the cuff, wherein the joint provides one or more of a roll degree of freedom, a pitch degree of freedom, or a yaw degree of freedom between the cuff and the forearm attachment portion of the tool frame, and wherein actuation of the end-effector control input on the handle assembly actuates the end-effector when the second handle portion is in any rotational position about the first axis relative to the first handle portion.

In general, any of these apparatuses may include an unlimited-roll handle assembly in which the shuttle body portion of the handle assembly is keyed to the knob/dial portion of the handle (e.g., second handle portion). Thus, the shuttle body may be coupled to the second handle portion so that it has one translational degree of freedom along the first axis direction relative to the second handle portion but is rotationally constrained about the first axis relative to the second handle portion. As mentioned above, the shuttle includes the structure(s) that couple(s) to the transmission member transmitting the end-effector control input (such as an end-effector actuation transmission) to the end-effector.

Also described herein are apparatuses including an unlimited-roll handle assembly in which the apparatus is configured to articulate, e.g., between the handle assembly and the tool shaft, with or without an arm attachment. For example, described herein are medical devices comprising: an end-effector at a distal end of an elongate tool frame; a handle assembly that provides unlimited roll to an end-effector, wherein the handle assembly includes: a first handle portion, a second handle portion coupled to the first handle portion so that the second handle body has one rotational degree of freedom in a first axis relative to the first handle portion but is translationally constrained relative to the first handle portion along the first axis direction, a push rod within the first handle portion and coupled to the first handle portion so that it has one translational degree of freedom along the first axis direction relative to the first handle portion but is rotationally constrained about the first axis relative to the first handle portion, a shuttle body within the second handle portion, wherein the shuttle body is coupled to the push rod so that it has one rotational degree of freedom about the first axis relative to the push rod but is translationally constrained along the first axis direction relative to the push rod, further wherein the shuttle body is coupled to the second handle portion so that it has one translational degree of freedom along the first axis direction relative to the second handle portion but is rotationally constrained about the first axis relative to the second handle portion, and an end-effector control input on the first handle portion coupled to the push rod and configured to translate the push rod along the first axis direction, wherein rotation of the second handle portion is transmitted to the end-effector so that the end-effector rotates with the second handle portion; and an input joint between the handle assembly and the tool frame configured to capture motion of the handle about a pitch axis of rotation relative to the tool frame for transmission to an output joint, and further configured to capture motion of the handle about a yaw axis of rotation relative to the tool frame for transmission to an output joint, wherein the pitch axis of rotation and the yaw axis of rotation intersect in a center of rotation; wherein the end-effector is coupled to the tool frame by the output joint. Typically, actuation of the end-effector control input on the handle assembly may actuate the end-effector when the second handle portion is in any rotational position relative to the first handle portion.

As mentioned above, the center of rotation may be posterior to the handle assembly, and may be, for example, a virtual center of rotation that would be located within a user's arm or wrist when the apparatus is held by a user. Any of these apparatuses may also include an arm (e.g., forearm) attachment. For example, any of these apparatuses may include a forearm attachment portion at a proximal end of the tool frame and a cuff having a passage therethrough that is configured to hold a wrist or forearm of a user, wherein the cuff is configured to couple to the forearm attachment portion of the tool frame. The forearm attachment may include a joint between the forearm attachment portion of the tool frame and the cuff, wherein the joint is configured to provide one or more rotational degrees of freedom between the cuff and the forearm attachment portion of the tool frame.

The input joint between the handle assembly and the tool frame/tool shaft may be referred to herein as a pitch and yaw input joint, and may comprise a pitch motion path and a yaw motion path, as described above. For example, the pitch motion path and the yaw motion path may be independent and coupled in parallel between the handle assembly and the tool frame, wherein the pitch motion path captures pitch motion of the handle assembly relative to the tool frame for transmission to the output joint but does not capture yaw motion of the handle assembly relative to the tool frame for transmission to the output joint, and wherein the yaw motion path captures yaw motion of the handle assembly relative to the tool frame for transmission to the output joint but does not capture pitch motion of the handle assembly relative to the tool frame for transmission to the output joint.

For example, a medical device may include: an end-effector at a distal end of an elongate tool frame; a handle assembly that provides unlimited roll to an end-effector, wherein the handle includes: a first handle portion, a second handle portion coupled to the first handle portion so that the second handle body has one rotational degree of freedom in a first axis relative to the first handle portion but is translationally constrained relative to the first handle portion along the first axis direction, a push rod within the first handle portion and coupled to the first handle portion so that it has one translational degree of freedom along the first axis direction relative to the first handle portion but is rotationally constrained about the first axis relative to the first handle portion, a shuttle body within the second handle portion, wherein the shuttle body is coupled to the push rod so that it has one rotational degree of freedom about the first axis relative to the push rod but is translationally constrained along the first axis direction relative to the push rod, further wherein the shuttle body is coupled to the second handle portion so that it has one translational degree of freedom along the first axis direction relative to the second handle portion but is rotationally constrained about the first axis relative to the second handle portion, and an end-effector control input on the first handle portion coupled to the push rod and configured to translate the push rod along the first axis direction, wherein rotation of the second handle portion is transmitted to the end-effector so that the end-effector rotates with the second handle portion; and an input joint between the handle and the tool frame, the input joint comprising a pitch motion path and a yaw motion path, further wherein the pitch motion path and the yaw motion path are independent and coupled in parallel between the handle assembly and the tool frame, wherein the pitch motion path captures pitch motion of the handle relative to the tool frame about a pitch axis of rotation for transmission to the output joint but does not capture yaw motion of the handle assembly relative to the tool frame for transmission to the output joint, and wherein the yaw motion path captures yaw motion of the handle assembly relative to the tool frame about a yaw axis of rotation for transmission to the output joint but does not capture pitch motion of the handle assembly relative to the tool frame for transmission to the output joint, wherein the pitch axis of rotation and the yaw axis of rotation intersect in a center of rotation that is proximal to the handle; wherein the end-effector is coupled to the tool frame by the output joint.

Any of these apparatuses may include an unlimited-roll handle assembly and an end-effector configured as a jaw assembly, either with or without an arm (e.g., forearm) attachment, and/or be configured as an articulating device (e.g., including an input joint such as a pitch and yaw input joint). For example, described herein are medical devices including: an end-effector at a distal end of an elongate tool frame; a handle assembly that provides unlimited roll to an end-effector, wherein the handle assembly includes: a first handle portion, a second handle portion coupled to the first handle portion so that the second handle body has one rotational degree of freedom in a first axis relative to the first handle portion but is translationally constrained relative to the first handle portion along the first axis direction, a push rod within the first handle portion and coupled to the first handle portion so that it has one translational degree of freedom along the first axis direction relative to the first handle portion but is rotationally constrained about the first axis relative to the first handle portion, a shuttle body within the second handle portion, wherein the shuttle body is coupled to the push rod so that it has one rotational degree of freedom about the first axis relative to the push rod but is translationally constrained along the first axis direction relative to the push rod, further wherein the shuttle body is coupled to the second handle portion so that it has one translational degree of freedom along the first axis direction relative to the second handle portion but is rotationally constrained about the first axis relative to the second handle portion, and an end-effector control input on the first handle portion coupled to the push rod and configured to translate the push rod along the first axis direction, wherein rotation of the second handle portion is transmitted to the end-effector so that the end-effector rotates with the second handle portion; wherein the end-effector includes a second end-effector portion that is movably coupled to a first end-effector portion; and a transmission cable connecting the shuttle body to the second end-effector portion so that actuation of the end-effector control input moves the second end-effector portion relative to the first end-effector portion when the second handle portion is in any rotational position with respect to the first axis relative to the first handle portion. As mentioned, the end-effector may be a jaw assembly configured so that actuation of the end-effector control input opens or closes the jaw assembly. For example, the second end-effector portion may comprise a jaw member that is pivotally hinged to the first end-effector portion. The jaw assembly may also include a third end-effector portion that is pivotally hinged to the first end-effector portion and coupled to the transmission cable. The second end-effector portion is further coupled to a third end-effector portion such that actuation of the end-effector control input on the handle moves the second and third end-effector portions relative to the first end-effector portion.

As described above, any of these apparatuses may include a forearm attachment portion at a proximal end of the tool frame and a cuff having a passage therethrough that is configured to hold a wrist or forearm of a user, wherein the cuff is configured to couple to the forearm attachment portion of the tool frame; the apparatus may also include a joint between the forearm attachment portion of the tool frame and the cuff, wherein the joint is configured to provide one or more rotational degrees of freedom between the cuff and the forearm attachment portion of the tool frame.

For example, a medical device may include: an end-effector at a distal end of an elongate tool frame; a handle assembly that provides unlimited roll to an end-effector, wherein the handle assembly includes: a first handle portion, a second handle portion coupled to the first handle portion so that the second handle body has one rotational degree of freedom in a first axis relative to the first handle portion but is translationally constrained relative to the first handle portion along the first axis direction, a push rod within the first handle portion and coupled to the first handle portion so that it has one translational degree of freedom along the first axis direction relative to the first handle portion but is rotationally constrained about the first axis relative to the first handle portion, a shuttle body within the second handle portion, wherein the shuttle body is coupled to the push rod so that it has one rotational degree of freedom about the first axis relative to the push rod but is translationally constrained along the first axis direction relative to the push rod, further wherein the shuttle body is coupled to the second handle portion so that it has one translational degree of freedom along the first axis direction relative to the second handle portion but is rotationally constrained about the first axis relative to the second handle portion, and an end-effector control input on the first handle portion coupled to the push rod and configured to translate the push rod along the first axis direction, wherein rotation of the second handle portion is transmitted to the end-effector so that the end-effector rotates with the second handle portion; wherein the end-effector comprises a jaw assembly including a first end-effector portion that is movably coupled to a second end-effector portion, wherein the second end-effector portion comprises a jaw member; and a transmission cable connecting the shuttle body to the second end-effector portion so that actuation of the end-effector control input moves the second end-effector portion relative to the first end-effector portion when the second handle portion is in any rotational position with respect to the first axis relative to the first handle portion to open or close the jaw assembly of the end-effector.

Described herein are apparatuses (e.g., mechanisms, devices, tools, machines, systems, etc.) including handle assemblies with an unlimited-roll mechanism which may incorporate certain degrees of freedoms and degrees of constraints between bodies in the handle assembly and/or in the end-effector assembly, such that there is an efficient transmission of articulation (pitch/yaw), roll, as well as end-effector actuation. These apparatuses may also incorporate certain degrees of freedoms and degrees of constraints between bodies in the handle assembly and/or in the end-effector assembly by utilizing independent transmission members. These transmission members may be end-effector articulation transmission members, end-effector roll trans-
mission members and/or end-effector actuation transmission
members. These transmission members may be indepen-
dent, or two or more independent transmission members
may be combined to act like a single transmission member
if it helps with efficient transmission of various functionali-
ties.

Various embodiments of handle assemblies are based on
the constraint map presented in FIG. 1 of U.S. Pat. No.
9,814,451 (FIG. 24A in this patent application). Certain of
these embodiments may consist of components, namely, a
handle body, a dial, a push rod and a shuttle. This constraint
map represents the structural construction of the handle
assemblies. The constraint map provides a genus based on
which several species or embodiments can be generated. The
constraint map shown in FIG. 24A is extended in FIG. 24B.
Handle assemblies mapped to the constraint map from FIG.
24B may contain two additional components, namely, a
closure input and a roll input. One objective of describing
these additional embodiments is to present alternate forms of
handle assemblies.

Various embodiments of handle assemblies based on new
constraint maps are presented in FIG. 31A-B. The constraint
maps are different from that of FIG. 1 of U.S. Pat. No.
9,814,451 (as well as those of FIG. 24A-B of this applica-
tion), and includes four components/bodies namely, a handle
body, a closure input, a roll input, and a shuffle. These
embodiments present various joints/mechanisms present
between the closure input and handle body that provide at
least one degree of freedom.

Various embodiments of handle assemblies based on a
constraint map are presented in FIG. 39. In addition to the
constraint map of FIG. 24A-B, the constraint map of FIG. 39
shows the presence of an articulation input joint within the
handle assembly such that there exists a three degree of
freedom (3 DoF) (pitch, yaw and roll) joint(s) between the
handle body and articulation-roll input.

In an embodiment, a roll handle assembly may include a
handle body, a roll body, a closure body, and a shuttle body.
The roll body is coupled to the handle body. The roll body
has a rotational degree of freedom about a roll axis relative
to the handle body. The roll body is translationally con-
strained along the roll axis relative to the handle body. The
closure body is coupled to the handle body. The closure body
has one or more degrees of freedom of motion relative to the
handle body. The shuttle body is coupled to the roll body and
is coupled to the closure body. The shuttle body has a
translational degree of freedom along the roll axis relative to
the roll body. The shuttle body is rotationally constrained
about the roll axis relative to the roll body. The shuttle body
has a rotational degree of freedom about the roll axis relative
to the closure body.

In an embodiment, a roll handle assembly may include a
handle assembly, a frame, and an input joint. The handle
assembly may include a handle body, a roll body, and a
shuttle body. The roll body is coupled to the handle body.
The roll body has a rotational degree of freedom about a roll
axis relative to the handle body and is translationally con-
strained along the roll axis relative to the handle body. The
shuttle body is coupled to the roll body and has a transla-
tional degree of freedom along the roll axis relative to the
roll body. The shuttle body is rotationally constrained about
the roll axis relative to the roll body. The input joint provides
a pitch rotation and a yaw rotation between the handle
assembly and the frame.

BRIEF DESCRIPTION OF THE DRAWINGS

The novel features of the disclosure are set forth in the
claims. A better understanding of the features can be obtained by reference to the following detailed description
that sets forth illustrative embodiments, in which the prin-
ciples of the disclosure are utilized, and the accompanying
drawings of which:

FIGS. 3I.1 through 3I.4 respectively illustrate a needle
thrust bearing, a roller thrust bearing, a roller bearing, and an
angular contact roller bearing, each of which may be used as
part of an unlimited-roll handle assembly.

FIG. 15 is another example of an unlimited-roll handle assembly coupled to an end-effector configured as a jaw assembly.

FIG. 27 depicts a handle assembly consisting of a screw mechanism as a closure input mechanism.

DETAILED DESCRIPTION

Described herein are apparatuses including an unlimited-roll handle assembly. Although the unlimited-roll handle assemblies described herein may be incorporated into any apparatus (e.g., device, tool, system, machine, etc.), described herein in particular are apparatuses including unlimited-roll handles assemblies at a proximal region of an elongate tool frame (e.g., a tool shaft or including a tool shaft) having an end-effector at the distal end of the tool frame. The apparatus may include a forearm attachment at the proximal end; the forearm attachment may allow one or more degrees of freedom between the user's forearm and the tool frame while the user's hand grips the unlimited-roll handle assembly. The apparatus may be articulating; for example, the tool frame may include an input joint between the unlimited-roll handle assembly and the tool frame that may capture movement (e.g., pitch and yaw movements) between the handle assembly and the tool frame for transmission to an output joint between the tool frame and an end-effector, so that the end-effector may be moved as the handle assembly is moved. Although any appropriate end-effector may be used, in some variations the end-effector is a jaw assembly that includes at least a pair of jaws (end-effector portions), which move to open and/or close the jaws when actuated by an end-effector control input on the handle assembly of the device.

In general, the unlimited-roll handle assemblies described herein may be configured to have four (though in some cases only three) or more parts that interact together to provide unlimited rotation of a knob or dial portion of the handle assembly about a central axis relative to a palm grip portion of the handle assembly, while still permitting the actuation of an end-effector control input to actuate the end-effector from any rotational position of the dial portion relative to the palm grip. Rotation of the knob or dial portion of the apparatus causes rotation of the end-effector, and in some cases, also causes rotation of the tool frame.

Figure 1:
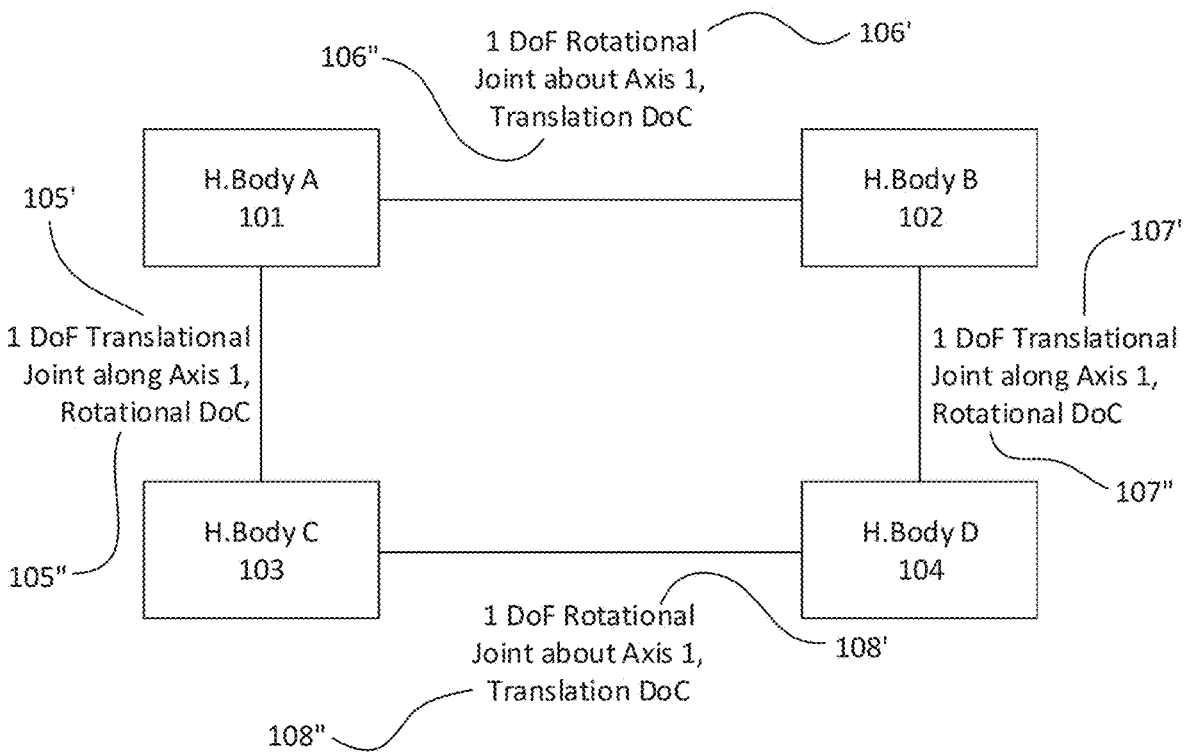
FIG. 1 is a constraint map of an unlimited-roll handle
assembly (handle assembly) having four parts, illustrating
the degrees of freedom and degrees of constraint between
the coupled components.

A constraint map of an unlimited-roll handle assembly or handle assembly is shown in FIG. 1, illustrating a conceptual model of the relative degrees of freedom (DoF) and degrees of constraint (DoC) between various bodies. In general, a degree of freedom (DoF) between two bodies implies that a particular relative motion in a specific direction between these two bodies is allowed. A degree of constraint (DoC) between two bodies implies that a particular motion in a specific direction between these two bodies is constrained and therefore transmitted. The handle assembly typically comprises rigid bodies that are generically referred to as: H.Body A 101, H.Body B 102, H.Body C 103, and H.Body D 104. H.Body A 101 may be referred to as the reference ground, in that the motion of all other bodies may be described with respect to H.Body A 101. For example, H.Body A 101 may be a palm grip. In general, any other of these bodies may be used as the ground reference for describing the motion of the remaining bodies. At a high level, the functionality of the handle assembly is independent of which body is assumed to reference ground.

Using H.Body A 101 as the ground reference, H.Body C 103 has a single translational degree of freedom (DoF) 105' with respect to H.Body A 101 along a first axis direction (e.g., Axis 1) and has rotational constraint (DoC) 105" with respect to H.Body A 101 about Axis 1. This implies that relative translation along Axis 1 direction is allowed between H.Body C 103 and H.Body A 101. However, relative rotation about Axis 1 is not allowed between the two, and therefore transmitted from one to the other and vice versa. H.Body B 102 has a rotational DoF 106' with respect to H.Body A 101 about Axis 1 and has translational constraint (DoC) 106" with respect to H.Body A 101 along Axis 1 direction. H.Body D 104 has a single translational DoF 107' with respect to H.Body B 102 along Axis 1 direction and rotational DoC constraint 107" with respect to H.Body B 102 about Axis 1. H.Body D 104 has a rotational DoF 108' with respect to H.Body C 103 about Axis 1 and translational constraint (DoC) 108" with respect to H.Body C 103 along Axis 1 direction.

Figure 2:
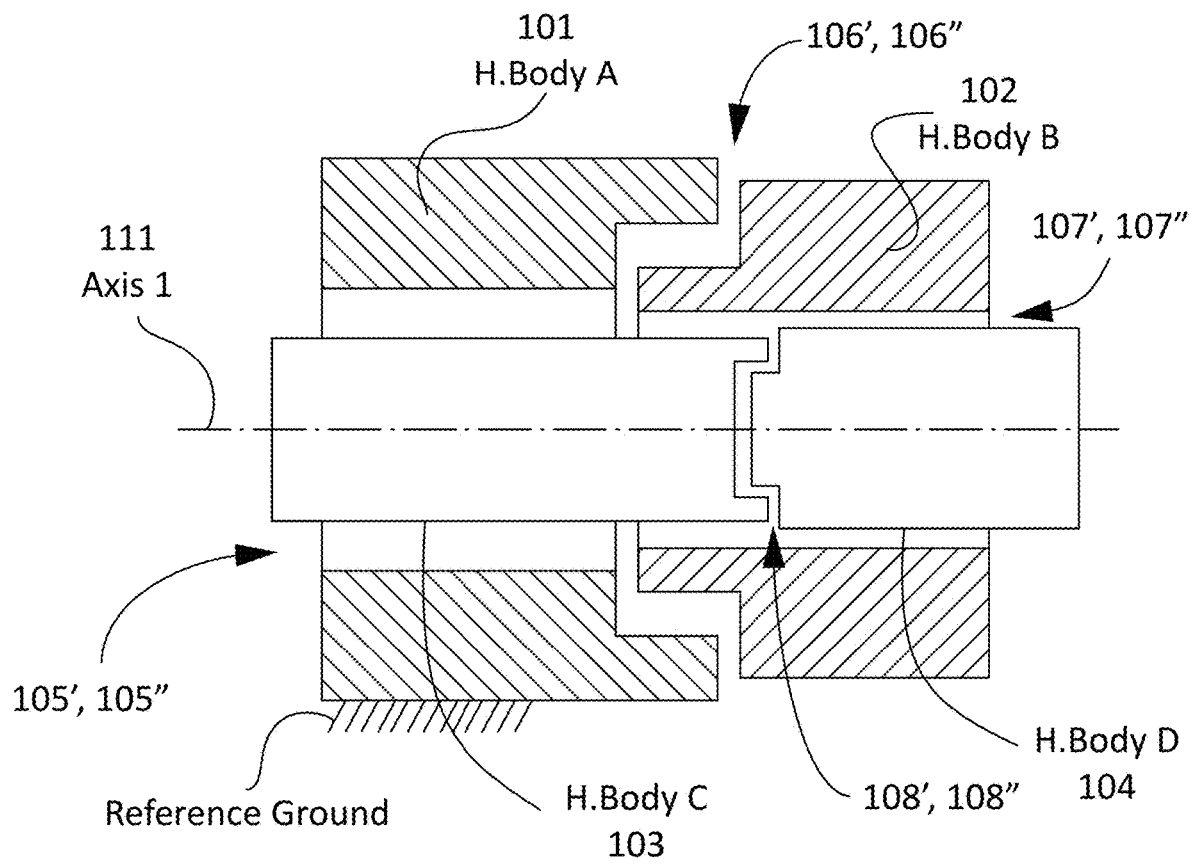
FIG. 2 is a schematic of a conceptual model of an
unlimited-roll handle assembly, illustrating the attributes of
each interface of four bodies forming the handle assembly.

FIG. 2 illustrates one example of an unlimited-roll handle assembly fitting the constraint map shown in FIG. 1. Even though FIG. 2 shows H.Body A 101 and H.Body B 102 to be cylindrical in shape, the schematic diagram of FIG. 2 does not depict the actual geometric features of each bodies, and these bodies can be of any general shapes as long as they satisfy the joint conditions/constraints between the various bodies as mentioned above.

The constraint map of FIG. 1 results in the following functionality of the handle assembly: using H.Body A 101 as a reference (i.e., assuming it to be stationary), this mechanism allows for the independent rotation of H.Body B 102 with respect to H.Body A 101 about Axis 1 111. While this happens, H.Body D 104 rotates along with H.Body B 102, also about Axis 1 111, and since rotation of H.Body C 103 is coupled to rotation of H.Body A 101, H.Body C 103 does not rotate. At the same time, any axial translation of the non-rotating H.Body C 103 with respect to the stationary H.Body A 101 along Axis 1 111 direction is transmitted to H.Body D 104, even as H.Body B 102 and H.Body D 104 rotate about Axis 1 111.

The joints between the bodies within the unlimited-roll handle assembly typically comprise interfacing geometries which allow or prevent rotation with respect to one another. Also, these joints typically comprise interfacing geometries which allow or prevent translation with respect to one another. For those joints which enable rotation of one body with respect to another, this joint may comprise one or more cylindrical surfaces, and these surfaces can be enabled by a bearing, bushing, or lubricious surface treatment which minimizes frictional resistances. For translating joints, these surfaces may also comprise a linear bearing or lubricious surface treatment. As an overall mechanism, reduced frictional resistances to both translation and rotation mean that simultaneous motion of H.Body D 104 can occur in both rotation and translation while H.Body C 103 only translates and H.Body B 102 only rotates, all with respect to H.Body A 101. Thus, another way of describing the functionality of this constraint map is that the rotation of H.Body B 102 and translation of H.Body C 103 are transmitted to H.Body D 104. Considering this in reverse: H.Body D 104 has two DoFs with respect to H.Body A 101, translation along Axis 1 111 direction and rotation about Axis 1 111. Any arbitrary combination of these two motions can be separated into translation only at H.Body C 103 and rotation only at H.Body B 102.

Any of the joints described herein may be captured for transmission to an output (e.g., output joint). The transmission may be done mechanically, electrically, or otherwise. For example, sensors may be positioned at these two bodies, e.g., a linear displacement sensor on H.Body C 103 and a rotary sensor on H.Body B 102 may give discrete/individual values for arbitrary combination of rotation and translation applied at H.Body D 104. These electrical signals could then be transmitted via wired or wireless means to a mechatronic, robotic, electronic, or computer-controlled system. These sensors may use various types of encoding techniques (e.g. electrical, optical, etc.). Alternatively, instead of sensors, one could place actuators at these locations, e.g., a linear translational actuator between H.Body A 101 and H.Body C 103 and a rotary actuator between H.Body A 101 and H.Body B 102. Any arbitrary discrete/individual motion inputs at these two bodies get added into a combined motion at H.Body D 104 with respect to H.Body A 101.

In general, a degree of freedom (DoF) implies that a particular relative motion between two bodies in a specific direction is allowed, a degree of constraint (DoC) implies that a particular relative motion between two bodies in a specific direction is constrained and therefore transmitted. All motions in FIG. 1 are defined with respect to Axis 1 111 (not shown), which is the axis of rotation of a handle dial (corresponding to H.Body B 102) with respect to a handle shell (corresponding to H.Body A 101). Any motion direction not explicitly mentioned could be a DoF or DoC.

As used to describe degrees of freedom here, axis refers to a specific line in space. A body may rotate with respect to (w.r.t.) another body about a certain axis. A body may translate w.r.t. another body along a certain direction. A direction is not defined by a particular axis and is instead commonly defined by multiple parallel axes. Thus, X axis is a specific axis defined and shown in a figure, while X direction refers to the direction of this X axis. Multiple different but parallel X axes can have the same X direction. Direction only has an orientation and not a location in space.

Figure 3A:
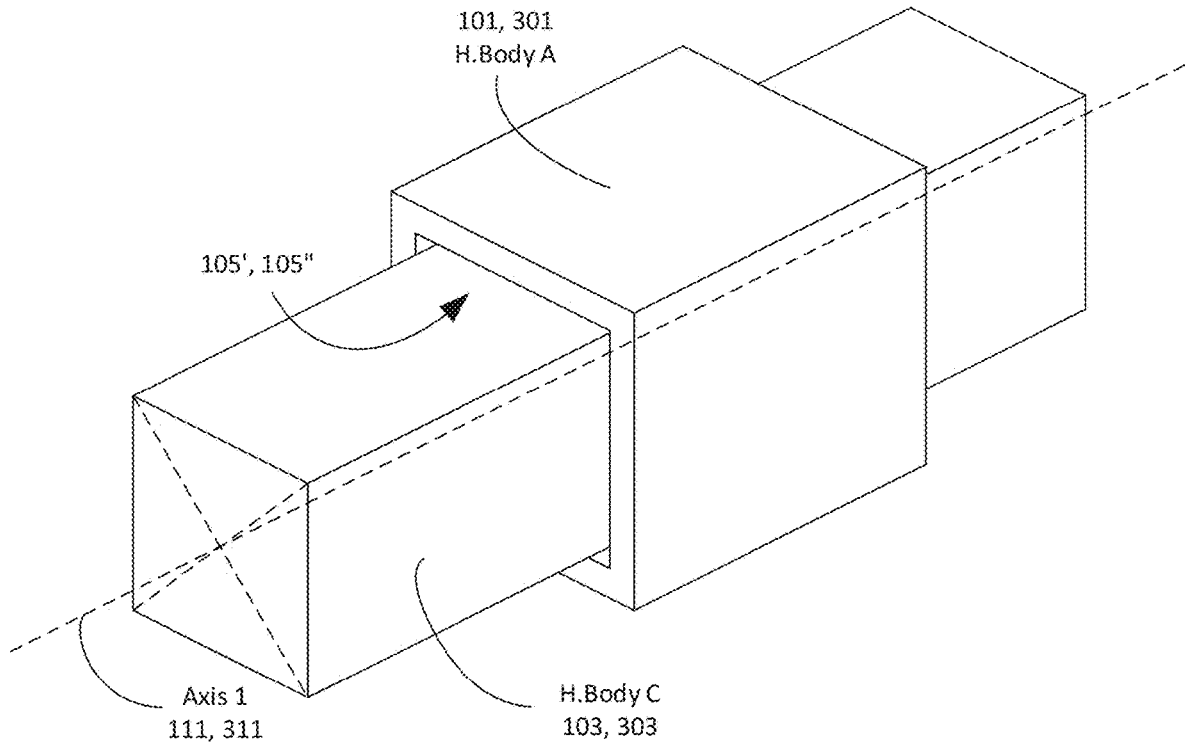
FIG. 3A shows an example of an interface between two
bodies of an exemplary unlimited-roll handle assembly (e.g.,
H.Body A and H.Body C) shown as a square slot and square
key feature.

In FIG. 1, H.Body C 103 is shown having a single translational DoF 105' along Axis 1 111 (not shown) direction with respect to H.Body A 101 and vice versa. H.Body C 103 also has a rotational constraint (DoC) 105" about Axis 1 111 with respect to H.Body A 101 and vice versa. This type of joint, between H.Body A 101 and H.Body C 103, can be accomplished through a variety of embodiments. In one embodiment, the interfacing bodies have a keying feature between them which restricts relative rotation about Axis 1 111 and simultaneously allows for relative translation along Axis 1 111 direction. FIG. 3A schematically describes a joint which might exist between H.Body A 101 and H.Body C 103. Referring to FIG. 3A, an outer body with a square longitudinal slot may correspond to H.Body A 101, 301 while the inner square key may correspond to H.Body C 103, 303. Considering that H.Body A 101, 301 is fixed to the reference ground, H.Body C 103, 303 will be allowed to translate along Axis 1 111, 311 direction while unable to rotate about Axis 1 111, 311 due to the interferences posed by the square cross-sectional joint. One might consider that this joint can also have a rectangular cross-section which can provide the same single axis (Axis 1 111, 311) rotational constraint and single axis (Axis 1 111, 311) translational DoF.

Figure 3B:
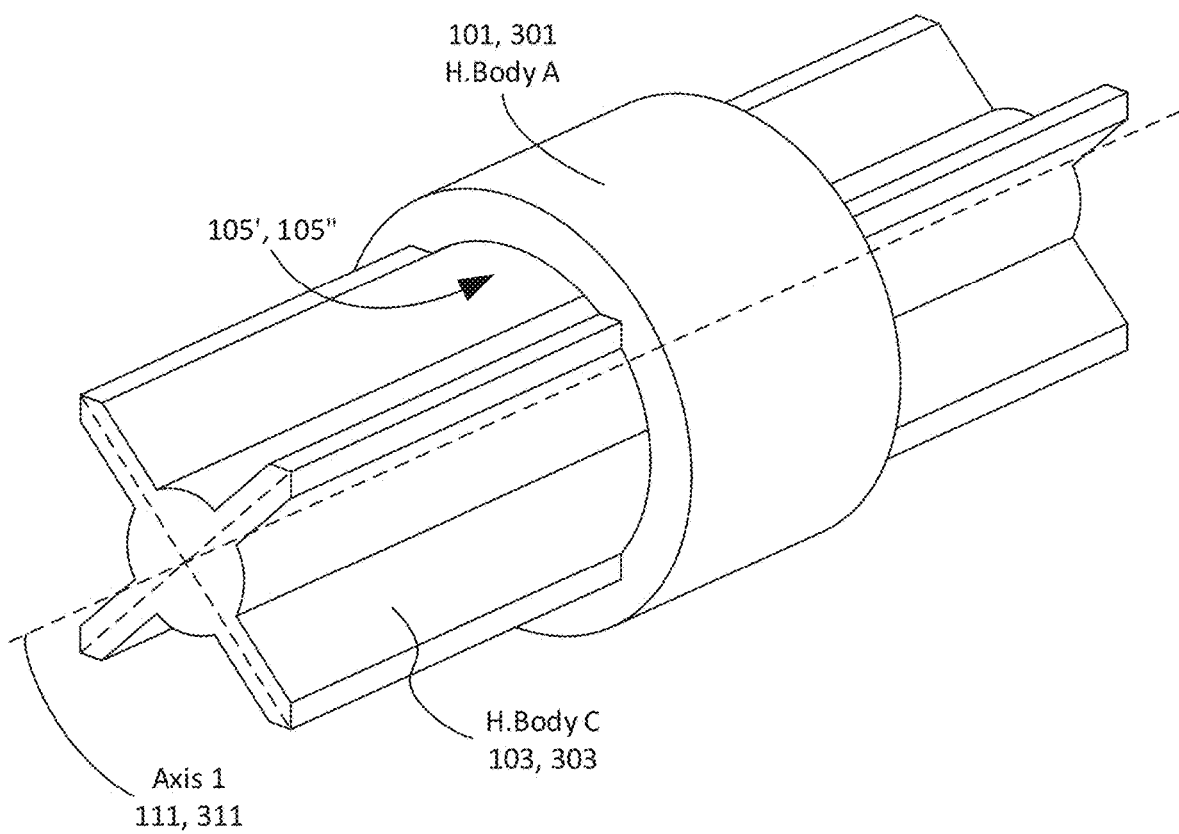
FIG. 3B shows an example of an interface between two
bodies of an exemplary unlimited-roll handle assembly (e.g.,
H.Body A and H.Body C) with minimal keying surface
between bodies causing a rotational constraint.

A functional aspect of this joint is a low friction relative sliding motion along Axis 1 111, 311 direction between H.Body A 101, 301 and H.Body C 103, 303. To achieve this, the surface contact between both bodies (H.Body A 101, 301 and H.Body C 103, 303) may need to be minimal so as to avoid large frictional contact between surfaces of H.Body A 101, 301 and H.Body C 103, 303. Therefore, one way of achieving the same joint between H.Body A 101, 301 and H.Body C 103, 303 with less friction contact is to minimize the contact surface area between two bodies. FIG. 3B shows one way to reduce the surface contact between H.Body A 101, 301 and H.Body C 103, 303 by interfacing the spokes of H.Body C 103, 303 with corresponding slots in H.Body A 101, 301.

Figure 3C:
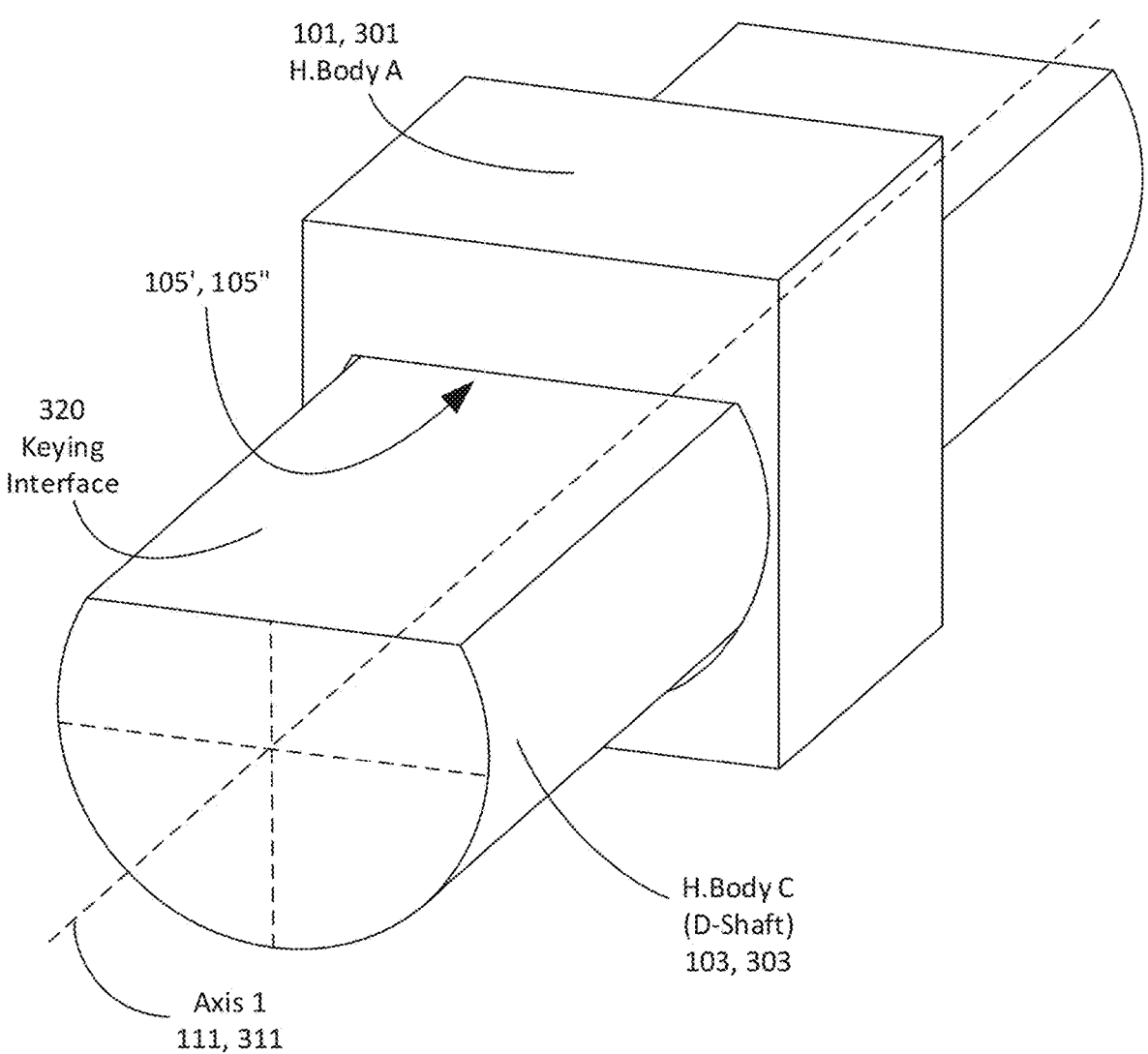
FIG. 3C is an example of an interface between two bodies
of an exemplary unlimited-roll handle assembly (e.g.,
H.Body A and H.Body C) shown as a D-Shaft and corre-
sponding slot feature.

FIGS. 3A and 3B show examples of achieving the constraint and DoF between H.Body A 101, 301 and H.Body C 103, 303, but they can have different geometric shapes provided that the constraints and DoFs are met. For example, FIG. 3C shows one way this joint can be achieved by essentially providing a keying surface 320 via the flat end of the D-Shaft 303 (H.Body C 103, 303) that engages with a corresponding slot present in H.Body A 101, 301.

H.Body B 102, 302 and H.Body D 104, 304 have a rotational DoC 107" about Axis 1 111, 311 and a single translational DoF 107' along Axis 1 111, 311 direction. This is the same type of rotational DoC 105" and translational DoF 105' that is present between H.Body A 101, 301 and H.Body C 103, 303. Therefore, each one of the ways to attain the joint between H.Body A 101, 301 and H.Body C 103, 303 are also applicable to the joint between H.Body B 102, 302 and H.Body D 104, 304; given the constraint and DoF requirements are fulfilled.

Any of the joints between H.Body A 101, 301 and H.Body C 103, 303 as well as between H.Body B 102, 302 and H.Body D 104, 304 may include or require a low friction surface contact between the bodies. This, along with a single rotational constraint (DoC) 105", 107" about Axis 1 111, 311 and a single translational DoF 105', 107' along Axis 1 111, 311 direction, may completely define the joint between these bodies. Similarly, a single DoC, a single DoF, and functional requirements define the joint between H.Body A 101, 301 and H.Body B 102, 302 as well as between H.Body C 103, 303 and H.Body D 104, 304. H.Body A 101, 301 and H.Body B 102, 302 may have a single rotational DoF 106' about Axis 1 111, 311 relative to each other and a single translational constraint (DoC) 106" along Axis 1 111, 311 direction. H.Body A 101, 301 and H.Body B 102, 302 may also have a functional requirement of providing low friction joint between them while they rotate relative to each other about Axis 1 111, 311. This functional requirement comes from the fact that either of the duos, H.Body A 101, 301 and H.Body B 102, 302 or H.Body C 103, 303 and H.Body D 104, 304, can be under compressive or tensile loading while fulfilling the rotational DoF 106', 108' about Axis 1 111, 311 and translational constraint (DoC) 106", 108" along Axis 1 111, 311 direction.

Figure 3D:
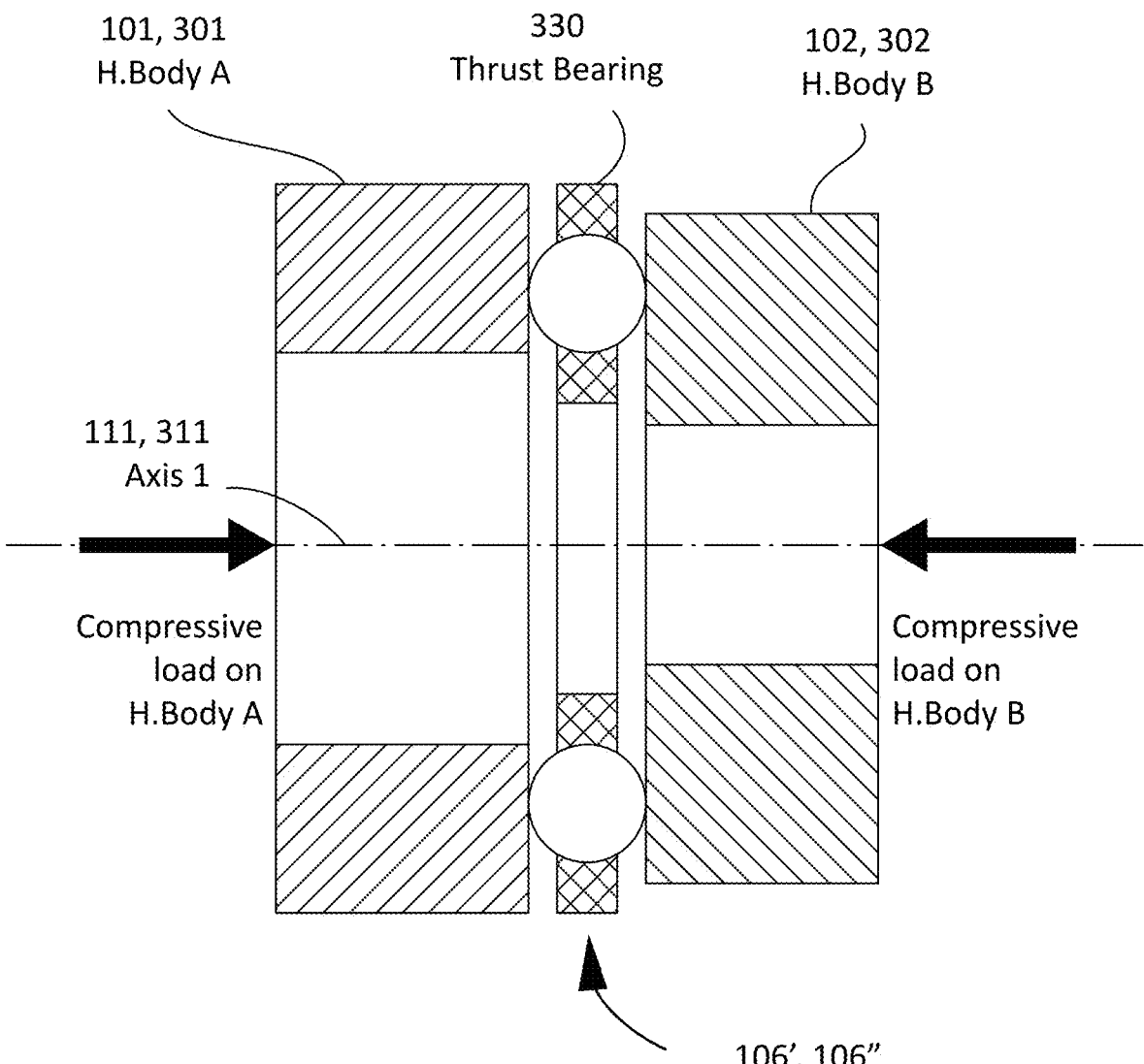
FIG. 3D is an example of a thrust bearing acting as
interface between two bodies of an unlimited-roll handle
assembly (e.g., H.Body A and H.Body B).
Figure 3E:
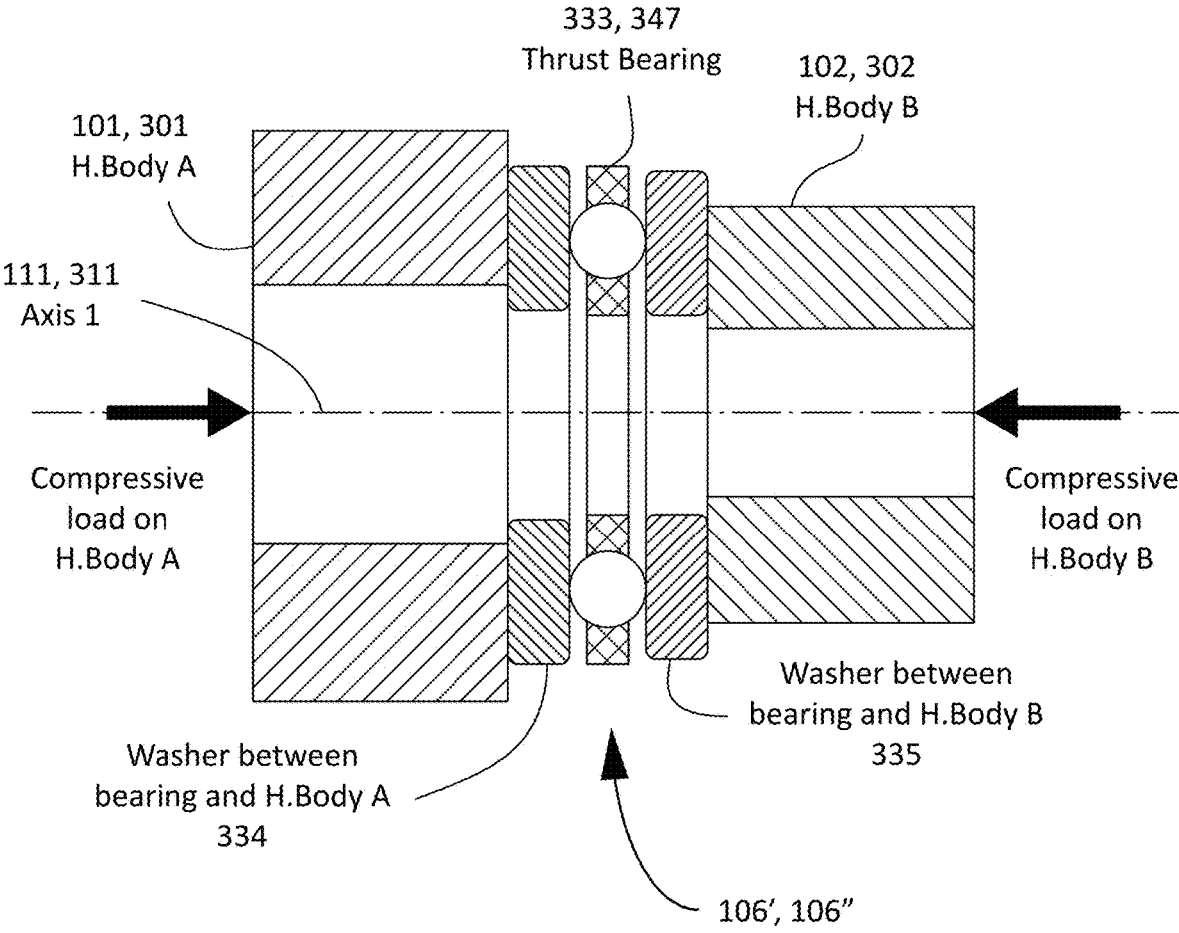
FIG. 3E shows an example of a portion of an unlimited-
roll handle assembly including a thrust bearing with side
washers acting as interface between H.Body A and H.Body
B.
Figure 3F:
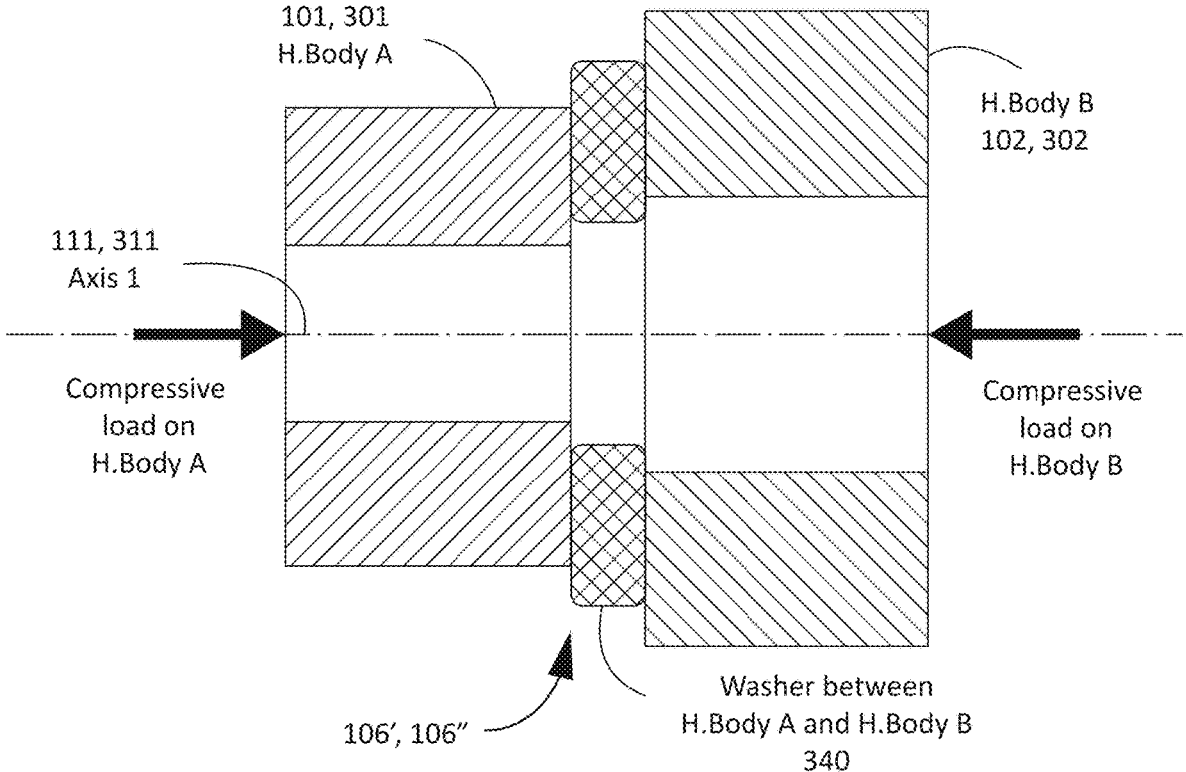
FIG. 3F shows an example of a washer acting as interface
between H.Body A and H.Body B in one example of an
unlimited-roll handle assembly.
Figure 3G:
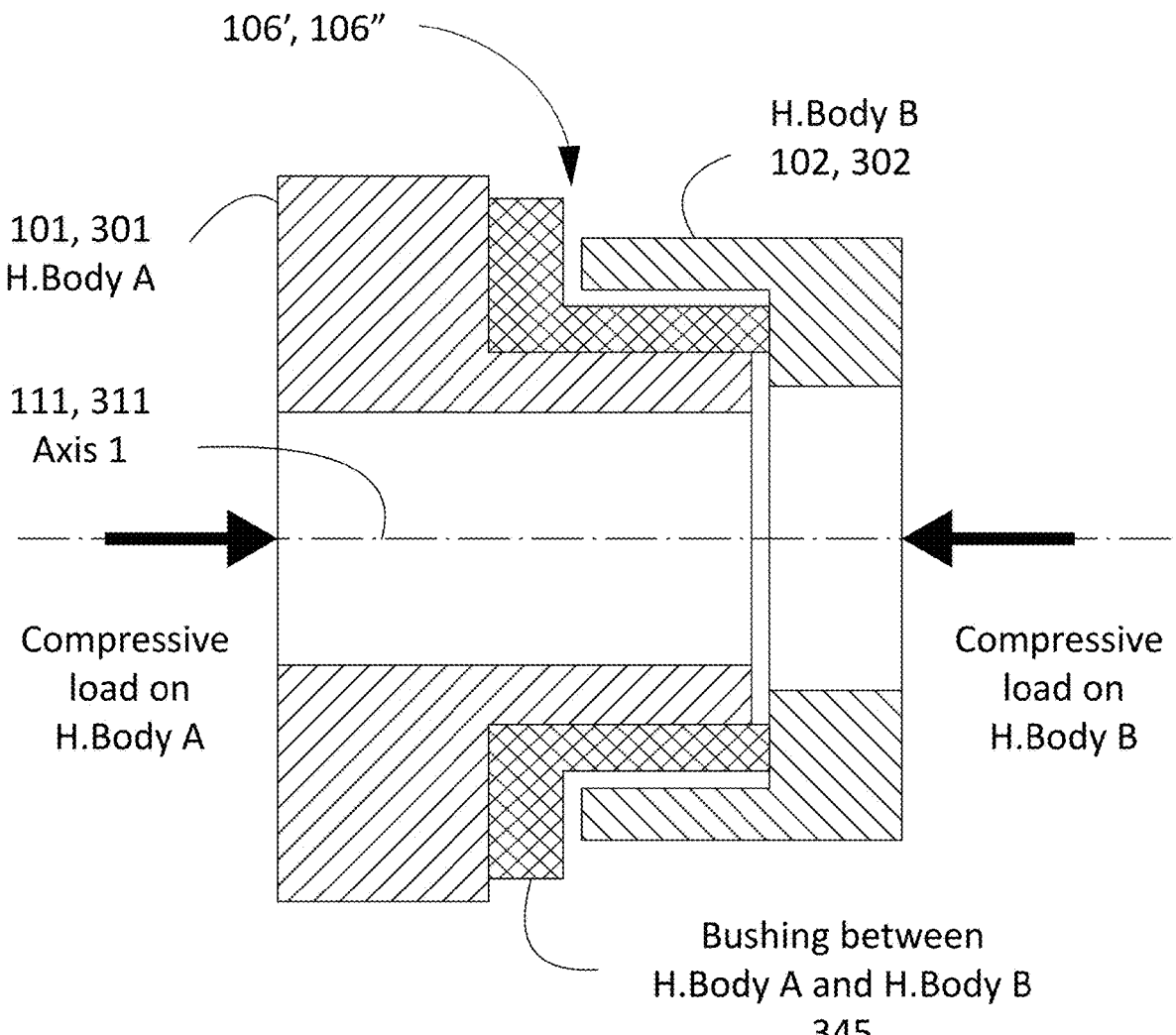
FIG. 3G shows a bushing acting as interface between an
H.Body A and H.Body B of an unlimited-roll handle assem-
bly.

For example, if H.Body A 101, 301 and H.Body B 102, 302 are placed such that their surfaces normal to Axis 1 111, 311 are under compression, they need to overcome the normal forces acting on each bodies' surfaces to provide the rotational DoF 106' about Axis 1 111, 311. Therefore, to provide the rotational DoF 106' about Axis 1 111, 311 and the translational constraint 106" along Axis 1 111, 311 direction, the surfaces of H.Body A 101, 301 and H.Body B 102, 302 may need to provide low friction contact such that the bodies can rotate relative to each other about Axis 1 111, 311. FIG. 3D shows one way of obtaining the desired rotational DoF 106' and translational constraint (DoC) 106" by providing low friction surface contact. In this example, a thrust bearing 330 is used to provide the rotational DoF 106' along with maintaining low friction contact between surfaces of H.Body A 101, 301 and H.Body B 102, 302 by holding the thrust load between the two bodies. Similarly, this functionality can be achieved in many other ways that fulfill the rotational DoF 106' and translational constraint 106" requirement. For example, either an angular contact ball bearing or a roller ball bearing, each capable of holding the required radial and thrust loads can also be used between H.Body A 101, 301 and H.Body B 102, 302. Alternatively, a bushing between two bodies can be used to provide radial support as well as capacity to bear thrust load. FIG. 3E shows one way in which the thrust load can be supported by having a thrust bearing 333 between H.Body A 101, 301 and H.Body B 102, 302 along with washers 334, 335 on each side of the bearing 333. FIG. 3F shows another way of supporting thrust loads while providing the rotational DoF 106' about Axis 1 111, 311 by using a single washer 340 between H.Body A 101, 301 and H.Body B 102, 302 made of material with low friction coefficient like Teflon (PTFE), nylon, etc. In another alternative embodiment, FIG. 3G shows a bushing 345 placed between the interfacing surfaces of H.Body A 101, 301 and H.Body B 102, 302, such that it is capable of holding thrust load, thereby providing a translational constraint (DoC) 106" along Axis 1 111, 311 direction.

Figure 3H:
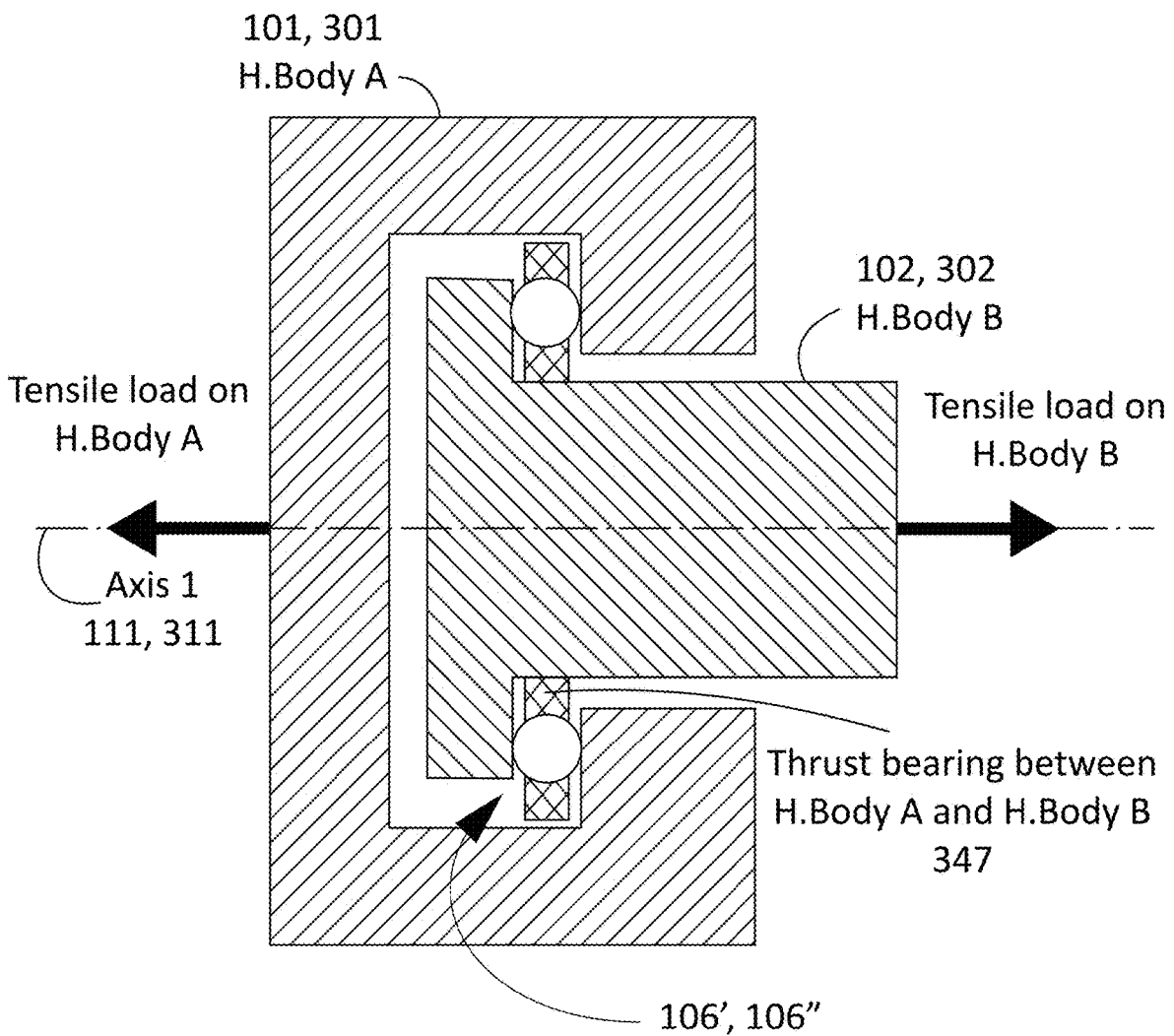
FIG. 3H illustrates an exemplary H.Body A and H.Body
B under tensile load with thrust bearing acting as interface
between them as part of an unlimited-roll (e.g., roll) handle
assembly.

The same system of two bodies with an intermediate member carrying thrust load and providing a rotational DoF 106' about Axis 1 111, 311 and providing a translational constraint (DoC) 106" along Axis 1 111, 311 direction, shown in FIGS. 3D, 3E, and 3F also works well when there is a tensile load—as opposed to compressive load—between H.Body A 101, 301 and H.Body B 102, 302. An example is illustrated in FIG. 3H with an embodiment similar to that illustrated in FIG. 3D, wherein a thrust bearing 347 is located between H.Body A 101, 301 and H.Body B 102, 302, facing normal to Axis 1 111, 311. The thrust bearing 347 between H.Body A 101, 301 and H.Body B 102, 302 can be of various types, e.g., thrust needle bearing, thrust roller bearing, roller bearing, tapered roller bearing, angular contact bearing, etc., some of which are illustrated in FIGS. 3I.1 through 3I.4. For example, FIG. 3H shows a thrust roller bearing 347 acting as joint between H.Body A 101, 301 and H.Body B 102, 302. Also, H.Body C 103, 303 and H.Body D 104, 304 may have the same type of joint as H.Body A

101, 301 and H.Body B 102, 302 and comply with all the aforementioned joint types mentioned in this section.

Figure 3J:
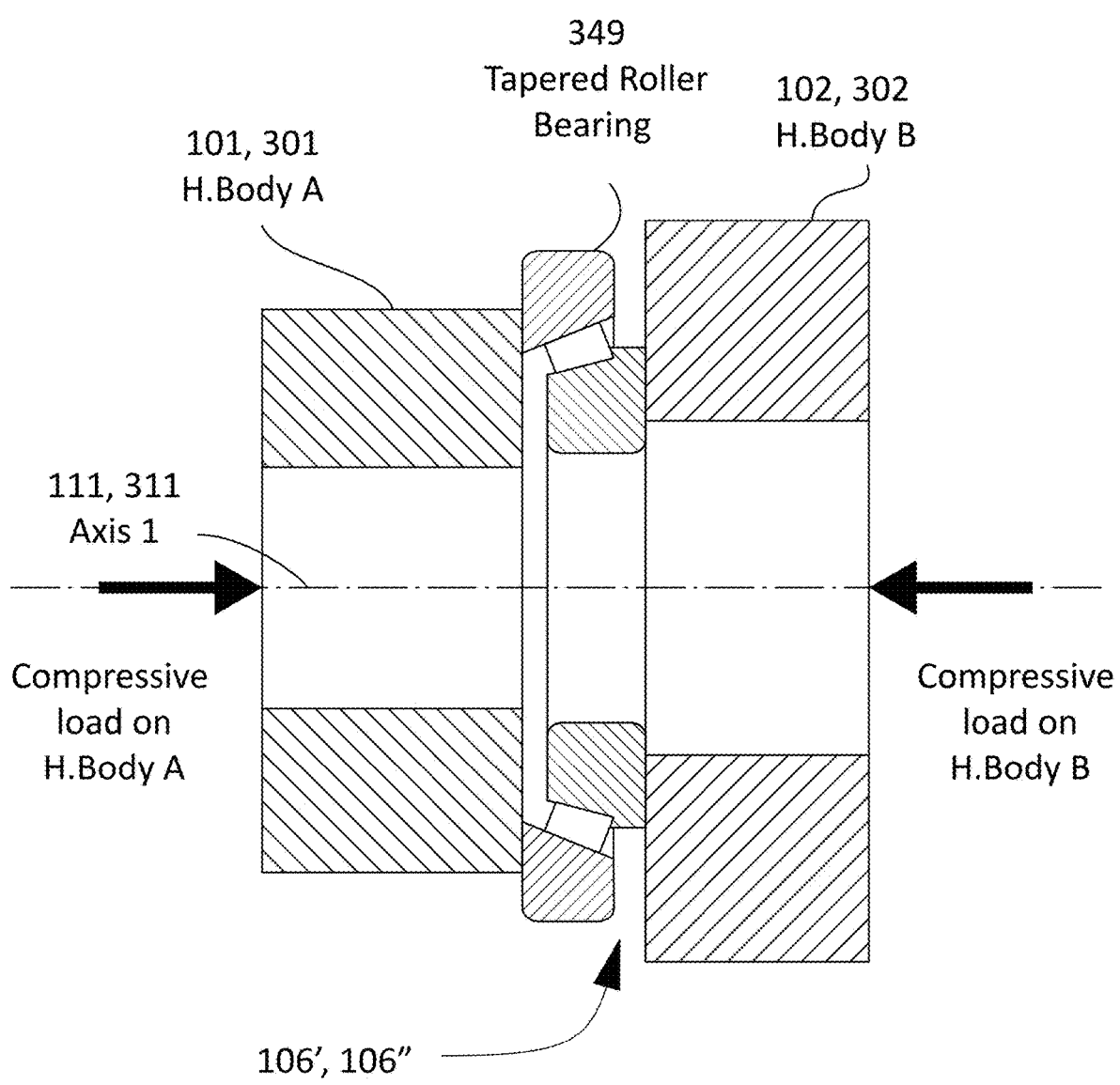
FIG. 3J illustrates an example of a tapered roller bearing
that may be used as part of an unlimited-roll handle assem-
bly.
Figure 3K:
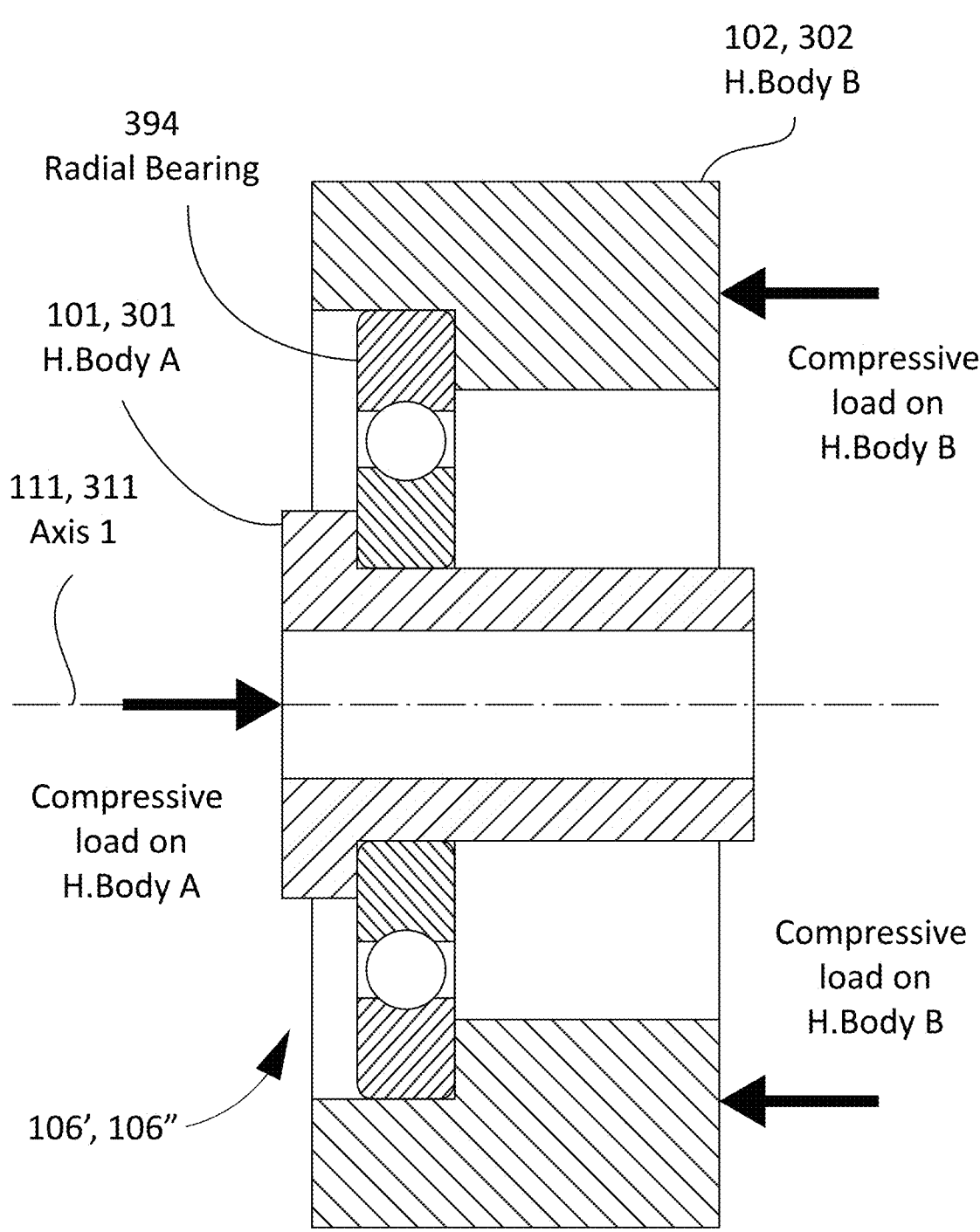
FIG. 3K shows a radial bearing that may be used as part
of an unlimited-roll handle assembly.

As illustrated in FIGS. 3I.1 through 3I.4 and FIGS. 3J and 3K, other types of bearings may be used as alternatives to, or in combination with, the above-described thrust bearings 330, 333, 347, for example, tapered roller bearings 349, radial ball bearings 394, etc.

Figure 3L:
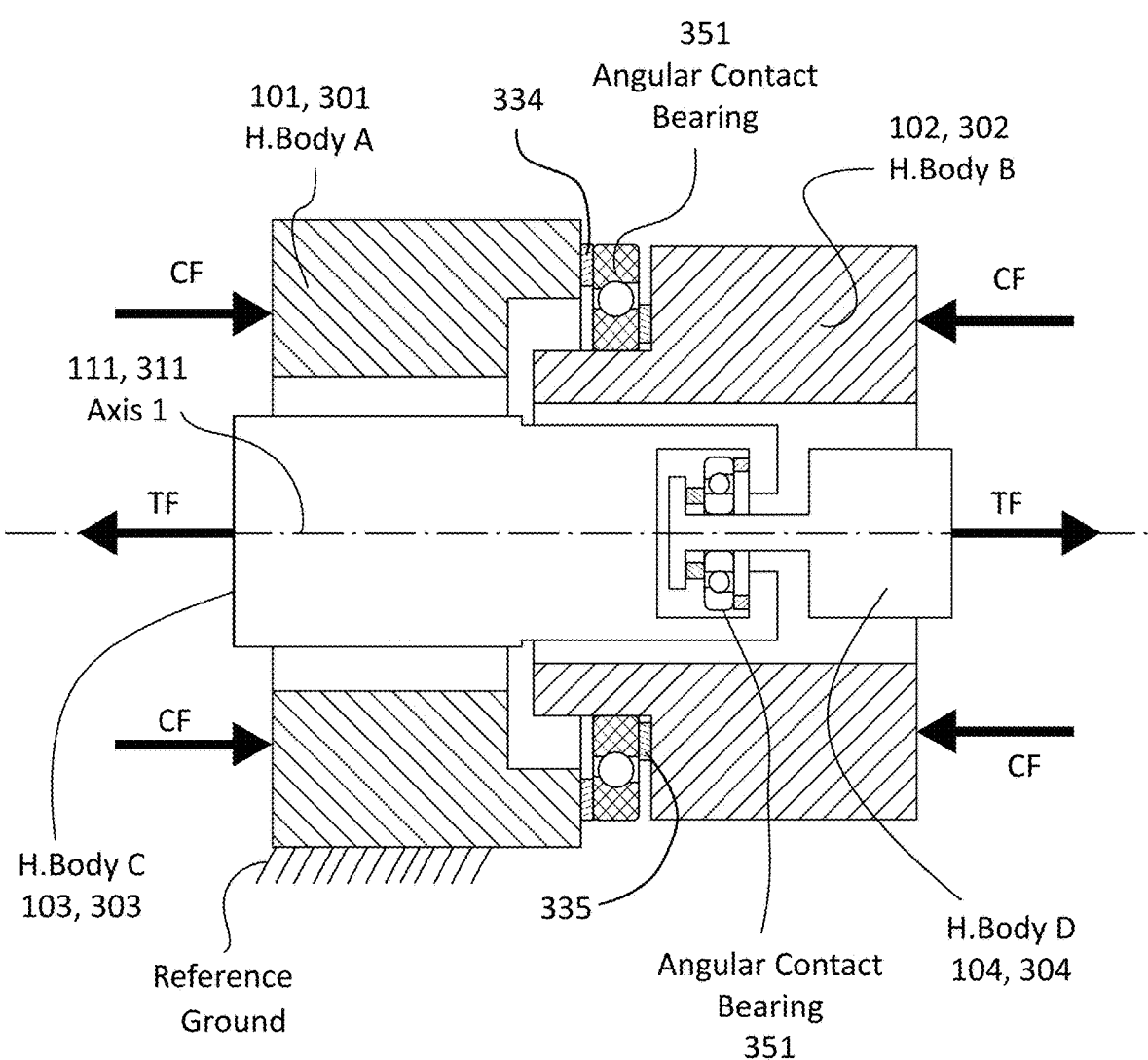
FIG. 3L illustrates exemplary loading conditions applied
on different bodies of an unlimited-roll handle assembly.

Accordingly, H.Body A 101, 301 and H.Body B 102, 302 can be under compressive or tensile load along Axis 1 111, 311. Similarly, H.Body C 103, 303 and H.Body D 104, 304 can also be under compressive or tensile load along Axis 1 111, 311 direction. This gives two possible combinations for the whole system presented with schematic diagram in FIG. 1 (to be under tensile load or compressive load). Either of the system of two bodies, H.Body A 101, 301 and H.Body B 102, 302, or H.Body C 103, 303 and H.Body D 104, 304 can be under tensile or compressive load. As presented in FIG. 1, with H.Body A 101, 301 serving as the reference ground, H.Body B 102, 302 can be under tension or under compression with respect to H.Body A 101, 301. However, H.Body C 103, 303 is free to move along Axis 1 111, 311 direction with respect to H.Body A 101, 301 and has rotational constraint about Axis 1 111, 311 with respect to H.Body A 101, 301. H.Body C 103, 303 can be under compression or tension with respect to H.Body D 104, 304, and H.Body D 104, 304 is free to translate along Axis 1 111, 311 direction with respect to H.Body B 102, 302 and has rotational constraint about Axis 1 111, 311 with respect to H.Body B 102, 302. FIG. 3L illustrates a configuration where H.Body B 102, 302 is under compressive load with respect to H.Body A 101, 301 and H.Body C 103, 303 is under tensile load with respect to H.Body D 104, 304. In this example, an angular contact bearing 351 is used between H.Body A 101, 301 and H.Body B 102, 302. This accounts for a joint between H.Body A 101, 301 and H.Body B 102, 302 that provides the associated translational constraint (DoC) 106" and rotational DoF 106' requirements mentioned above, along with the functional requirement of providing low friction between surfaces contacting one another. Similarly, a thrust bearing 330, 333, 347, 349, 394, 351 may be used between H.Body C 103, 303 and H.Body D 104, 304. This accounts for a joint between H.Body C 103, 303 and H.Body D 104, 304 that provides the associated translational constraint (DoC) 108" and rotational DoF 108' requirements mentioned above, along with the functional requirement of providing low friction surface contact.

In some of these examples, even though the bodies have been illustrated as being cylindrical in shape, the constraint map (FIG. 1) doesn't imply any restriction on geometric shapes of these bodies, provided that the functionality, DoFs, and constraints are satisfied.

Figure 4A:
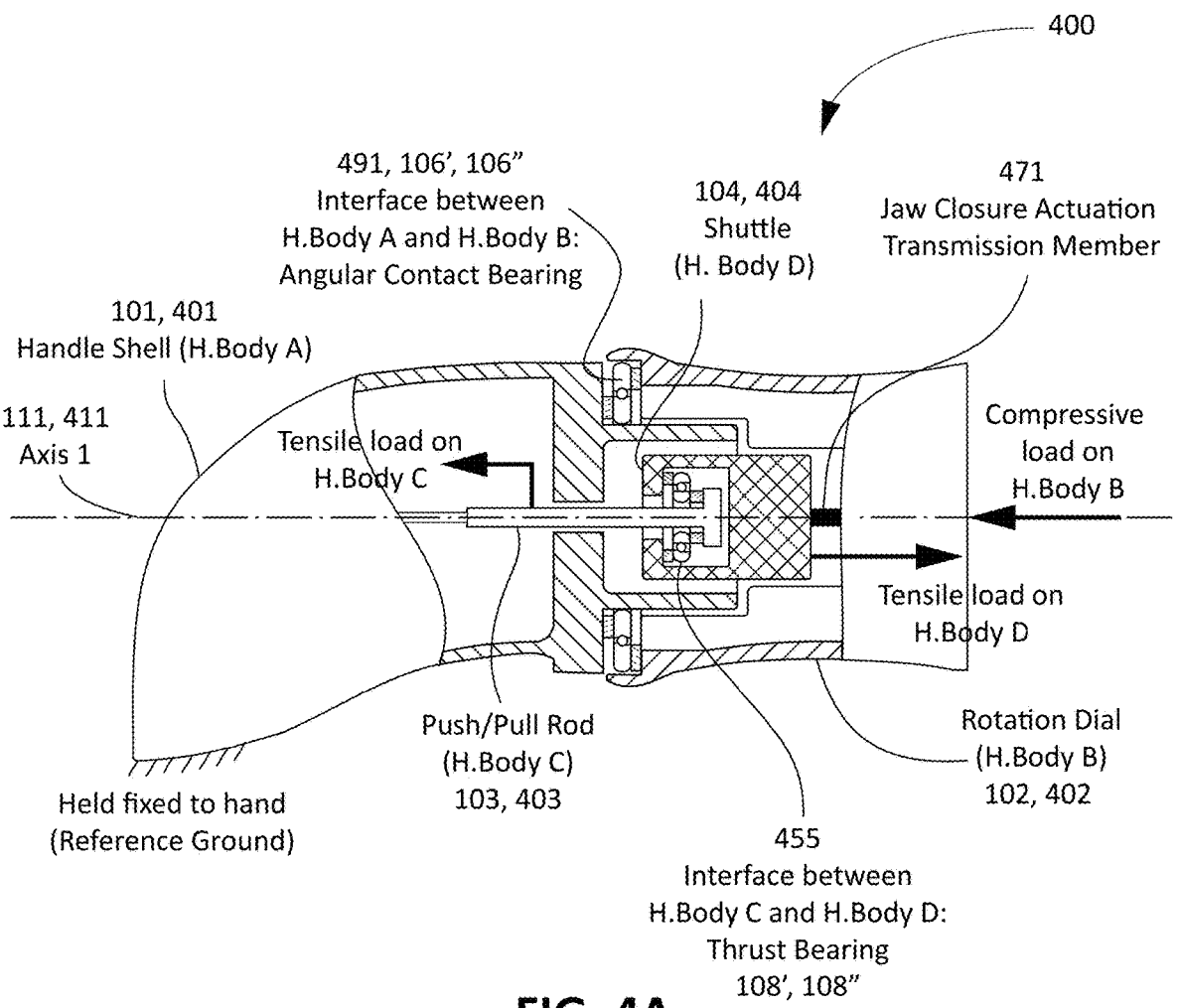
FIG. 4A shows an example of an unlimited ("infinity")
handle as described herein, which is one realization of the
constraint map shown in FIG. 1 as an ergonomic handle.
Figure 4B:
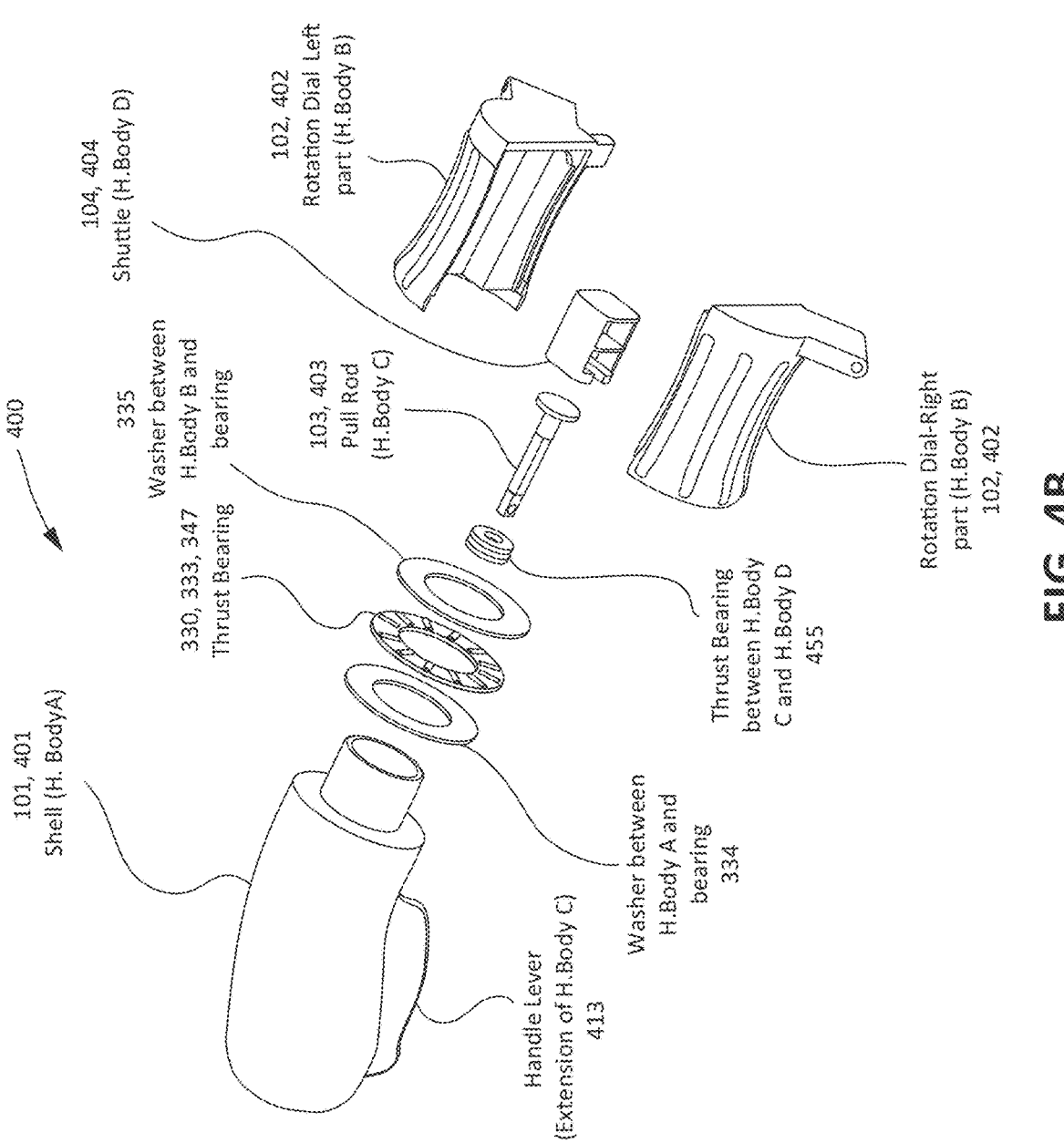
FIG. 4B is an exploded view of the unlimited-roll handle
assembly of FIG. 4A, in which a first handle portion is
configured as a palm grip (H.Body A), a second handle
portion is configured as a dial (H.Body B), a push rod
(H.Body C) is within the palm grip, and a shuttle (H.Body
D) is within the second handle portion. An end-effector
control input (e.g., handle lever) may be attached to the palm
grip to actuate the end-effector.

FIGS. 4A and 4B show an example of an ergonomic handle assembly 400 (unlimited-rotation handle assembly) that utilizes the mechanism illustrated in FIG. 3L involving both compressive and tensile loading conditions. This handle assembly 400 is an embodiment of the constraint map shown in FIG. 1. Via joint 491, the rotation dial 402 (H.Body B 102, 402) is under a rotational degree of freedom (DoF) 106' about Axis 1 111, 411 and translational constraint (DoC) 106" along Axis 1 111, 411 direction with respect to Handle Shell 401 (H.Body A 101, 401). The rotation dial 402 transmits this rotation about Axis 1 111, 411 to H.Body D 104, 404, which is also referred as shuttle 404. This is possible because shuttle 404 (H.Body D 104, 404) is under rotational constraint (DoC) 107" about Axis 1 111, 411 with respect to rotation dial 402 (H.Body B 102, 402) and therefore, has no relative rotation about Axis 1 111, 411. The shuttle 404 (H.Body D 104, 404) is further interfaced with H.Body C 103, 403 (referred as push rod or pull rod, i.e. push/pull rod 403) via a joint 455 which allows rotational DoF 108' about Axis 1 111, 411 and translational constraint (DoC) 108" along Axis 1 111, 411 direction. The translation of shuttle 404 (H.Body D 104, 404) along Axis 1 111, 411 direction is further transmitted to the moving jaw of an end-effector via an end-effector transmission 471. When the end-effector is configured as a jaw assembly, the latter may alternatively be referred to as a jaw closure transmission member 471 or jaw closure actuation transmission member 471. In some variations, it may simply be referred to as a transmission cable (when it is a compliant cable, for example). This jaw closure actuation transmission member 471 can be either rigid or non-rigid body, or a combination of a rigid and non-rigid members. For example, the transmission member can be either the shaft of an apparatus (e.g., of a laparoscopic instrument) or a rod passing internally through the shaft, a cable under tension that connects to the end-effector at the distal end of the laparoscopic instrument, or a combination of a non-rigid body and a rigid body (e.g., a rod along with a cable under tension). The push/pull rod 403 (H.Body C 103, 403) and shuttle 404 (H.Body D 104, 404) are under tensile load and the rotation dial 402 (H.Body B 102, 402) is under compressive load and the latter does not translate along Axis 1 111, 411 direction with respect to handle shell 401 (H.Body A 101, 401). The push/pull rod 403 (H.Body C 103, 403) is actuated by the user by activating handle lever 413, which is a mechanical extension of the push/pull rod 403 (H.Body C 103, 403) via a transmission mechanism that may comprise a linkage, cams, springs, etc.

Another variation of an ergonomic handle assembly 400 shown in FIGS. 4A and 4B can be constructed via a flexure-based design, also known as a compliant mechanism, that realizes the constraint map of FIG. 1 by employing compliant or flexure joints between the bodies H.Body A 101, H.Body B 102, H.Body C 103, and H.Body D 104 to achieve the necessary constraints.

Figure 5:
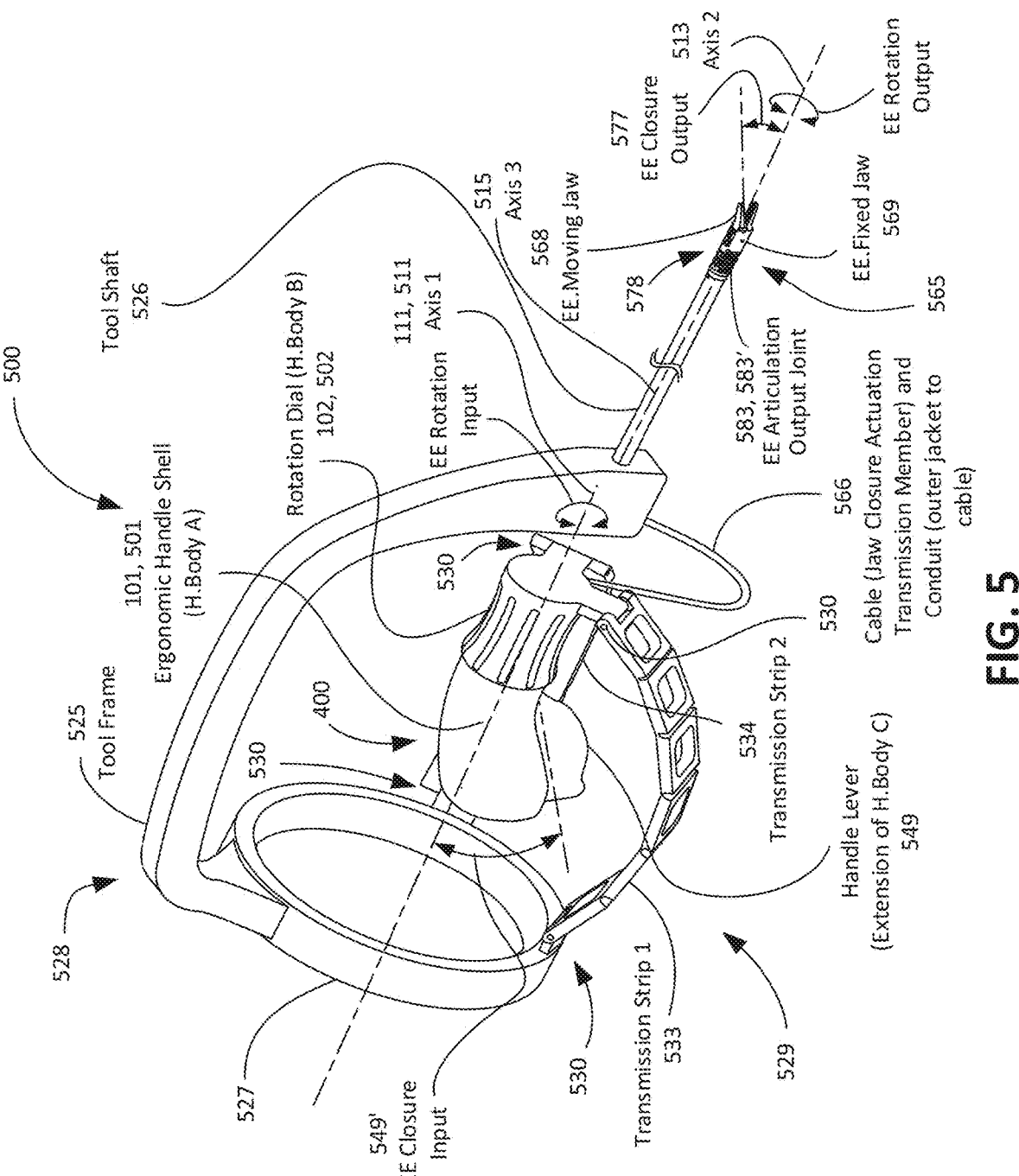
FIG. 5 illustrates one example of a medical device (e.g.,
a laparoscopic device) incorporating an unlimited-roll
handle assembly such as the one shown in FIGS. 4A-4B and
described herein. This medical device is an embodiment of
a tool apparatus in the beta configuration.
Figure 7:
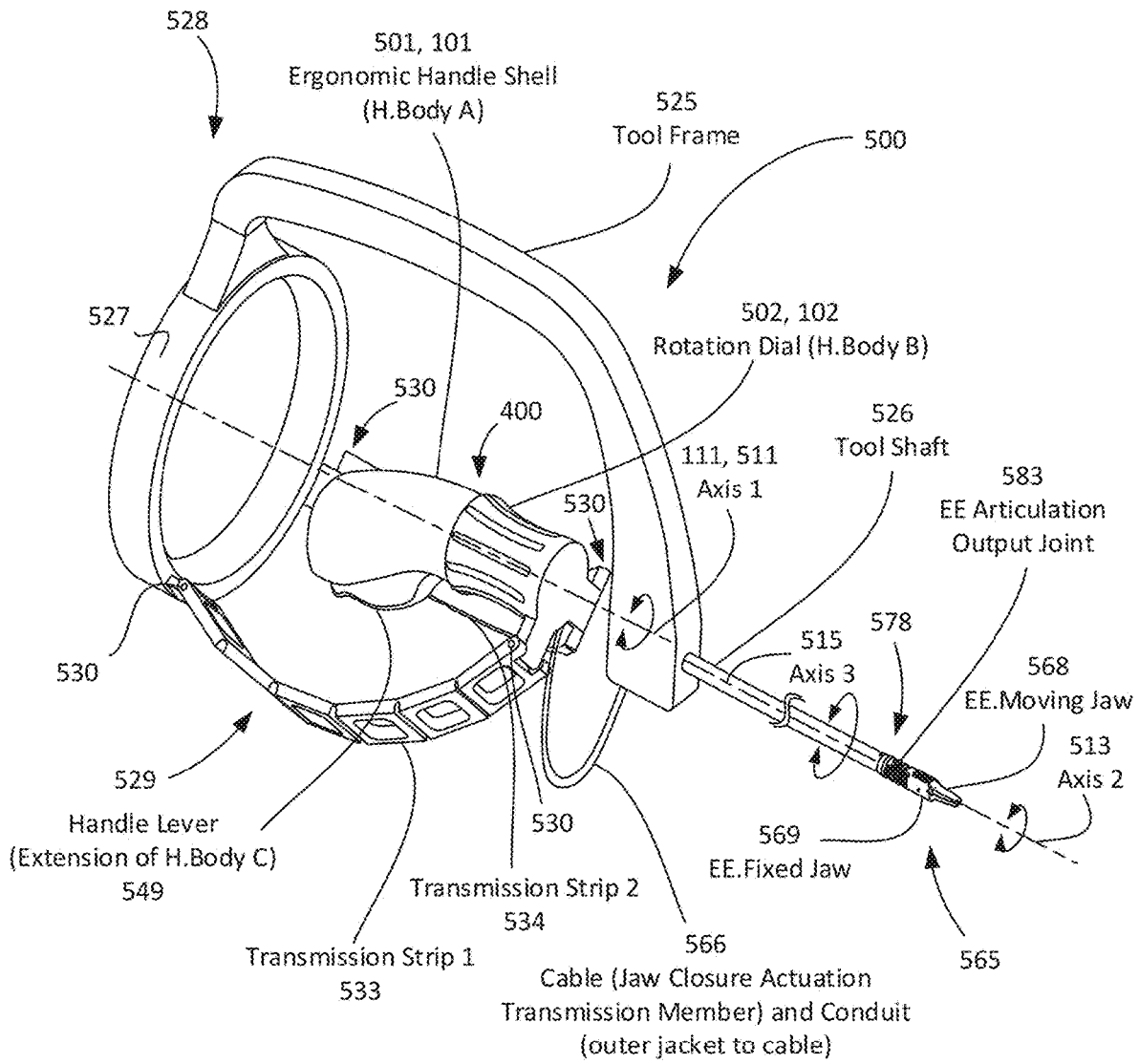
FIG. 7 shows another example of a medical device having an unlimited-roll handle assembly and a jaw assembly end-effector, such as the one shown in FIG. 5 but in a closed-jaw configuration. This medical device is an embodiment of a tool apparatus in the beta configuration.
Figure 8:
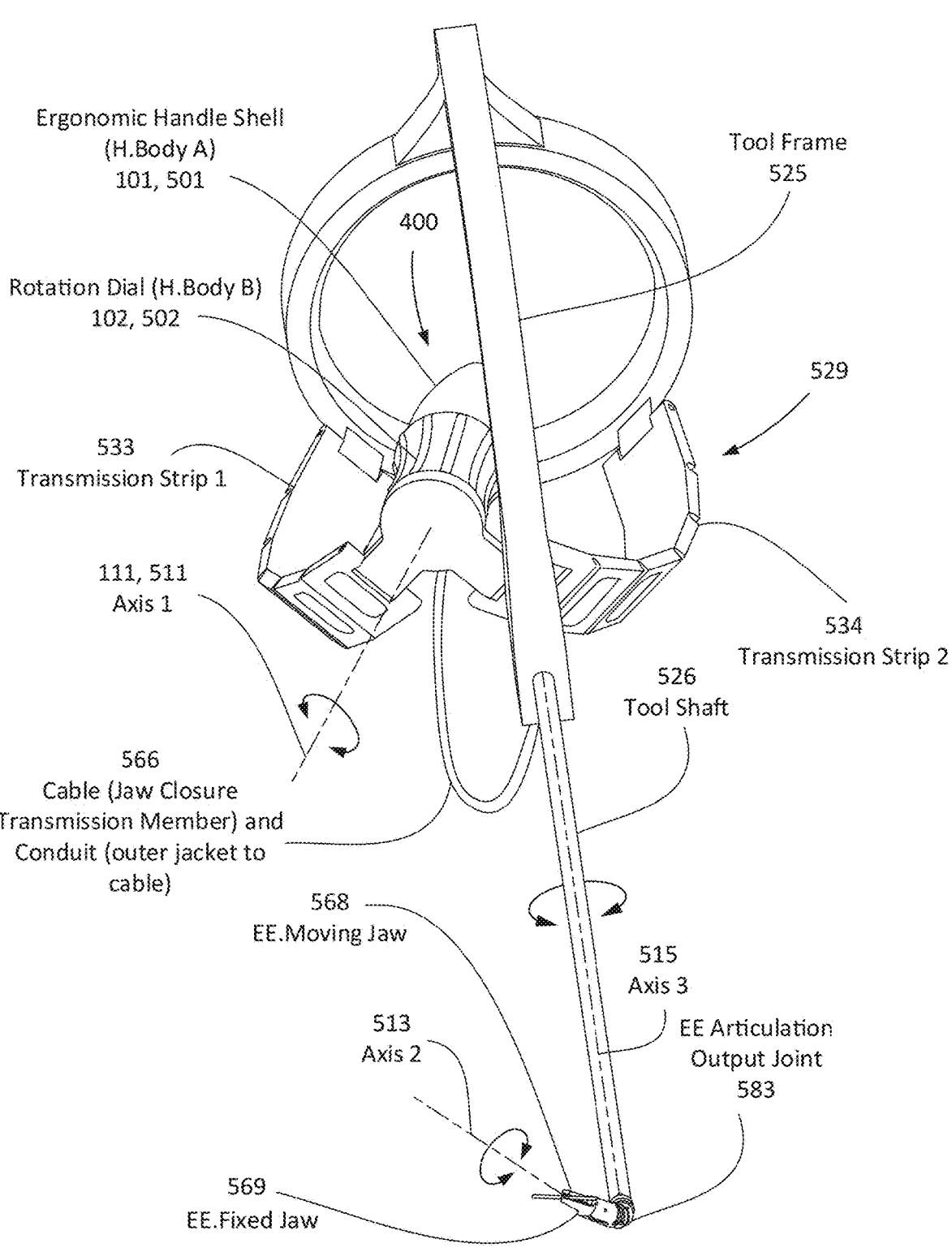
FIG. 8 is another view of a medical device having both an unlimited-roll handle assembly and a distal end-effector configured as a jaw assembly, wherein the distal end-effector is shown in an articulated position with closed jaws clamping on a needle-like object, and the unlimited-roll handle assembly is similar to that shown in FIGS. 4A-4B. This medical device is an embodiment of a tool apparatus is the beta configuration.

An apparatus incorporating the unlimited-roll handle assemblies illustrated in FIGS. 4A and 4B is shown in FIGS. 5, 7, and 8 as part of a medical device (specifically a laparoscopic device). These embodiments depict apparatuses in the beta configuration (defined later). More particularly, FIGS. 5, 7, and 8 show a laparoscopic surgical instrument having an end-effector configured as a jaw assembly; wherein in FIG. 5 the jaws are open, in FIG. 7 the jaws are shown closed, and in FIG. 8. the jaws are closed on a needle-like object and the end-effector assembly is articulated.

Figure 6:
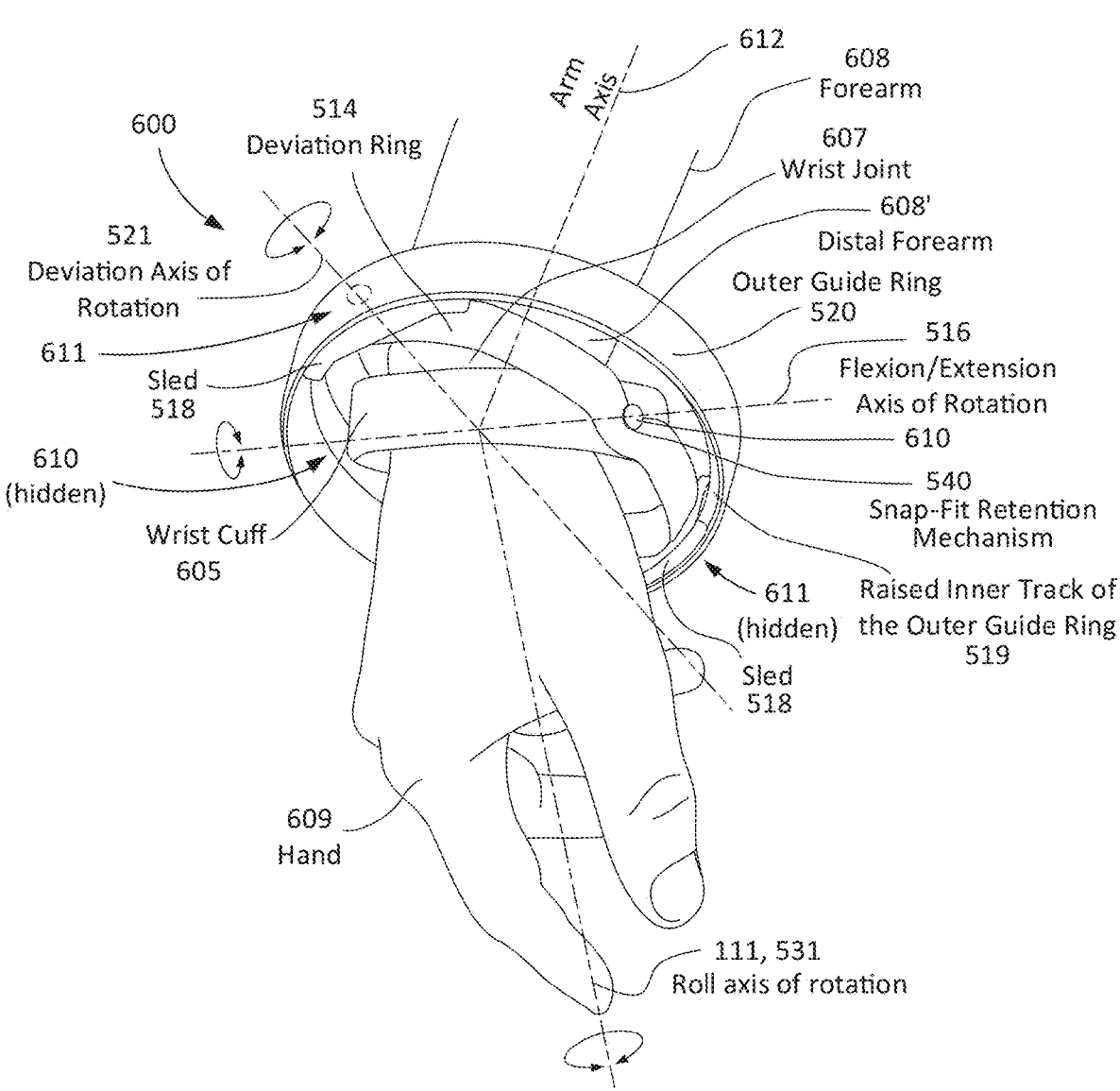
FIG. 6 shows an example of a cuff that can couple with a forearm attachment portion of a tool shaft of a medical device including an unlimited-roll (roll) handle assembly. The cuff includes a passage therethrough that is configured to hold a wrist or forearm of a user, wherein the cuff is configured to couple to the forearm attachment portion of the tool frame.

Referring to FIGS. 5 through 8, the exemplary apparatus 500 in beta configuration (defined later) includes a tool frame 525, the latter of which includes a tool shaft 526 and a forearm attachment portion 527 at the proximal end 528 of the tool frame 525. FIG. 6 shows an example of a wrist cuff 605—having a passage therethrough—that is configured to hold a wrist 607 or forearm 608 of a user and may be coupled to the forearm attachment portion 520, 527. For example, in some embodiments, the wrist cuff 605 is operatively coupled to the forearm attachment portion 520, 527 of the tool frame 525 via a bearing therebetween that allows the wrist cuff 605 to slide or roll so that there is a roll rotational degree of freedom between the tool frame 525 and the wrist cuff 605 about a tool axis 515 (Axis 3 515). A proximal unlimited-roll handle assembly 400—for example, as shown in FIGS. 4A and 4B—may be connected to the tool frame 525 by an input joint 529, the latter of which may be configured to capture motion between the tool frame 525 and the unlimited-roll handle assembly 400, as shown in FIGS. 5, 7 and 8. In this example, the input joint 529 includes a pair of transmission strips 533, 534 that are connected between the unlimited-roll handle assembly 400 and the forearm attachment portion 527 by corresponding associated hinged joints 530, and that may be connected in parallel to respective pivoting joints (not shown) in order to provide for separately receiving pitch and yaw rotations of the unlimited-roll handle assembly 400 relative to the tool frame 525. An output joint 583 (shown as an end-effector articulation output joint) between an end-effector 565 and the tool shaft 526receives transmission input (pitch and yaw motion) from the input joint 529 to articulate the end-effector 565.

In this example, the unlimited-roll handle assembly 400 includes an ergonomic palm grip portion 101, 501 (handle shell 501) that connects to the rotation dial 102, 502, which enclose an internal push rod and shuttle (not visible), wherein these four elements are constrained per the constraint map shown in FIG. 1. The unlimited-roll handle assembly 400 also includes an end-effector control input such as a handle lever 549 and an associated closure actuation 549' (see FIG. 5). This control input (i.e., handle lever 549) is as a mechanical extension (e.g., via a mechanism) of the internal push rod. In alternate configurations, the handle lever 549 is coupled to the push rod via a transmission mechanism that may comprise a linkage, cams, springs, etc. A transmission cable 566 connects to the shuttle and acts as a jaw closure actuation transmission member 471 extending from the shuttle and through the tool shaft 526 to the end-effector 565. This transmission cable 566 may be enclosed by a protective and/or supporting sheath or cover or conduit for some or entire portion of its length. The end-effector 565 itself is a jaw assembly including a first end-effector portion 569 (ground), in this example, including a fixed jaw 569 to which a pivoting second end-effector portion (moving jaw 568) is attached. The transmission cable 566 may couple to the moving jaw 568 at the end-effector closure output 577.

In FIG. 5, when the user's forearm 608 is mounted to the proximal end 528 of the tool frame 525 and the palm grip portion 101, 501 is held in the user's hand 609 so that the user can rotate the rotation dial 102, 502 between the thumb and fingers, rotation of the dial portion 102, 502 of the unlimited-roll handle assembly 400 rotates the entire tool frame 525, and therefore the end-effector 565 that is attached to the distal end 578 of the tool frame 525 via an end-effector output articulating joint 583. Thus, the handle shell 101, 501 may rotate about a first axis 111, 511 referred to as handle articulated roll axis 511 (Axis 1), so as to cause the tool shaft 526 to rotate about a third axis 515 referred to as the tool shaft roll axis 515 (Axis 3), which in turn causes the end-effector 565 to roll about a second axis 513, referred to as an end-effector articulated roll axis 513 (Axis 2).

The rotation dial 102, 502 (H.Body B) as shown in FIG. 5 is rotated about Axis 1 111, 511. The rotation of H.Body B 102, 502 leads to a rotation of the tool frame 525 via the transmission strips 533, 534 (as they constrain rotation DoF between H.Body B 102, 502 and tool frame 525), which in turn causes a rotation of the tool shaft 526 (about Axis 3 515) operatively coupled to the tool frame 525, and a rotation of the end-effector 565 (about Axis 2 513) operatively coupled to the tool shaft 526. When the handle shell 101, 501 is articulated using the input articulation joint 529, the end-effector 565 articulates via the end-effector output articulation joint 583, wherein the end-effector articulated roll axis 513 (Axis 2) is distinct from the tool shaft roll axis 515 (Axis 3).

The above description is also relevant when describing apparatuses that either do not attach to the forearm 608 or that attach to the forearm 608 via a roll joint, so that rotation of the dial portion 102, 502 of the unlimited-roll handle assembly 400 leads to roll rotation of a forearm attachment apparatus 600 about the wrist 607 via the transmission strips 533, 534 (as they constrain the roll rotation), leading to a rotation of tool frame 525, the tool shaft 526, and eventually the end-effector 565. FIG. 6 illustrates an example of an embodiment of a forearm attachment apparatus 600 comprising a 3-axis gimbal assembly including a wrist cuff 605 that securely attaches to the user's wrist 607/forearm 608, leaving the user's hand 609 free to move (e.g., to grasp the handle shell 101, 501 and manipulate the rotation dial 102, 502 and actuate the end-effector control input 549). In this embodiment, the forearm attachment apparatus 600 allows pitch, yaw, and roll degrees of freedom; the wrist cuff 605 pivotally attaches to a deviation ring 514 with a first pair of pins 610 that provide for rotation about flexion/extension axis of rotation 516. The deviation ring 514 is in turn pivotally attached to a sled 518 with a second pair of pins 611 that provide for rotation about a deviation axis of rotation 521, wherein the sled 518 is configured to roll within a raised inner track 519 of an outer guide ring 520 about a corresponding roll axis of rotation 531. Accordingly, the forearm attachment apparatus 600 provides for pitch, yaw, and roll degrees of freedom between the wrist cuff 605 and the tool frame 525 when coupled to the tool frame 525 of the apparatus 500. For example, in one set of embodiments, the outer guide ring maybe formed as part of the forearm attachment portion 527 of the apparatus 500, or it may be attached thereto. The wrist cuff 605 may be releasably coupled into the deviation ring 514 via a snap-fit coupling 540 or some other type of coupling.

FIG. 8 shows another view of the beta configuration (defined later) laparoscopic instrument of FIGS. 5-7 with the end-effector 565 in an articulated position and holding a needle that may be used to suture tissues. The end-effector fixed jaw 569 (ground) and the end-effector moving jaw 568 can be rotated about the end-effector articulated roll axis 513 (Axis 2) such that the tool shaft 526/tool frame 525 rotates about the tool shaft roll axis 515 (Axis 3) while the handle assembly is rotated about the handle articulated roll axis 511 (Axis 1); all while simultaneously holding the needle securely by forcing the end-effector moving jaw 568 towards the end-effector fixed jaw (ground) 569 via a jaw closure actuation transmission member 471 connected to H.Body D 104, 404 within the unlimited-roll handle assembly 400. The apparatus 500 shown in FIGS. 5-8 may fit a constraint map such as the one shown in FIG. 20A.

Figure 9:
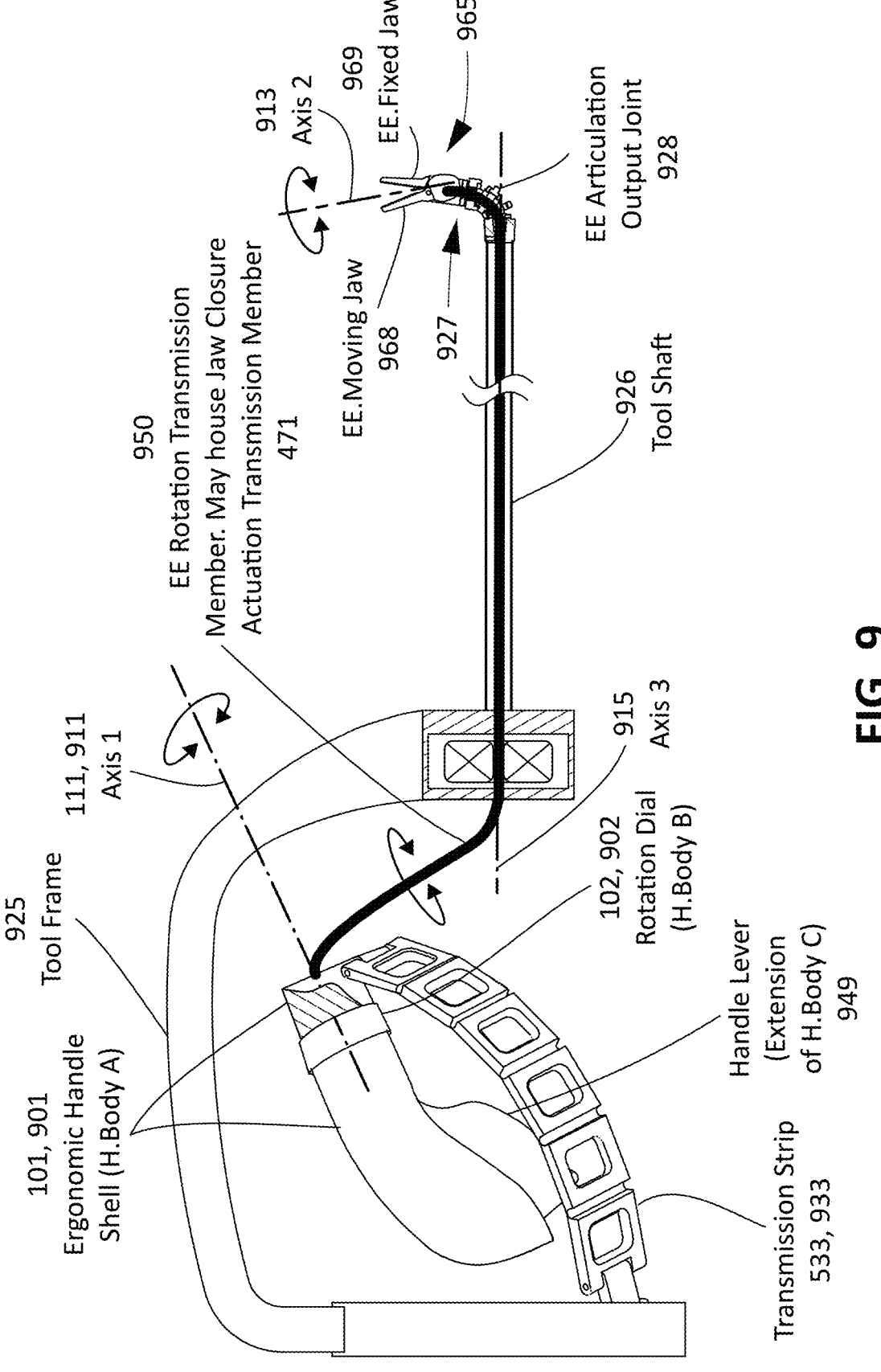
FIG. 9 shows another example of a medical device having both an unlimited-roll handle assembly and a distal end-effector configured as a jaw assembly, illustrating an end-effector transmission connecting the rotation dial (H.Body B) to the end-effector. This medical device is an embodiment of a tool apparatus in the alpha configuration.

Another variation of an apparatus incorporating the unlimited-roll handle assemblies illustrated in FIGS. 4A and 4B that conform to the constraint map illustrated in FIG. 1 is shown in FIG. 9. FIG. 9 illustrates a tool apparatus in the alpha configuration. In this example, the rotation of a rotation dial 102, 902 (H.Body B) about Axis 1 111, 911 leads to rotation of an associated end-effector assembly 965 (shown here as a jaw assembly including a moving jaw 968 and a fixed jaw 969) about Axis 2 913. Here, the tool frame 925 including the tool shaft 926 does not rotate about their associated axis (Axis 3 915) thereof when the rotation dial (H.Body B) rotates with respect to the handle shell (H.Body A) about Axis 1. The tool frame 925 may still be connected to a wrist cuff 605 mounted on a user's forearm 608 via a forearm attachment apparatus 600 that may provide for a pitch and/or yaw rotational DoF, as described hereinabove. The end-effector assembly 965 has a rotational DoF with respect to the distal end 927 of the associated end-effector articulation output joint 928 about Axis 2 913 (similar to that between H.Body A 101, 901 and H.Body B 102, 902 about Axis 1 111, 911) and an end-effector rotation transmission member 950 connects H.Body B 102, 902 directly to the end-effector assembly 965 via the torsionally stiff end-effector rotation transmission member 950. This may also be the jaw closure actuation transmission member 471 or may house and therefore route, a flexible jaw closure actuation transmission member 471, for example, a hollow flexible shaft (end-effector rotation transmission member 950) that is torsionally stiff that can transmit rotation from one end to another, housing a cable that is flexible in bending (jaw closure actuation transmission member 471) there within.

Figure 10:
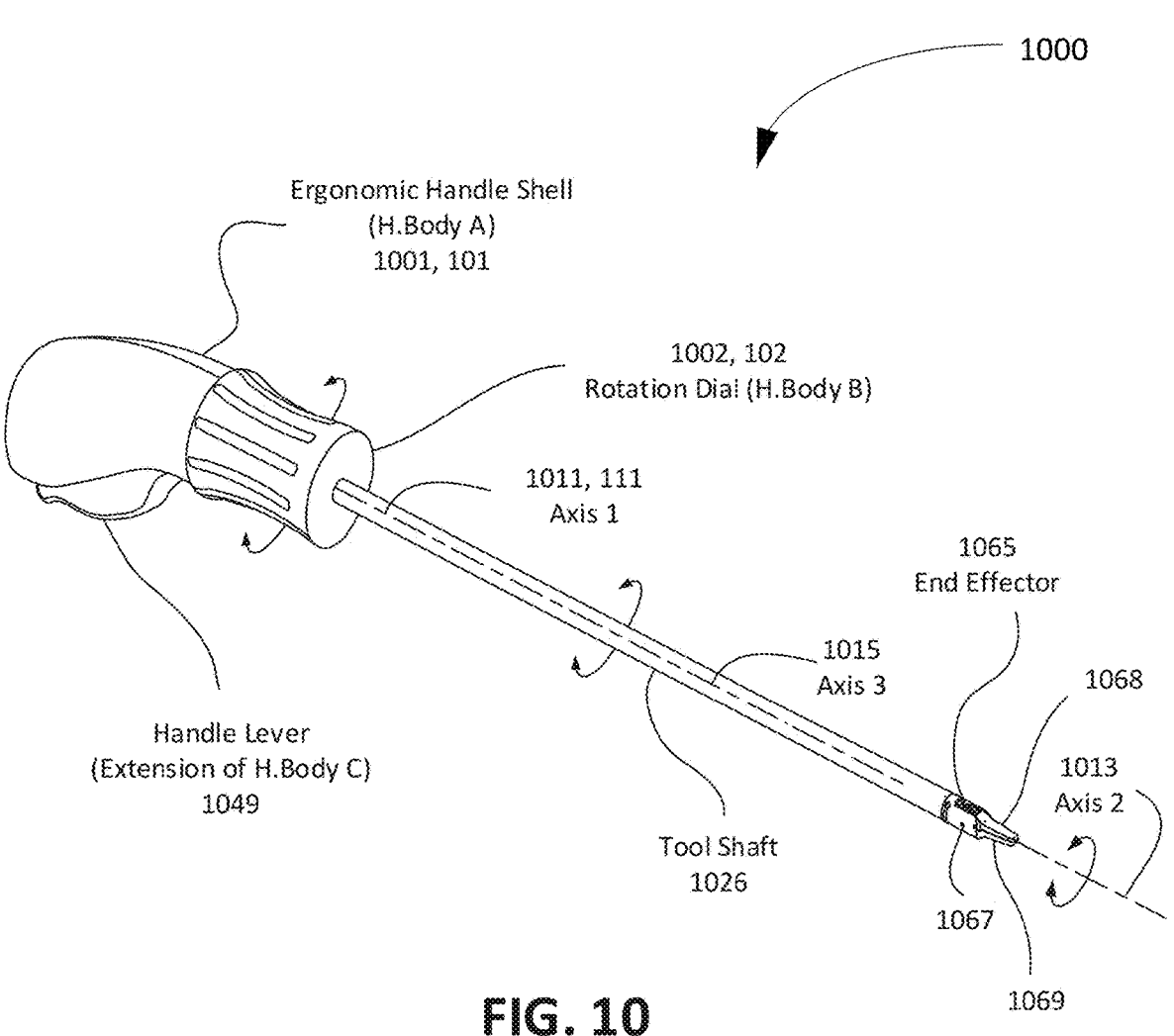
FIG. 10 shows an example of another apparatus including an unlimited-roll handle assembly and a distal end-effector configured as a jaw assembly, wherein the apparatus is a non-articulating "straight stick" laparoscopic device.

Another example of an apparatus 1000 incorporating the above-described unlimited-roll handle assembly 400 of FIGS. 4A and 4B is shown in FIG. 10. This apparatus 1000 is configured as a straight stick device with a non-articulating end-effector 1065. Other straight stick apparatuses—for example, as described in U.S. Pat. Nos. 4,712,545, 5,626, 608, and 5,735,874—may benefit from incorporation of the unlimited-roll handle apparatuses, for example, the unlimited-roll handle assembly 400 illustrated in FIGS. 4A and 4B. FIG. 10 shows an example of a surgical instrument comprising an unlimited-roll handle assembly 400 (including a palm grip portion 101, 1001 and a dial portion 102, 1002), a tool shaft 1026, and the non-articulating end-effector 1065 configured as a jaw assembly, wherein, for example, there is a rotation joint 1067 between the moving jaw 1068 and fixed jaw 1069 of the non-articulating end-effector 1065. The non-articulating end-effector 1065 connects to the rotation dial 102, 1002 (H.Body D) via a jaw closure actuation transmission member (not visible in FIG. 10). This apparatus 1000 provides the functionality of closing and opening the non-articulating end-effector 1065 by moving the moving jaw 1068 relative to the fixed jaw 1069. The apparatus 1000 may also provide the rotation of the non-articulating end-effector 1065 about the handle axis 1011 (Axis 1 111), wherein the shaft axis 1015 (Axis 3) remains parallel to the handle axis 1011 (Axis 1 111) under rotation of the H.Body B 102, 1002, tool shaft 1026, and the non-articulating end-effector 1065 attached hereto.

Figure 11:
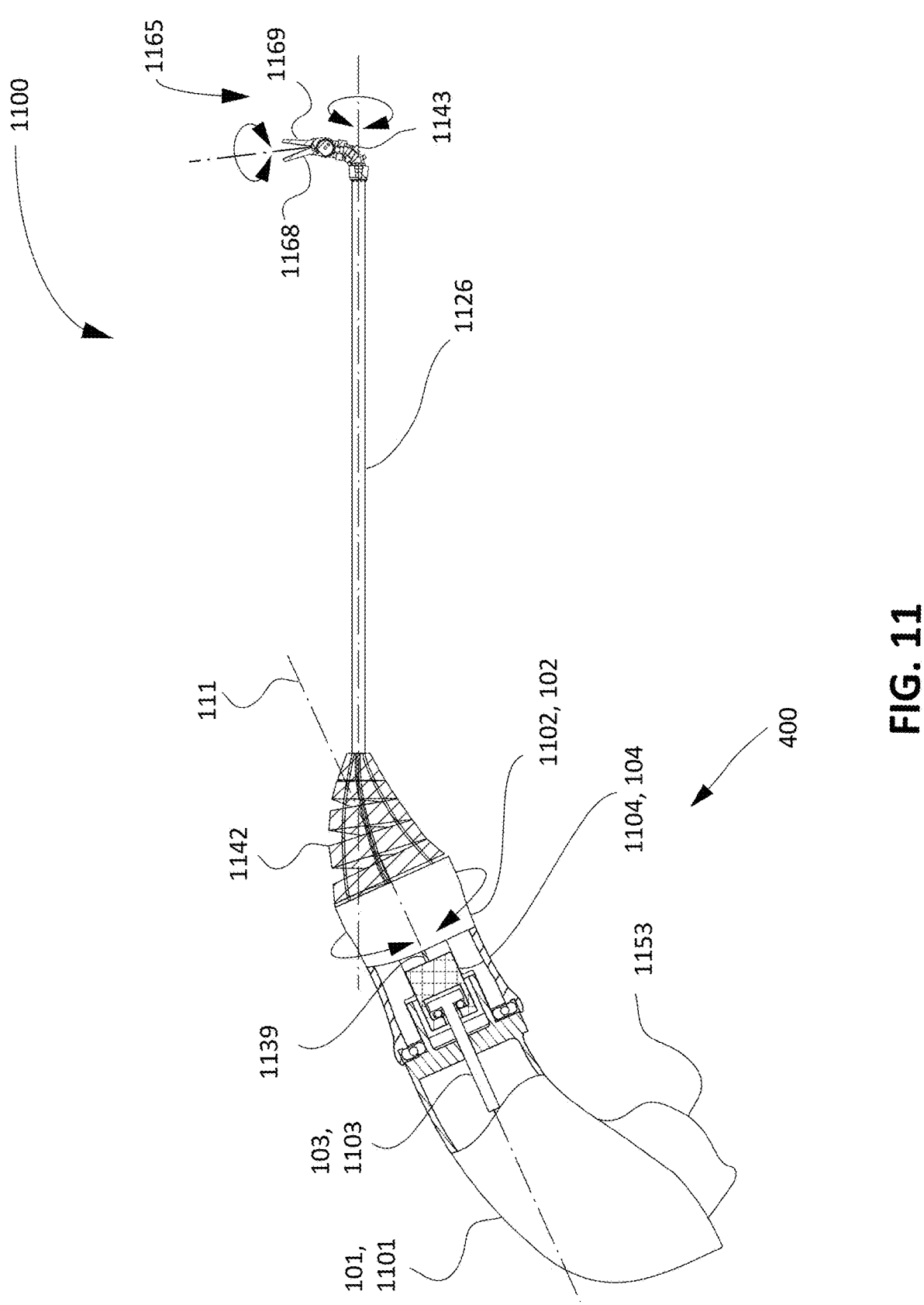
FIG. 11 shows an example of another articulating medical device using an unlimited-roll handle assembly such as the one shown in FIGS. 4A-4B.

Referring to FIG. 11, in accordance with another set of embodiments that incorporate the unlimited-roll handle assembly 400 illustrated in FIGS. 4A and 4B, articulation at the input joint 529 is captured via either a serial kinematic input articulation joint or a parallel kinematic input articulation joint. For example, FIG. 11 shows an articulating laparoscopic device 1100. Such devices include a handle shell 101, 1101, handle lever 1153, handle dial 102, 1102, shuttle 104, 1104, pull/push rod 103, 1103, jaw closure actuation transmission member 1139, tool shaft 1126 and an articulating end-effector 1165. Similar to the above-described non-articulating laparoscopic device 1000, the articulating laparoscopic device 1100 also incorporates an end-effector rotation joint 1067 (open/close functionality) operative between a moving jaw 1168 and a fixed jaw 1169, and in addition to this open/close end-effector rotation joint 1067, also contains an output articulation joint 1143 for end-effector articulation and a corresponding associated input articulation joint 1142. The input articulation joint 1142 may be implemented as either a serial kinematic (S-K) input joint or parallel kinematic (P-K) input joint. Some articulating instruments that consist of serial kinematic (S-K) input joint (such as the one shown in FIG. 11) can be found, for example, in U.S. Pat. Nos. 8,465,475; 5,713,505, 5,908,436, U.S. application Ser. No. 11/787,607 and U.S. Pat. No. 8,029,531. Examples of articulating instruments incorporating a parallel kinematic (P-K) input joint may be found, for example, in U.S. patent application publication No. 2013/0012958. In such devices, although the end-effector may be a jaw assembly and may be shown in an open jaw condition, an associated articulating instrument can also perform rotation with the end-effector rotation joint in a closed jaw condition or with the output articulation joint in an articulated condition.

Figure 12:
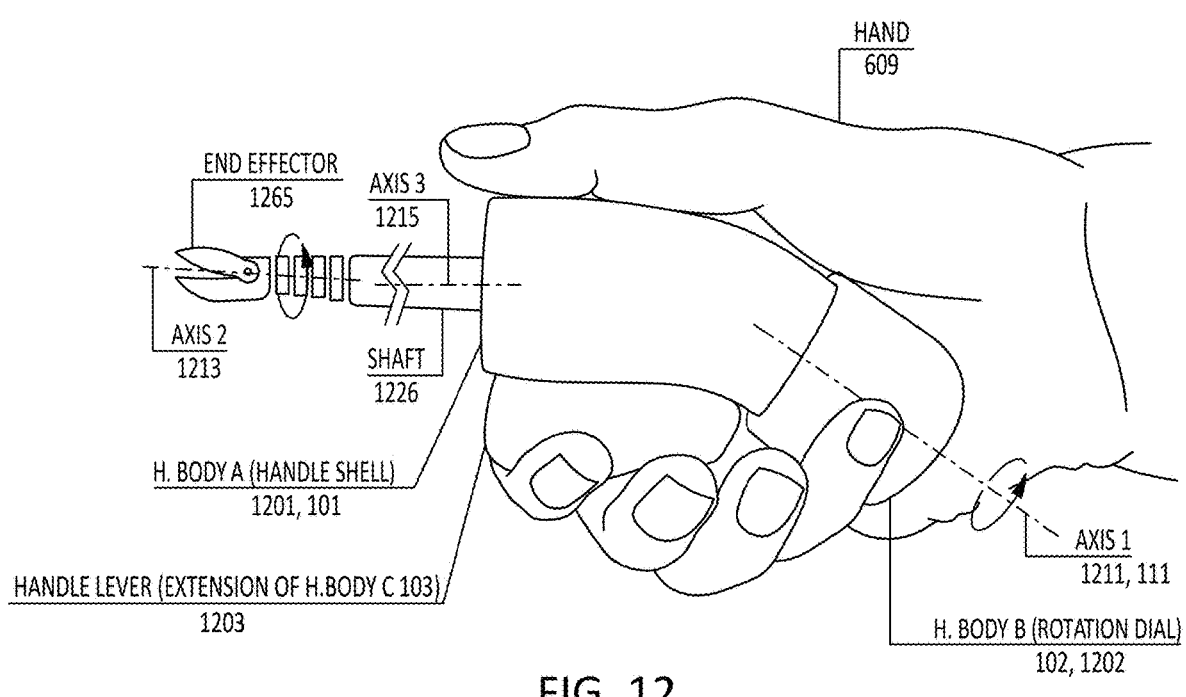
FIG. 12 is an example of an alternative unlimited-roll handle assembly in which the palm grip/handle shell (H.Body A) is distal to the rotation dial (H.Body B).
Figure 13:
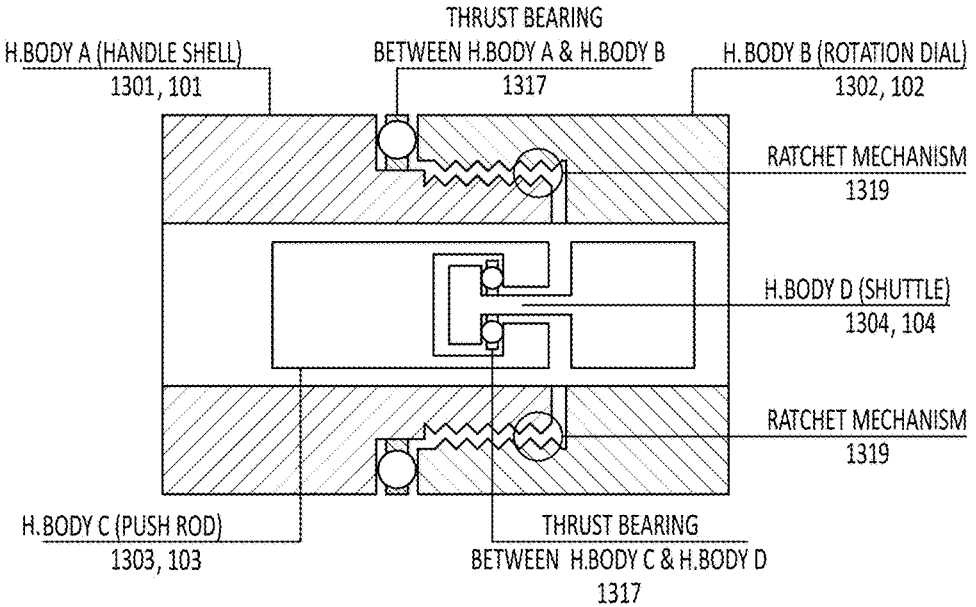
FIG. 13 illustrates the use of a ratchet mechanism for providing discrete rotational positioning of the associated rotation dial of an unlimited-roll handle assembly.

FIGS. 12 and 13 illustrate other unlimited-roll handle assembly variations that follow the constraint map illustrated in FIG. 1. These handle assembly variations may be used with any of the other apparatus components described herein (including with other device architectures and/or constraint maps). For example, in FIG. 12, the rotation dial 102, 1202 is proximal to the palm grip/handle shell portion 101, 1201. The apparatus may include a shaft 1226 and an end-effector 1265 and may include the same axes as described above (first Axis 111, 1211, second Axis 1213, and third Axis 1215). As indicated in the constraint map of FIG. 1, joint characteristics (DoFs and DoCs) between H.Body A 101, 1201 and H.Body C 103 (Handle Lever 1203 is a mechanical extension of H.Body C 103) are the same as the ones between H.Body B 102, 1202 and H.Body D 104 (not shown in FIG. 12). Also, joint characteristics (DoFs and DoCs) between H.Body A 101, 1201 and H.Body B 102, 1202 are the same as the ones between H.Body C 103 and H.Body D. Any of the four bodies can be referred as ground reference. In FIG. 12, when mapped to the constraint map of FIG. 1, H.Body B 102, 1202 is located away from to the tool shaft 1226 and towards the proximal end of the hand 609. H.Body A 101, 1201 is located towards the proximal end of the tool shaft 1226. H.Body B 102, 1202 is rotated w.r.t. H.Body A 101, 1201 about axis 1 1211, 111. Here, H.Body C 103 rotates with respect to H.Body D 104. Another way of explaining this embodiment (shown in FIG. 12) is that the handle assembly's rotation dial is now placed at the proximal end of the handle assembly.

Any of the apparatuses described herein may include a rotation lock/ratcheting mechanism, as illustrated in FIG. 13. The handle assembly shown here follows the constraint map of FIG. 1 and consists of a joint 1317 between H.Body A 101, 1301 and H.Body B 102, 1302 that provides a rotational DoF about Axis 1 111. This rotation can be made more tactile by the application of a ratcheting feature 1319 between H.Body A 101, 1301 and H.Body B 102, 1302. Ratcheting between H.Body A 101, 1301 and H.Body B 102, 1302 can provide a sense of discrete rotation steps while rotating about Axis 1. FIG. 13 illustrates a ratchet mechanism 1319 along with a thrust bearing 1317 (that provides rotational DoF 106' and translational DoC 106'') located between the palm grip/handle shell 101, 1301 and the rotation dial 102, 1302. The shuttle 104, 1304 and push rod 103, 1303 otherwise operate per the constraint diagram of FIG. 1 and handle assembly 400 of FIG. 4.

Figure 14:
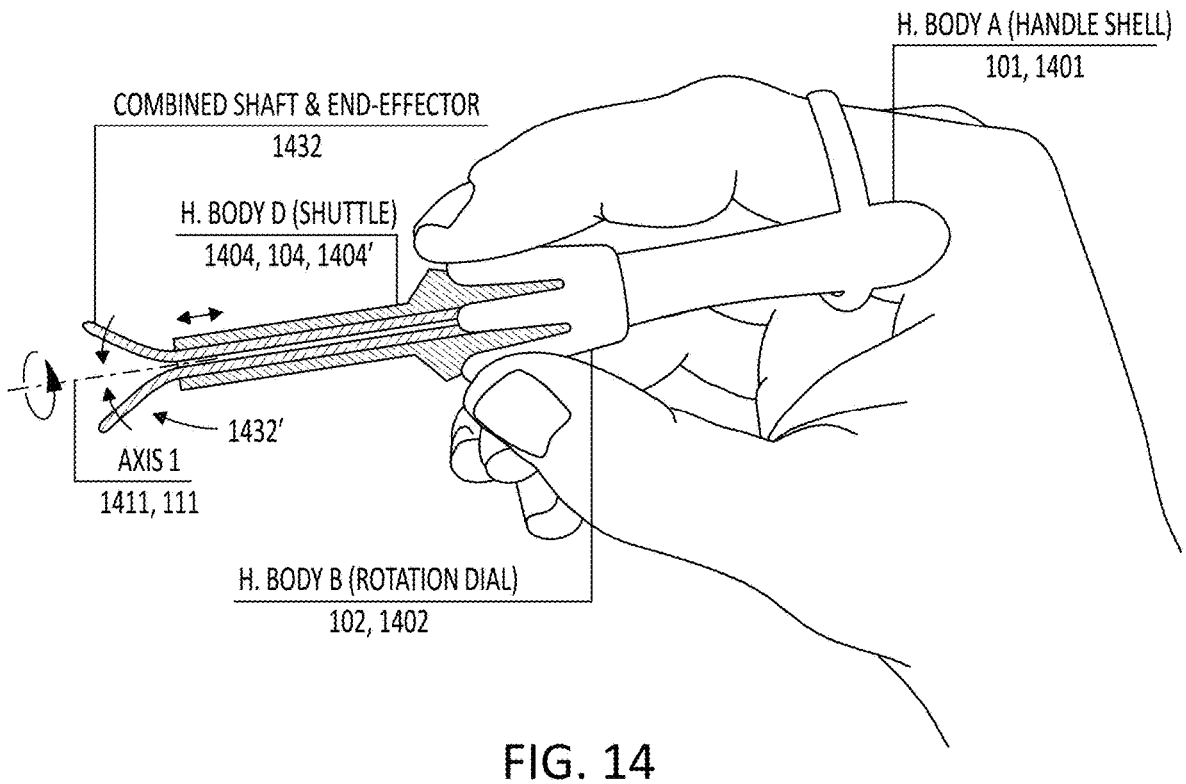
FIG. 14 illustrates another embodiment of an apparatus using an unlimited-roll handle assembly.

The unlimited-roll handle assemblies described herein may also be used with an apparatus configured to provide a pecking motion at the end-effector. For example, referring to FIG. 14, other embodiments of an unlimited-roll handle assembly 400 of FIG. 4 (fitting the constraint map of FIG. 1) may provide for the opening and closing of an end-effector jaw triggered directly by radially pressing the rotation dial 102, 1402 (H.Body B). For example, the embodiment illustrated in FIG. 14 comprises a handle shell 101,

1401 (H.Body A), held in a hand 609 of the user, and may include a rotation dial 102, 1402 (H.Body B) that can rotate relative to handle shell 101, 1401 (H.Body A) about Axis 1 111, 1411. The rotation dial 104, 1404 (H.Body B), when radially pressed, pushes a shuttle 104, 1404 (H.Body D) along Axis 1 111, 1411 direction in accordance with the translational DoF of the shuttle 104, 1404 (H.Body D) with respect to the rotation dial 104, 1404 (H.Body B) along Axis 1 111, 1411. This closes a combined shaft and end-effector 1432 that may be rigidly connected to the rotation dial 102, 1402 (H.Body B), as shown in FIG. 14. The flexible nature of the body representing combined shaft and end-effector 1432 directs the movement of shuttle 104, 1404 (H.Body D)—as a sleeve 1404'—over the combined shaft and end-effector 1432. This sleeve 1404'/shuttle 104, 1404 (H.Body D), controls the opening and closing of the associated end-effector 1432', the latter of which acts as a double action jaw that can have various applications in open surgery, for example, in eye surgery, or in minimal invasive surgery. The push/pull rod (H.Body C, which can't be seen in FIG. 14) may be keyed to the interior of the handle shell 101, 1401 (H.Body A) and attached via a spring, so that after the push/pull rod (H.Body C) is moved relative to handle shell 101, 1401 (H.Body A), it retracts back to its original position with the help of the spring. Accordingly, this provides for the motion of the push/pull rod (H.Body C) and shuttle 104, 1404 (H.Body D) along Axis 1 111, 1411 direction when the shuttle 104, 1404 (H.Body D) is pushed along Axis 1 direction by radially pressing the rotation dial 104, 1404 (H.Body B), and provides for retracting both the shuttle 104, 1404 (H.Body D) and the push/pull rod (H.Body C) to their original position thereafter. Accordingly, for this embodiment, the combined end-effector 1432 can be rotated about Axis 1 (111, 1411), and the associated end-effector 1432' can be used to grab or clamp external bodies by pecking the shuttle 104, 1404 (H.Body D), which closes of the end-effector 1432', and can then be used to release the external body by releasing the shuttle 104, 1404 (H.Body D), which opens the end-effector 1432'.

Referring to FIG. 15, in accordance with another embodiment, an apparatus 1500 utilizing a pull-pull configuration for jaw closure transmission incorporates an unlimited-roll handle assembly 400 such as was shown in FIG. 4A, including a shuttle 104, 404 (H.Body D) keyed to H.Body B 102, 402. An associated jaw closure (open/close) actuation transmission member 1530 is first pulled to close an end-effector moving jaw 1567 with respect to a corresponding end-effector fixed jaw 1568, and is then subsequently released to open the end-effector moving jaw 1567 with respect to the end-effector fixed jaw 1568. The jaw closure (open/close) actuation transmission member 1530 is attached to H.Body D 104, 404 where H.Body D can translate with respect to H.Body B 102, 402 as a result of the translational DoF 107' along Axis 1 111, 411 direction, but has a translational constraint (DoC) 108'' with respect to H.Body C 103, 403. Once H.Body D 104, 404 moves along Axis 1 111, 411 direction to pull the jaw closure (open/close) actuation transmission member 1530 to close the jaws 1567, 1568 (i.e., bringing the end-effector moving jaw 1567 and end-effector fixed jaw 1568 together), a second jaw closure (open/close) actuation transmission member 1532 is pulled to open the end-effector moving jaw 1567. To open the jaws 1567, 1568 the second jaw closure actuation transmission member 1532 may be pulled. In one embodiment, the second jaw closure actuation transmission member 1532 can be pulled using a pull spring 1513, grounded at a reference frame called "Spring Reference Ground 1512". Depending on how the roll transmission member is routed throughout the whole assembly, "Spring Reference Ground 1512" can occur at different locations in the assembly, as follows: (1) If roll transmission is by means of an input articulating joint 529, a tool frame/tool shaft 1526, and an output articulating joint 583, then the "spring reference ground 1512" can occur at the H.Body B 102, 402, or the tool frame/tool shaft 1526, or the end-effector fixed jaw 1568; (2) If roll transmission is by means of an independent roll transmission member routed across the input articulating joint 529, through tool frame/tool shaft 1526, and through the output articulating joint 583 (given an extra roll DoF between output joint distal end and end-effector base), then the "spring reference ground 1512" can occur at H.Body B 102, 402 or at the end-effector fixed jaw 1568.

Figure 16:
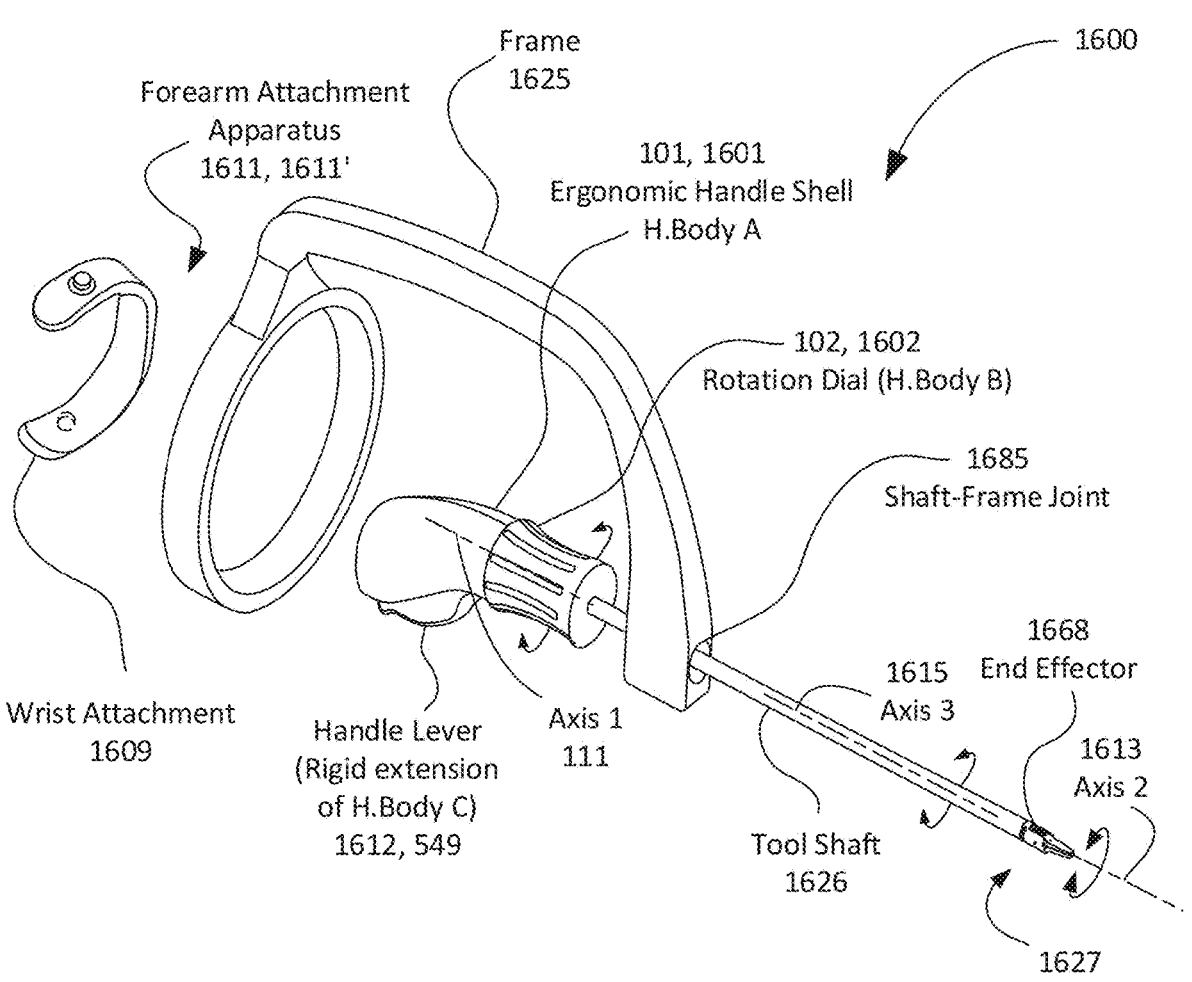
FIG. 16 is a front perspective view of an exemplary surgical device incorporating an unlimited-roll handle assembly and an arm (forearm) attachment. This surgical device is an embodiment of a tool apparatus in the alpha configuration.

In some variations, the unlimited-roll handle assembly is generally configured to include a forearm attachment apparatus 600. The unlimited-roll handle apparatus 1600 may provide the ability for simultaneously transmitting roll and closure action to H.Body D 104 with respect to H.Body A 101. Such a variation that includes a forearm attachment apparatus 600 that provides for addition degrees of freedom (DoFs) was described above in FIGS. 5-8, and another example is shown in FIG. 16. FIG. 16 illustrates a tool apparatus embodiment in the alpha configuration (defined later). In this example, a (one) joint—referred to as a forearm attachment apparatus 1611—exists between a wrist attachment/wrist cuff 1609 and a tool frame 1625. The forearm attachment apparatus 1611 (similar to 600 shown in FIG. 6) may be used to couple the wrist attachment/wrist cuff 1609 to the tool frame 1625, allowing either zero, or one, or more degrees of freedom between the user's forearm and the unlimited-roll handle apparatus 1600, depending upon the nature of the forearm attachment apparatus 1611. The forearm attachment apparatus 600 may be used with either articulating devices or non-articulating devices. For example, one embodiment can include a roll DoF by providing a roll rotation joint 1611' between the wrist attachment/wrist cuff 1609 and the tool frame 1625. This joint may use a "sled 518"—for example, as illustrated in FIG. 6—which can provide for a roll rotational DoF about the roll axis 111, 531 or the arm axis 612. Another embodiment can provide for a pitch DoF by providing a rotation joint to allow rotation about the flexion/extension axis of rotation 516. Another embodiment can provide for a yaw DoF by providing a rotation joint to allow rotation about the deviation axis of rotation 521. Another embodiment can provide for both pitch and yaw DoF by providing one or more rotation joints that allow rotation about the flexion/extension axis of rotation 516 and rotation about the deviation axis of rotation 521, respectively, for example, by incorporating an intermediate body referred to as a deviation ring 514, for example, as illustrated in FIG. 6. Another embodiment can provide for roll (about the arm axis 612), pitch (about the flexion/extension axis of rotation 516), and yaw (about the deviation axis of rotation 521) degrees of freedom (DoFs). Also as shown in FIG. 16, a joint exists between the tool frame 1625 and the tool shaft 1626, called a shaft-frame joint 1685, which may have a zero DoF joint (i.e., a rigid connection between the tool shaft 1626 and the tool frame 1625), which, for the embodiments disclosed herein, is the default configuration. The device 1600 illustrated in FIG. 16 includes a handle palm grip 101, 1601 (H.Body A), a rotation dial 102, 1602 (H.Body B), an end-effector input 1612 (e.g. a handle lever 549), a shaft-frame joint 1685, an end-effector 1668 at a distal end 1627 of the tool shaft 1626, for which are defined an associated handle axis 111 (Axis 1), an associated tool shaft axis 1615 (Axis 3) and an associated end-effector axis 1613 (Axis 2).

Some variations of a non-articulating instrument 1600 that is forearm mounted and that incorporates the unlimited-roll handle assembly 400 of FIGS. 4A and 4B may include a separate tool frame 1625 and a separate tool shaft 1626. In one such configuration, the tool frame 1625 and wrist attachment/wrist cuff 1609 may be rigidly attached (i.e., 0 DoF). In this case, if the tool shaft 1626 is rigidly connected to the rotation dial 102, 1602 (H.Body B), then the device 1600 may be configured so that there is at least one roll rotation DoF between the tool shaft 1626 and the tool frame 1625. Furthermore, a shaft-frame joint 1685 can have a roll DoF, a pitch DoF, and/or a yaw DoF.

Figure 17:
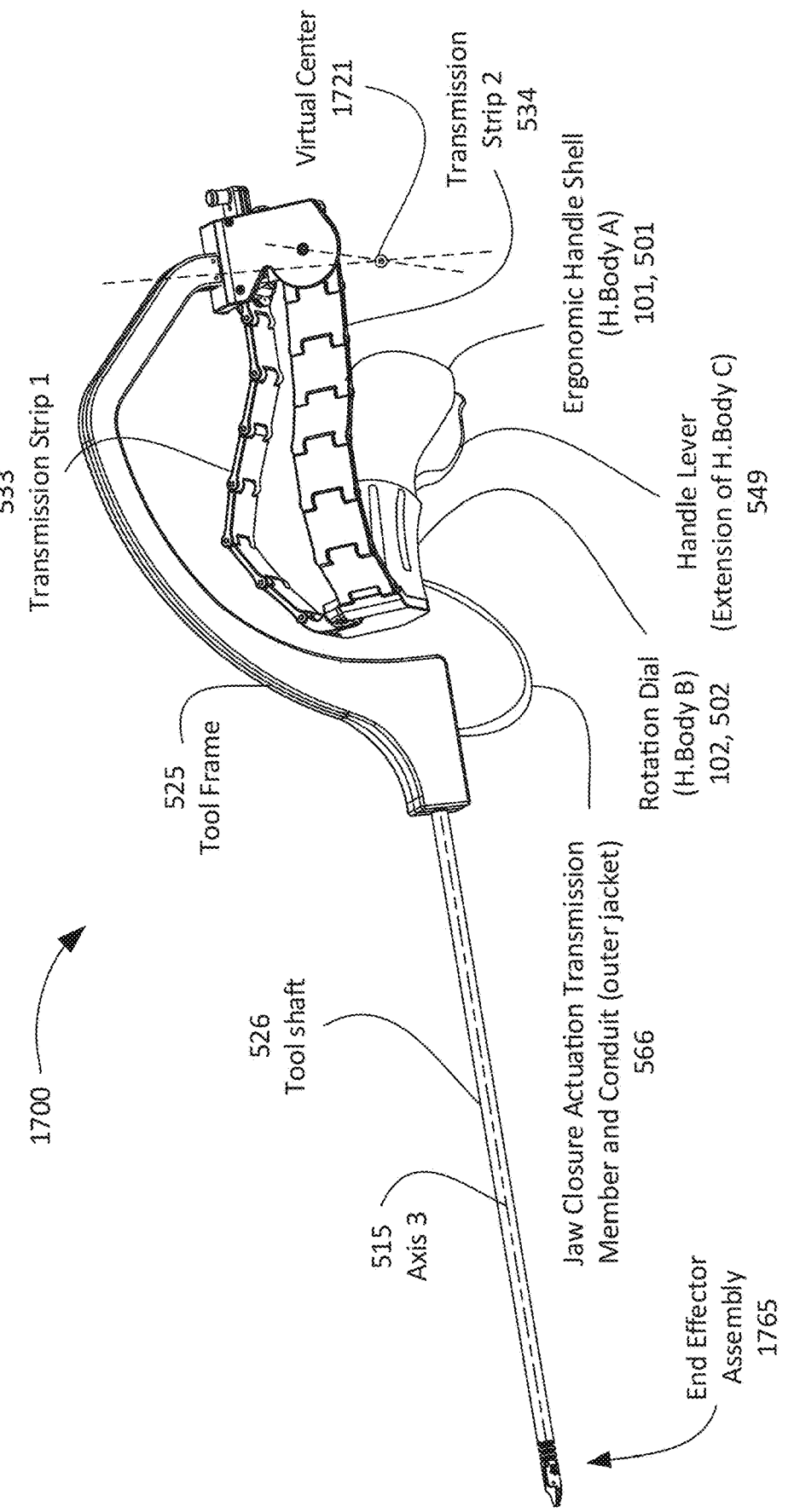
FIG. 17 is a side perspective view of an exemplary surgical device incorporating an unlimited-roll handle assembly and an input joint capturing pitch and yaw articulation by a parallel kinematic mechanism, which transmits pitch and yaw motions to an output joint located between the tool frame and the end-effector (shown configured as a jaw assembly). This surgical device is an embodiment of a tool apparatus in the beta configuration.

Any of the apparatuses incorporating an unlimited-roll handle assembly described herein may also include a virtual center (VC) 1721 associated with an input articulation joint, for example, as shown in FIG. 17. This device 1700 can have either a serial or parallel kinematic input joint, with the associated joint axes intersecting at the virtual center (VC) 1721. This device 1700 is similar to that shown in FIGS. 5, 7, and 8, but explicitly shows the virtual center (VC) 1721. The device 1700 also includes an end-effector assembly 1765 that is also configured as a jaw assembly.

Example: Medical Device

Figure 18A:
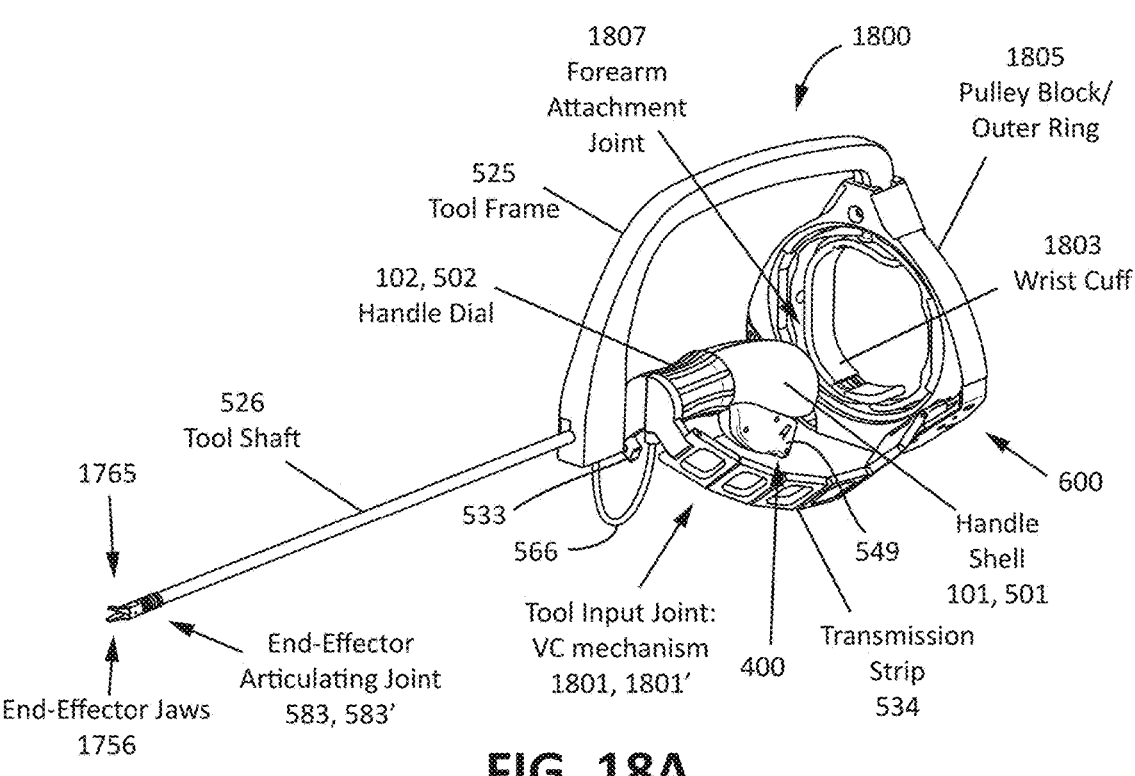
FIGS. 18A-18D show front perspective, left side perspective, back perspective, and right side perspective views, respectively, of a medical device including an unlimited-roll handle assembly, an end-effector assembly configured as a jaw assembly, a tool shaft, a tool frame, a proximal forearm attachment and an input joint providing pitch and yaw articulation of the handle assembly with respect to the tool frame. is the pitch and yaw articulation of the input joint are transmitted to an output joint articulating the end-effector. The input joint has a center of rotation—located where the pitch and yaw axes intersect—that provides for a virtual center of rotation located approximately within a user's wrist when the apparatus is attached to the user. This medical device is an embodiment of a tool apparatus in the beta configuration.
Figure 18B:
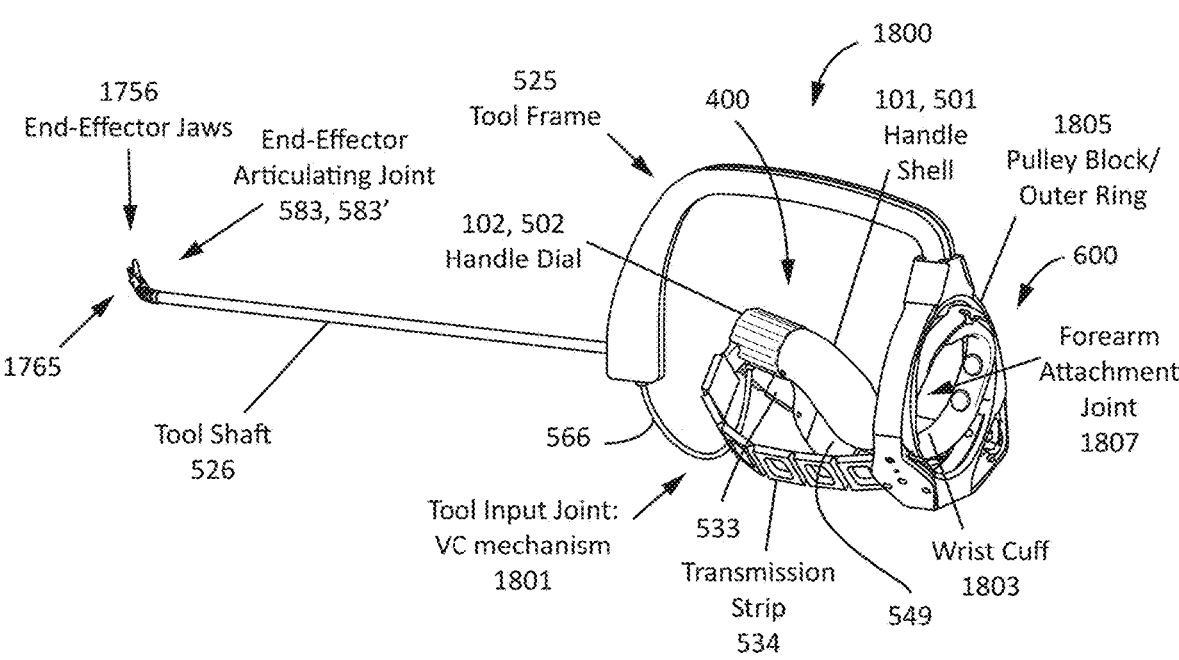
Figure 18C:
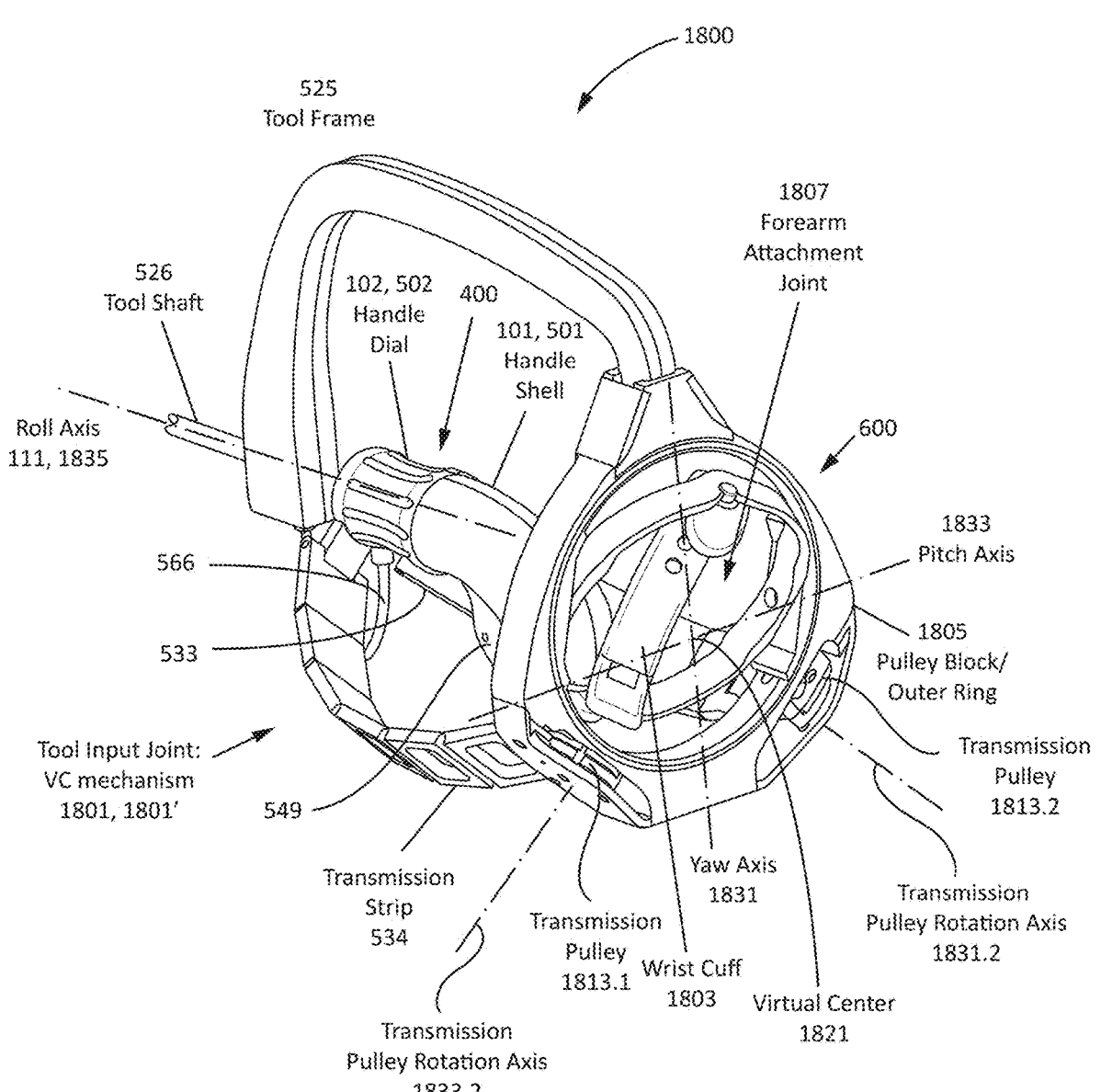
Figure 18D:
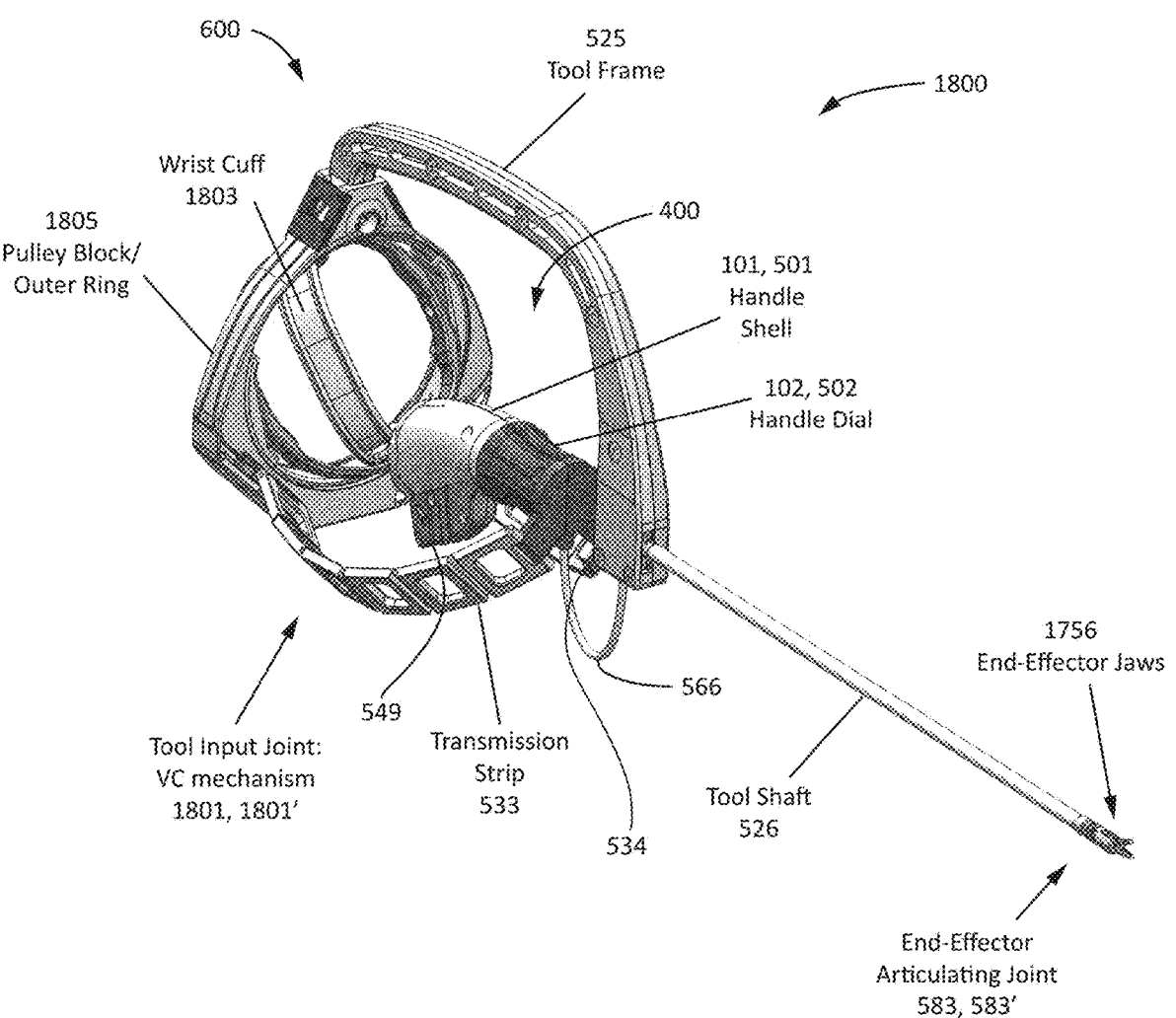
Figures 19A, 19B:
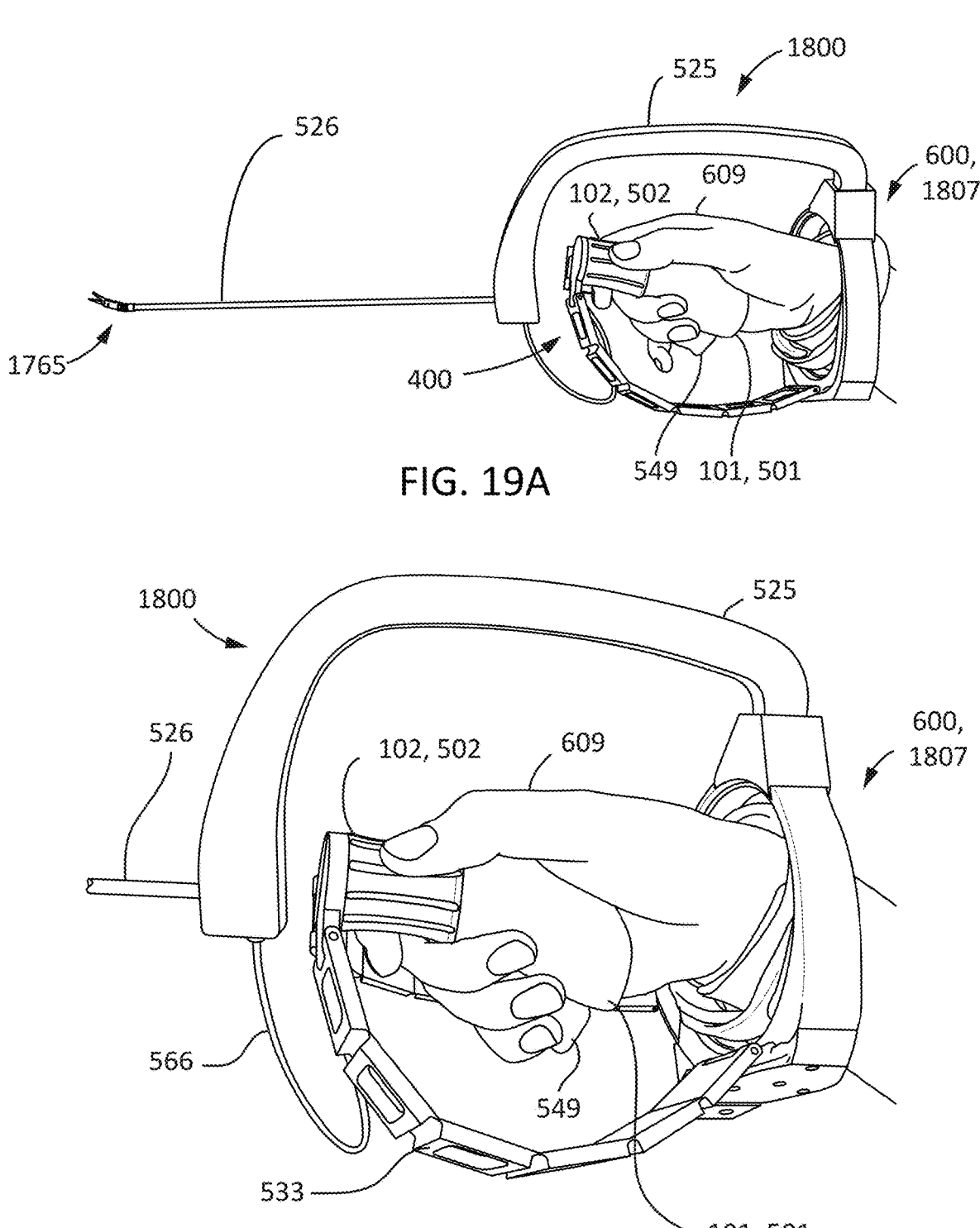
FIG. 19A shows a side view of a portion of a medical device corresponding to that shown in FIGS. 18A-18D, coupled to a user's forearm with the unlimited-roll handle assembly held in the user's hand. This medical device is an embodiment of a tool apparatus in the beta configuration.
FIG. 19B shows a slightly enlarged view of the device of FIG. 19A.
Figure 19C:
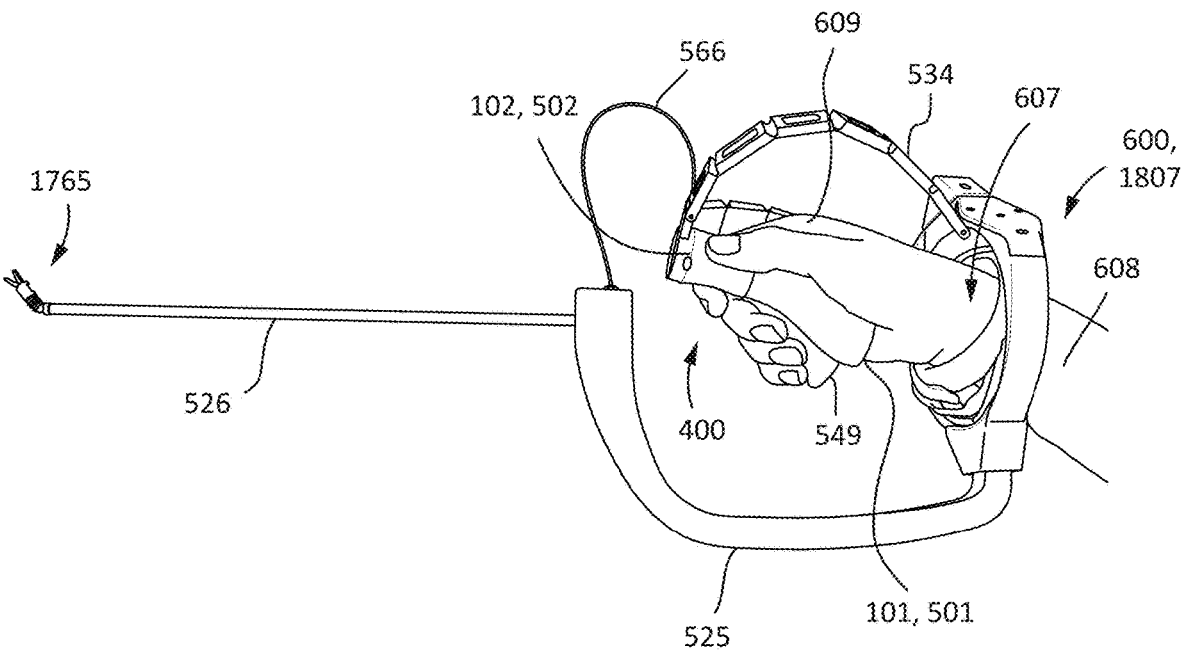
FIG. 19C shows the device of FIG. 19A, in which the user is articulating the handle assembly in pitch and yaw relative to the tool frame, illustrating that the end-effector assembly track the handle orientation, with the tool frame rotated relative to the orientation shown in FIGS. 19A and 19B.
Figure 20A:
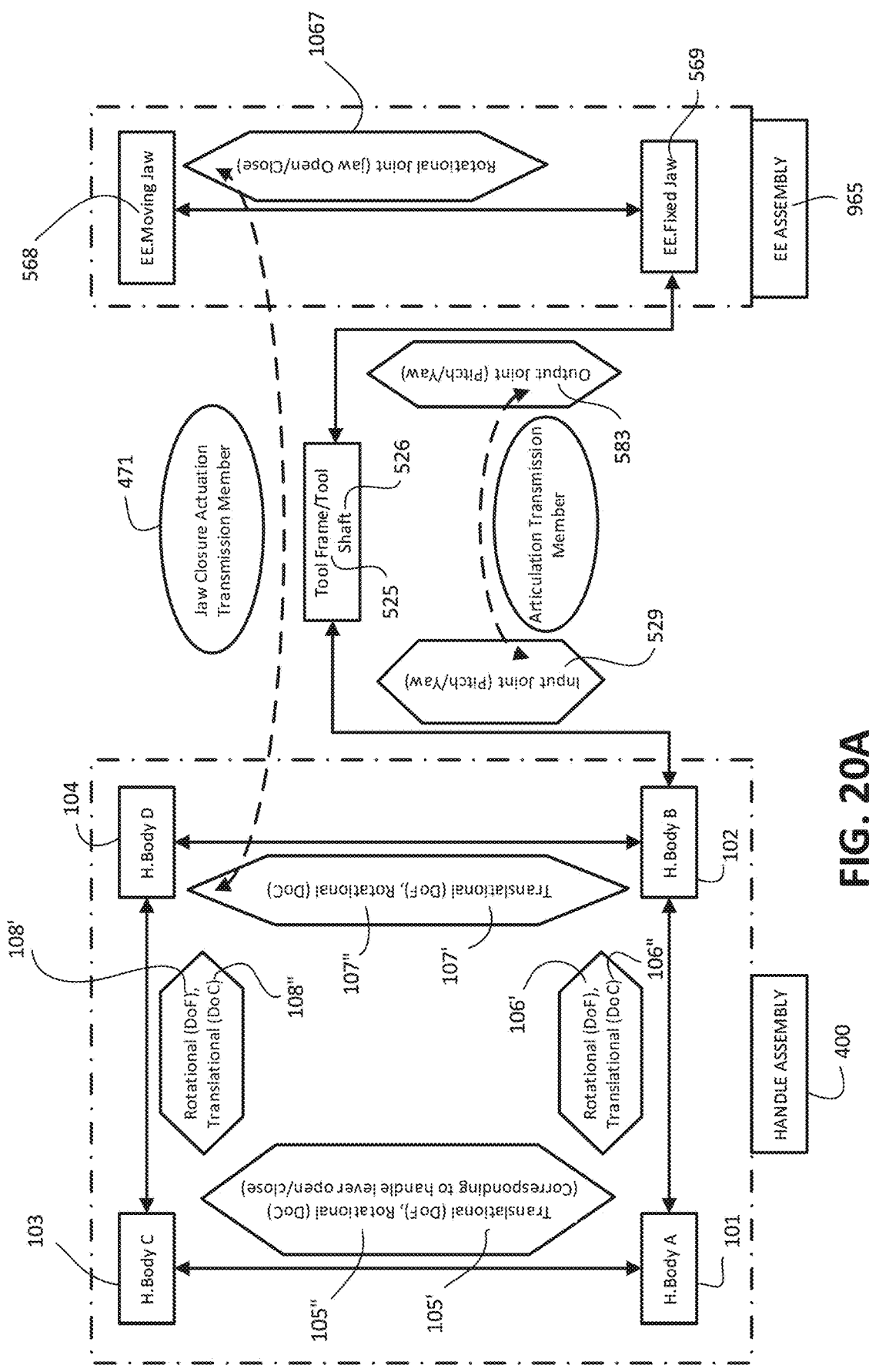
FIG. 20A is a constraint map of the apparatus shown in FIGS. 18A-18D that includes an unlimited-roll handle assembly, an input joint, an output joint, and an end-effector configured as a jaw assembly.
Figure 20B:
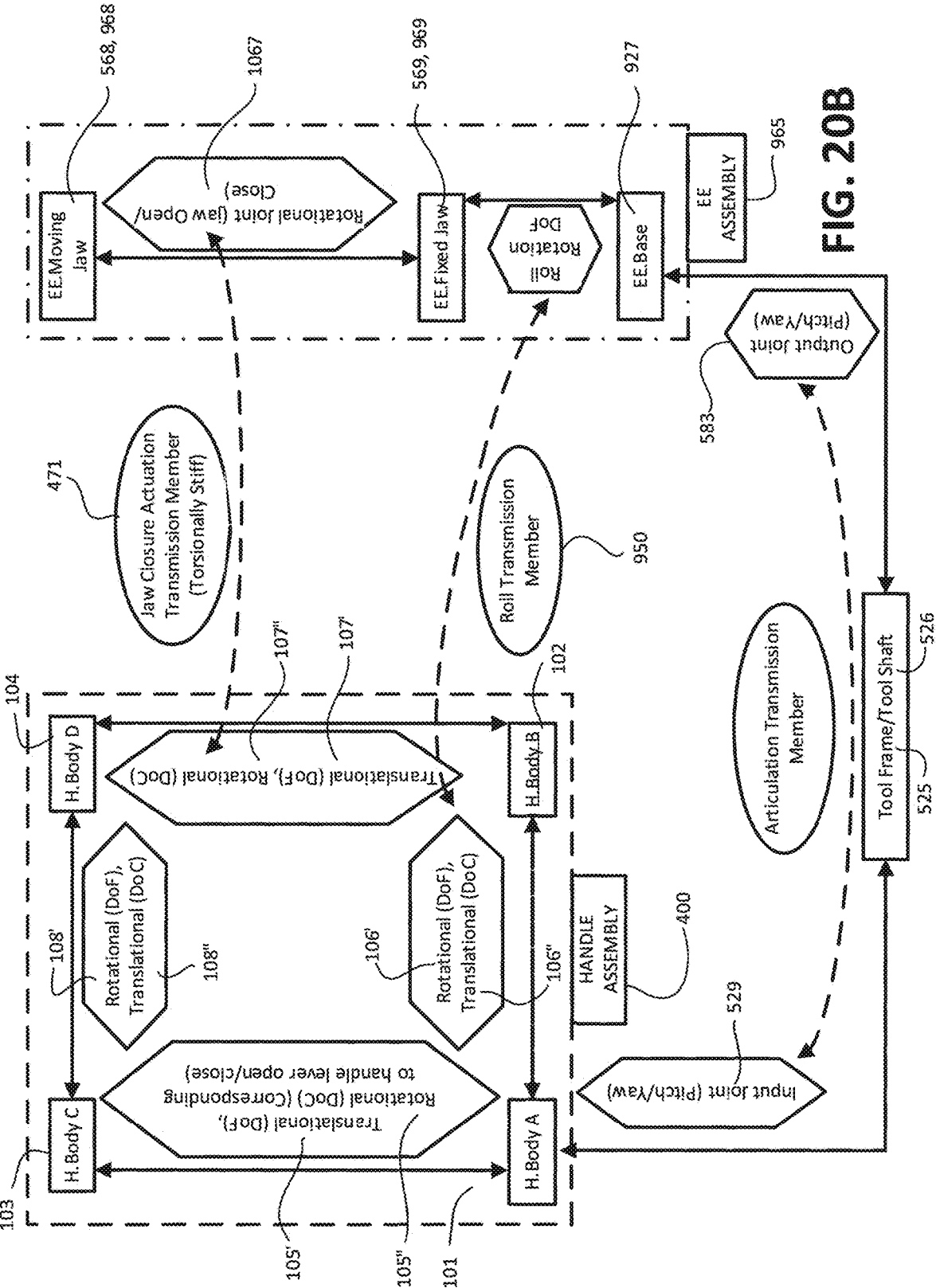
FIG. 20B shows an alternative constraint map for another apparatus described herein.

FIGS. 18A-18D illustrate one example of a medical device 1800 configured as a laparoscopic apparatus including an unlimited-roll handle assembly 400 (similar to that illustrated in FIGS. 4A and 4B), an elongate tool frame 525, a forearm attachment apparatus 600 (similar to that illustrated in FIG. 6) having multiple degrees of freedom between the user's arm and the tool frame 525, an end-effector assembly 1765 configured as a jaw assembly, and an input joint 1801 that captures pitch and yaw rotation of the unlimited-roll handle assembly 400 for transmission to an output joint 583, e.g. an end-effector output articulating joint 583', so that the end-effector assembly 1765 may articulate in the same direction as does the unlimited-roll handle assembly 400, for example, as illustrated in FIGS. 19A-19C. A schematic constraint diagram for the medical device 1800 shown in FIGS. 18A-18D is shown in FIG. 20A, corresponding to beta configuration (defined later). An alternative constraint diagram for a medical device 1800 as described herein is shown in FIG. 20B, which corresponds to alpha configuration (defined later).

Referring again to FIGS. 18A-18D, the overall medical device 1800 comprises a pulley block 1805, a tool frame 525 including a tool shaft 526 (the tool shaft 526 may be considered a portion of the tool frame 525), all rigidly inter-connected to one another. The pulley block 1805 serves as the outer ring 1805 of a forearm attachment joint 1807 that interfaces with the distal forearm 608' of a user via a wrist cuff 1803, as described above.

In this example, the wrist cuff 1803 and the outer ring 1805 are all part of the forearm attachment joint 1807 (corresponding to the forearm attachment apparatus 600 of FIG. 6). The forearm attachment joint 1807 comprises the outer ring 1805, a sled 518, a deviation ring 514, and the wrist cuff 1803 (all connected in series), as illustrated in FIG. 6 and described hereinabove, and provide three rotational degrees of freedom (DoFs) between the wrist cuff 1803 and the outer ring 1805, i.e., roll, pitch, and yaw. Roll is the rotation direction about the axis of the outer ring 1805, which is the same as the axis of the tool shaft 526. Pitch and yaw are orthogonal rotations about the pitch axis 1833 and yaw axis 1831, respectively, as illustrated in FIG. 18C. These axes can assume any orientation and one of these orientations may align with the transmission pulley axes. In this particular orientation, the pitch axis of rotation (1833) aligns with the rotation axis of transmission pulley 1813.1 and the yaw axis of rotation aligns with the rotation axis of transmission pulley 1813.2. These axes, namely transmission pulley rotation axis 1833.2 and transmission pulley rotation axis 1831.2, are shown in FIG. 18C. When the medical device 1800 is mounted on the forearm 608 (i.e., the wrist cuff 1803 is attached to the forearm 608/wrist 607 of a user), the forearm attachment joint 1807 provides the above three rotational degrees of freedom between the tool frame 525 and user's/surgeon's forearm 608.

The tool frame 525 extends from the outer ring 1805/pulley block 1805 and is shaped around the unlimited-roll handle assembly 400 to accommodate a user's hand 609 (over its entire range of articulation) while supporting the unlimited-roll handle assembly 400. The tool frame 525 rigidly connects to the tool shaft 526, which further extends in a distal direction (i.e., away from the forearm attachment joint 1807 and the user). A two-DoF articulating joint (also referred to as the output joint 583/end-effector articulating joint 583') is located at the end (also referred to as the output of the medical device 1800) of the tool shaft 526. These two degrees of freedom are pitch rotation and yaw rotation, which are controlled/actuated by articulating the input joint 1801 (discussed below) between the unlimited-roll handle assembly 400 and the pulley block 1805. Additionally, the end-effector assembly 1765 is equipped with a pair of jaws 1756 that can be opened and closed in response to a handle lever 549 of the unlimited-roll handle assembly 400.

The input joint 1801 is located between the unlimited-roll handle assembly 400 and the pulley block 1805 at the proximal end 528 of the medical device 1800 and provides for two rotational degrees of freedom (DoF) (pitch rotation and yaw rotation) therebetween. The input joint 1801 is a parallel kinematic mechanism comprising two flexure transmission strips 533, 534 and two transmission pulleys 1813.1, 1813.2 (a pitch pulley 1813.1 and a yaw pulley 1813.2, shown in FIG. 18C). The axes of the pulleys 1813.1, 1813.2, when extrapolated, intersect at a virtual center (VC) 1821 in space. For this reason, the parallel kinematic input joint 1801' of the medical device 1800 is also referred to as a Virtual Center mechanism 1801' or a Virtual Center input joint 1801'. When the medical device 1800 is mounted on a user's forearm 608 via the forearm attachment joint 1807 and the user's hand 609 holds the handle shell 101, 501 of the unlimited-roll handle assembly 400, the overall geometry of the medical device 1800 is such that the virtual center (VC) 1821 produced by the parallel kinematic input joint 1801' approximately coincides with the center of rotation the user's wrist joint 607. This ensures a natural, comfortable, unrestricted articulation of the surgeon's wrist 607 while using the medical device 1800.

Given the above configuration of the medical device 1800, the yaw and pitch rotations of the user's wrist 607 with respect to his/her forearm 608 are translated to the corresponding rotations of the unlimited-roll handle assembly 400 with respect to the pulley block 1805/tool frame 525. The parallel kinematic design of the virtual center mechanism 1801' is such that the two rotation components (pitch and yaw) of the handle shell 101, 501 with respect to the pulley block 1805 are mechanically separated/filtered into a pitch-only rotation at the pitch pulley 1813.1 and a yaw-only rotation at the yaw pulley 1813.2. The pitch pulley 1813.1 and yaw pulley 1813.2 are respectively pivoted (and mounted) with respect to the pulley block 1805 about the corresponding associated pitch rotation axis 1833 and yaw rotation axis 1831, respectively. The pitch and yaw rotations of the unlimited-roll handle assembly 400 (and therefore, of the surgeon's wrist 607) thus captured at the pitch 1813.1 and yaw 1813.2 transmission pulleys are then transmitted as corresponding rotations of the end-effector articulating joint 583 via cables that originate at the transmission pulleys 1813.1, 1813.2 and run through the pulley block 1805, tool frame 525, and tool shaft 526 all the way to the end-effector assembly 1765. These cables may or may not be continuous.

In addition to the yaw and pitch rotational degrees of freedom (DoFs) provided by the input joint 1801, the input joint also provides/allows for an axial translational degree of freedom along the roll axis 111, 1835, which provides/allows for a range of user hand 609 sizes to be accommodated by the medical device 1800, and ensures free and unrestricted hand 609/wrist 607 articulation.

Furthermore, the flexure transmission strips 533, 534 are stiff in twisting about the roll axis 111, 1835, which ensures that the input joint 1801 constrains (and therefore transmits) roll rotation from the distal end of the unlimited-roll handle assembly 400 (i.e., the dial) via the flexure transmission strips 533, 534 to the pulley block 1805. Note that pulley block 1805 serves as the outer ring 1805 of the forearm attachment joint 1807, which provides a well-defined low-resistance rotation about roll axis 111, 1835 with respect to the wrist cuff 1803 shown in FIG. 18C. This implies that when the user holds the handle shell 101, 501 in his/her palm, he/she can articulate the handle shell 101, 501 in any desired yaw and pitch directions, resulting in corresponding articulation of the end-effector assembly 1765. Then he/she can twirl the dial portion 102, 502 of the unlimited-roll handle assembly 400—i.e. the rotation dial 102, 502—with his/her thumb and fingers (typically index finger) while keeping the articulation of the unlimited-roll handle assembly 400 fixed. The twirling of the rotation dial 102, 502 (i.e., roll rotation) is transmitted to the pulley block 1805/outer ring 1805 via the parallel kinematic input joint 1801' (i.e. via the flexure transmission strips 533, 534 of the Virtual Center mechanism 1801'). The pulley block 1805 then rotates about the roll axis 111, 1835 with respect to the wrist cuff 1803, which is attached to the forearm 608 of the user. As a result, the entire tool frame 525 rotates about the roll axis 111, 1835 with respect to the forearm 608 of the user. Since the tool shaft 526 is rigidly connected to the tool frame 525, the tool shaft 526 also rotates about the roll axis 111, 1835. The roll rotation of the tool shaft 526 is transmitted to the end-effector assembly 1765 as well via the output joint 583 (i.e. via the end-effector articulating joint 583'). Because the articulation of the end-effector assembly 1765 (at the output joint 583) is controlled by the corresponding articulation of the unlimited-roll handle assembly 400 (about the input joint 1801), if the latter is held fixed, the former is also held fixed, while roll rotation is transmitted all the way from the twirling motion of the surgeon's fingers to the end-effector assembly 1765. This particular mode of operating the medical device 1800 is referred to as articulated roll.

In addition to producing end-effector roll via twirling of the surgeon's thumb and fingers (resulting in rotation of the rotation dial 102, 502 with respect to the handle shell 101, 501), another way to produce this roll is when the surgeon rotates (about the roll axis 111, 1835) the entire unlimited-roll handle assembly 400 by pronating and supinating his/her hand 609 and forearm 608. This roll motion is also transmitted to the tool frame 525 via the flexure transmissions strips 533, 534 of the Virtual Center mechanism 1801' and the pulley block 1805, and subsequently transmitted to the end-effector assembly 1765 via the tool shaft 526. However, the amount of roll motion achieved in this manner is limited by the range of pronation/supination allowed by the user's (i.e. surgeon's) hand 609/forearm 608.

On the other hand, by having two distinct components in the unlimited-roll handle assembly 400—the handle shell 101, 501 and the rotation dial 102, 502—this limitation is overcome. The handle shell 101, 501, which remains fixed in the user's hand 609, is indeed limited in its roll angle by the pronation/supination limit of the user's hand 609/forearm 608. However, the user can—via his/her fingers—endlessly, or infinitely, roll-rotate the rotation dial 102, 502 with respect to the handle shell 101, 501. This infinite-roll rotation is then transmitted to the end-effector assembly 1765, as described above. This infinite-roll capability provides significant and unique functionality to the surgeon in complex surgical procedures, such as when sewing, knot-tying, etc.

As noted already, the unlimited-roll handle assembly 400 comprises a rotation dial 102, 502 and a handle shell 101, 501, which are connected by a rotation joint therebetween which has a single rotational DoF about the roll axis 111, 1835. Additionally, the unlimited-roll handle assembly 400 also houses an end-effector actuation mechanism that is actuated by the handle lever 549, wherein as the handle lever 549 is depressed (by the user's fingers, typically middle, ring, and pinky fingers) with respect to the handle shell 101, 501, the end-effector actuation mechanism translates this action into a pulling action of a transmission cable 566 of an end-effector transmission 471. This pulling action is transmitted through the rotating interface/joint between the handle shell 101, 501 and the rotation dial 102, 502 to the end-effector assembly 1765 via the transmission cable 566 within a flexible conduit between the rotation dial 102, 502 and tool frame 525, then through the tool shaft 526, and finally to the end-effector jaws 1756 of the end-effector assembly 1765 via the end-effector articulating joint 583. A jaw closure mechanism in the end-effector assembly 1765 closes the end-effector jaws 1756 responsive to the pulling action of the transmission cable 566, as would be needed to operate shears, graspers, a needle-holder, etc.

The virtual center (VC) 1721 provided by the input joint 1801 coincides with the center of rotation of the wrist joint 607 of the user operating the medical device 1800. Furthermore, the three rotational axes of the corresponding three rotational degrees of freedoms (yaw axis 1831, pitch axis 1833, and roll axis 1835) provided by the forearm attachment joint 1807 may all intersect at one point, referred to as the center of rotation of the forearm attachment joint 1807. This center of rotation of the forearm attachment joint 1807 may coincide with the center of rotation of the input joint 1801 (i.e. the virtual center (VC) of rotation 1721 of the unlimited-roll handle assembly 400 with respect to the pulley block 1805).

Accordingly, the center of rotation of the forearm attachment joint 1807 may also coincide with the center of rotation of the user's wrist joint 607 when the medical device 1800 is mounted on a user's forearm 608.

In particular, when the user's wrist 607 in not articulated (i.e., is in a nominal position) the forearm axis should coincide with the axis of the outer ring 1805, which should coincide with the axis of the tool shaft 526, which should coincide with the axis of the end-effector assembly 1765. This is when the unlimited-roll handle assembly 400 is not articulated with respect to the pulley block 1805 (i.e., is nominal) and therefore the end-effector assembly 1765 is not articulated with respect to the tool shaft 526.

To facilitate the ease of performing an infinity roll of the medical device 1800, the overall weight of the medical device 1800 may be distributed such that its center of gravity lies close to the roll axis 111, 1835 of the medical device 1800, which ensures that as the user rolls the medical device 1800 (as described above), he/she is not working with or against gravity. With the weight of the medical device 1800 supported at the user's forearm 608 and a trocar on the patient's body, locating the center of gravity of the medical device 1800 on the roll axis 111, 1835 makes driving the roll rotation relatively effortless because gravity no longer has an effect on the roll rotation.

In addition to all the functionality mentioned above, the overall design and construction of the medical device 1800 also helps filter out hand tremors and prevent them from reaching the end-effector assembly 1765. In the medical device 1800, the handle assembly 400—and therefore surgeon's hand 609—are isolated from the pulley block 1805/tool frame 525/tool shaft 526 by means of the flexure transmission strips 533, 534, which because of their material and/or construction, prevent any hand tremors from reaching the tool shaft 526 and end-effector assembly 1765. The tool frame 525 is mounted on the forearm 608 via the forearm attachment joint 1807. Therefore, the tool shaft 526, which is connected to the tool frame 525, is controlled by the forearm 608 of the surgeon. Not only does this help drive power motions (translating the tip of the shaft in three directions), but the forearm 608 has many fewer tremors compared to the hand 609, so the shaft will experience fewer tremors as well.

Thus the flexure transmission strips 533, 534 may help separate out the yaw and pitch rotation components of the rotation of the handle shell 101, 501 (and handle assembly 400) with respect to the pulley block 1805 (equivalently, the yaw and pitch rotations of the hand 609 with respect to the forearm 608), and separately transmit these components of rotation to the corresponding pitch 1813.1 and yaw 1813.2 transmission pulleys, the latter of which are mounted on the pulley block 1805. The flexure transmission strips 533, 534 also help transmit the roll rotation from the unlimited-roll handle assembly 400 to the pulley block 1805, tool frame 525, tool shaft 526, all the way to the end-effector assembly 1765, and also help filter out or block hand tremors from reaching the pulley block 1805, and therefore from reaching the tool frame 525, and therefore from reaching the tool shaft 526, and finally, therefore, from reaching the end-effector assembly 1765.

The use of an unlimited-roll handle assembly 400 enables surgeons to have better control of the surgical instrument during surgery as a result of being able to transfer natural, ergonomic, and intuitive motion from the surgeon's hand 609/wrist 607/forearm 608 to the end-effector assembly 1765. The Virtual Center mechanism 1801' (i.e. the input joint) allows the pitch and yaw rotations of the surgeon's wrist 607 to be mapped and transferred intuitively and fluidly to corresponding rotations of the end-effector articulation joint 583. Without the benefit of the unlimited-roll handle assembly 400 to perform a roll of the end-effector assembly 1765, the surgeon would otherwise be limited to pronation and supination of his/her forearm 608, which is inherently biomechanically limited in its range of roll rotation.

However, with the addition of the unlimited-roll handle assembly 400, the surgical instruments described herein can intuitively and ergonomically provide for the end-effector assembly 1765 to directly inherit or receive the yaw, pitch, and roll of the input of the medical device 1800. In addition to roll resulting from pronation and supination of the surgeon's forearm 608/wrist 607, roll is also achieved with the rolling of the rotation dial 102, 502 by the surgeon's thumb/fingers. Roll produced from both these sources is transferred or transmitted to the end-effector assembly 1765. When the surgeon articulates his wrist 607, i.e. his hand 609 is in an articulated position with respect to his/her forearm 608, the handle shell 101, 501 held by the surgeon's hand is in an articulated position with respect to the tool frame (such articulation provided by the input articulation joint). Articulation of this input joint results in articulation of the output joint. This implies that the axis of the end-effector assembly 1765 (i.e. Axis 2) is no longer aligned with the axis of the tool shaft 526 (i.e. Axis 3). In such an articulated configuration of the end-effector assembly 1765 (e.g. shown in FIG. 18B), the surgeon is able to ergonomically perform an articulated roll by maintain his wrist 607 in a fixed articulated orientation, and rolling the rotation dial 102, 502 with his/her thumb/fingers by an unlimited amount. This enables an articulated roll in any and every orientation of the wrist 607. The roll of the end-effector assembly 1765 is no longer limited by the surgeon's biomechanical limitation in pronation and supination of his forearm 608/wrist 607. By controlling the roll of the instrument's end-effector assembly 1765 from the rotation dial 102, 502 by his thumb/fingers, the surgeon is able to perform an infinite amount of roll while still being able to use the actuate the handle lever 549 of the end-effector actuation mechanism to control the open/close actuation of the end-effector assembly 1765 in any articulated orientation of his wrist 607.

Furthermore, the unlimited-roll handle assemblies described herein enable simultaneous and predictable control of all the minimal access tool's advanced features with an ergonomic interface. This handle features power motions, finesse motions, and intuitive control of articulation. These three actions are individually aligned to optimal regions of the user's hand 609. Power motions such as gripping the handle body and lever to close the end-effector jaw assembly are provided by the palm and fingers (particularly the middle finger, ring finger and litter finger). Finesse motions such as rotating the rotation dial 102, 502 are provided by the thumb and index finger (although middle finger can also contribute to this action). The separation of power and finesse actions to these regions of the hand 609 minimizes user fatigue. This also reduces the cognitive load for the user, reducing their mental fatigue. Similar to using a computer joystick, articulation is controlled by directing the handle assembly held in the user hand 609 to the desired angle by articulating the user wrist 607.

Yet further, the unlimited-roll handle assemblies described herein enable the simultaneous actions of open/close, roll rotation, and articulation (or any combination). Like one's own hand 609, motions are fluid and natural. Performing a "running stitch" by rotating the rotation dial 102, 502 in continuous direction without unwinding, unlocking, or other intermediate steps is a novelty compared with other suturing instruments. This is made possible by weight balancing the instrument about the tool shaft axis (e.g., Axis 3) and simplifying the mechanics of instrument rotation as described herein. When the rotation dial 102, 502 on the unlimited-roll handle assembly 400 is rotated, the entire instrument rotates or orbits in the same direction around the user's wrist 607. During this process, the frame also rotates but the virtual center associated with the input joint remains located at the center of the user's wrist 607.

Consequently, performance is consistent and predictable, even during complex moves like an articulated roll rotation.

As perceived by the user, the unlimited-roll handle assembly apparatuses described herein enable a finesse roll of the associated unlimited-roll handle assembly while engaging the end-effector closure mechanism and end-effector articulation. Initially, the unlimited-roll handle assembly as previously described comprises optimized bearings between the various bodies within the mechanism. It is by way of the bearings between various bodies of the handle assembly that the surgeon notices minimal or very little difference in the resistance to rotate when the jaw closure lever is engaged or disengaged. Infinite rotation of the unlimited-roll handle assembly is enabled by a swivel joint and several keying features within the handle assembly which prevent the jaw closure cable from twisting upon itself during rotation.

During use, these unlimited-roll handle-based assemblies may allow the surgeon to perform an articulation of the end-effector assembly 1765 of the overall medical device 1800 by articulating their own wrist 607 while comfortably holding the handle shell 101, 501 and handle lever 549. Articulation of the unlimited-roll handle assembly leverages the distal end of the rotation dial 102, 502, to drive (i.e. rotate) the flexure transmission strips 533, 534 along with their associated transmission pulleys 1813.1, 1813.2, whose axes are centered at the surgeon's wrist 607 in accordance with what is also referred to as the Virtual Center mechanism 1801'. Rotation of the two transmission pulleys 1813.1, 1813.2 drives associated articulation cables within the frame to provide for controlling the corresponding articulation of the end-effector assembly 1765, about the end-effector output articulation joint 583'. Once an articulated position is established, the surgeon may choose to close the jaw by actuating the handle lever 549 on the handle assembly 400. The process of suturing with a needle requires that the surgeon roll-rotate the end-effector assembly 1765 about its articulated axis, thereby driving the needle about its curvature axis through various tissue planes. These unlimited-roll handle-based assemblies may (in conjunction with the other features described herein) provide the surgeon with easy access to the rotation dial 102, 502 that provides for rotating both the associated flexure transmission strips 533, 534 and the associated transmission pulleys 1813.1, 1813.2 about the surgeon's wrist 607, as enabled by an associated three-axis wrist gimbal (i.e., the forearm attachment joint 1807). The three-axis wrist gimbal constrains and centers the medical device 1800 about the surgeon's wrist 607 so that rotation of the rotation dial 102, 502 and Virtual Center mechanism 1801' drives a predictable concentric rotation of the pulley block 1805, tool frame 525, tool shaft 526, and end-effector assembly 1765 about the surgeon's wrist 607.

These devices provide for finesse rotation control with relatively low resistances to rotation both within the unlimited-roll handle assembly (addressed via bearings) and at the wrist gimbal (addressed via minimized contact surfaces and low friction plastic materials), with overall balance of the device (addressed by establishing a center of gravity on the axis of rotation and redistribution of weight throughout the device), and with the use of flexure transmission strips 533, 534 which offer little compliance in torsion/twisting about roll axis 111, 1835.

Furthermore, basic definitions are now provided for certain terms as used herein.

Mechanism and joint—There is a certain equivalence between the terms "mechanism" and "joint." A "joint" may also be alternatively referred to as a "connector" or a "constraint." All of these can be viewed as allowing certain motion(s) along a certain degree(s) of freedom (DoF) between two bodies and constraining the remaining motions. A mechanism generally comprises multiple joints and rigid bodies. Typically, a joint is of simpler construction, while a mechanism is more complex as it can comprise multiple joints. But what is simple and what is complex depends on the context. A mechanism under consideration may appear simple or small in the context of a much bigger mechanism or machine, in which case the particular mechanism under consideration may be called a joint. Thus, what was viewed as a mechanism may also be viewed as a joint. Also note that "joint" here refers to a mechanical connection that allows motions as opposed to a fixed joint (such as welded, bolted, screwed, or glued jointly). In the latter case, the two bodies are fused with each other and are considered one and the same in the kinematic sense (because there is no relative motion allowed or there are no degree of freedoms). The term "fixed joint" is used herein to refer to this kind of joint between two bodies. When reference to the term "joint" is made, it means a connection that allows certain motions, e.g., pin joint, a pivot joint, a universal joint, a ball, and socket joint, etc. Thus, the joint that we are referring to here interfaces one body with another in a kinematic sense.

Axis and direction—Axis refers to a specific line in space. A body may rotate with respect to (w.r.t.) another body about a certain axis. Alternatively, a body may translate w.r.t. another body in a certain direction. A direction is not defined by a particular axis and is instead commonly defined by multiple parallel axes. Thus, X-axis is a specific axis defined and shown in a figure, while X direction refers to the direction of this X-axis. Multiple different but parallel X axes can have the same X direction. Direction only has an orientation and not a location in space. In this sense "axis" is more precision, "direction" is more general. If one specifies an axis, the direction is defined because axis has a direction. If one specifies a direction, there need not be any axis defined. Here, axis 1 and direction 1 are defined further which are used to define motion and constraints of the described system.

Degree of freedom (DoF)—As noted already, a joint or mechanism allows certain motions between two bodies and constrains the rest. "Degrees of freedom" is a technical term to capture or convey these "motions." In all, there are six independent degrees of freedom possible between two rigid bodies when there is no joint between them: three translations and three rotations. A joint will allow anywhere between 0 and 6 DoF between the two bodies. For the case when the joint allows 0 DoF, this effectively becomes a "fixed joint," described above, where the two bodies are rigidly fused or connected to each other. From a kinematic sense, the two bodies are one and the same. For the case when the joint allows 6 DoF, this effectively means that there is no joint, or that the joint really does not constrain any motions between the two bodies such as when two bodies are connected via a spring or members that are compliant in all directions. Any practical joint allows 1, or 2, or 3, or 4, or 5 DoF between two rigid bodies. If it allows one DoF, then the remaining 5 possible motions are constrained by the joint. If it allows 2 DoF, then the remaining 4 possible motions are constrained by the joint and so on.

Degree of constraint (DoC)—Degree of constraint refers to directions along which relative motion is constrained between two bodies. Since relative motion is constrained, these are directions along which motion that can be transmitted from one body to the other body. Since the joint does not allow relative motion between the two bodies in the DoC direction, if one body moves in the DoC direction, it drives along with it the other rigid body as well along that direction. In other words, load (e.g., force or torque) and motion are transmitted from one rigid body to another in the DoC directions.

Local ground—In the context of an assembly of bodies (or a multi-body system, or a mechanism) including multiple bodies and joints, one or more bodies may be referred to as the "reference" or "ground" or "local ground" or "reference ground." The body referred to as the local ground is not necessarily an absolute ground (i.e., attached or bolted to the actual ground). Rather, the body that is selected as a local ground simply serves as a mechanical reference with respect to which the motions of all other bodies is described or studied. Also, selecting a body in an assembly/multi-body system/mechanism as the local ground doesn't limit the functionality of the assembly/multi-body system/mechanism. E.g., in case of the handle assemblies described here, the Handle Body may be chosen as the local ground and motion of other bodies may be defined with respect to the Handle Body (i.e., assuming the Handle Body is kept stationary). However, this does not mean that the handle assembly is only functional when the Handle Body is held stationary. Rather, at a high level, the functionality of the handle assembly is independent of which body is assumed to local ground.

Body—Body is a discrete component that is part of an assembly, possibly inter-connected by joints or mechanism. This discrete component is rigid and thereby, facilitates rigid body motion transmission. This means that there is no loss in transmission when force travels through the body along DoC. In certain scenarios, a body may be compliant (not rigid). In such cases, exception to the baseline definition will be specifically mentioned herein. In certain scenarios, the term body maybe used for an assembly of bodies. Specific features of the body that are relevant to the discussion will be specified while describing a body. Also, body is used as a common term describing a discrete component that is part of an assembly or a mechanism. As described further, structural components that are used to form an assembly or sub-assembly are terms as "bodies." The term "body" and "component" may be interchangeably used throughout the description and hold the same meaning.

Transmission member—A transmission member is a rigid/compliant body that transmits motions from one body to another body. A transmission member maybe a compliant wire/cable/cable assembly, flexible shaft, etc.

User interface—A user interface acts as an input interface that user interacts with to produce certain output at the other end of a machine or instrument or mechanism. User interface is generally an ergonomic feature on a body, which is part of an instrument, that is triggered by the user. E.g., a knob on a car dashboard can be rotated by a user to increase/decrease speakers' volume. In this example, the knob and specifically, knurled outer circumference (feature) of the knob is the user interface.

Handle assembly terminologies—Components named in U.S. Pat. No. 9,814,451B2 (FIG. 1 in the application) are given alternate equivalent names in this application for clarity purposes. "H.Body A" is referred to as "Handle Body," "H.Body B" is referred to as "Dial," "H.Body C" is referred to as "Push Rod" and "H.Body D" is referred to as "Shuttle."

Axis 1—Axis 1 refers to the axis about which Dial rotates w.r.t. the Handle Body. This axis is also defined as the axis about which the Push Rod has a rotational DoF w.r.t. the Shuttle.

Direction 1—This is the direction along which the Shuttle translates w.r.t. the Dial. This is also the direction along which the Push Rod translates w.r.t. the Handle Body.

Handle body—Handle Body refers to a body in the handle assembly which is considered as a local ground while describing the handle assembly and associated mechanisms. The Handle Body is held by the user while other bodies within handle assembly are put in motion with respect to (w.r.t.) the Handle Body. Handle Body described herein may also be referred to as "palm grip", "palm grip portion", or "handle shell."

Closure body—Closure Body refers to a body in the handle assembly which has at least 1 degree of freedom motion w.r.t. the Handle Body and in certain embodiments can be rotationally constrained (DoC) w.r.t. the Handle Body about axis 1. Closure Body may also interface with another body called Closure Input. Once the Closure Input is actuated w.r.t. the Handle Body, it may lead to translation of the Closure Body w.r.t. the Handle Body along direction 1. The Closure Body, when it has a translation degree of freedom relative to the Handle Body along axis 1, is termed a Push Rod. Push Rod is also described in U.S. Pat. No. 9,814, 451B2.

Shuttle—Shuttle refers to a body in the handle assembly which rotates w.r.t. the Push Rod about axis 1 and translates w.r.t. the Dial along direction 1. The Shuttle is also rotationally constrained w.r.t. the Dial about axis 1.

Roll body—Roll Body refers to a body in the handle assembly which has rotational DoF w.r.t. the Handle Body. Roll Body, in certain handle assembly embodiments, can be a visible (an external component accessible by the user) component of the handle assembly. Apart from the function and structure of Dial that is described in U.S. Pat. No. 9,814,451B2, Roll Body may also interface with another body called Roll Input. Once the Roll Input is rotated w.r.t. the Handle Body about its roll axis, it may lead to rotation of the Roll Body w.r.t. the Handle Body about axis 1. The terms "dial" or "knob" are used interchangeably for the term Roll Body.

Tool frame—Tool frame refers to a structural body that is part of a tool apparatus. In certain tool apparatuses, it may be connected to a handle assembly and/or an elongated tool shaft. The terms "tool frame" and "frame" may be used interchangeably throughout the document.

Figure 21A:
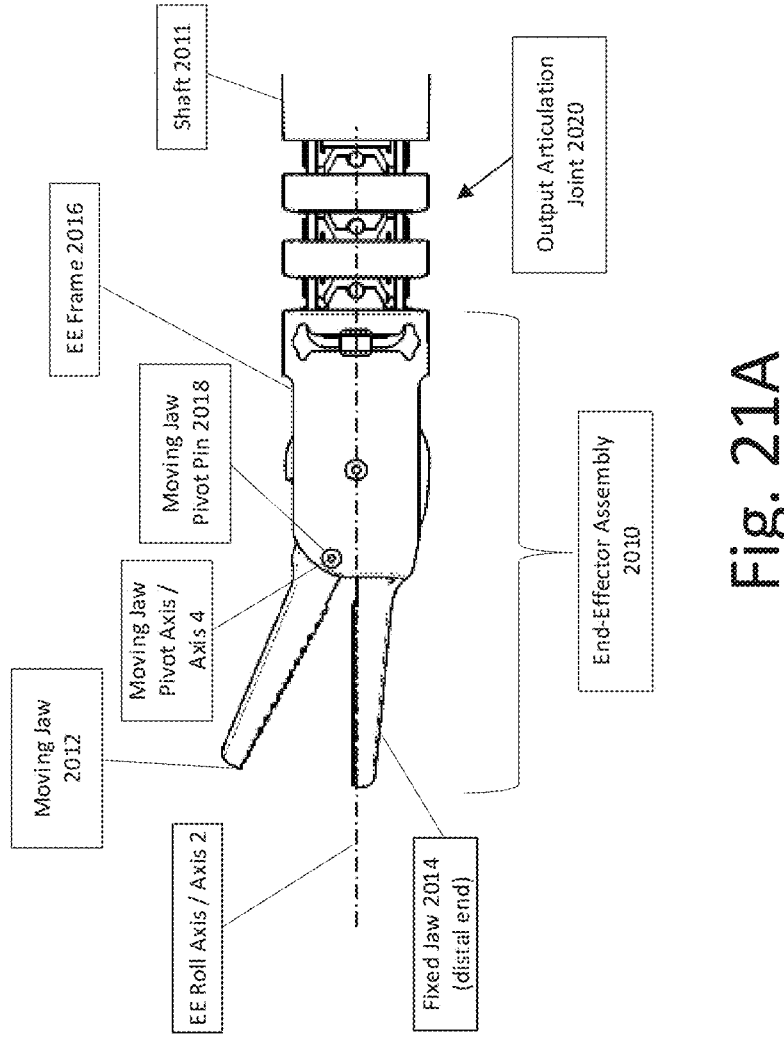
FIGS. 21A-B depict types of end-effector assemblies used in tool apparatuses in beta configuration (A) and used in tool apparatuses in alpha configuration (B).
Figure 21B:
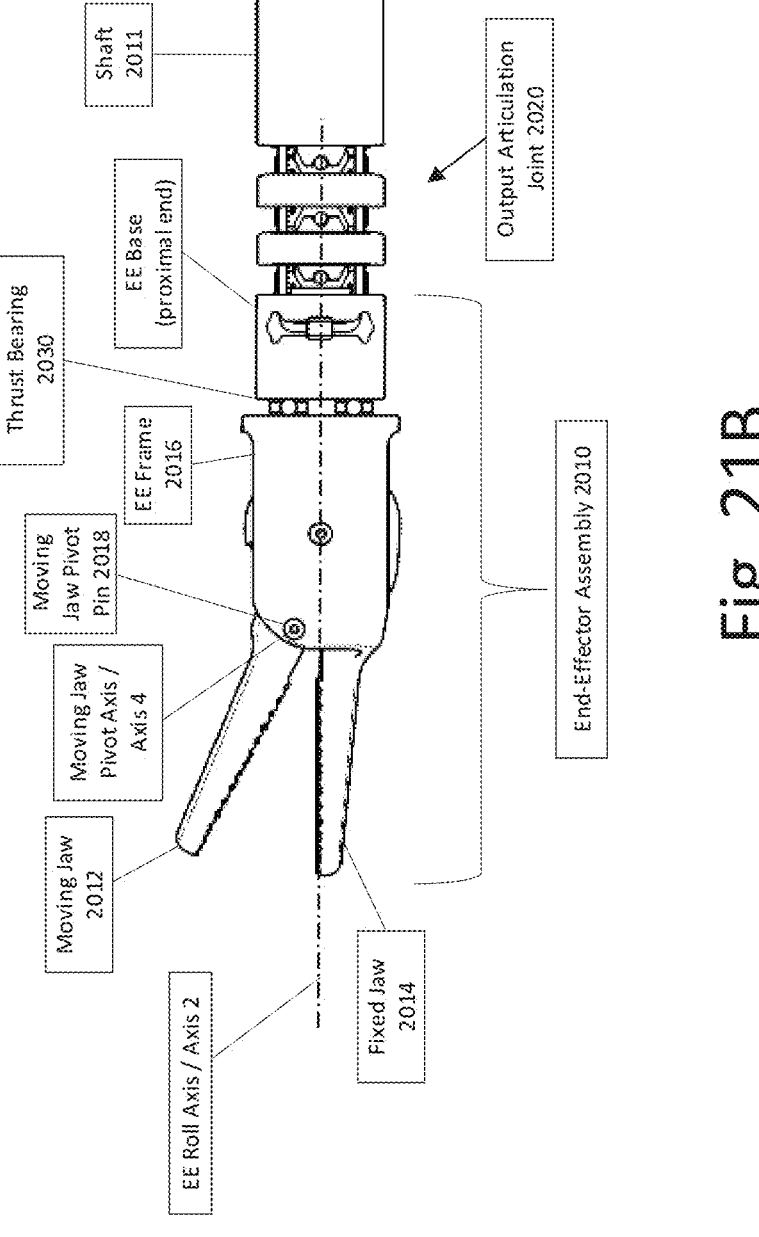

EE (end-effector) assembly—With general reference to FIGS. 21A and 21B, EE assembly 2010 or end-effector assembly or jaw assembly exists at the distal end of the elongated tool shaft 2011. An EE assembly may contain one or more jaws (or EE jaws). There are two types of EE assembly 2010. The first type of EE assembly 2010 consists of two EE jaws, namely "Moving Jaw" 2012 and "Fixed Jaw" 2014. There also exists "EE Frame" 2016 that acts as a local reference ground for Moving Jaw 2012 and any other moving body within the EE assembly 2010. In this assembly, Moving Jaw 2012 moves relative to EE Frame 2016 by rotating about a pivot pin 2018 shown in FIG. 21A. This motion of Moving Jaw 2012 w.r.t. EE Frame 2016 is termed as "jaw closure motion." Jaw closure motion and "jaw open/close motion" maybe used interchangeably throughout the description. In FIG. 21A, Fixed Jaw 2014 is also coupled to EE Frame 2016 such that it is a rigid extension of the EE Frame 2016. While describing this EE assembly 2010 that is shown in FIG. 21A, Fixed Jaw 2014 is treated as a local reference like EE Frame 2016. This is because Fixed Jaw 2014 is a rigid extension of EE Frame 2016 in this EE assembly 2010. In other EE assemblies, Fixed Jaw 2014 may have one or more DoF joint w.r.t. the EE Frame 2016.

The EE Frame 2016 is further coupled to the tool shaft 2011 via an output articulation joint 2020 in case the EE assembly 2010 is part of a tool apparatus that provides articulation function.

"EE roll motion" is the second output motion at the EE assembly 2010. EE roll motion can refer to two separate rotations of EE assembly 2010 about different axes. Rotation about axis 2 refers to rotation of EE assembly 2010 about EE assembly's roll axis. Rotation about axis 3 refers to rotation of EE assembly 2010 about the tool shaft 2011 roll axis. In the case of the EE assembly 2010 shown in FIG. 21A, upon rotation of the overall tool apparatus including handle assembly 2022 and tool shaft 2011 about axis 3, EE assembly 2010 also rotates about axis 3. Whereas, roll motion that is generated by rotation of Dial 2024 w.r.t. Handle Body 2026 about axis 1 leads to rotation of tool shaft 2011 about axis 3 and rotation of EE assembly 2010 about axis 2. This is further described while presenting various tool apparatus configurations in the description.

The second type of EE assembly 2010 consists of two EE jaws, namely "Moving Jaw" 2012 and "Fixed Jaw" 2014. The assembly also contains EE Frame 2016. In this assembly, Moving Jaw 2012 moves relative to EE Frame 2016 by rotating about a pivot pin 2018 shown in FIG. 21B. Fixed jaw 2014 is also coupled to EE Frame 2016 such that it is a rigid extension of the EE Frame 2016. While describing this EE assembly 2010 that is shown in FIG. 21B, Fixed Jaw 2014 is treated as a local reference like EE Frame 2016. This is because Fixed Jaw 2014 is a rigid extension of EE Frame 2016 in this EE assembly 2010. The assembly also consists of a body/component proximal to the EE assembly called "EE base" 2028. The EE base 2028 has a 1 DoF rotation joint to the EE Frame 2016. This rotation joint provides a roll DoF about axis 2. This joint can be formed by a thrust bearing, roll bearing, plain bearing, etc. FIG. 21B shows a thrust bearing 2030 between EE Frame 2016 and EE base 2028. EE base 2028 is coupled to tool shaft 2011 via an articulation output joint 2020. In the case of the second type of EE assembly 2010, rotation of Fixed Jaw 2014/EE Frame 2016 w.r.t. EE base 2028 does not lead to rotation of output articulation joint 2020 and thereby, does not lead to rotation of tool shaft 2011 about axis 3. Whereas in first type of EE assembly 2010, rotation of Fixed Jaw 2014/EE Frame 2016 involves rotation of the output articulation joint 2020. In the first type of EE assembly 2010, the output articulation joint 2020 provides a roll rotation DoC between Fixed Jaw 2014/EE Frame 2016 and tool shaft 2011 axis 2 in order to transmit roll motion.

In case of EE assembly 2010 shown in FIG. 21B, upon rotation of the overall tool apparatus including handle assembly 2022 and tool shaft 2011 about axis 3, EE assembly 2010 also rotates about axis 3. Whereas, roll motion that is generated by rotation of Dial 2024 w.r.t. Handle Body 2026 about axis 1 leads to rotation of EE Frame 2016/Fixed Jaw 2014 and Moving Jaw 2012 about axis 2. It does not lead to rotation of tool shaft 2011 about axis 3. This corresponds to an alpha configuration, which is further described while presenting various tool apparatus configurations in the description.

Also, the entire EE assembly 2010 may rotate about its roll axis termed as "EE roll axis" or "axis 2" w.r.t. to the EE base 2028. EE assembly 2010 may be interchangeably referred to as "jaw assembly" or "end-effector assembly" in this document.

Roll input—"Roll Input" or "Rotation input" refers to the body that is part of the handle assembly 2022 which is rotated or activated to produce rotation of the EE assembly 2010 about axis 2 (EE roll axis). Here, both handle assembly 2022 and EE assembly 2010 are part of a tool apparatus where handle assembly 2022 is proximal to the user and EE assembly 2010 is distal to the user. Roll Input, in its simplest form, is the Dial 2024 which is part of the handle assembly 2022. Roll Input, in another scenario, may be an assembly that may consist of an external Roll Input body which is visible or externally accessible by the user. In this scenario, Roll Input acts as a user interface. This assembly may also consist of the Dial 2024 which mates with the Shuttle such that the Shuttle has a rotational DoC w.r.t. Dial 2024 about axis 1 and translational DoF w.r.t. Dial 2024 along direction 1. The Dial 2024 also has rotational DoF w.r.t. Handle Body 2026 about axis 1. In the case Roll Input is an assembly, rotation of external Roll Input may be transmitted to Dial 2024 via roll transmission mechanism. This mechanism may include mechanical transmission components including but not limited to linkages, pulley, compliant mechanisms/members, cable, threaded screw, pneumatic and/or gears. This mechanism may be an electromechanical transmission mechanism that may include sensors (rotation/position/force), actuators (rotary motors, linear motors, solenoids), and/or transducers.

Closure input—This refers to the body that is part of the handle assembly 2022 which is triggered or activated to cause actuation of member(s) of the EE assembly 2010. Closure Input, in its simplest form, is the Push Rod which is part of the handle assembly 2022. This is the first scenario where Closure Input is the Push Rod itself. Closure Input, in a second scenario, may be an assembly which includes an external Closure Input which is visible or externally accessible by a user. In this scenario, Closure Input acts as a user interface. This assembly may also consist the Push Rod which mates with the Shuttle such that Shuttle has a rotation DoF w.r.t. Push Rod about axis 1 and a translational DoC w.r.t. Push Rod along direction 1. Therefore, translation of Push Rod leads to translation of Shuttle. In the case Closure Input is an assembly, 1 DoF motion of external Closure Input w.r.t. Handle Body 2026 is transmitted to Push Rod via a closure transmission mechanism. This mechanism may be a mechanical transmission mechanism which may use linkages, pulley, compliant mechanisms/members, cable, threaded screw, pneumatic and/or gears. This mechanism may be an electromechanical transmission mechanism that may include sensors (rotation/position/force), actuators (rotary motors, linear motors, solenoids) and/or transducers. This second scenario is shown via various embodiments that follow the constraint map shown in FIG. 31B.

In a third scenario, Closure Input may just be an external Closure Input component. In this scenario, Closure Input has at least 1 DoF w.r.t. Handle Body 2026 and interfaces with Shuttle such that Shuttle has a translational DoF w.r.t. Dial along direction 1 and a rotational DoC w.r.t. Dial about axis 1. Motion of external Closure Input may be transmitted to Shuttle via a closure mechanism. This mechanism may be a mechanical transmission mechanism which may use linkages, pulley, compliant mechanisms/members, cable, threaded screw, pneumatic and/or gears. This mechanism may be an electromechanical transmission mechanism that may include sensors (rotation/position/force), actuators (rotary motors, linear motors, solenoids) and/or transducers. This third scenario is shown via various embodiments that follow the constraint map shown in FIG. 31.

Jaw closure transmission member (TM)—This transmission member/body helps transmit translation of Shuttle w.r.t. Dial 2024 along direction 1 to the jaw closure motion within the EE assembly 2010. The transmission member can be a mechanical component, e.g., a solid wire (sometimes also called piano wire) or a flexible braided cable. This member may be torsionally stiff along its centroidal axis. E.g., a Nitinol wire which is stiff against a torsional load but flexible against bending load. Whereas a braided steel cable made with individual steel filaments, which is flexible in bending, not torsionally stiff and may wound on itself upon rotation about its centroidal axis. "Jaw closure transmission member" and "Jaw closure actuation transmission member" may be used interchangeably herein.

Roll Transmission Member (TM)—This transmission member helps transmit rotation of rotation input or Dial 2024 w.r.t. Handle Body 2026 to produce EE roll motion.

Articulation Transmission Member—This transmission members that help transmit articulation (pitch and yaw motion) from the articulation input joint, which may exist between handle assembly 2022 and tool shaft 2011, to the articulation output joint 2020 (present between tool shaft 2011 and EE assembly 2010). Typically, these articulation transmission members may comprise cables, crimps, pulleys, etc.

Jaw closure transmission assembly—Jaw Closure Transmission Assembly refers to bodies, joints, mechanisms, and/or jaw closure transmission member(s) that exist between the handle assembly 2022 and EE assembly 2010 and facilitate Jaw Closure Motion. Specifically, the body within the handle assembly 2022 that produces output motion (e.g., Shuttle) is coupled to the proximal body that is part of jaw closure transmission assembly. Similarly, the moving jaw within the EE assembly 2010 is coupled to the distal most body that is part of the jaw closure transmission assembly. Terms "jaw closure transmission assembly" and "jaw actuation transmission assembly" may be used interchangeably throughout the description.

EE roll transmission assembly—EE Roll Transmission Assembly refers to bodies, joints, mechanisms and/or roll transmission member(s) that exist between the handle assembly 2022 and EE assembly 2010 and facilitate EE Roll Motion.

Articulation transmission assembly—Articulation Transmission Assembly refers to bodies, joints, mechanisms and/or articulation transmission member(s) that help transmit input motion (pitch and yaw rotation motion) generated by the user via input articulation joint to the output articulation joint 2020. Specifically, the body that couples with the body within the tool apparatus that receives input from the user is the proximal body of the articulation transmission assembly. Similarly, the body that couples with either the EE Frame 2016 or EE Base 2028 depending on the type of EE assembly 2010 under consideration is the distal-most body within the articulation transmission assembly.

Figure 22A:
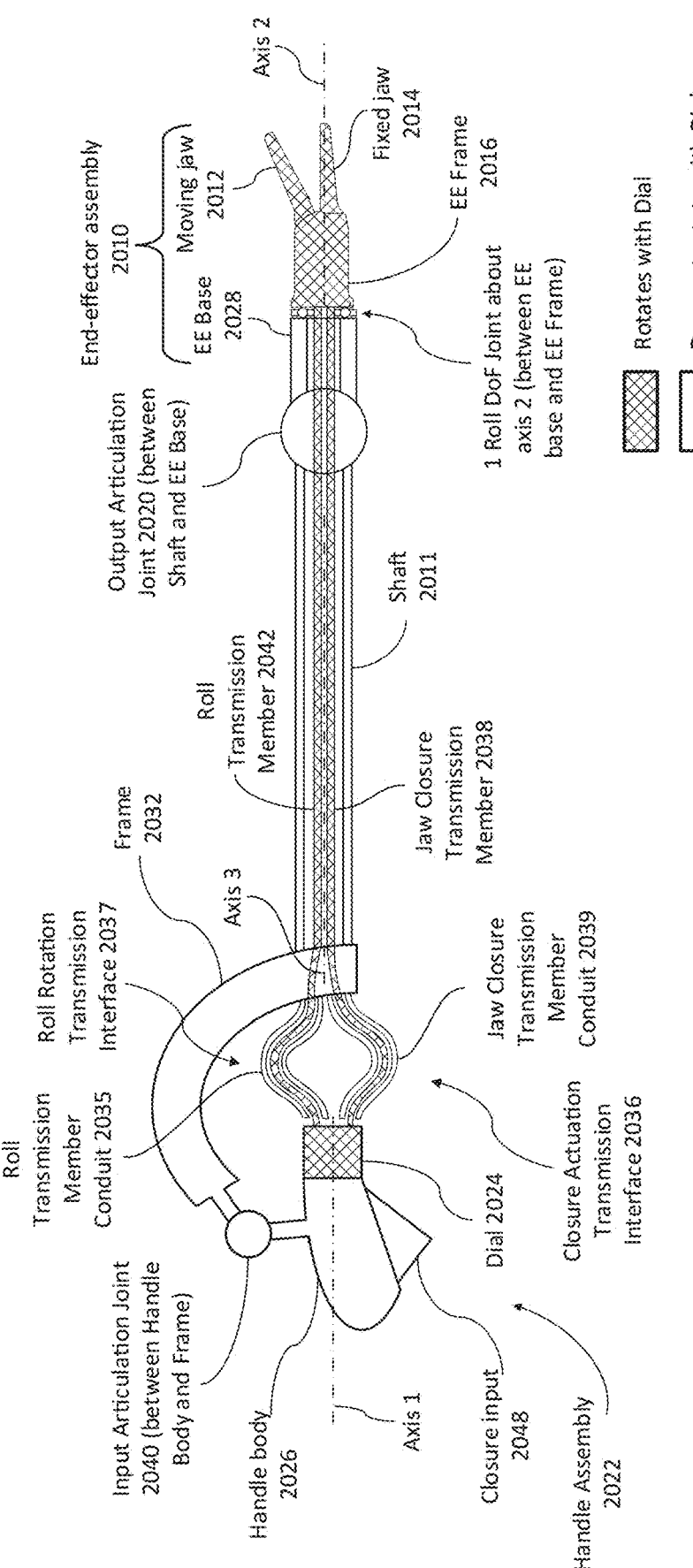
FIGS. 22A-B depict (A) tool apparatus in alpha configuration and (B) tool apparatus in beta configuration.
Figure 22B:
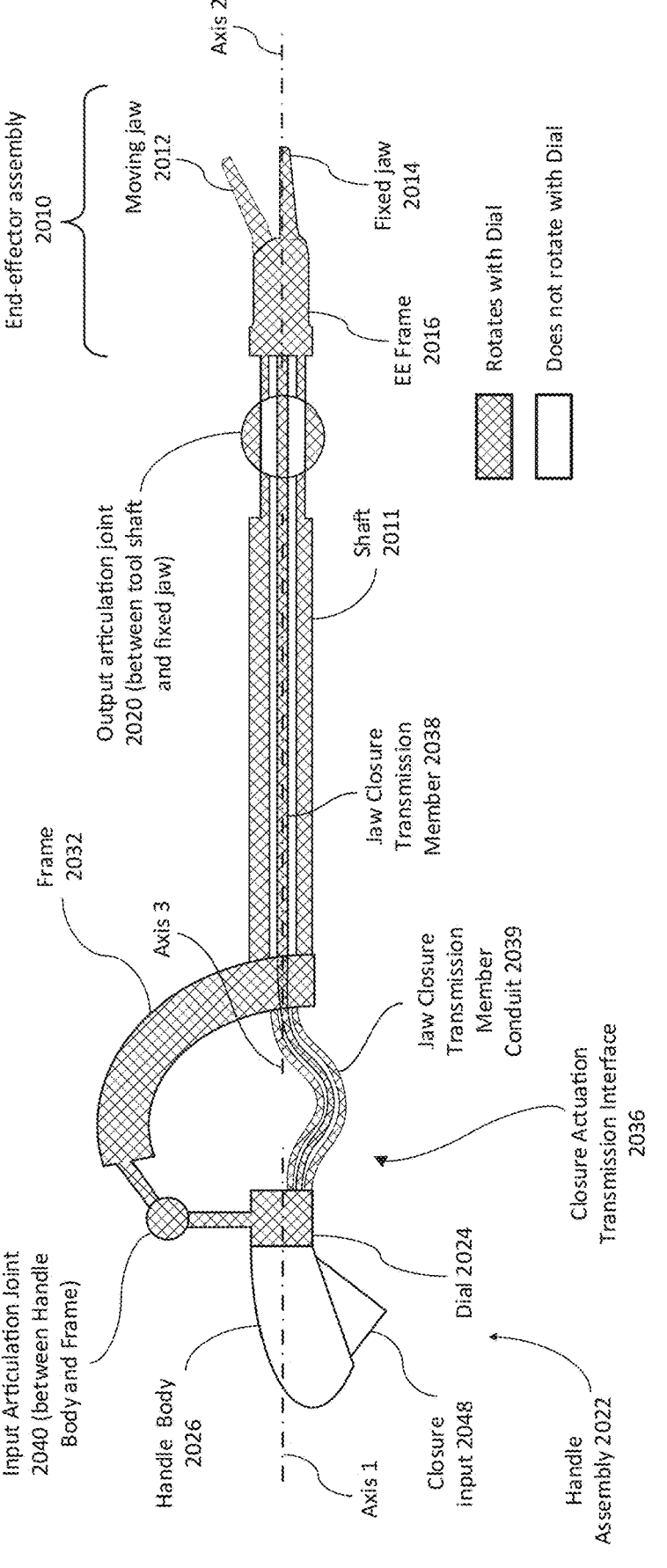

Tool Apparatus, Its Functions and Its Configurations (FIGS. 22A and 22B)

Handle assembly 2022 described herein may be part of a tool apparatus which can include the handle assembly 2022, a tool frame 2032, the elongated tool shaft 2011, which is a rigid extension of the tool frame 2032, and the EE assembly 2010 located at the distal end of the tool shaft 2011. The tool apparatus may provide various functions which correspond to following output motions: i) jaw closure motion at the EE assembly 2010; ii) articulation motion (pitch and yaw rotation) of the EE assembly 2010; iii) rigid body motion of the tool shaft 2011 and EE assembly 2010; and iv) articulated roll motion of the EE assembly 2010 (or portion thereof).

This apparatus can have different configurations. Two configurations that are used herein to describe the tool apparatus functions are shown in FIGS. 22A-B. In both these configurations, handle assembly 2022 consists of at least a closure input 2048, handle body 2026, and dial 2024. There exists a closure actuation transmission interface 2036 between dial 2024 and frame 2032. This closure actuation transmission interface 2036 comprises a jaw closure transmission member 2038 and a jaw closure transmission member conduit 2039 (e.g. flexible sheath or conduit, also shown in FIG. 23) between the dial and the frame that guides the jaw closure transmission member 2038. The jaw closure transmission member conduit 2039 may be coupled to (e.g. rigidly connected to or seated against) the Frame 2032 on it distal end and coupled to (e.g. rigidly connected to or seated against) the Handle Body 2026 on its proximal end. Alternatively, on its proximal end, the jaw closure transmission member conduit 2039 may be coupled to the Dial 2024 via an interface that seats the conduit's proximal end against Dial 2024 axially but allows relative roll rotation between the two. The jaw closure transmission member 2038 facilitates the transmission of the relative motion of the Closure Input 2048 w.r.t. the Handle Body 2026 to the EE assembly 2010. This relative motion leads to motion of the Moving Jaw 2012 w.r.t. the Fixed Jaw 2014 about a pivot pin 2018 (with an Axis 4) to produce jaw closure motion. In certain tool apparatus configurations, translation motion of jaw closure transmission member 2038 at the distal end of tool apparatus requires to be converted to rotation of the Moving Jaw 2012 w.r.t. the Fixed Jaw 2014 about Axis 4. Therefore, there may exist bodies, e.g., rack-pinion transmission assembly, pulleys, gears, linkage, cams, pins, etc. to convert the translation motion of jaw closure transmission member 2038 to rotation motion of the Moving Jaw 2012 w.r.t. the Fixed Jaw 2014.

Articulation function of the tool apparatus is a function in which pitch and yaw rotations (i.e. output motions) are produced at the EE assembly 2010 at distal end of the tool apparatus. These output motions are generated by pitch and yaw rotation input motion of the handle assembly 2022. There exists a 2-DoF output articulation joint 2020 that exists between the shaft 2011 (also referred as the tool shaft) and EE assembly 2010. There also exists a 2-DoF input articulation joint 2040 that exists between the handle assembly 2022 and frame 2032. Articulation motion of the handle assembly 2022 w.r.t. frame 2032 is transmitted to the articulation motion of the EE assembly 2010 w.r.t. tool shaft 2011 via various intermediate joints, mechanisms and/or transmission members (i.e. articulation transmission members). There may exist two different configurations for the tool apparatus that are shown in FIGS. 22A-B.

FIG. 22A shows a tool apparatus configuration and embodiment where the input articulation joint 2040 exists between handle body 2026 and frame 2032. Also, the EE assembly 2010 is similar to the one shown in FIG. 21B. EE assembly 2010, in this case, consists of bodies namely, EE base 2028, Moving Jaw 2012, and Fixed Jaw 2014. In FIGS. 21A-B and 22A-B, the Fixed Jaw 2014 is shown as a rigid extension of EE Frame 2016. In other instances, the Fixed Jaw 204 can be separate body coupled to EE Frame 2016. There exists the output articulation joint 2020 between the proximal portion of the EE assembly 2010 (which in this embodiment is the EE base 2028) and the distal end of the shaft 2011. The need for EE base 2028 and a 1-DoF roll rotation joint between EE base 2028 and EE frame 2016 is discussed while describing EE roll motion in the following paragraphs. This configuration is termed as "alpha configuration." Also depicted in the embodiment shown in FIG. 22A are two transmission interfaces—roll transmission interface 2037 and closure actuation transmission interface

2036. Associated with these two transmission interfaces are two respective transmission members, namely a roll transmission member 2042 and the jaw closure transmission member 2038. Although illustrated as two separate transmission interfaces and therefore two separate transmission members, in some scenarios, a single transmission interface and a single associated transmission member may be used. In such scenarios, the single transmission member has adequate axial and torsional stiffness can be used to transmit both roll rotation as well as jaw closure actuation from the handle assembly to the end-effector assembly.

FIG. 22B shows an alternate tool apparatus configuration and embodiment where the input articulation joint 2040 exists between the dial 2024 and the frame 2032. Also, the EE assembly 2010 is similar to the one shown in FIG. 21A. In this configuration, the EE assembly 2010 consists of bodies namely, Moving Jaw 2012 and Fixed Jaw 2014. Once again, the Fixed Jaw 2014 shown here is a rigid extension of the EE frame 2016 but in other instances these two may be separate bodies that are coupled to each other. There exists an output articulation joint 2020 between the proximal portion of the EE assembly 2010 and the distal portion of shaft 2011. In this embodiment, the proximal portion of the EE assembly 2010 is the EE Frame 2016. This configuration is termed as "beta configuration."

Each of the 2-DoF input and output articulation joint(s), 2040 and 2020 respectively, can be either a parallel kinematic input joint or a serial kinematic input joint. Examples of tool apparatus with parallel kinematic input joint is shown in U.S. Pat. No. 8,668,702, U.S. patent application publication No. 2013/0012958 and U.S. Pat. No. 10,405,936. Examples of tool apparatus with serial kinematic input joints are U.S. Pat. Nos. 5,908,436; 6,994,716; and U.S. application Ser. No. 11/787,607. The center of rotation of the input articulation joint 2040 can lie proximal or distal to the handle assembly 2022. Here the "distal" represents the direction where the end-effector assembly lies w.r.t. the tool shaft/tool frame, and "proximal" represents the direction where the handle assembly lies w.r.t. the tool shaft/tool frame.

In both configurations and embodiments shown, motion of the frame 2032 w.r.t. an external reference ground such as a patient's bed or body is transmitted to the tool shaft 2011 and the EE assembly 2010. Therefore, shaft 2011 has 3 translation DoFs (along X, Y, and Z axis direction) and 3 rotation DoFs (pitch, yaw, and roll rotation) w.r.t. the reference ground. The interface between the instrument shaft 2011 and the patient's body (e.g. via a trocar or cannula) eliminates some of these 6 DoFs. When the EE assembly 2010 is not articulated, roll rotation of the EE assembly 2010 and tool shaft 2011 takes place about axis 3. In this scenario, axis 1, axis 2, and axis 3 are all colinear. In another scenario where EE assembly 2010 is articulated, roll rotation of EE assembly 2010 takes place about axis 2 while the roll rotation of the shaft 2011 takes place about axis 3, and the roll rotation of dial 2024 takes place about axis 1. In this articulated condition or scenario of the tool apparatus, axis 1, axis 2 and axis 3 are no longer collinear. This roll rotation function of the end-effector when it is articulated is referred to as "articulated roll."

In both tool apparatus configurations shown in FIGS. 22A and 22B, the legend on the bottom right of the figure indicates that any body or component that is shown with a "cross-hatch pattern fill" rotates in roll a respective axis (Axis 1, Axis 2, or Axis 3) in response to roll rotation of the dial 2024 whereas any body or component that is show without a "cross-hatch pattern fill" does not rotate with the dial 2024. In the case of the alpha configuration, roll rotation of handle body 2026 about axis 1 w.r.t. an external reference ground leads to rigid body roll motion of the frame 2032 and tool shaft 2011 about axis 3, and EE assembly 2010 about axis 2. In this configuration, the input articulation joint 2040 as well as the output articulation joint 2020, both transmit roll. In other words, roll rotation is a Degree of Constraint (DoC) for both these joints. Separately, roll rotation of dial 2024 w.r.t. handle body 2026 about axis 1 leads to rotation of only the EE frame 2016 (and its extension Fixed Jaw 2014) w.r.t. EE Base 2028 about axis 2, while the rest of the frame 2032 and shaft 2011 do not roll w.r.t. the handle body 2026. This rotation of EE Frame 2016 (and therefore Fixed Jaw 2014) w.r.t. EE Base 2028 is possible because there exists a 1 roll DoF joint between the EE frame 2016 and the EE Base 2028 that provides roll motion of the EE Frame 2016 (along with the rest of the proximal portion of EE assembly 2010) about axis 2. This rotation of dial 2024 leading to rotation of EE Frame 2016 is transmitted via a roll transmission interface 2037, comprising a roll transmission member 2042. When the EE assembly 2010 is not articulated, axis 2 is collinear with axis 3. When the handle body 2026 is articulated w.r.t. the frame 2032, and as a result EE assembly 2010 is articulated w.r.t. the shaft 20111, and therefore axis 2 is no longer collinear with axis 3. In this articulated condition, when the dial 2024 is rotated w.r.t. handle body 2026 about axis 1, this leads to the rotation of EE Frame 2016 w.r.t. EE Base 2028 about axis 2, which is no longer collinear with axis 3. This motion is called "articulated roll".

Thus, in the case of the alpha configuration, there are two roll transmission assemblies. To produce rotation of frame 2032, tool shaft 2011, and EE Base 2028, the whole handle assembly 2022 (including the handle body 2026) is rotated about axis 1 w.r.t. an external reference ground. This roll rotation is transmitted via input articulation joint 2040 to rigid bodies (namely frame 2032 and tool shaft 2011), and further via output articulation joint 2020 all the way to the EE Base 2028. Input articulation joint 2040 and output articulation joint 2020 provide a DoC in roll rotation direction in order to transmit roll motion to the EE assembly 2010. All these input and output articulation joints, and tool frame and shaft rigid bodies are part of first roll transmission assembly. Here, EE assembly 2010 whether articulated w.r.t. the tool shaft 2011 or not, rotates about the tool shaft roll axis or axis 3 and not about its own roll axis (axis 2).

In the alpha configuration, to produce relative roll motion of EE Frame 2016 w.r.t. EE Base 2028 about axis 2, dial 2024 can be rotated w.r.t. handle body 2026 about axis 1. This is accomplished via the second roll transmission assembly, which consists of a proximal body (e.g. shown in FIG. 25C) that couples with dial 2024 (or roll body), which is part of the handle assembly 2022. This proximal body is either integral to or coupled to the proximal end of the roll transmission member 2042, which may be guided through a roll transmission member conduit 2035 that is part of the roll transmission interface 2037 (see FIG. 22A). When a roll transmission member conduit is employed, the roll transmission member conduit 2035 may be coupled to the Frame 2032 on it distal end and coupled to the Handle Body 2026 on its proximal end. Alternatively, on its proximal end, the roll closure transmission member conduit 2035 may be coupled to the Dial 2024 via an interface that allows relative roll rotation between the two. In some instances, a roll transmission member conduit may not be employed at all. The roll transmission member 2042 may further pass through a portion of the tool frame 2032, the tool shaft 2011, through the output articulation joint 2020, and through the EE Base 2028. The distal portion of this roll transmission member 2042 terminates at and is coupled to the EE Frame 2016. When the dial 2024 is rotated w.r.t. handle body 26 about axis 1 (in any articulated orientation of the handle assembly 2022 w.r.t. frame 2032), this roll rotation of dial is transmitted via the second roll transmission assembly to the end-effector assembly 2010 such that the EE frame EE Frame 2016 rotates w.r.t. EE Base 2028 about axis 2. Thus, there are two distinct roll transmission assemblies in the alpha configuration. There can be a version of the alpha configuration where there is only one roll transmission assembly e.g. the second roll transmission assembly. In this version of alpha configuration, either the input articulation joint 2040 does not provide a DoC about the roll rotation, or the output articulation joint 2020 does not provide a DoC about the roll rotation, or neither provide a DoC about the roll rotation. As a result, transmission of roll rotation is no longer possible via the first roll transmission assembly, and only functional roll transmission assembly is the second roll transmission assembly described above.

In the case of the beta configuration (FIG. 22B), rotation of dial 2024 w.r.t. handle body 2026 about axis 1 leads to rigid body roll rotation of the entire frame 2032, tool shaft 2011, and EE frame 2016. The EE frame 2016 always rotates about axis 2. When the EE assembly 2010 is not articulated w.r.t. shaft 2011, the axis 2 is collinear with axis 3. When the EE assembly 2010 is in an articulated position, axis 2 is at an articulation angle w.r.t. axis 3. This roll rotation is transmitted from the Dial 2024 via input articulation joint 2040, rigid bodies (namely frame 2032 and tool shaft 2011), and output articulation joint 2020. In the case, the input articulation joint 2040 and output articulation joint 2020 each provide a DoC in the roll rotation direction in order to transmit roll motion from the Dial 2024 to the EE frame 2016. When the handle assembly 2022 is articulated w.r.t. the frame 2032 and thereby EE assembly 2010 is articulated w.r.t. the shaft 2011, roll rotation of the dial 2024 w.r.t. handle body 2026 about axis 1 leads to roll rotation of the EE frame 2016 about axis 2. Roll rotation of the EE frame 2016 causes roll rotation of the whole EE assembly 2010 (which includes Moving Jaw 2012 and Fixed Jaw 2014) about axis 2. In this articulated configuration, axis 2 and axis 3 are no longer collinear.

In the beta configuration, EE roll motion is transmitted via a single roll transmission assembly consisting of roll motion transmission via rigid body roll rotation of the frame and shaft, and via input and output articulation joints. Whereas, in alpha configuration, EE roll motion transmission can take place via two roll transmission assemblies, as described above.

Figure 23:
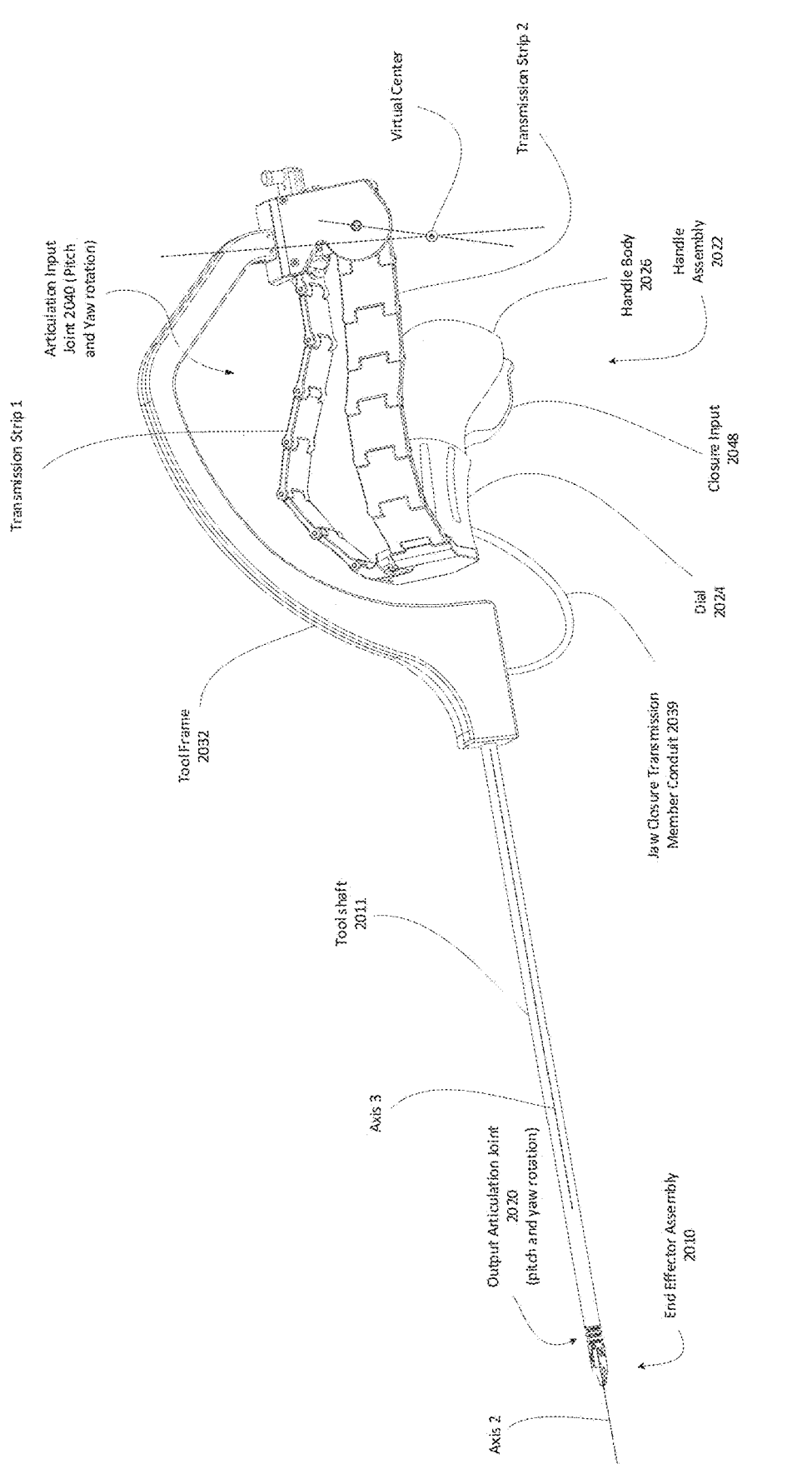
FIG. 23 depicts an embodiment of a tool apparatus in beta configuration.

FIG. 23 shows an embodiment of a tool apparatus which includes a parallel kinematic input articulation joint that has a center of rotation (Virtual Center) proximal to the handle assembly 2022. This tool apparatus embodiment is based on the beta configuration that has been discussed above. There exists the handle assembly 2022 within this tool apparatus along with frame 2032, tool shaft 2011 and EE assembly 2010. The handle assembly 2022 that is part of this tool apparatus is discussed in detail in sections below.

Handle Constraint Maps A and B

Figure 24A:
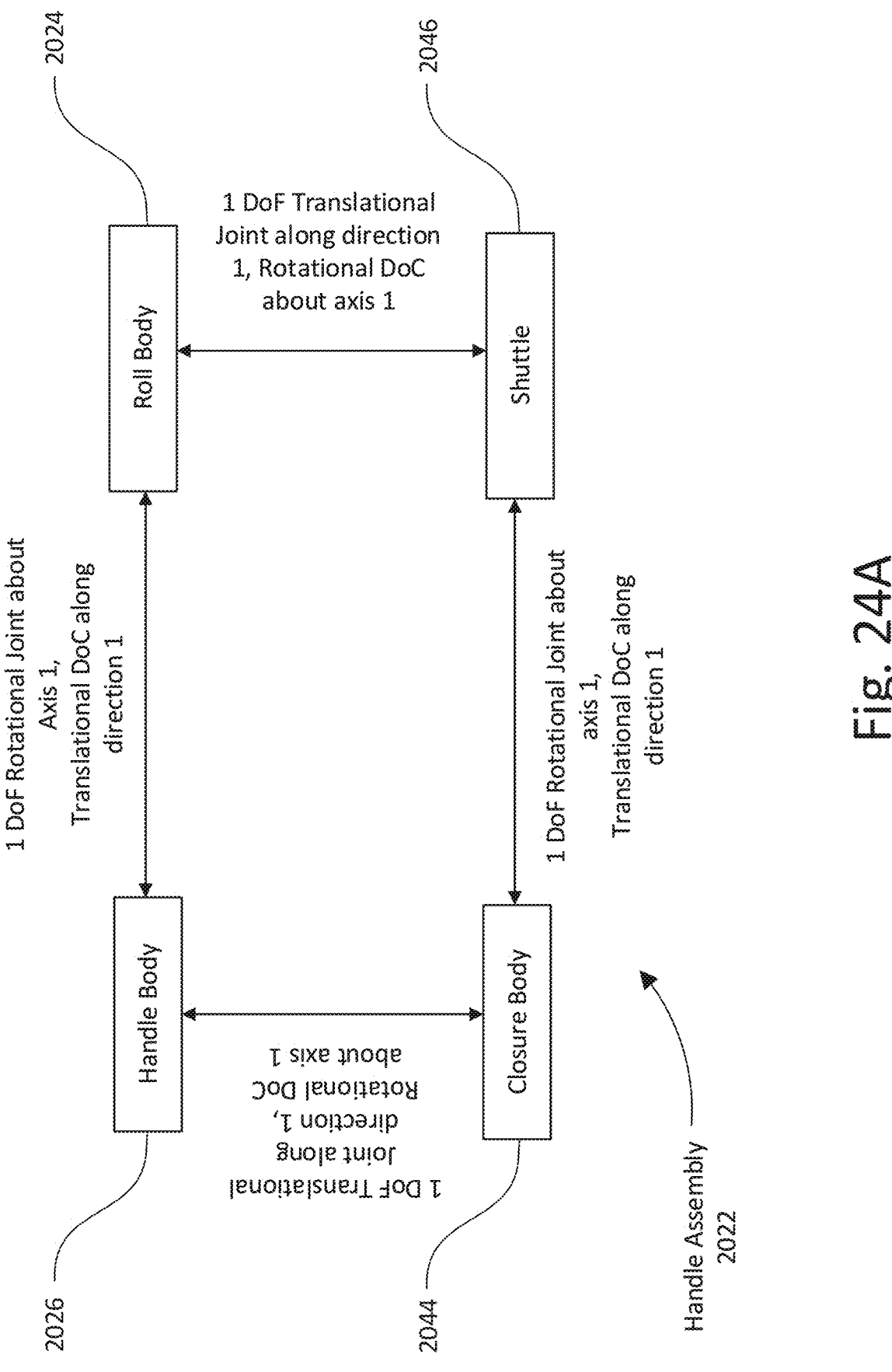
FIGS. 24A-B depict constraint map A and constraint map B for a handle assembly.

FIG. 24A represents a constraint map termed as "constraint map A" that is used to describe the relationship between various bodies that constitute the handle assembly 2022. The handle assembly 2022 may consist of four bodies namely, Handle Body 2026, Dial 2024, Push Rod 2044, and Shuttle 2046. In the embodiments of handle assembly that map to the constraint map shown in FIG. 24A, Handle Body 2026 can be considered as the local ground.

Closure Body (i.e., Push Rod) 2044 has a 1-DoF translational joint w.r.t. Handle Body 2026 along direction 1. Push Rod 2044 also has a rotational DoC w.r.t. Handle Body 2026 about axis 1. In other words, the Push Rod 2044 is rotationally constrained (e.g., keyed) w.r.t. Handle Body 2026 and if Handle Body 2026 is rotated about axis 1, it rotates the Push Rod 2044 along with itself. The Roll Body (i.e. Dial) 2024 has a 1 DoF rotational joint w.r.t. Handle Body 2026. Dial 2024 rotates about axis 1 relative to Handle Body 2026. Dial 2024 also has 1 translational DoC w.r.t. Handle Body 2026 along direction 1. Therefore, translation of Handle Body 2026 along direction 1 leads to translation of the Dial 2024 as well. The Shuttle 2046 has a 1 DoF rotational joint w.r.t. Push Rod 2044, i.e., Shuttle 2046 can rotate about axis 1 w.r.t. Push Rod 2044. The Shuttle 2046 also has a translational DoC w.r.t. Push Rod 2044 along direction 1. Therefore, along direction 1, translation of the Push Rod 2044 is transmitted to Shuttle 2046. The Shuttle 2046 has a 1 DoF translational joint w.r.t. Dial 2024 along direction 1. The Shuttle 2046 also has a 1 rotational DoC w.r.t. Dial 2024 about axis 1. Therefore, rotation of Dial 2024 w.r.t. Handle Body 2026 about axis 1 leads to rotation of Shuttle 2046 about axis 1 due to the presence of rotational DoC between Shuttle 2046 and Dial 2024.

Figure 24B:
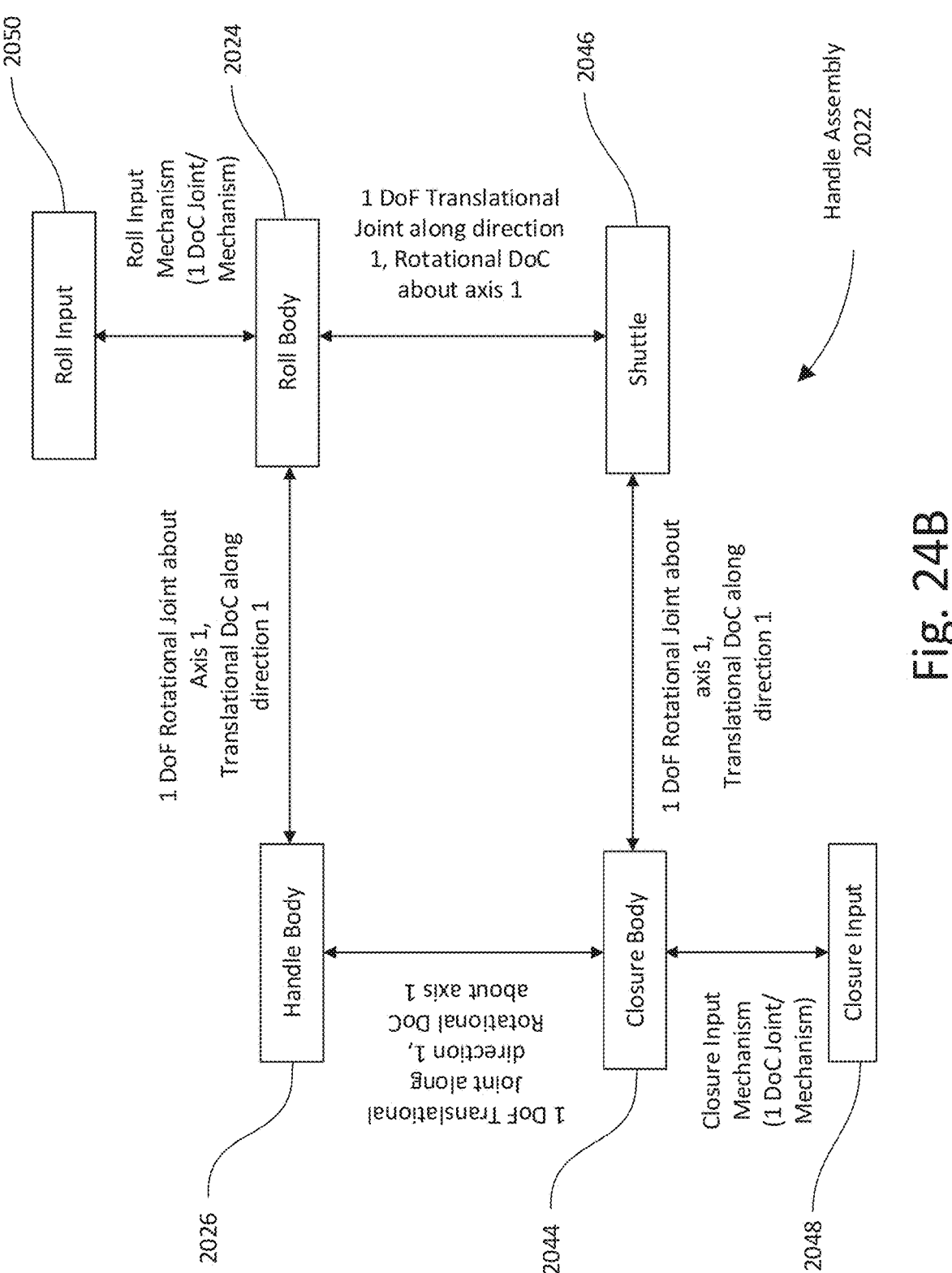

As seen in FIG.24B, which shows "constraint map B", handle assembly 2022 may also comprise additional bodies, such as Closure Input 2048 and Roll Input 2050. Closure Input 2048 may be coupled to the Push Rod 2044 via a direct structural connection or via a Closure Input Mechanism that transmits the input motion of the Closure Input 2048 w.r.t. the Handle Body 2026 to the translation along direction 1 of Push Rod 2044 w.r.t. Handle Body 2026. In the former scenario, where the Closure Input 2048 has a direct structural connection to Push Rod 2044, the Push Rod 2044 itself serves as the Closure Input 2048. Here the Closure Input 2048 is integral to or an extension of the Push Rod 2044. However, in other scenarios, the Closure Input 2048 may be coupled to the Push Rod 2044 via a Closure Input Mechanism (which is shown via various embodiments in the next section). Actuation of the Closure Input 2048 may be done manually by the user, or by using an electro-mechanical actuator, or pneumatic actuator, or hydraulic actuator, or another actuator. Additional mechanical transmission components (such as gears, pulleys, levers, tension cables, etc.) may be used between the actuator and the Closure Input 2048. Such mechanical transmission components may also be included in the Closure Input Mechanism.

Roll Input 2050 may be coupled to the Dial 2024 via a direct structural connection or via a Roll Input Mechanism that transmits the input motion of the Roll Input 2050 w.r.t. the Handle Body 2026 to the rotation about axis 1 of Dial 2024 w.r.t. Handle Body 2026. In the former limiting case, where the Roll Input 2050 has a direct structural connection to the Dial 2024, the Dial 2024 itself serves as the Roll Input 2050. Roll Input 2050 is integral to or an extension of the Dial 2024. However, in a more general case, the Roll Input 2050 is coupled to the Dial 2024 via a Roll Input Mechanism (which shall be described in detail later). Actuation of the Roll Input 2050 may be done by the user manually, or by using electro-mechanical actuator, or pneumatic actuator, or hydraulic actuator, or another actuator. Mechanical transmission components and systems (namely, gears, pulleys, levers, tension cables, etc.) may be used between such actuator and the Roll Input 2050, and/or within the Roll Input Mechanism.

Input received at Closure Input 2048 leads to translation of Shuttle 2046 along direction 1 w.r.t. Handle Body 2026. Input received at Roll Input 2050 leads to rotation of Shuttle 2046 about axis 1 w.r.t. Handle Body 2026. These inputs can simultaneously be received by the handle system shown in FIG. 24A-B in order to produce a combined or simultaneous translation and rotation of Shuttle 2046.

Tool Apparatus Configuration Maps

When the handle assembly of FIG. 24B is employed in a tool apparatus, inputs received at the Closure Input 2048 and Roll Input 2050 lead to jaw closure motion and EE roll motion, respectively, at the EE assembly 2010. Based on the input provided by the user to the handle assembly 2022 at Closure Input 2048, the output motion of the handle assembly 2022 is a translation of Shuttle 2046 along direction 1 w.r.t. Dial 2024 as well as w.r.t. Handle Body 2026. Based on input provided by the user to the handle assembly 2022 at the Roll Input 2050, the output motion of the handle assembly 2022 is a rotation of Shuttle 2046 about axis 1 w.r.t. Handle Body 2026. Therefore, the handle assembly 2022 is such that two separate and independent inputs lead to a combined translation and rotation output motion at a single body, namely, the Shuttle 2046. The main benefit of providing independent inputs to the handle assembly 2022 is the ability to independently optimize bodies, joints, mechanisms, and transmission members that are part of roll transmission assembly and jaw closure transmission assembly.

Tool apparatus in beta configuration shown in FIG. 23 includes handle assembly 2022 that follows the constraint map shown in FIG. 24B, the elongated tool shaft 2011 which is distal to the handle assembly 2022, and the EE assembly 2010 that exists at the distal end of the tool shaft 2011. Translation of Shuttle 2046 (e.g. shown as Shuttle 104, 404 in FIGS. 4A and 4B) w.r.t. Dial 2024 (e.g. shown as Rotation Dial 102, 402 in FIGS. 4A and 4B) along direction 1 leads to open/close actuation of Moving Jaw 2012 w.r.t. Fixed Jaw 2014 (e.g. shown in FIG. 21A). As part of jaw closure transmission assembly, there exists the jaw closure transmission member 2038 (routed via jaw closure transmission member conduit 2039) that transmits translation of shuttle 2046 to produce jaw closure motion at the End-Effector Assembly 2010. This jaw closure transmission member 2038 has to have adequate stiffness along direction 1 at the location where it couples with the Shuttle, and more generally along its entire length in order to capture and transmit translation of the shuttle 2046. This jaw closure transmission member 2038 may be a flexible (bendable) solid wire (e.g., piano wire, Nitinol wire) which may or may not be torsionally stiff when rotated about its centroidal axis; it may be a solid rod that may not be flexible in bending and/or torsion; it may be a braided cable assembly, which is flexible in bending and/or torsional, or it may be a member with a combination of these attributes. All these transmission members offer relatively high axial stiffness along their respective lengths.

Also, rotation of Dial 2024 w.r.t. Handle Body 2026 about axis 1 leads to rotation of Shuttle 2046 about axis 1. In this case (similar to the beta configuration of FIG. 22B), roll transmission assembly consists of rigid bodies (frame 2032, tool shaft 2011), and input and output articulation joint 2040, 2020.

In this case, jaw closure and roll transmission assemblies are independent and thus can be independently analyzed, designed, and optimized. E.g., bodies, joints, and mechanisms that belong to the jaw closure transmission assembly can be independently optimized for mechanical advantage, forces, materials used, efficiency, etc. without an impacting roll rotation transmission. Similarly, bodies, joints, and mechanisms that belong to the roll transmission assembly can be independently optimized to transmit roll efficiently without impacting the jaw closure transmission.

As part of the handle assemblies that map to constraint maps A and B, the Shuttle 2046 is pulled by the Push Rod (or Closure Body) 2044 towards the proximal end of the handle assembly 2022 (also shown as 400 in FIGS. 4A and 4B). The Closure Input 2048 may be a a rigid extension of the Push Rod 2044, in which case the Closure Input 2048 may translate w.r.t. Handle Body 2026 along direction 1. () In other instances, the Closure Input 2048 may be coupled to the Push Rod 2044 via a Closure Input Mechanism. In these instances, motion of the Closure Input 2048 w.r.t. the Handle Body 2026 may lead to translation of the Push Rod 2044 w.r.t. Handle Body 2026 along direction 1. This leads to actuation of the Moving Jaw 2012 w.r.t. Fixed Jaw 2014 in EE assembly 2010.

In case of some tool apparatuses, actuating the Moving Jaw 2012 w.r.t. the Fixed Jaw 2014 may require a high amount of force due to the requirement of high clamping loads between the two jaws or due to high losses and/or resistance between bodies within the jaw closure transmission assembly. This means that the Push Rod 2044 needs to pull the Shuttle 2046 with a high force along direction 1. Rotating Shuttle 2046 w.r.t. Push Rod 2044 simultaneously while the interface between the Push Rod 2044 and the Shuttle 2046 is under high load (due to various reasons mentioned above) may turn out to be hard to perform and inefficient due to high resistance if there is no well-defined and intentional load bearing interface between the Shuttle 2046 and Push Rod 2044.

In case of a handle assembly 2022 that follows the constraint map shown in FIGS. 24A-B, there exists a well-defined bearing interface between Shuttle 2046 and Push Rod 2044 that lets the two bodies have a relative rotation in the presence of the high axial load. This well-defined load bearing interface may consist of a thrust bearing, a roller bearing, or a lubricious plain bearing (e.g. FIGS. 3D, 3E, 3F) that helps mitigate the impact of high axial load on the rotation of the Shuttle 2046 with respect to the Push Rod 2044, and eventually on the roll rotation of the EE assembly 2010 when the Moving Jaw 2012 is actuated w.r.t. the Fixed Jaw 2014. Therefore, the presence of a well-defined bearing interface within the handle assembly 2022 that makes roll transmission efficient without impacting jaw closure transmission is a functional need of an efficient instrument/apparatus.

Figure 25A:
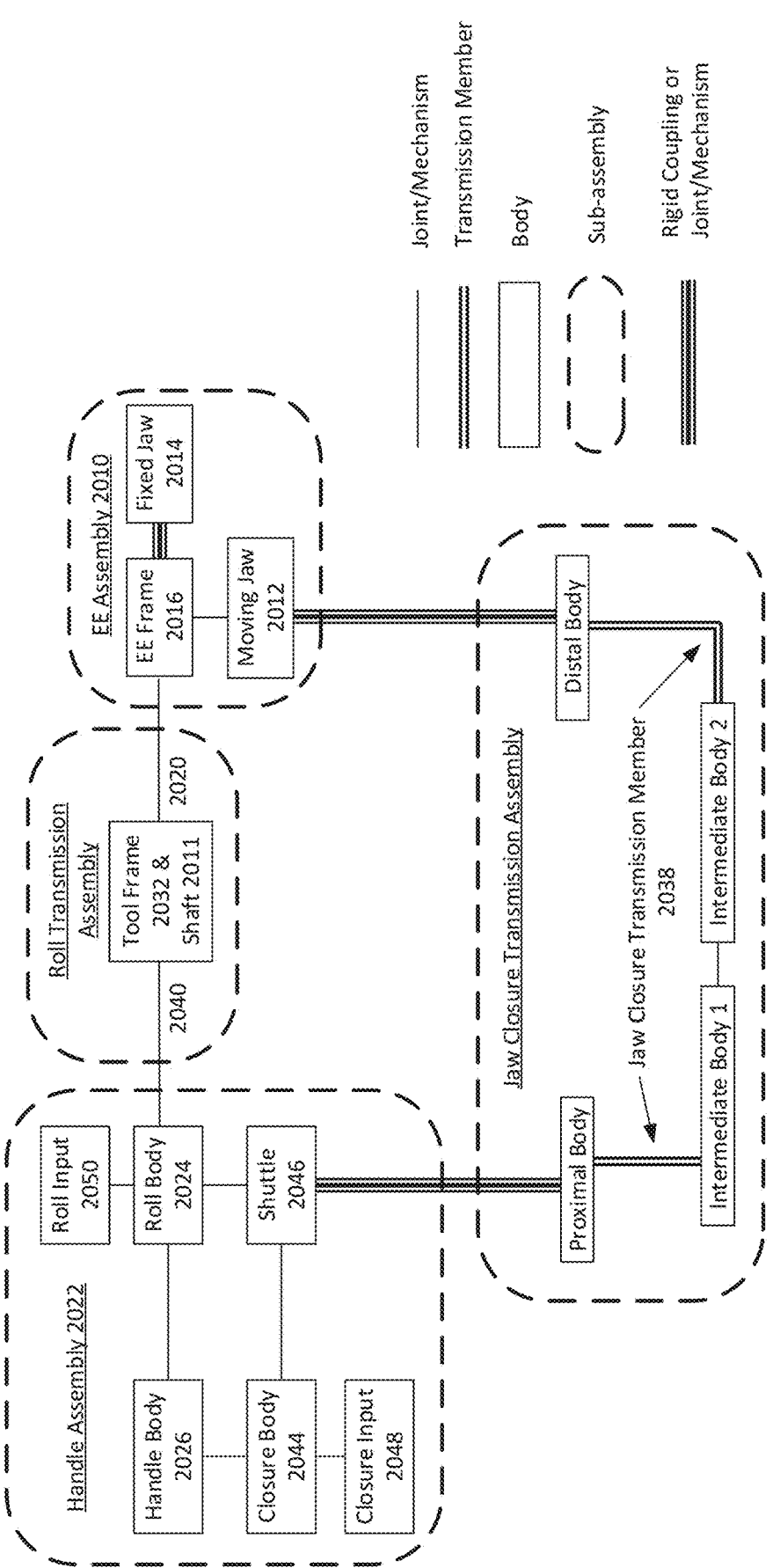
FIGS. 25A-C depict possible configuration maps for the tool apparatuses that incorporate an unlimited-roll handle assembly.

FIG. 25A shows a tool apparatus configuration map (i.e. schematic drawing) that incorporates the handle assembly 2022 based on constraint map B of FIG. 24B. This tool apparatus configuration map correlates to the beta configuration of tool apparatus presented in FIG. 22B. In this configuration, there exist two independent transmission assemblies, namely jaw closure transmission assembly and roll transmission assembly. Actuation of Closure Input 2048 relative to Handle Body 2026 leads to translation of Closure Body or Push Rod 2044 along direction 1. Since the Shuttle 2046 has a translation DoC w.r.t. Push Rod 2044 along direction 1, translation of the Push Rod w.r.t. the Handle Body leads to translation of Shuttle 2046 w.r.t. the Handle along direct 1. The legend on the bottom right of FIGS. 25A-C indicate the following: A single-line represents a joint or mechanism that offers at least 1 DoF (e.g. input articulation joint, output articulation joint, etc.) between bodies, components, or sub-assemblies; a double-line represents a transmission member (e.g. cables) that transmits a motion from one body/component/sub-assembly to another; a triple-line represents an interface that may be either a rigid/direct coupling between two bodies/components/sub-assemblies or a joint/mechanism that offers at least 1 DoF between two bodies/components/sub-assemblies; and a dashed single-line represents a sub-assembly.

Referring to FIG. 25A, Proximal Body, which is part of the jaw closure transmission assembly, is coupled to and therefore translates along with Shuttle 2046, and thereby transmits motion to jaw closure transmission member 2038 which is attached or coupled to the Proximal Body. At the distal end, jaw closure transmission member 2038. On its distal end, the jaw closure transmission member is coupled to Distal Body, which in turn is coupled to the Moving Jaw 2012 in the end-effector assembly 2010, either directly or via a mechanism that converts the translation of the Distal Body into rotation of the Moving Jaw 2012 w.r.t. EE Frame 2016 (and Fixed Jaw 2014) about pivot axis 4 to produce jaw closure motion. The Proximal Body, jaw closure transmission member(s), and various intermediate bodies (e.g. Intermediate Body 1 and Intermediate Body 2) are all part of the Jaw Closure Transmission Assembly. The Proximal Body may be coupled to the Shuttle either via a rigid/direct coupling or via a joint/mechanism, as represented by a triple-line. Similarly, the Distal Body may be coupled to the Moving Jaw either via a direct/rigid coupling or via joint/mechanism. FIG. 25A shows "Intermediate Body 1" and "Intermediate Body 2" and a joint/mechanism between them to depict the diverse types of components that can exist within the jaw closure transmission assembly. There may exist more than two Intermediate Bodies, joints/mechanisms, and transmission members within a transmission assembly.

In a tool apparatus that maps to the configuration map shown in FIG. 25A, EE roll motion is produced by rotation of Roll Input 2050 relative to Handle Body 2026. This configuration map correlates to the beta configuration of tool apparatus presented in FIG. 22B. Transmission of EE roll motion from the handle assembly 2022 to the EE assembly 2010 for this beta configuration is described above. . At the input end, the Shuttle 2046 has a roll DoC about axis 1 w.r.t. the Dial 2024. Therefore, as the user rotates the Dial 2024, the Shuttle 2046 also rotates. There also exists a roll DoF between the Push Rod 2044 and Shuttle 2046 about axis 1 such that Shuttle 2046 can rotate relatively freely without being impacted by jaw closure transmission that also originates within the handle assembly 2022 (at Closure Input 2048). The presence of Shuttle 2046, a discrete body within handle assembly 2022, maintains the independence between jaw closure transmission assembly and roll transmission assembly.

Figure 25B:
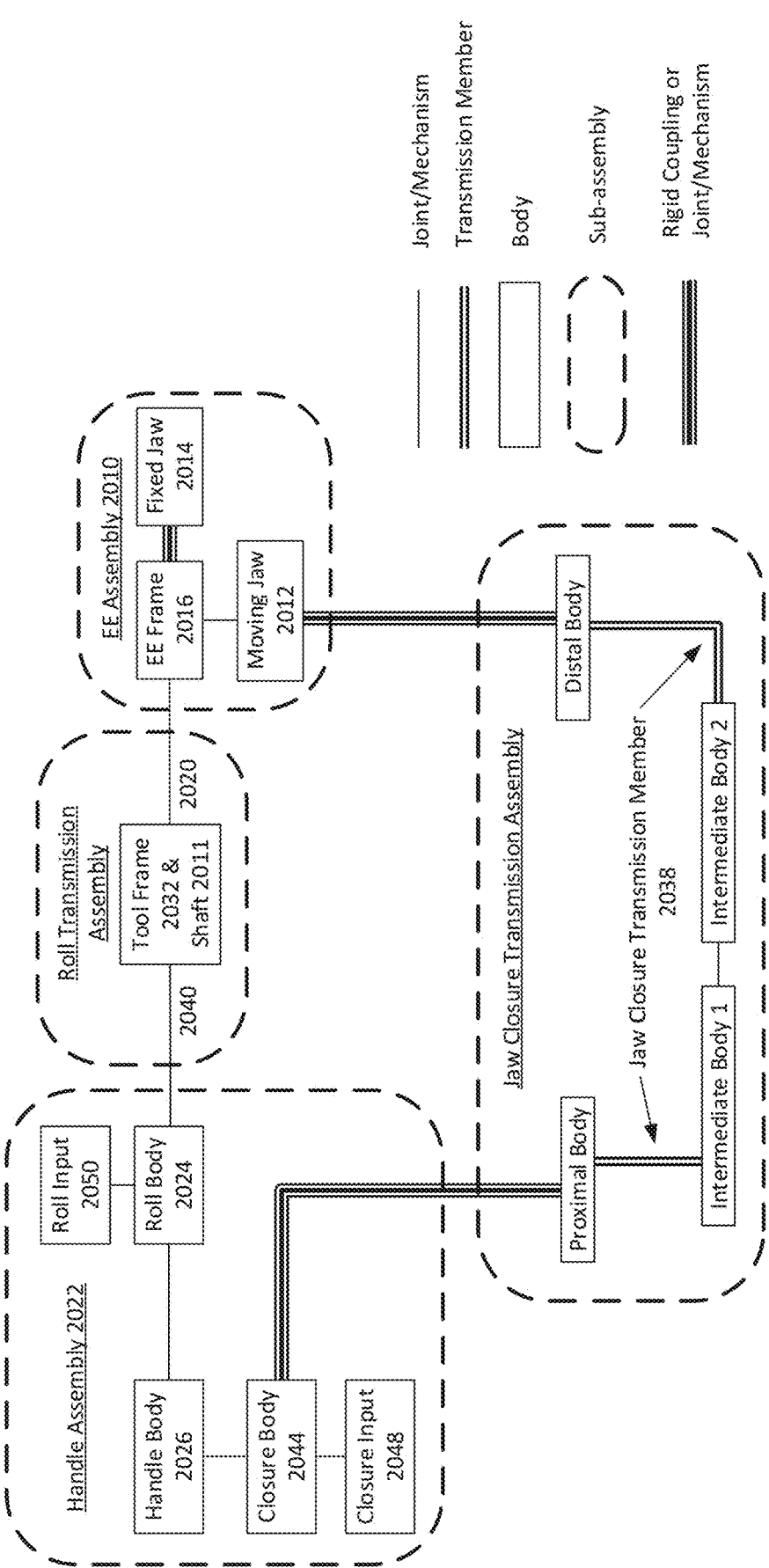

In the prior art, there exist tool apparatuses that follow another tool apparatus configuration map shown in FIG. 25B which lacks Shuttle 2046 within the handle assembly 2022. This configuration map does not incorporate a handle assembly based on the constraint maps of FIG. 24A or 24B. With the exception of the shuttle, all the other bodies and associate joints within the handle assembly 2022 shown in FIG. 25B correspond to the handle assembly constraint map shown in FIG. 24B. Jaw closure motion is transmitted from the proximal end of tool apparatus to the EE assembly 2010 by actuation of Closure Input 2048 leading to translation of Push Rod 2044 w.r.t. Handle Body 2026 along direction 1. Closure Body or Push Rod 2044 is further connected to the jaw closure transmission member 2038 with Proximal Body. This Proximal Body or proximal end of transmission member has a translation DoC w.r.t. Push Rod 2044 along direction 1. Therefore, the translation of the Push Rod 2044 is transmitted to the Proximal Body and/or the proximal end of the transmission member, both of which exist within the jaw closure transmission assembly. Proximal Body is rigidly connected or coupled to the proximal end of the jaw closure transmission member 2038. Alternatively, Proximal Body may simply be the a relatively rigid end proximal end of the jaw closure transmission member 2038. Within the jaw closure transmission assembly, there may either be a Distal Body rigidly coupled to the distal end of the jaw closure transmission member 2038, or a Distal body that itself is the distal end of the jaw closure transmission member 2038. Further, as in the case of FIG.25A, this Distal Body may be coupled to the Moving Jaw 2012 of the EE assembly 2010 either directly or via a mechanism that converts the translation of jaw closure transmission member 2038 (and therefore the Distal Body) to the rotation of Moving Jaw 2012 relative to EE Frame/Fixed Jaw. This mechanism may contain linkages, rack and pinion assembly, pulleys, cams, pins, etc.

In certain scenarios of FIG. 25B, the Distal Body or the distal end of the jaw closure transmission member 2038 may have a roll DoC (e.g. via a keying feature or a pin) w.r.t. the Moving Jaw 2012 about axis 2 such that rotation of Moving Jaw 2012 about axis 2 leads to rotation of the Distal Body or the distal end of the jaw closure transmission member 2038. EE roll motion is produced by rotation of Roll Input 2050 (or directly of the Dial 2024) relative to Handle Body 2026. This configuration map (FIG. 25B) also aligns with the beta configuration of tool apparatus presented in FIG. 22B. Transmission of EE roll rotation of the Roll Input 2050 (Dial 2024) relative to Handle Body 2016 (all part of the handle assembly 2022) to tool frame 2032 and shaft 2011 via the input articulation joint 2040 and further to the EE assembly 2010 via the output articulation join 2020, for this beta configuration is described above. Eventually, the roll rotation of the EE assembly 2010 causes the EE Frame 2016, Fixed Jaw 2014, and Moving Jaw 2012 to also roll rotate about axis 2.

As noted above, rotation of Moving Jaw 2012 about axis 2 may also lead to rotation of the Distal Body or the distal end of the jaw closure transmission member 2038 due to presence of a roll DoC about axis 2. Though jaw closure transmission member 2038 does not transmit roll rotation in this configuration, it rotates nevertheless due to the EE roll motion about its centroidal axis. Rotation of jaw closure transmission member 2038 initiated at the distal end of the instrument should ideally have a corresponding, matching rotation at the proximal end where it interfaces with the Proximal Body. In case rotation of the distal end does not have a matching rotation on the proximal end, it may lead to unnecessary storage and wastage of energy as well as other functionality issues such as jamming due to twisting of the jaw closure transmission member 2038 and, as a result can impact EE roll motion and jaw closure motion. This highlights the importance of a distinct Shuttle component present in the configuration map of FIG. 25A but absent in FIG. 25B.

For the tool apparatus configuration map of FIG. 25B, the jaw closure transmission member 2038 (and more generally the jaw closure transmission assembly) has to have certain design characteristics. Even though it does not transmit roll rotation, it has to be torsionally stiff about its centroidal axis along with being axially stiff. It also has to have low friction or frictionless interface throughout its length along the shaft before it interfaces with the Closure Body or Push Rod 2044. It also has to have a roll DoF at its proximal end w.r.t. Push Rod 2044 about axis 1. This roll DoF joint helps allow the same rotation of Proximal Body (or proximal end of the jaw closure transmission member 2038) as that of the Distal body (or distal end of the jaw closure transmission member 2038).

Thus, the lack of Shuttle 2046 (as in case of Prior Art) is acceptable only when there is an efficient roll DoF joint between the Proximal Body (or proximal end of the jaw closure transmission member 2038) w.r.t. Push Rod 2044 and that the jaw closure transmission member 2038 (as well as the jaw closure transmission assembly) is adequately stiffness in torsion (i.e. about its centroidal axis or the roll rotation axis). This is necessary ensure that the jaw closure transmission member can rotate freely without twisting about its centroidal axis and without impacting the EE roll motion or the jaw actuation. Presence of Shuttle 2046 and a roll DoC between Shuttle 2046 and Dial 2024 about axis 1 provides an efficient solution and relieves the need for the above design characteristics namely high torsional stiffness and axial stiffness for jaw closure transmission member 2038. This means that a cable that is axially stiff but is not stiff in torsion can be used as a jaw closure transmission member in tool apparatus of the beta configuration. The advantage of using such a jaw closure transmission member is that it also flexible in bending, which allows for a tight bend radius and large range of articulation at the output articulation joint 2020.

Figure 25C:
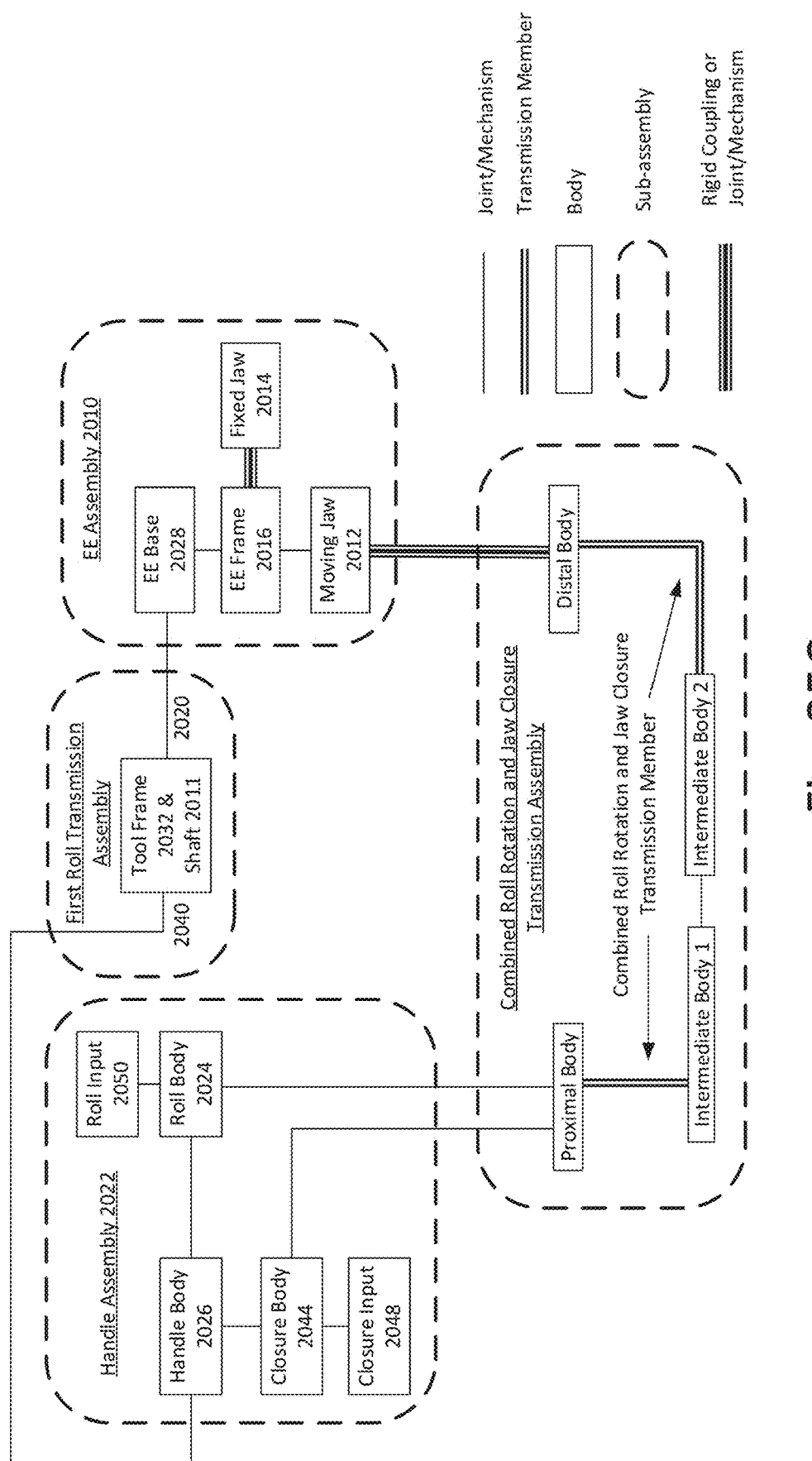

In contrast to the tool apparatus configuration map shown in FIG. 25A, there exists tool apparatuses that are based on another configuration map (FIG. 25C) where the handle assembly 2022 does not include Shuttle 2046. In FIG. 25C, with the exception of the shuttle, all other bodies and associated joints within the handle assembly 2022 are mapped to the constraint map shown in FIG. 24B. This tool apparatus configuration of FIG. 25C aligns with the alpha configuration of tool apparatus shown in FIG. 22A. As noted in the description of the alpha configuration, there can be two transmission interfaces and associated transmission assemblies and transmission members—one for jaw closure transmission and one for roll rotation transmission. These two transmission interfaces and associated transmission members can either be distinct or combined. In other words, the same transmission member can serve as the jaw closure transmission member as well as the roll rotation transmission member. This latter case is illustrated in the tool apparatus configuration map of FIG. 25C. Here, Proximal Body, which is part of the "combined roll rotation and jaw closure transmission assembly" is either rigidly connected/coupled to the distal end of the to the "combined roll rotation and jaw closure transmission" member. Roll rotation of the Roll Input 2050 is transmitted to Dial 2024 via a Roll Input Mechanism (described later). Roll Rotation is transmitted from Dial 2024 to the roll to the Proximal Body (or proximal end of the combined roll rotation and jaw closure transmission member) via a joint that provides roll DoC w.r.t. Dial 2024 about axis 1 and translation DoF along direction 1. Furthermore, this Proximal Body (or proximal end of the combined roll rotation and jaw closure transmission member) is connected to the Closure Body or Push Rod 2044 via joint that provides translational DoC along axis 1 and rotational DoF about axis 1. The Distal Body (or distal end of the combined roll rotation and jaw closure transmission member), which is part of the combined roll rotation and jaw closure transmission assembly, couples to the EE assembly 2010 (specifically the EE frame 2016 and Moving Jaw 2012) via a joint/mechanism. This mechanism allows relative translation of the Distal Body w.r.t. EE frame 2016 (i.e. DoF along axis 2) but constrains and therefore transmits roll between the two (i.e. DoC about axis 2 e.g. via a keying feature). This mechanism also couples the Distal Body (or distal end of the combined roll rotation and jaw closure transmission member) to the Moving Jaw 2012 so as to convert the translation of the former to rotation of the latter (i.e. Moving Jaw 2012) relative to EE Frame/Fixed Jaw about pivot axis 4 to produce jaw closure motion. This mechanism may contain linkages, rack and pinion assembly, pulleys, cams, pins, gears, cable, etc.

This functionality may call for the combined roll and jaw closure transmission member to have certain design characteristics. This Proximal Body or the proximal end of this transmission member should have a joint with at least 1 DoF (roll rotation) w.r.t. closure body or Push Rod 2044. This joint may be achieved via a bearing interface between the Proximal Body (or the proximal end of transmission member) and Push Rod 2044 using thrust bearing, lubricious plain bearing, etc. This transmission member also has to be torsionally stiff about its centroidal axis as well as axially stiff (both under tension and compression) to transmit both roll rotation and jaw closure actuation, respectively. The torsional stiffness has to be high not only to transmit roll but also so that any friction at the joint between Push Rod/Closure Body 2024 and the Proximal Body (or the proximal end of the transmission member), which is supposed to provide rotational DoF about axis 1 and translational DoC along axis 1, does not cause the transmission member to get twisted (i.e. torsionally wound up) especially when jaw closure actuation force is applied via the transmission member. These design characteristics of large axial and torsional stiffness also impact the transmission member's ability to bend, which limits the tool apparatus' ability to provide large range of articulation and tight bend radius at the output articulation joint 2020. For example, a braided cable with small diameter (while ideal in terms of bendability) is not ideal for this transmission member since such cables are neither torsionally stiff about their centroidal axis nor axially stiff when under compression. A stiffer transmission member (e.g. a solid wire, monofilament, or a thick braided cable with large diameter) provides the desirable high axial stiffness (in tension and compression) and torsional stiffness, it ends being too stiff in bending as well, thereby making large articulation and tight bend radius at the output articulation joint difficult to achieve. This shows the limitations of the prior art tool apparatuses that are based on the tool apparatus configuration map of FIG. 25C that lacks a distinct Shuttle body/component. In the absence of a Shuttle and its associated well defined and properly designed respective joints w.r.t. to the Roll Body and Closure Body, the combined jaw closure transmission member has to meet the above requirements of high axial and torsional stiffness. These requirements adversely impacts the bendability of this transmission member, thereby limiting range of articulation and tight bend radius of the output articulation joint.

In this configuration (FIG. 25C), there is not a well-defined bearing interface that provides the roll DoF about axis 1 between Push Rod/Closure Body 2044 and Proximal Body (or proximal end of the transmission member). Such a well-defined and properly designed bearing interface isolates the impact of high jaw closure transmission load (e.g. axial tension or force) on the transmission member. However, due to the lack of Shuttle body within handle assembly 2022 in this configuration, the combined roll and jaw closure transmission member needs the aforementioned design characteristics (e.g. adequately high torsional stiffness), which limits articulation performance.

Handle Assembly Embodiments—Mapping to Constraint Maps A and B

Figure 26:
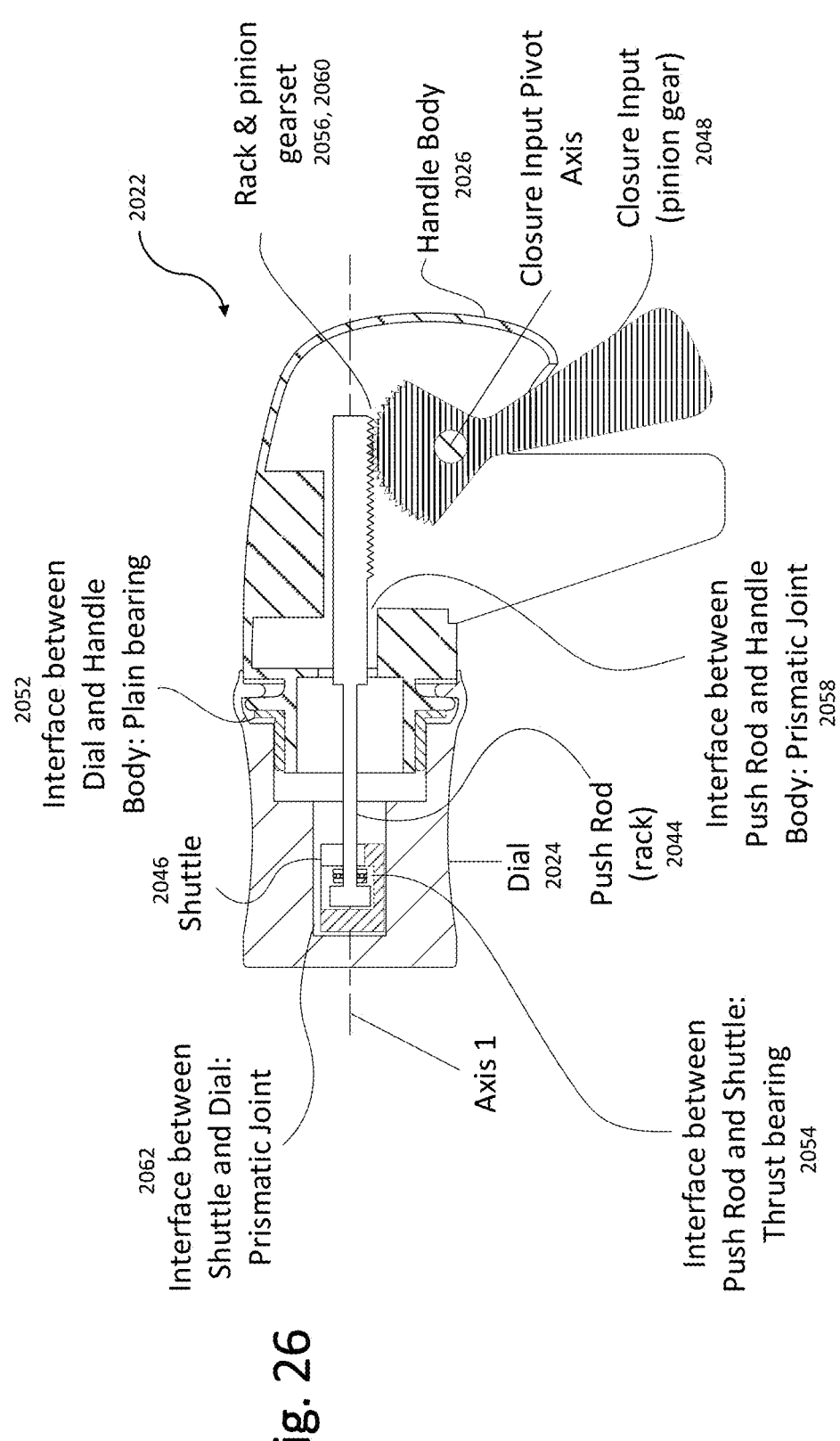
FIG. 26 depicts a handle assembly consisting of a rack and pinion gearset as a closure input mechanism.

FIG. 26 represents an embodiment of a handle assembly 2022 including Handle Body 2026, Closure Input 2048, Push Rod 2044, Dial 2024 and Shuttle 2046. This handle assembly 2022 is an embodiment that follows the constraint map shown in FIG. 24A-B. Roll Input 2050 is represented in its simplest form as Dial 2024 itself. Here, rotation of Dial 2024 w.r.t. Handle Body 2026 about axis 1 leads to rotation of Shuttle 2046 about axis 1. There exists a plain bearing 2052 made from lubricious material (e.g., Delrin, Teflon, PEEK, PTFE coated aluminum) between the Dial 2024 and Handle Body 2026. There exists a thrust bearing 2054 between Shuttle 2046 and Push Rod 2044. There exists a roll DoC joint between Dial 2024 and Shuttle 2046 about direction 1. There exists a Closure Input Mechanism 2056 between Closure Input 2048 and Push Rod 2044 such that actuation of the Closure Input 2048 leads to translation of Push Rod 2044 along direction 1, while the Push Rod 2044 has a roll DoC joint w.r.t. Handle Body 2026 about direction 1. Therefore, there exists a prismatic joint 2058 between the Push Rod 2044 and Handle Body 2026. If this roll DoC joint did not exist, the roll friction between the Push Rod 2044 and Shuttle 2046 will cause the Push Rod 2044 to transmit the frictional roll torque to the Closure Input 2048. This may lead to high force requirement to actuate the Closure Input 2048 due to introduction of reaction loads at the pivot joint between Closure Input 2048 and Handle Body 2026. In case of low roll friction between Push Rod 2044 and Shuttle 2046, this roll DoC may not be needed.

In the embodiment shown in FIG. 26, Closure Input mechanism 2056 is represented by a rack and pinion gearset 2060 transmission assembly. Here, Closure Input 2048 is a handle lever with an integrated pinion gear while Push Rod 2044 has a rack gear integrated into it. Upon rotation of Closure Input 2048 about its pivot axis w.r.t. Handle Body 2026 , the rack can move back and forth along direction 1. Further, presence of a prismatic joint 2062 provides translation DoF w.r.t. Handle Body 2026 along direction 1.

FIG. 27 represents another embodiment of a handle assembly 2022 that includes Handle Body 2026, Dial 2024, Push Rod 2044, Closure Input 2048, and Shuttle 2046. This handle assembly 2022 is an embodiment that follows the constraint map shown in FIGS. 24A-B. Roll Input 2050 is represented in its simplest form as Dial 2024 itself. Here, rotation of Dial 2024 w.r.t. Handle Body 2026 about axis 1 leads to rotation of Shuttle 2046 about axis 1. There exists a plain bearing 2064 made from lubricious material (e.g., Delrin, Teflon, PEEK, PTFE coated aluminum) between the Dial 2024 and Handle Body 2026. There exists a thrust bearing 2066 between Shuttle 2046 and Push Rod 2044. There exists a roll DoC joint about axis 1 between Dial 2024 and Shuttle 2046 as Dial 2024 acts as Roll Input 2050. There exists a Closure Input mechanism 2056 between Closure Input 2048 and Push Rod 2044 such that it leads to translation of Push Rod 2044 along direction 1 while the Push Rod 2044 has a roll DoC joint w.r.t. Handle Body 2026 about axis 1. Therefore, there exists a prismatic joint 2068 between the Push Rod 2044 and Handle Body 2026. The Closure Input Mechanism 2056 consists of a screw mechanism 2070 that exists between Closure Input 2048 and Push Rod 2044.

In the embodiment shown in FIG. 27, Closure Input 2048 acts as a screw whereas Push Rod 2044 acts as a nut as part of this screw mechanism 2070. Closure Input 2048 has a translational DoC joint w.r.t. Handle Body 2026 along direction 1 and a rotational DoF w.r.t. Handle Body 2026 about axis 1. Threads of the screw (here, Closure Input 2048), are mated with the nut (Push Rod 2044). Push Rod 2044 has a translational DoF w.r.t. Handle Body 2026 along direction 1 and a rotational DoC w.r.t. Handle Body 2026 about axis 1. Therefore, the rotation of screw leads to translation of the Push Rod 2044. This Closure Input 2048 (screw), may be operated by the user by turning the proximal end of the screw or via actuator (e.g., a stepper or servo motor). Also, the screw shown here may be a lead screw or a ball screw, depending on the other requirements of the application where this handle assembly 2022 is incorporated. Though FIG. 27 shows a bearing between Closure Input 2048 and Handle Body 2026 on the distal side, there may exist applications where a bearing interface between Closure Input 2048 and Handle Body 2026 may be required on the proximal side. Similarly, although a bearing between Shuttle 2046 and Push Rod 2044 is shown on the proximal side, there may exist applications where a bearing interface between Closure Input 2048 and Handle Body 2026 may be required on the distal side.

Figure 28A:
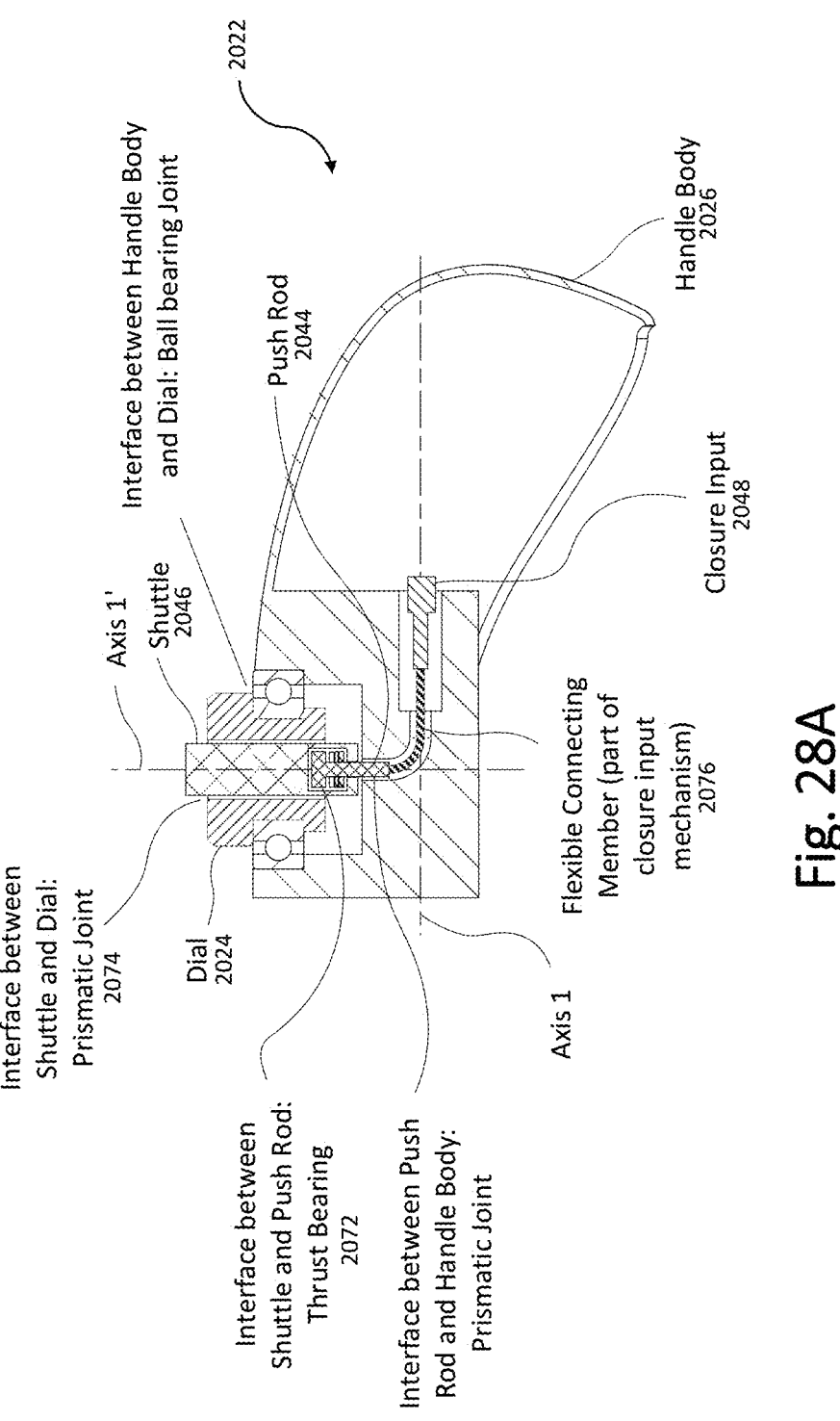
FIGS. 28A-C depict a handle assembly consisting of a flexible connecting member as a closure input mechanism (A); an embodiment of a pivot chain (B); and a handle assembly consisting of a pivot chain as a closure input mechanism (C).

FIG. 28A represents a handle assembly 2022 including Handle Body 2026, Push Rod 2044, Closure Input 2048, Dial 2024, and Shuttle 2046. This handle assembly 2022 is an embodiment that follows the constraint map shown in FIGS. 24A-B. Roll Input 2050 is represented in its simplest form as Dial 2024 itself. Here, rotation of Dial 2024 w.r.t. Handle Body 2026 about axis 1' leads to rotation of Shuttle 2046 about axis 1'. There exists a plain bearing (e.g. bushing) made from lubricious material (e.g. Delrin, Teflon, PEEK, PTFE coated aluminum) or a ball bearing between the Dial 2024 and Handle Body 2026. There exists a thrust bearing 2072 between Shuttle 2046 and Push Rod 2044. The Shuttle 2046 also translates w.r.t. Dial 2024 along direction 1' and thus, has a prismatic joint 2074 w.r.t. Dial 2024. There exists a roll DoC joint between Dial 2024 and Shuttle 2046 as Dial 2024 acts as Roll Input 2050. There exists a Closure Input Mechanism 2056 between Closure Input 2048 and Push Rod 2044 such that it leads to translation of Push Rod 2044 along a path which is not the same as direction 1. Also, the Push Rod 2044 has a roll DoC joint w.r.t. Handle Body 2026 about axis 1.

In the embodiment shown in FIG. 28A, this Closure Input Mechanism 2056 comprises a flexible member 2076 (e.g., flexible wire) which is able to bend along a certain angle θ (here 90 degrees) and translate along its centroidal axis direction. This axis is defined as axis 1'. This flexible wire, therefore, has a translational DoF w.r.t. Handle Body 2026 along axis 1' direction and is confined to move along this axis direction by guiding features of Handle Body 2026 present all around the wire. The flexibility of the wire provides the ability to bend but the wire needs to be stiff along its centroidal axis such that it transmits motion from Closure Input 2048 to the Push Rod 2044. This wire may be a Nitinol wire, a polymer composite which includes stiff member like spring steel and elastomeric resins, etc.

Figure 28B:
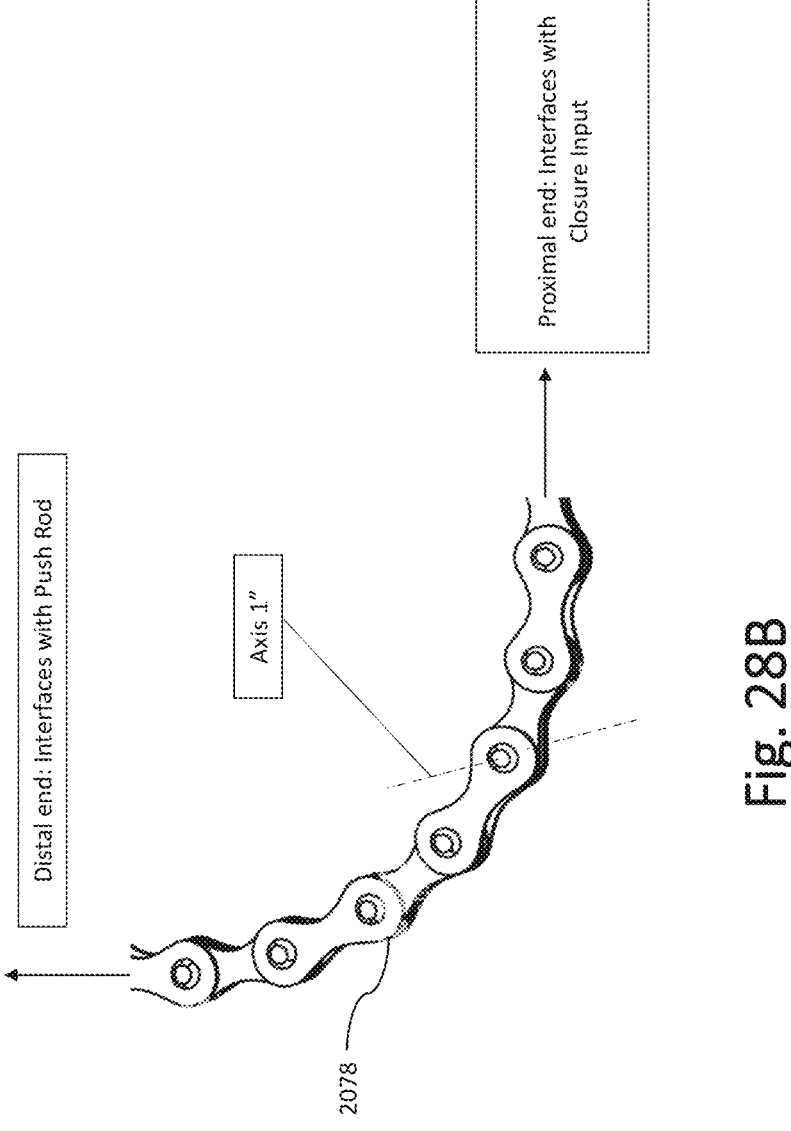
Figure 28C:
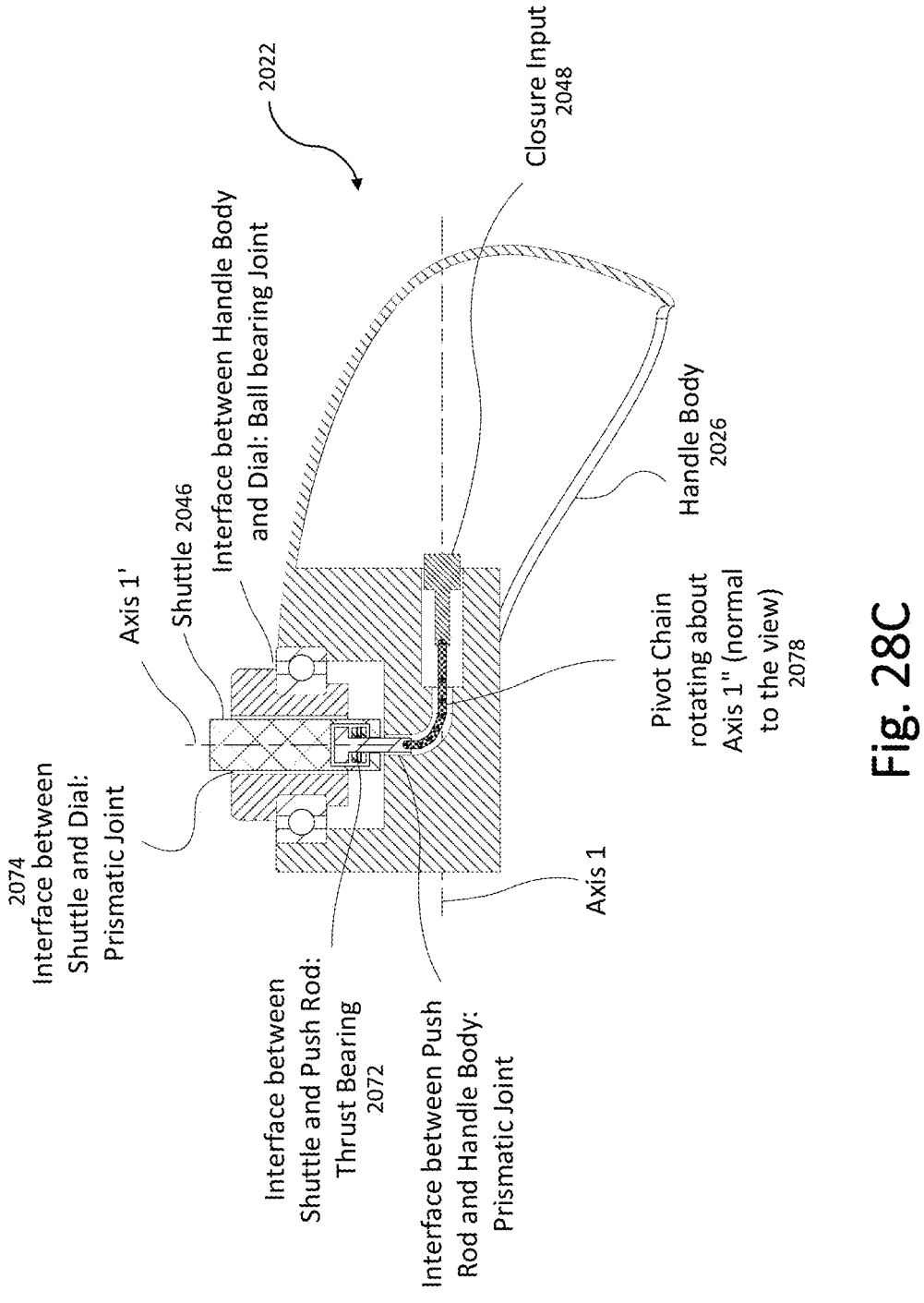

This Closure Input Mechanism 2056 may comprise a flexible wire which is flexible to bend but stiff along its centroidal axis or, as shown in FIG. 28B, may be a serial chain of single DoF pivot joints about axis 1", where axis 1" is perpendicular to both axis 1 and axis 1'. An embodiment showing a pivot chain 2078 with such pivot joints is shown in FIG. 28B. FIG. 28C shows the use of the pivot chain 2078 where Closure Input Mechanism 2056 consists of a serial chain 2078 of pivot joints that are guided by slot features present within the Handle Body 2026. At their two ends, the flexible wire or serial chain of joints may be rigidly connected to Closure Input 2048 and Push Rod 2044 respectively.

Figure 29A:
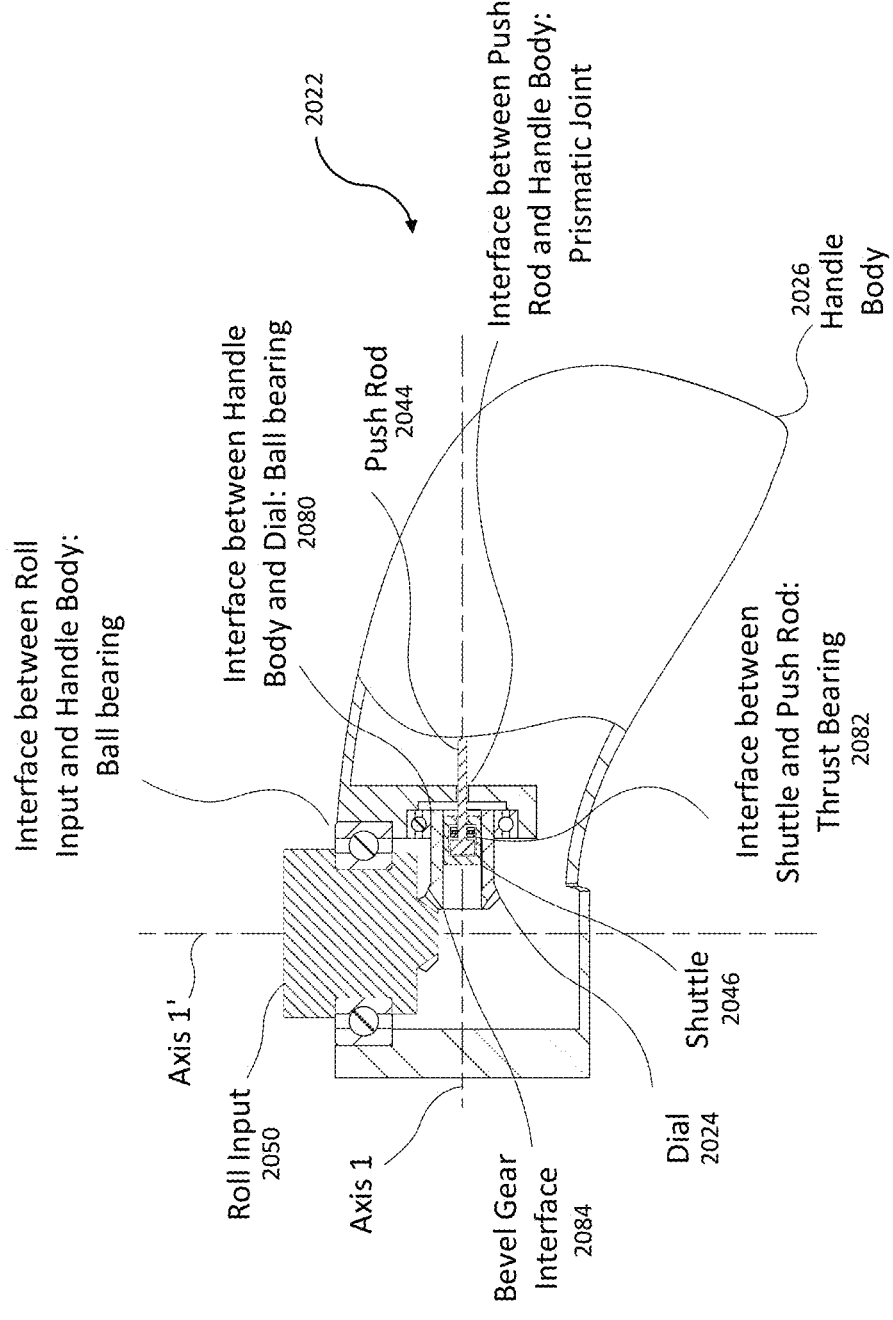
FIGS. 29A-B depict a handle assembly consisting of a bevel gearset as a roll input mechanism: (A) is a front view and (B) is an enlarged view.
Figure 29B:
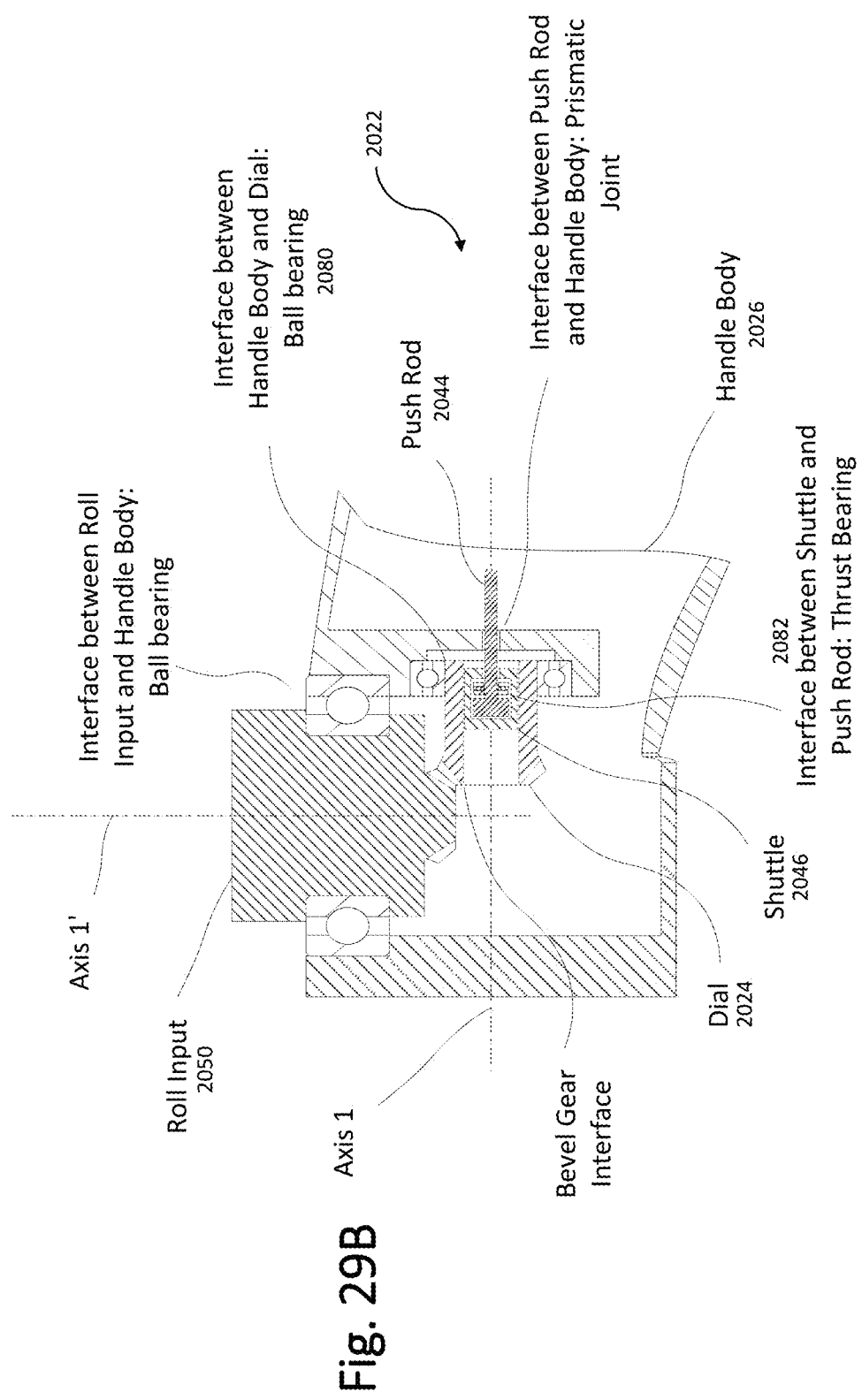

FIGS. 29A-B represents a handle assembly 2022 including Handle Body 2026, Push Rod 2044, Dial 2024, Roll Input 2050, and Shuttle 2046. The handle assembly 2022 is an embodiment that follows the constraint map shown in FIGS. 24A-B. There exists a ball bearing 2080 between Dial 2024 and Handle Body 2026. There exists a thrust bearing 2082 between Shuttle 2046 and Push Rod 2044. There exists a Roll Input 2050 which is a distinct component that interfaces with Dial 2024 via a Roll Input transmission. Rotation of Roll Input 2050 about axis 1', which perpendicular to axis 1 w.r.t. Handle Body 2026, is transmitted to Dial 2024 via a bevel gear assembly 2084. Roll Input 2050 and Dial 2024 act as a bevel gearset such that rotation of Roll Input 2050 about axis 1' is transmitted to the rotation of Dial 2024 w.r.t. Handle Body 2026 about axis 1. Here, these gears transmit rotation of Roll Input 2050 to Dial 2024 with the angle by 90° between the respective axis of Roll Input 2050 and Dial 2024 (axis 1). These gears may be designed to interface at other angles between axis 1 and axis 1'. This rotation of Dial 2024 leads to rotation of Shuttle 2046 about axis 1. The Shuttle 2046 also translates w.r.t. Dial 2024 along direction 1. Closure Input 2048 exists in form of the Push Rod 2044 in its simplest form. There exists a translation DoF between Push Rod 2044 and Handle Body 2026 along direction 1. Although FIG. 29 shows a bearing between Push Rod 2044 and Handle Body 2026 on the distal side, there may exist applications where a bearing interface between Closure Input 2048 and Handle Body 2026 may be called for on the distal side.

Figure 30A:
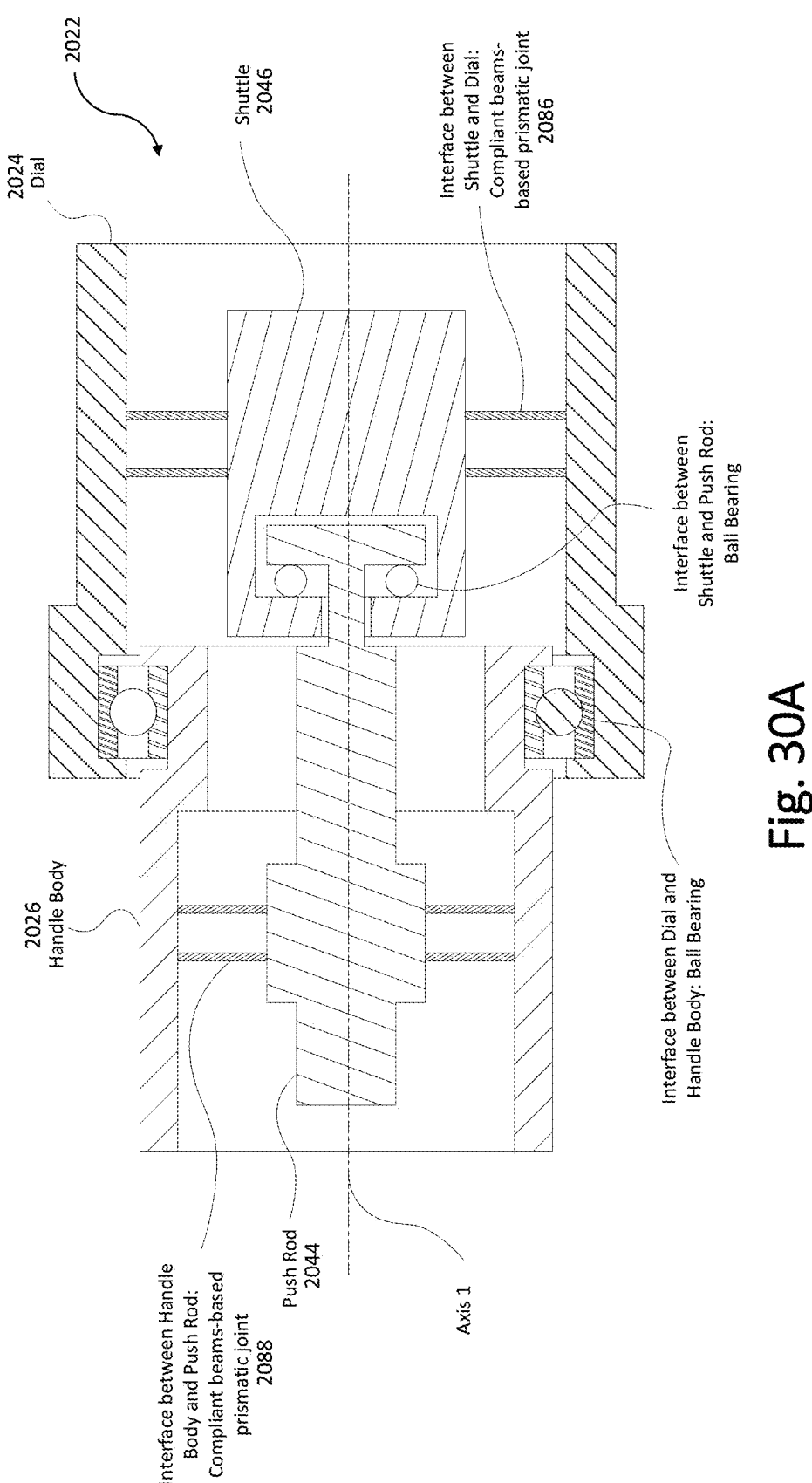
FIGS. 30A-E depict a handle assembly consisting of compliant (linear displacement) mechanisms (A); a compliant linear bearing interface between a shuttle and a dial (B); an ortho-planar bearing interface between a shuttle and a dial (C); an embodiment of a simple compliant mechanism between two bodies (D); and a compliant beams-based prismatic joint between two bodies (E).
Figure 30B:
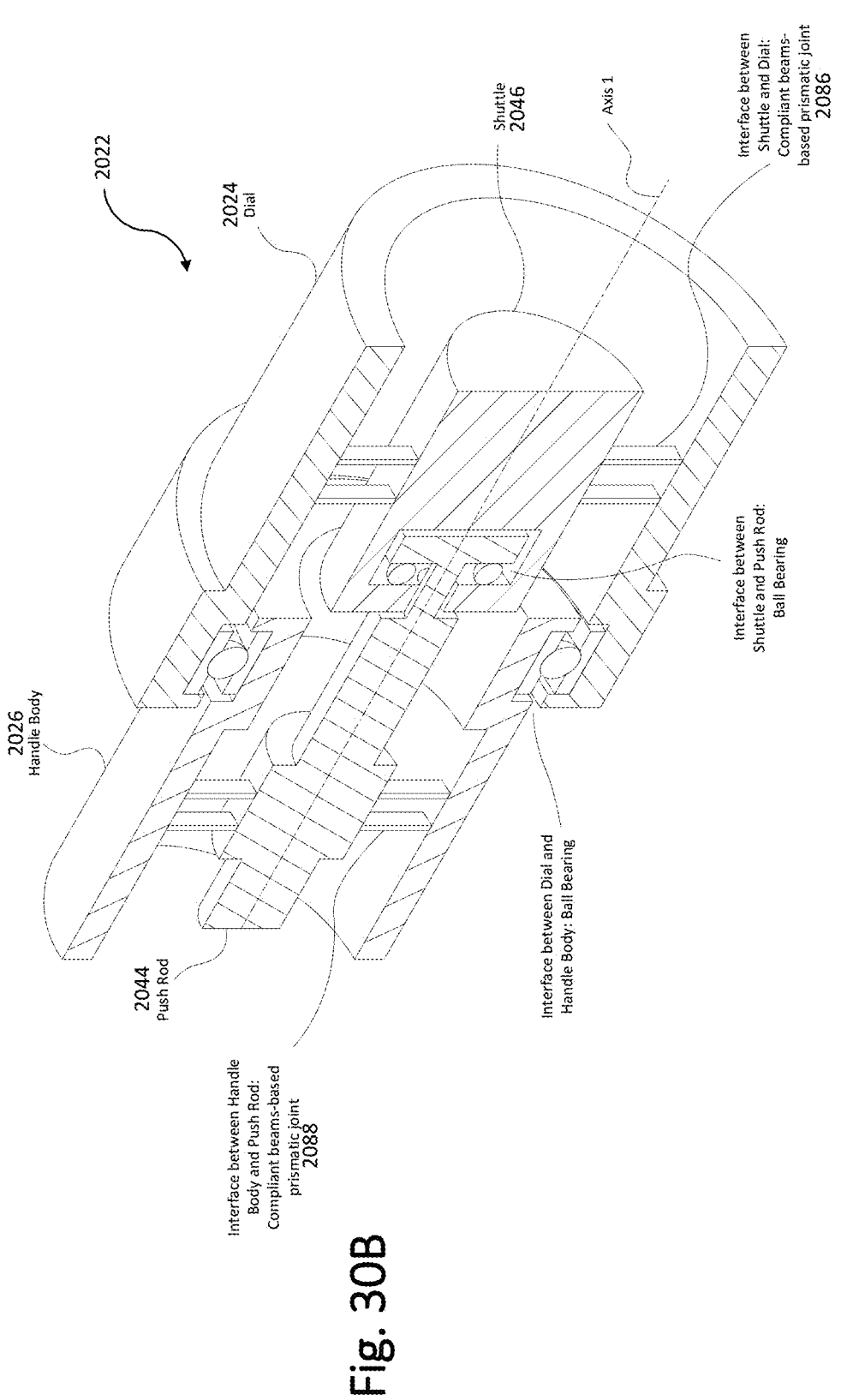

FIGS. 30A-B (front view and isometric view, respectively) represent a handle assembly 2022 including Handle Body 2026, Push Rod 2044, Dial 2024, and Shuttle 2046. This handle assembly 2022 is an embodiment that follows the constraint map shown in FIG. 24A. Here, rotation of Dial 2024 w.r.t. Handle Body 2026 about axis 1 leads to rotation of Shuttle 2046 about axis 1. Roll Input 2050 is represented in its simplest form as Dial 2024 itself. There exists a roll DoC joint between Dial 2024 and Shuttle 2046 as Dial 2024 acts as Roll Input 2050. The figure does not show the Closure Input 2048 and Closure Input Mechanism 2056. This embodiment represents a Dial-Shuttle interface to be a compliant mechanism 2086 that allows translation of Shuttle 2046 along direction 1. Also, Handle Body-Push Rod interface consists of a compliant mechanism 2088 that allows translation of Push Rod 2044 along direction 1 while the Push Rod 2044 has a roll DoC joint w.r.t. Handle Body 2026 about axis 1. This compliant mechanism (2086, 2088) may consist of 2 parallel beams that connect radially between Handle Body 2026 and Push Rod 2044; as well as radially between Dial-Shuttle. Also, there exists a roll DoF about axis 1 and translation DoC along direction 1 between Push Rod 2044 and Shuttle 2046.

Figure 30C:
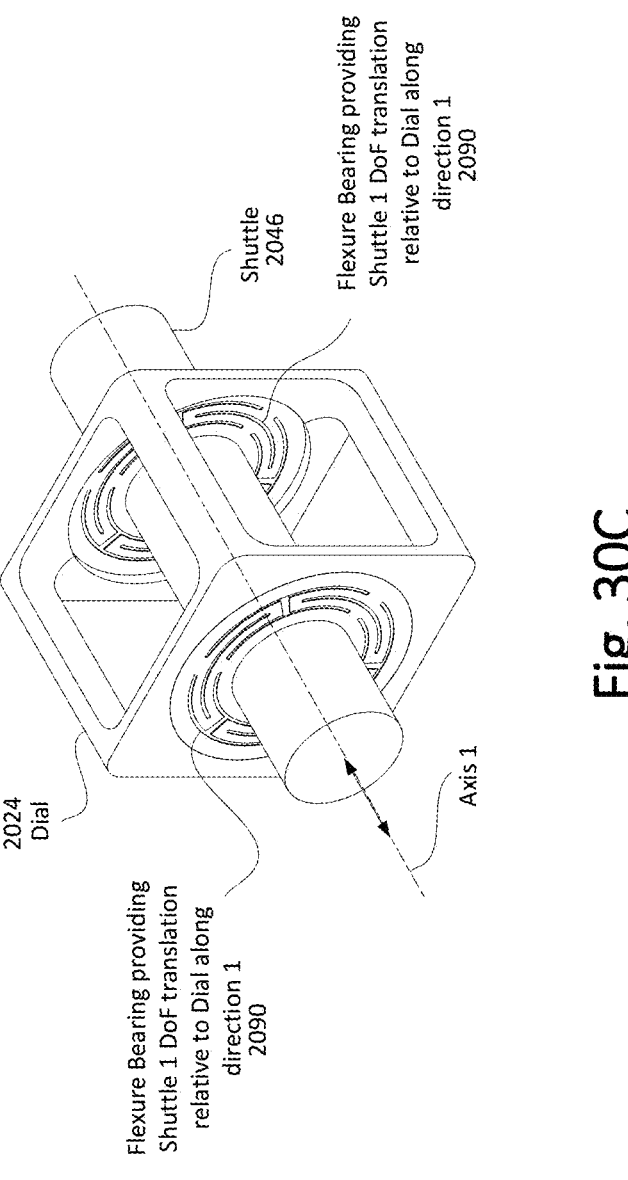
Figure 30D:
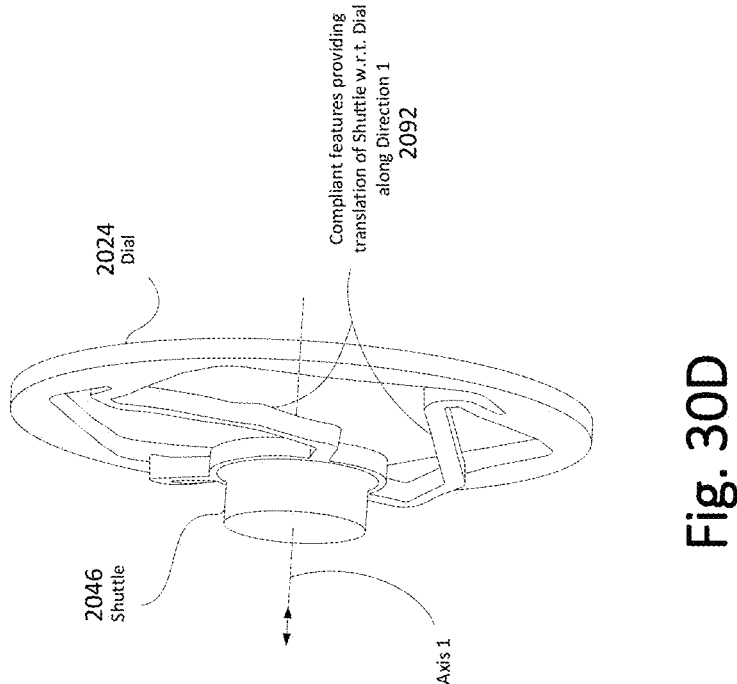
Figure 30E:
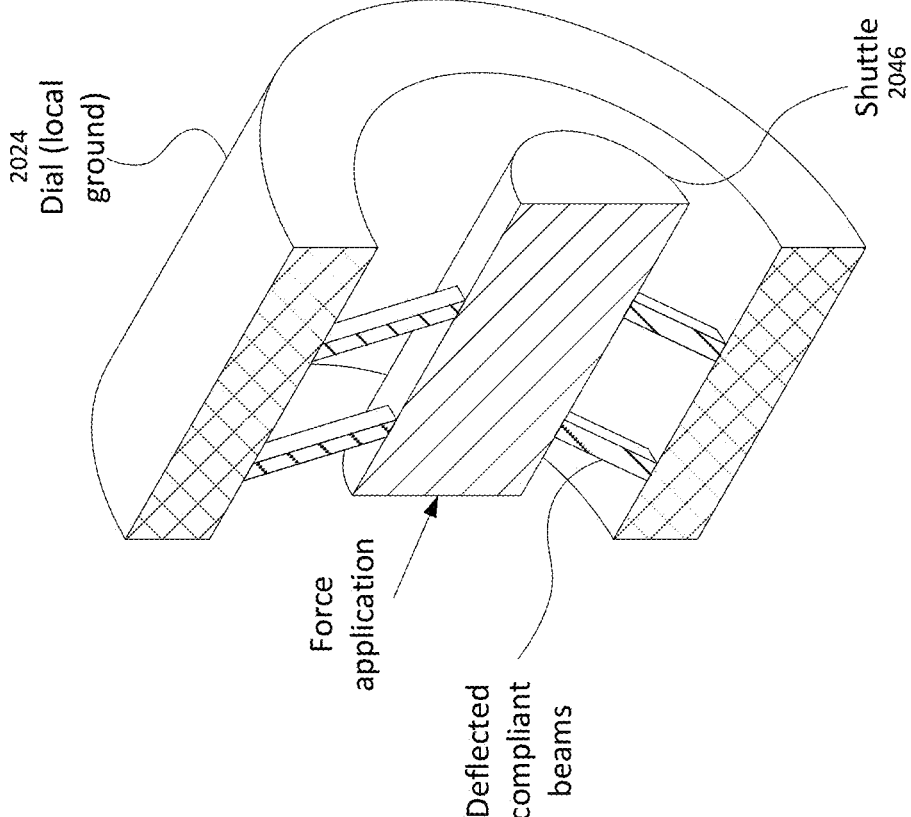

FIG. 30C, FIG. 30D and FIG. 30E show embodiments of flexure or compliant bearings that provide 1 DoF translation along direction 1. Such flexure bearing may be used as the interface between Dial 2024 and Shuttle 2046, and/or Handle Body 2026 and Push Rod 2044. FIG. 30C shows a linear 1-DoF linear flexure bearing 2090. FIG. 30D shows an ortho-planar spring 2092. When the inner ring is pushed along axis 1, ortho-planar spring 2092 helps a linear motion for the inner ring relative to the outer ring. Here, the outer ring can be integrated with the Dial 2024 whereas the inner ring can be connected to the Shuttle 2046. Similarly, the outer ring can be integral to the Handle Body 2026 whereas inner ring can be structurally connected to the Push Rod 2044.

Handle Assembly Constraint Map C

Figure 31A:
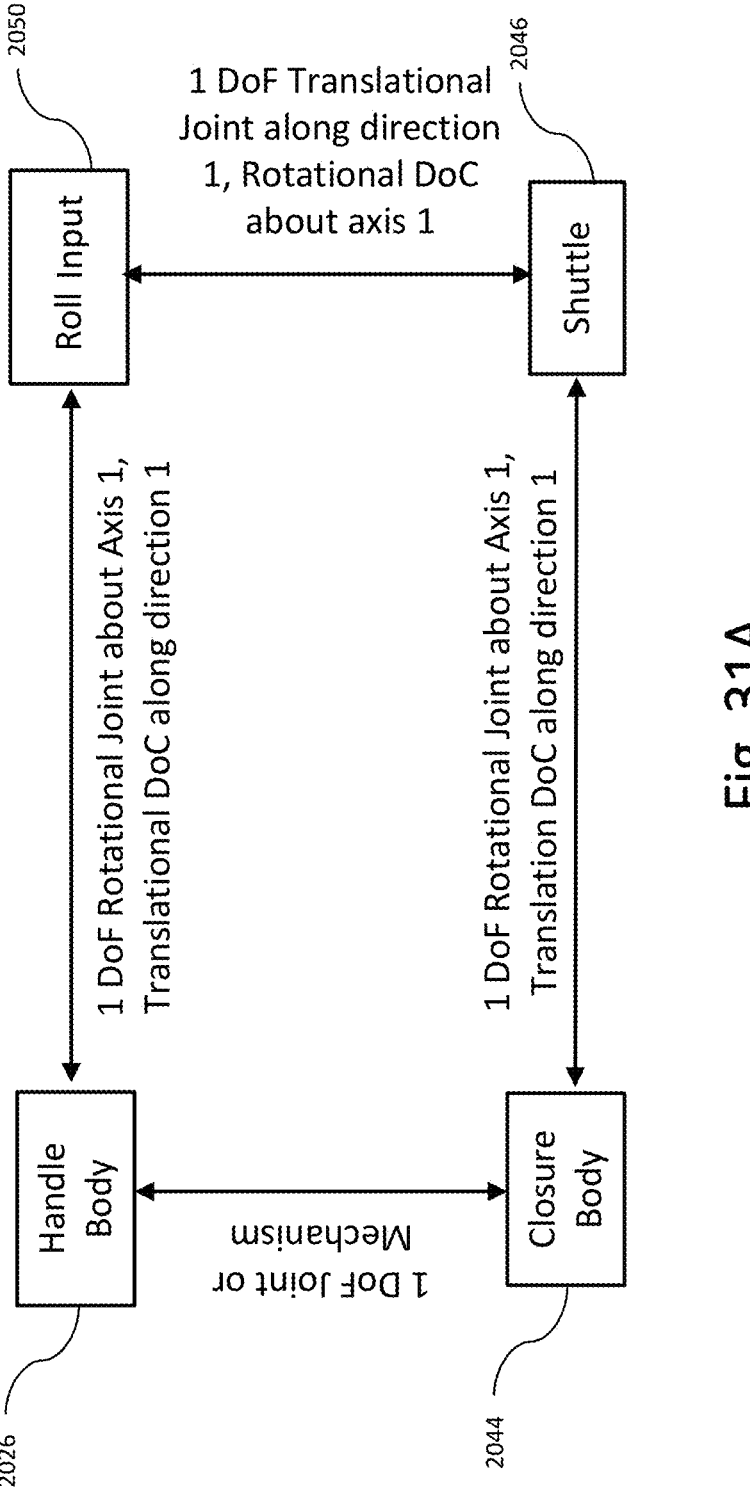
FIGS. 31A-B depict a constraint map C representing a handle assembly including a closure body, a handle body, a rotation input, a shuttle and joints/mechanisms between these bodies (A); and an extended constraint map C also including a closure input and a roll input (B).

FIG. 31A presents a constraint map showing a four-body system which includes Closure Body 2044, Handle Body 2026, Roll Input 2050, and Shuttle 2046. There exists at least 1-DoF joint or mechanism between Closure Body 2044 and Handle Body 2026. There exists a 1-DoF rotational joint providing rotation about axis 1 and 1 translational DoC along direction 1 between the Roll Input 2050 and Handle Body 2026. There also exists a 1-DoF translational joint along direction 1 and 1 rotational DoC joint constraining rotation about axis 1 between Shuttle 2046 and Roll Input 2050. Therefore, the output of the 1-DoF joint/mechanism that exists between Closure Body 2044 and Handle Body 2026 is transmitted to 1 DoF translation of Shuttle 2046 w.r.t. Roll Input 2050. This transmission may occur via a transmission member or by a one or more DoF joint that may exist between Shuttle 2046 and Closure Body 2044. This handle assembly 2022 may be a part of an apparatus/instrument that consists of an elongated tool shaft 2011 that has an EE assembly 2010 at its distal end (as shown in FIG. 23). The elongated tool shaft 2011 may lie distal to the handle assembly 2022. The EE assembly 2010, as described earlier, may consist of a Moving Jaw 2012 and a Fixed Jaw 2014. Translation of Shuttle 2046 w.r.t. Roll Input 2050 along direction 1 may lead to the relative motion of Moving Jaw 2012 w.r.t. Fixed Jaw 2014. Also, rotation of Roll Input 2050 may lead to rotation of EE assembly 2010 about its roll axis.

Figure 31B:
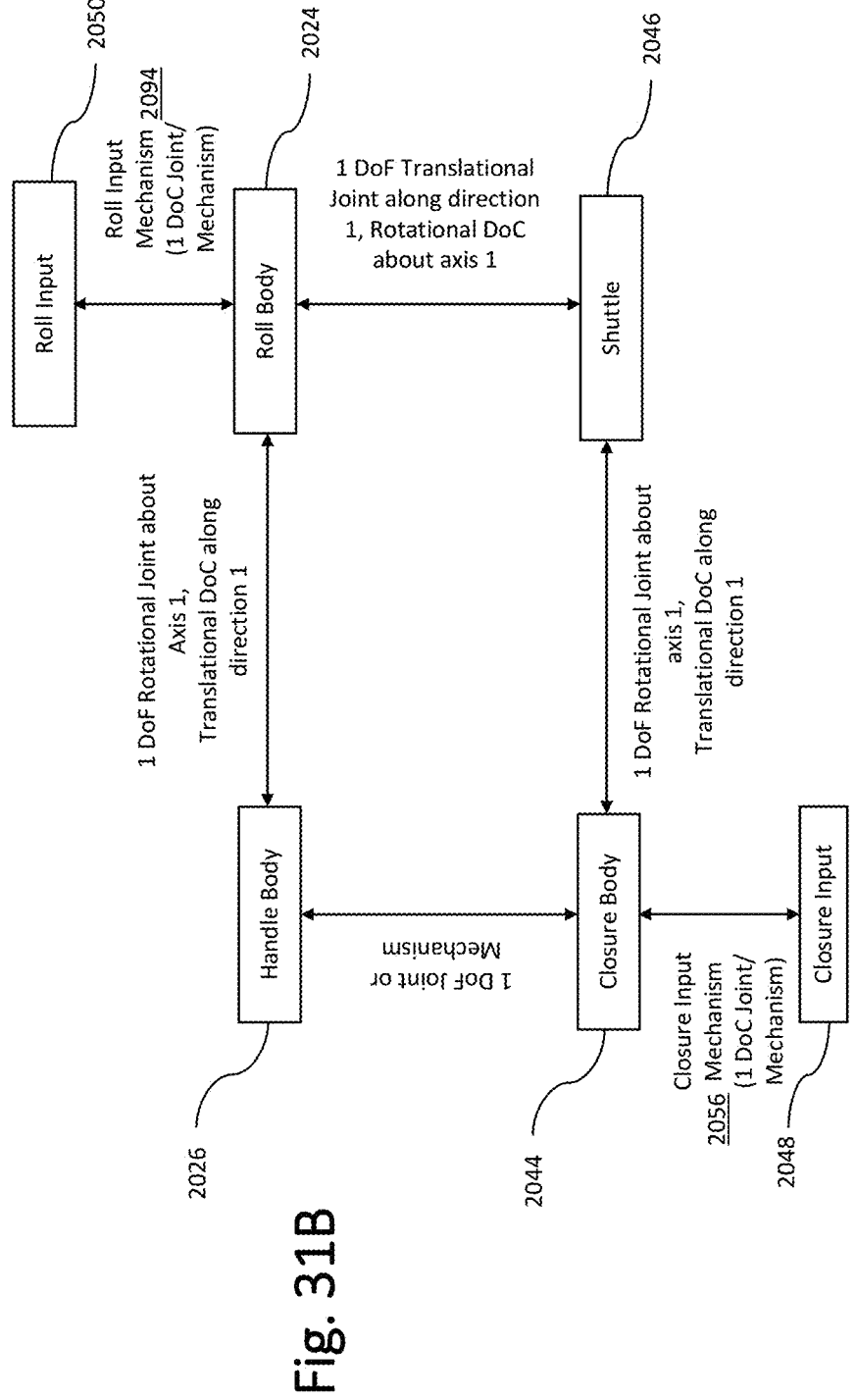

FIG. 31B presents an extended constraint map showing a six-body system which includes Closure Body 2044, Handle Body 2026, Roll Body 2024, Shuttle 2046, Closure Input 2048, and Roll Input 2050. There exists at least a 1-DoF joint or mechanism between Closure Body 2044 and Handle Body 2026. This constraint map C' is an extension of constraint map C shown in FIG. 31A. There exists a Closure Input Mechanism 2056 between Closure Input 2048 and Closure Body 2044 such that translation input can be transmitted via Closure Input 2048. There also exists a Roll Input Mechanism 2094 between Roll Input 2050 and Roll Body 2024 such that rotation input can be transmitted via Roll Input 2050. Each of these two mechanisms help transmit motion by providing a DoC between Closure Input 2048 and Closure Body 2044, and between Roll Input 2050 and Roll Body 2024. Embodiments shown in the following sections map to constraint map C. As constraint map B is an extension of constraint map A, similarly constraint map C' is an extension of constraint map C.

Handle Assembly Embodiments—Mapping to Constraint Map C

Figure 32A:
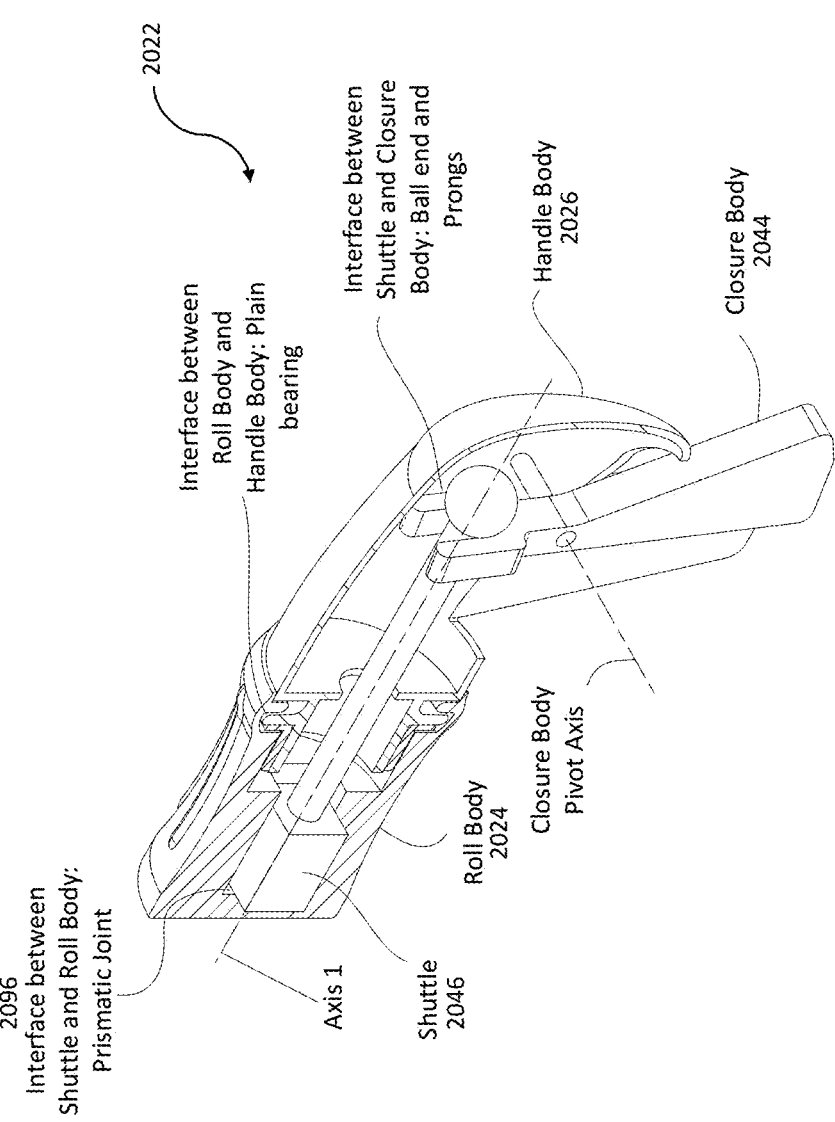
FIGS. 32A-B depict a handle assembly consisting of a ball and prong interface between a closure body and a shuttle—isometric sectional view (A); and a handle assembly consisting of a ball and prong interface between a closure body and a shuttle—sectional view (B).
Figure 32B:
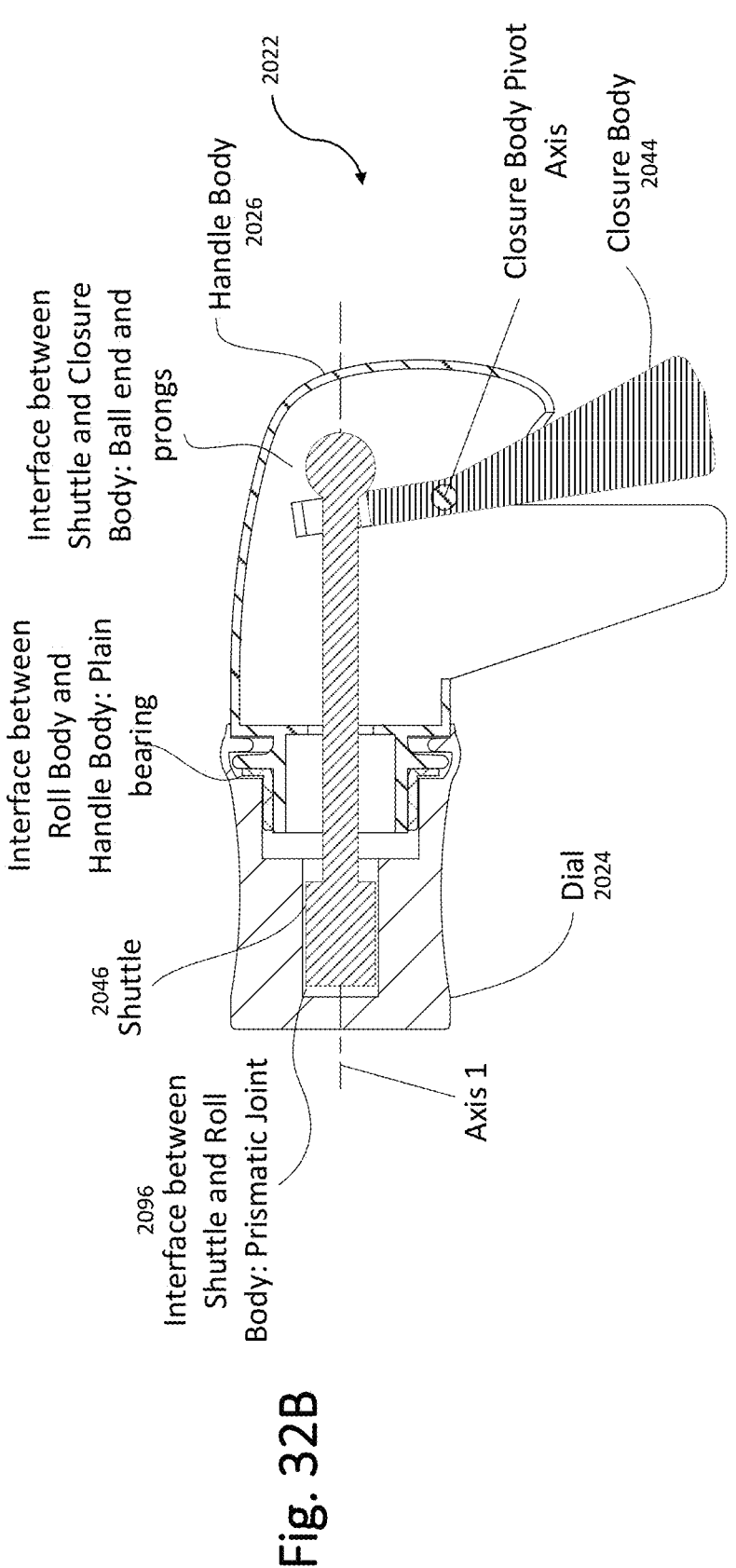

FIGS. 32A-B represents a handle assembly 2022 including Handle Body 2026, Closure Body 2044, Roll Input 2050, and Shuttle 2046. This embodiment maps to the constraint map shown in FIG. 31. Here, Roll Input 2050 can be termed as Roll Input 2050 as it is present in its simplest form. Rotation of Roll Input 2050 w.r.t. Handle Body 2026 about axis 1 leads to rotation of Shuttle 2046 about axis 1. Also, the Shuttle 2046 can translate w.r.t. Roll Input 2050 along direction 1. Therefore, the Shuttle 2046 has a prismatic joint 2096 w.r.t. Roll Input 2050. The Shuttle 2046 is an elongated member which extends towards the proximal end such that it has a ball/oval end which interfaces with the Closure Body 2044. Closure Body 2044 is shown as a level that has a 1-DoF rotation joint w.r.t. Handle Body 2026. The user triggers this input on one end of the pivot which leads to rotation of its other end about the pivot axis. This other end interfaces with the Shuttle 2046. Therefore, the ball end of the Shuttle 2046 interfaces with the Closure Body 2044.

Closure Body 2044 has two prongs or a wishbone-like or a slot feature which can pull the Shuttle 2046 by pulling the ball end of the Shuttle 2046. This feature on Closure Body 2044 may have features to pull the Shuttle's proximal end and/or push the proximal end of the Shuttle 2046.

As the Closure Body 2044 rotates about the pivot, its two-prong end rotates about the pivot joint axis. This end produces a translation of Shuttle's proximal end along direction 1. Translation of proximal end of Shuttle 2046 leads to translation of the distal end of the Shuttle 2046 which interfaces with the Roll Input 2050. Therefore, the interface between Shuttle 2046 and Closure Body 2044 is such that the proximal end of Shuttle 2046 translates w.r.t. Closure Body 2044 as the Closure Body 2044 (lever) rotates about its pivot axis in order to produce a translation w.r.t. Roll Input 2050 along direction 1. FIG. 32A and FIG. 32B represents a ball/oval end of the Shuttle 2046. This end may be conical or anchor-like or any other feature which can interface with Closure Body 2044 in order to produce a translation of Shuttle 2046 along direction 1. Also, this translation can be towards the proximal end and/or towards the distal end.

Figure 33:
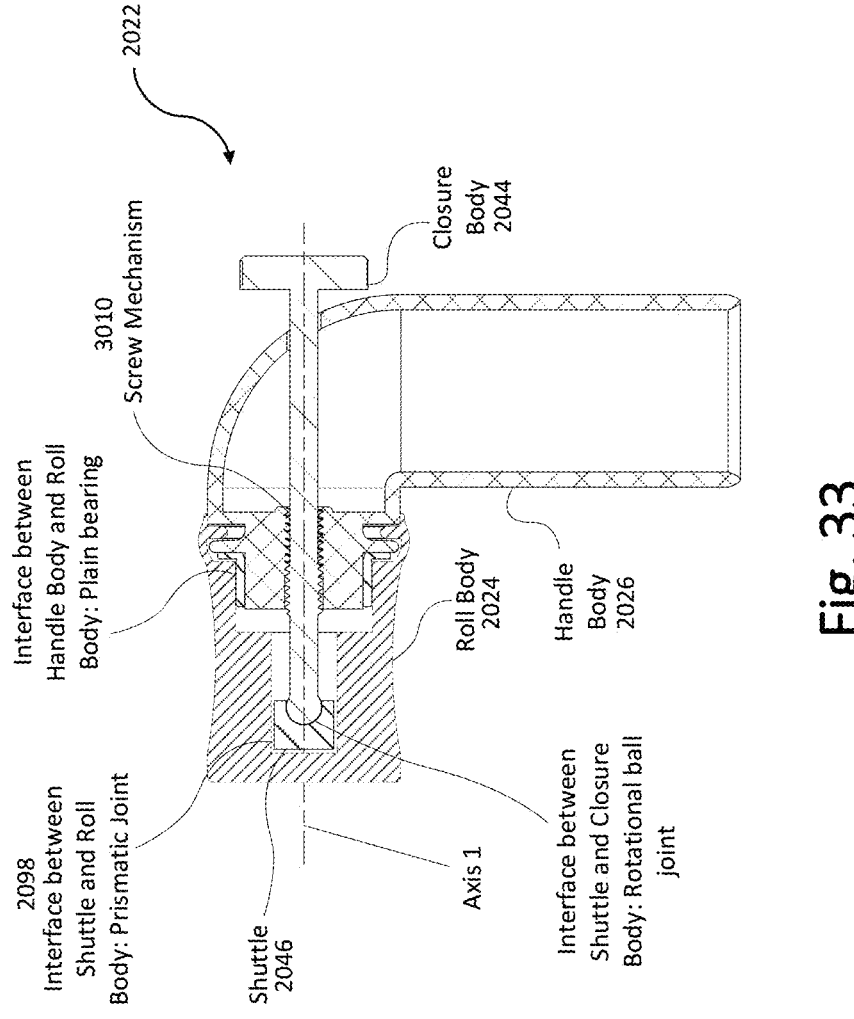
FIG. 33 depicts a handle assembly consisting of a screw mechanism between a closure body and a shuttle.

FIG. 33 represents a handle assembly 2022 that includes Handle Body 2026, Roll Input 2050, Closure Body 2044, and Shuttle 2046. This embodiment maps to the constraint map shown in FIG. 31. Here, Roll Input 2050 can be termed as Roll Input 2050 as it is present in its simplest form. Rotation of Roll Input 2050 w.r.t. Handle Body 2026 about axis 1 leads to rotation of Shuttle 2046 about axis 1. Also, the Shuttle 2046 can translate w.r.t. Roll Input 2050 along direction 1. Therefore, the Shuttle 2046 has a prismatic joint 2098 w.r.t. Roll Input 2050. There exists a screw mechanism 3010 between Closure Body 2044 and Handle Body 2026. Closure Body 2044 acts as a screw and Handle Body 2026 acts like a nut. Handle Body 2026 is held stationary by the user while the Closure Body 2044 (screw) is actuated by the user. Therefore, Closure Body 2044 moves w.r.t. Handle Body 2026 by rotating about axis 1 and translating along direction 1. Here, Handle Body 2026 acts as a local ground. At the distal end of the Closure Body 2044, there exists a ball joint between Closure Body 2044 and Shuttle 2046 such that Shuttle 2046 can rotate relative to Closure Body 2044 about axis 1. Also, due to the presence of this ball joint, rotation of the distal end of Closure Body 2044 (screw) w.r.t. Handle Body 2026 does not lead to transmission of rotation to the Shuttle 2046. Translation of distal end of Closure Body 2044 leads to the transmission of translation to Shuttle 2046. Therefore, the Shuttle 2046 translates along direction 1 w.r.t. Roll Input 2050. Here, the actuation of the screw may take place by rotation of the proximal end of Closure Body 2044 by the user manually or using a mechanical actuator or via an electromechanical actuator (e.g., linear motor).

Figure 34A:
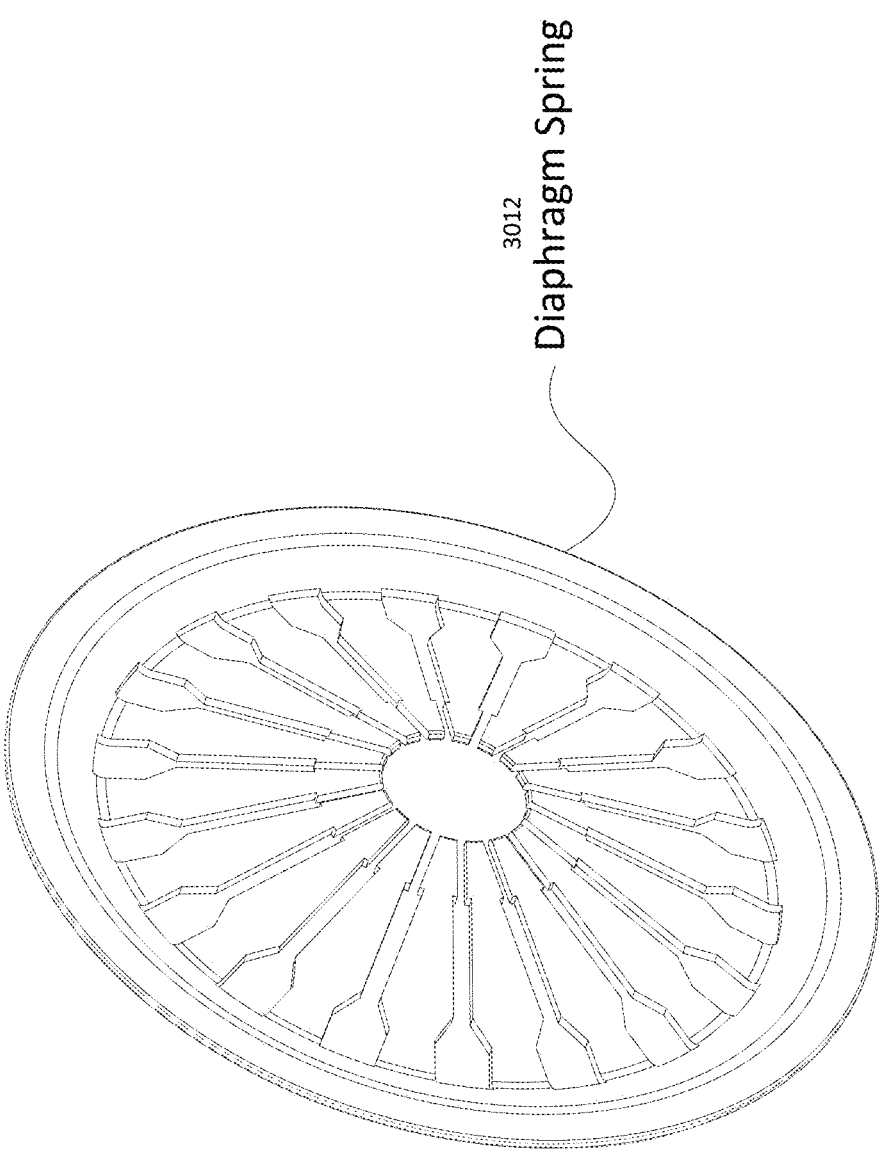
FIGS. 34A-C depict an embodiment of a diaphragm spring (A); a handle assembly consisting of a closure body which is a diaphragm spring—isometric sectional view (B); and a handle assembly consisting of a closure body which is a diaphragm spring—sectional view (C).

FIG. 34A represents a diaphragm spring 3012 which is commonly used in automotive applications as part of the clutch assembly. Diaphragm spring 3012 is pre-bent and is biased towards one direction. When the spring 3012 is deflected in the opposite direction, it tends to get back to its pre-bent configuration.

Figure 34B:
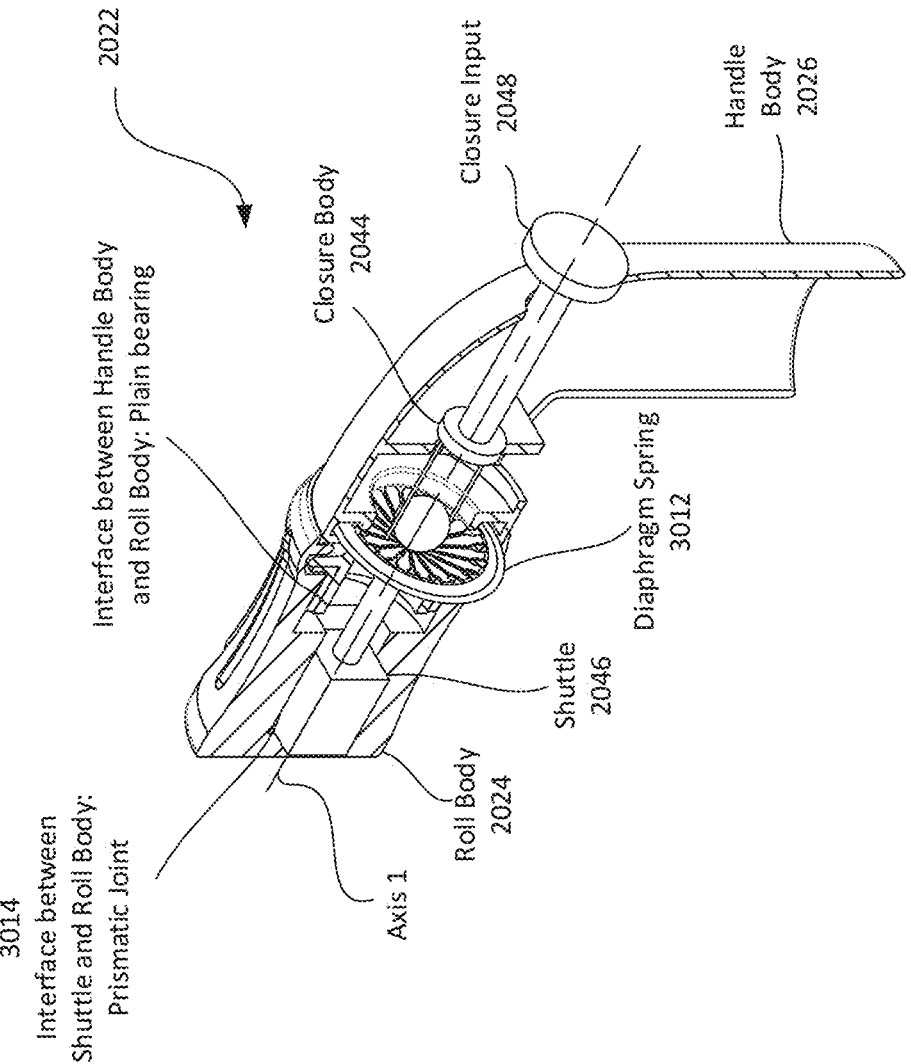
Figure 34C:
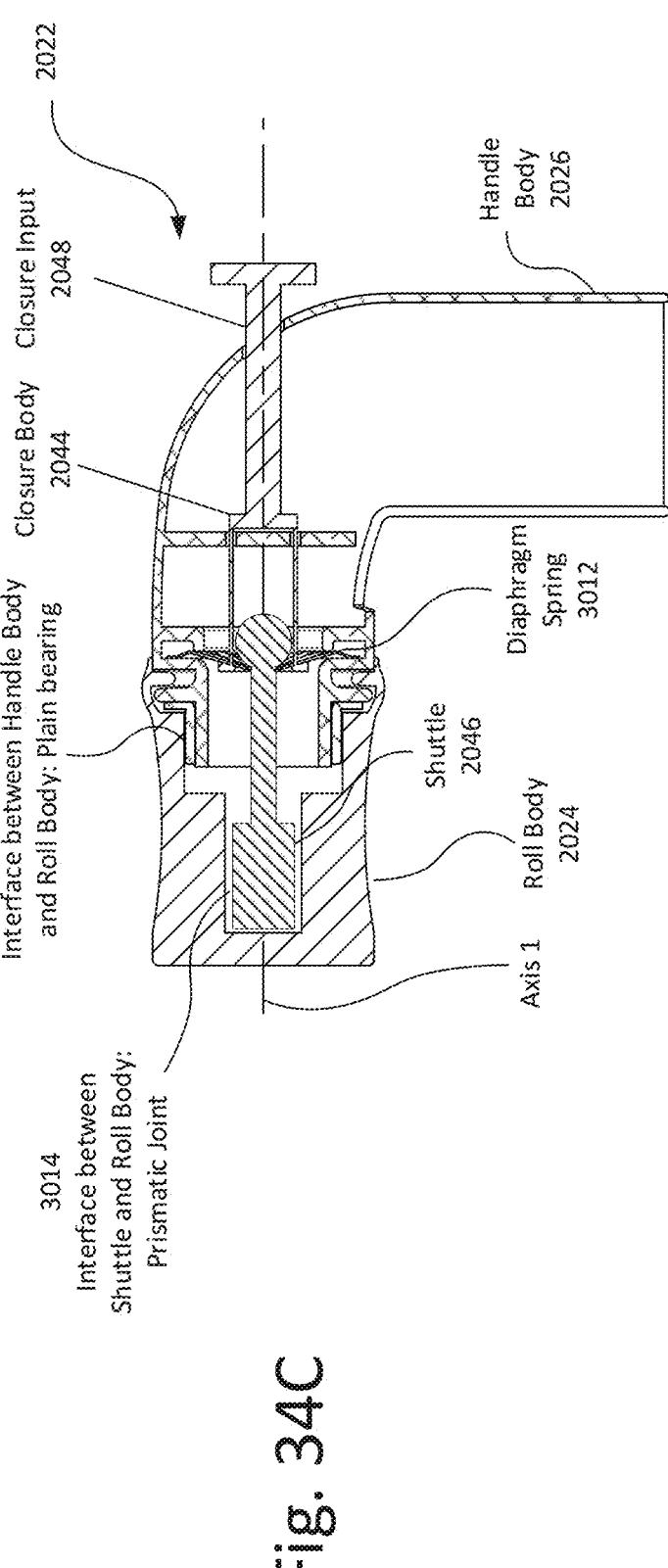

FIG. 34B and FIG. 34C (different views of the same assembly) represents a handle assembly 2022 including Handle Body 2026, Closure Body 2044, Roll Body 2024, and Shuttle 2046. This embodiment maps to the constraint map shown in FIG. 31. Here, Roll Body 2024 can be termed as Roll Input 2050 as it is present in its simplest form. Rotation of Roll Input 2050 w.r.t. Handle Body 2026 about axis 1 leads to rotation of Shuttle 2046 about axis 1. Also, the Shuttle 2046 can translate w.r.t. Roll Input 2050 along direction 1. Therefore, the Shuttle 2046 has a prismatic joint 3014 w.r.t. Roll Input 3050. There exists a Closure Body 2044 that interfaces with a diaphragm spring 3012. This spring 3012, as shown in FIG. 34A is meant to interface with Shuttle 2046 such that it produces the translation of Shuttle 2046 w.r.t. Roll Input 2050 along direction 1. Therefore, the Closure Body 2044 produces 1 DoF w.r.t. Handle Body 2026 (as mentioned in the constraint map C shown in FIG. 31). The spring 3012 consists of an outer ring which is constrained w.r.t. Handle Body 2026 and has an inner orifice. Between the outer ring and inner orifice, lies compliant radial beams which can deflect in order to produce a displacement of the inner orifice. The Closure Body 2044 may have an elongated member (Closure Input 2048, shown in FIGS. 34B-C) which the user can actuate and deflect the radial beams mentioned above.

The Shuttle 2046 is an elongated member that elongates proximal to the feature that mates with Roll Input 2050 via the prismatic joint 3014. The proximal end of the Shuttle 2046 may be a ball end or an oval end or similar feature that can be constrained to the inner orifice of the diaphragm spring 3012. Once the Shuttle 2046 is mated to this orifice, deflection of diaphragm spring 3012 w.r.t. Handle Body 2026 leads to translation of Shuttle 2046 via pulling of the proximal end of the Shuttle 2046. This deflection of the spring 3012 may take place via cables that pull around the inner orifice or via an elongated rigid member as shown in FIGS. 34A-B that extends external to the handle assembly 2022.

As mentioned, deflection of the spring 3012 can be carried out via pulling of cables, or a rigid extension of the diaphragm spring 3012. In the case where cables are used, the cables may be constrained along the direction 1 w.r.t. handle assembly 2022. The cable(s) mentioned here constitute the Closure Input Mechanism 2056. This Closure Input Mechanism 2056 may also consist of braided cable(s) or nitinol wire(s) or linkage mechanism or other similar means of transmission. Upon rotation of the Roll Input 2050, the ball end of the Shuttle 2046 will rotate relative to the diaphragm spring 3012 about axis 1. This sliding of the ball may require the presence of a thrust bearing or ball bearing interface w.r.t. the Closure Body 2044. Or the ball may be made out a lubricious material (e.g., POM/Acetal, PEEK, PTFE, etc.) in order to prevent impact on roll due to friction at this interface with Closure Body 2044.

Handle Assembly Embodiments—Discrete Dial Rotation (Rotation Resistance Force Members)

Figure 35A:
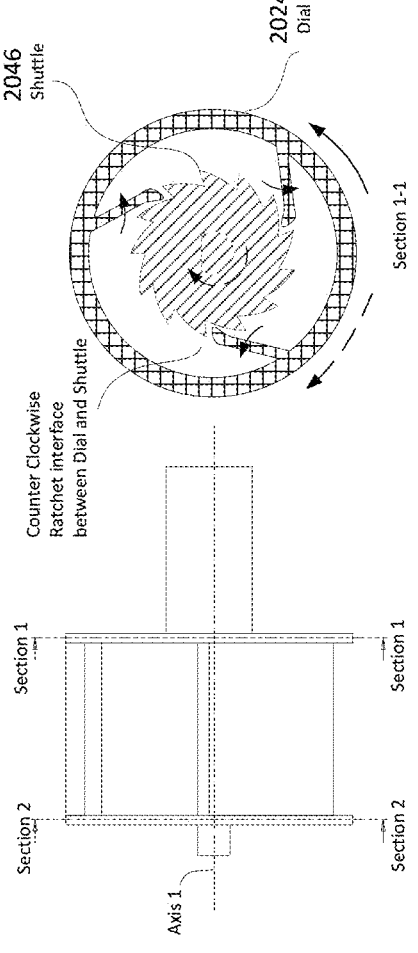
FIGS. 35A-C depict a counter-clockwise ratchet (A); a clockwise ratchet (B); and a dial-shuttle schematic diagram showing section 1 and section 2 locations (C).
Figure 35B:
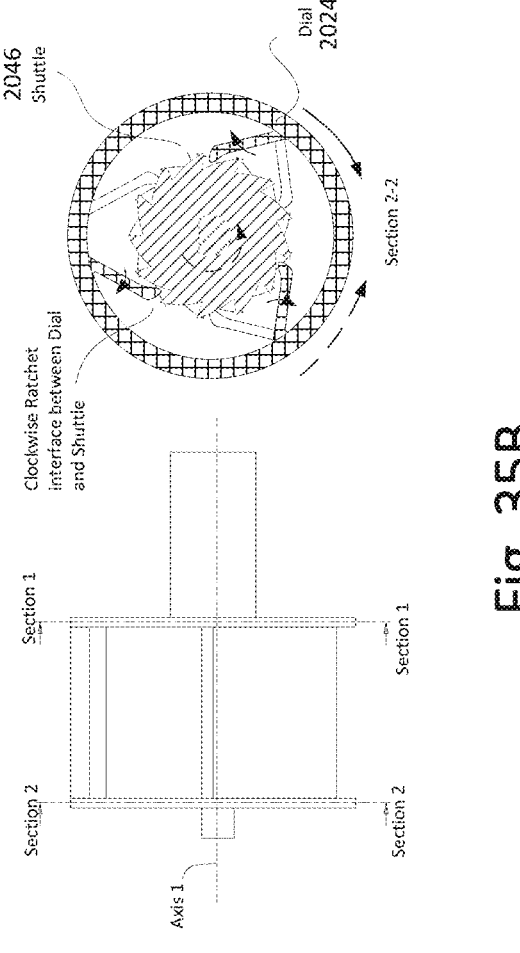
Figure 35C:
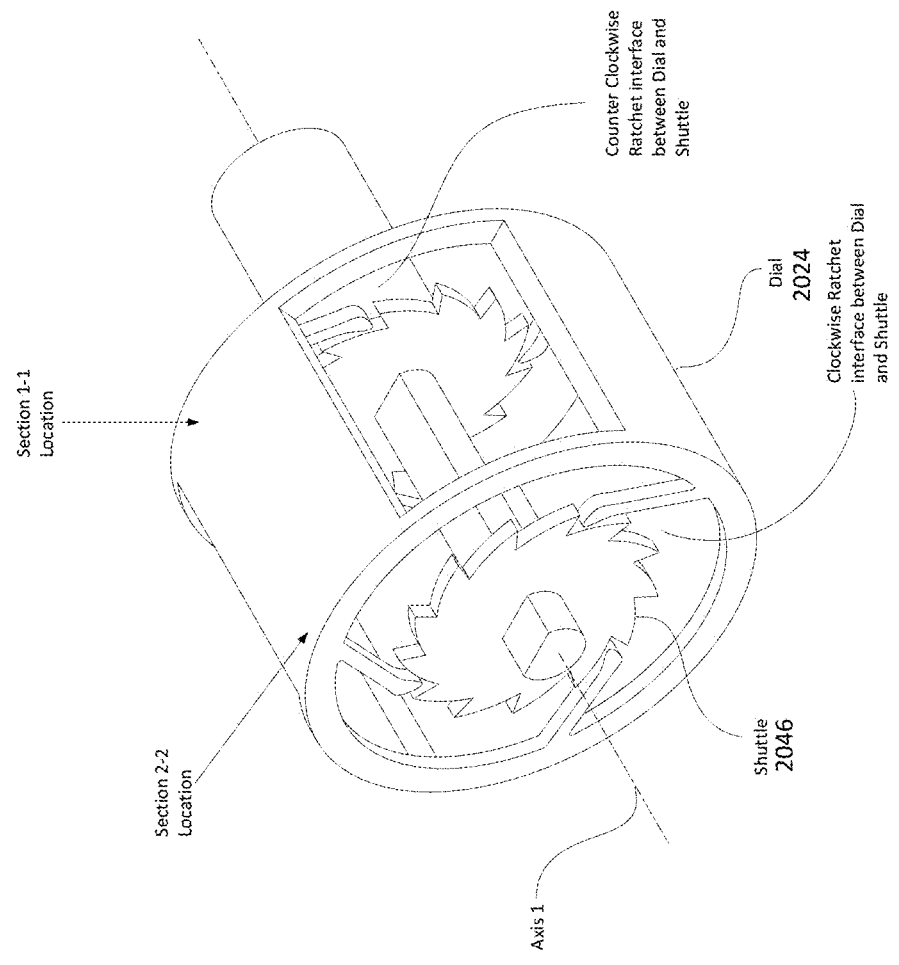

FIGS. 35A-C represent a configuration of Roll Input 2050 and Shuttle 2046 which can be part of a handle assembly 2022 that maps to any one of the constraint maps shown in FIG. 24A, FIG. 24B or FIG. 31. Here, Roll Input 2050 can be termed as Dial 2024 as it is present in its simplest form. Rotation of Dial 2024 w.r.t. Handle Body 2026 about axis 1 leads to rotation of Shuttle 2046 about axis 1. Also, the Shuttle 2046 can translate w.r.t. Dial 2024 along direction 1. Therefore, the Shuttle 2046 has a prismatic joint w.r.t. Dial 2024.

In this embodiment, the Dial 2024 and Shuttle 2046 interface forms two one-way ratchets. One benefit of the existence of a ratchet is to provide discrete motion feedback while the Dial 2024is rotated either clockwise (CW) or counterclockwise (CCW) about axis 1. FIG. 35A shows a configuration in which CCW rotation of Dial 2024 about axis 1 produces relative motion between Dial 2024 and Shuttle 2046. There exists a compliant clutch mechanism between Dial 2024 and Shuttle 2046 such that when the Dial 2024 is rotated CCW, the compliant portion of the Dial 2024 which serves as a pawl deflects and skips over the angled teeth profile present on the Shuttle 2046. Whereas, when the Dial 2024 is rotated CW, it leads to rotation of Shuttle 2046 along with its own rotation about axis 1. This embodiment is shown in FIG. 35A is termed as a counterclockwise ratchet.

FIG. 35B shows a configuration in which CW rotation of Dial 2024 about axis 1 produces relative motion between Dial 2024 and Shuttle 2046. There exists a compliant clutch mechanism between Dial 2024 and Shuttle 2046 such that when the Dial 2024 is rotated CW, the compliant portion of the Dial 2024 which serves as a pawl deflects and skips over the angled teeth profile present on the Shuttle 2046. Whereas when the Dial 2024 is rotated CCW, it leads to rotation of Shuttle 2046 along with its own rotation about axis 1. This embodiment is shown in FIG. 35B is termed as a clockwise ratchet.

FIG. 35C shows an embodiment showing the clutch mechanism shown in FIG. 35A and FIG. 35B as part of a single assembly where the Shuttle 2046 from FIG. 35A is coupled to Shuttle 2046 from FIG. 35B using a common shaft and common axis (axis 1). Also, Dial 2024 from FIG. 35A is coupled to Dial 2024 from FIG. 35B which are merged while being spaced axially along axis 1. FIG. 35C shows a configuration of the Dial-Shuttle interface in which CCW rotation of Dial 2024 about axis 1 will produce relative motion between Dial 2024 and Shuttle 2046 at section 1 and CW rotation of Dial 2024 about axis 1 will produce relative motion between Dial 2024 and Shuttle 2046 at section 2. Therefore, during CCW rotation of Dial 2024 about axis 1, discrete rotation feedback will be achieved via ratchet system present in section 1, and during CW rotation of Dial 2024 about axis 1, discrete rotation feedback will be achieved via ratchet system present in section 2. This way, a user may receive haptic, and/or audio, and/or visual feedback while rotating the Dial 2024. Also, when Dial 2024 is rotated with a high revolution per minute (rpm), it will come to halt relatively quickly when compared to a Dial-Shuttle configuration that lacks ratcheting.

Figure 36A:
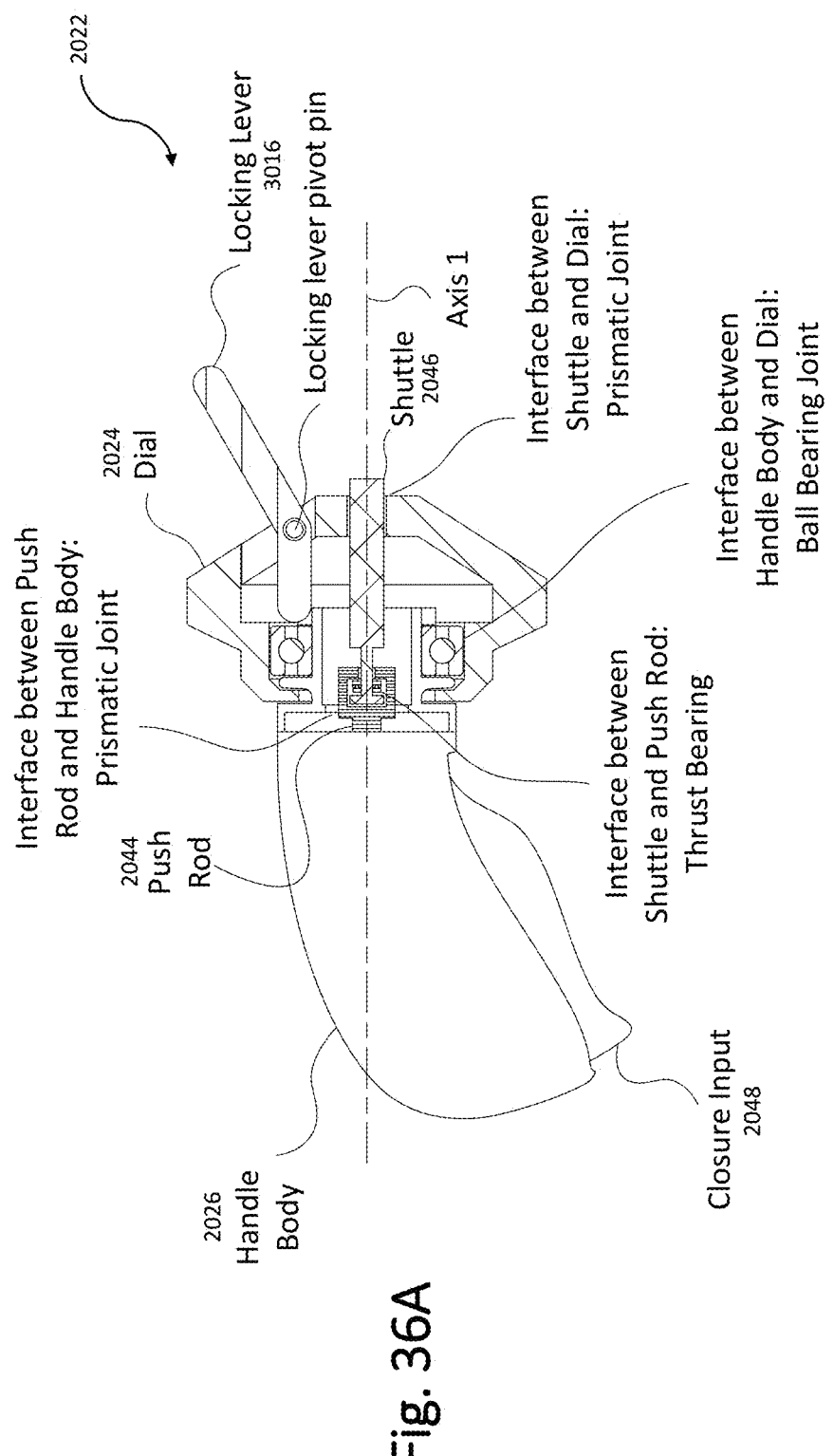
FIGS. 36A-D depict a handle assembly showing a locking lever for discrete dial rotation front view (A); a handle assembly showing a locking lever for discrete dial rotation—isometric view (B); a handle assembly showing the locking lever for discrete dial rotation—isometric view with transparent lever (C); and an isolated cross-section of a locking lever and mating slot features on a handle body.
Figure 36B:
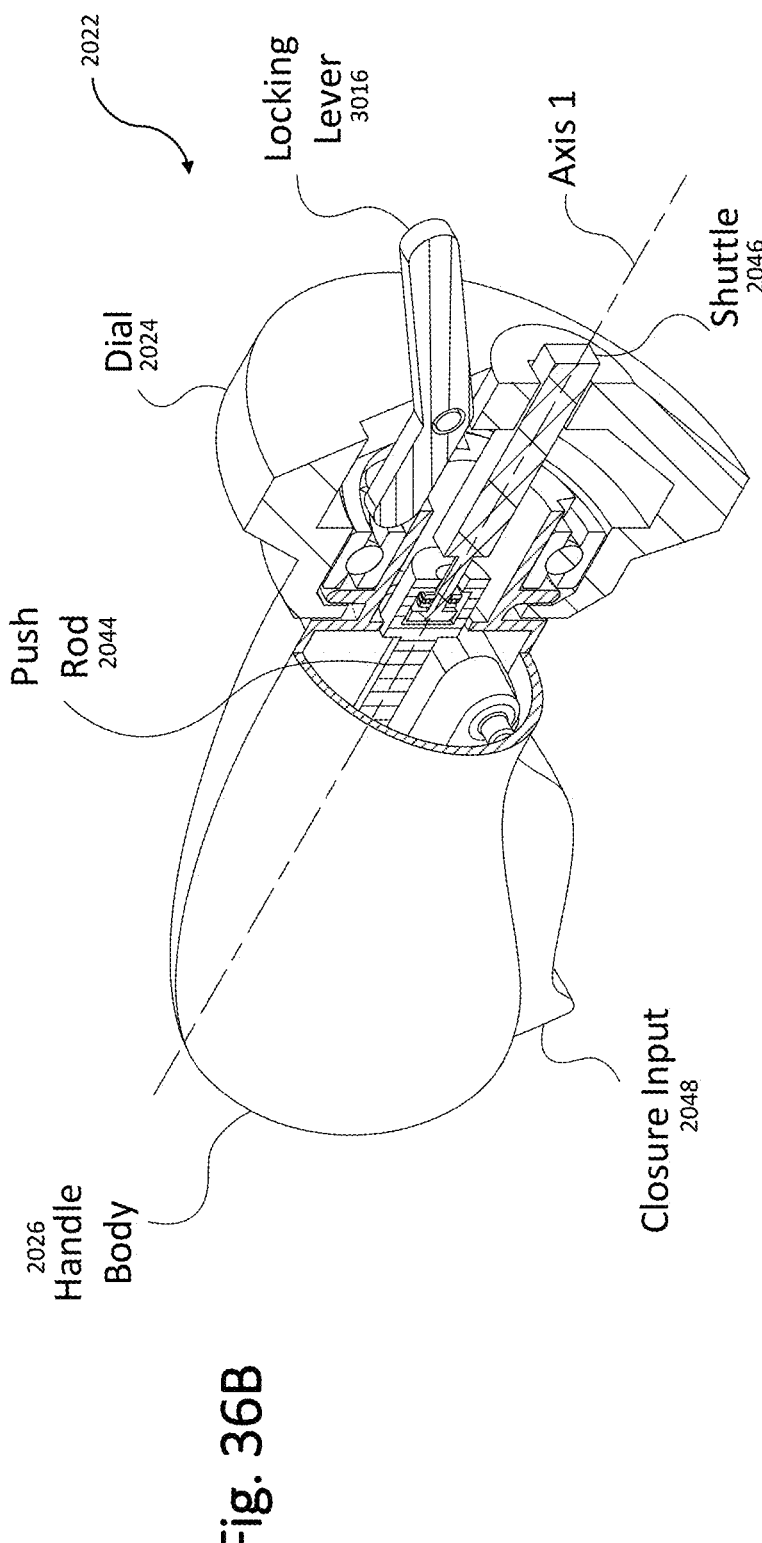
Figure 36C:
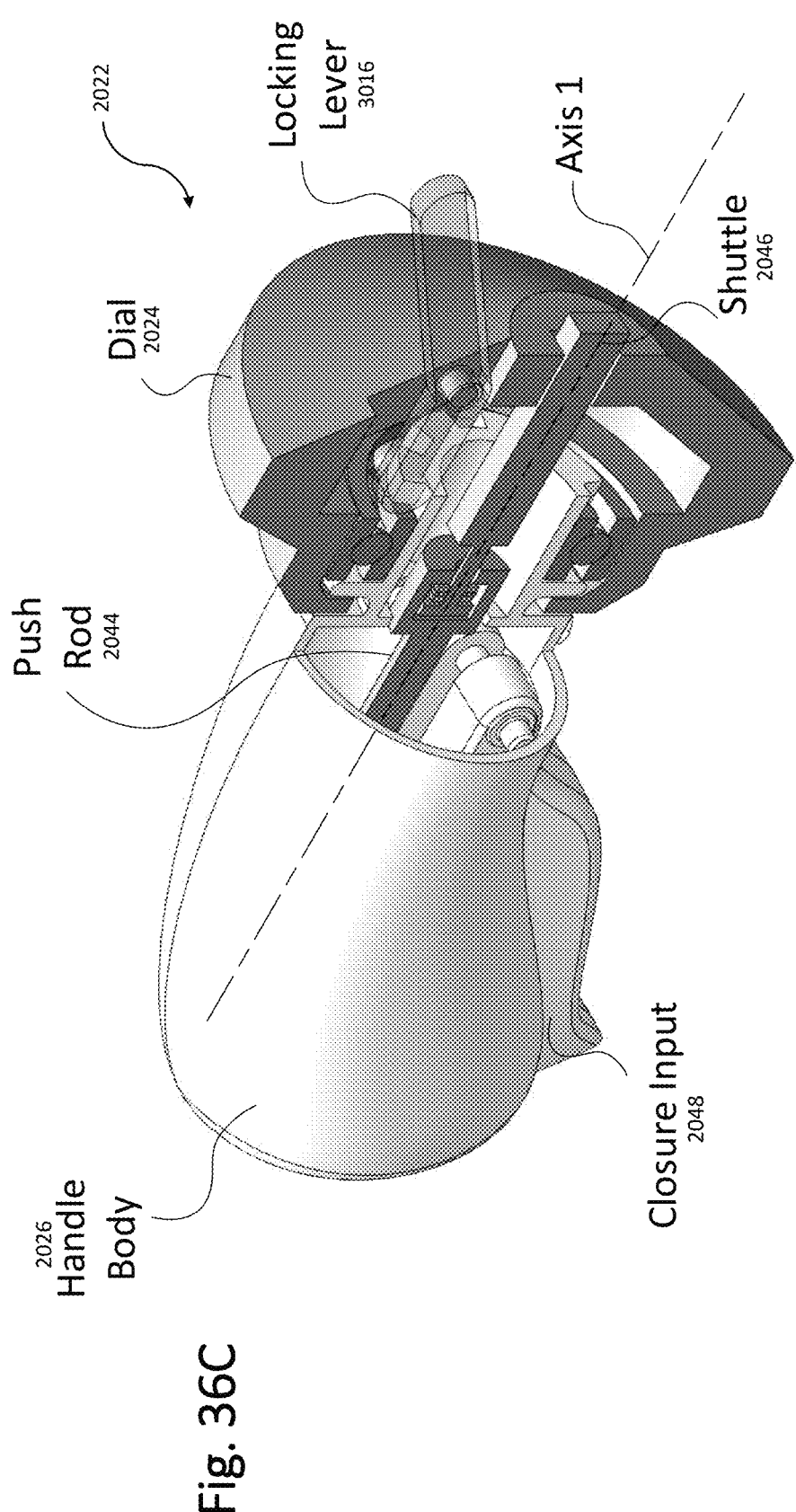

FIGS. 36A-C shows Handle Body 2026 and Dial 2024 which may be part of a handle assembly 2022 that may map to the constraint map shown in FIGS. 24A-B or FIG. 31. Here, Roll Input 2050 can be termed as Dial 2024 as it is present in its simplest form. Rotation of Dial 2024 w.r.t. Handle Body 2026 can be controlled such that angular orientation of Dial 2024 can be locked w.r.t. Handle Body 2026 via locking levers 3016.

In this embodiment, position locking levers 3016 are class I levers that are pivoted on the Dial 2024. These lever(s) 3016 may be singular or multiple (e.g., three locking levers located at an offset of one-hundred-and-twenty degrees (120°) that may be operated by the index finger, middle finger and/or thumb of the user). These levers 3016 may also be spring-loaded (e.g., via a torsion spring at the rotation pivot for each locking lever) such that it is always biased towards locking state. Each lever 3016 may have a peg that sits into one of many slots present on Handle Body 2026.

Figure 36D:
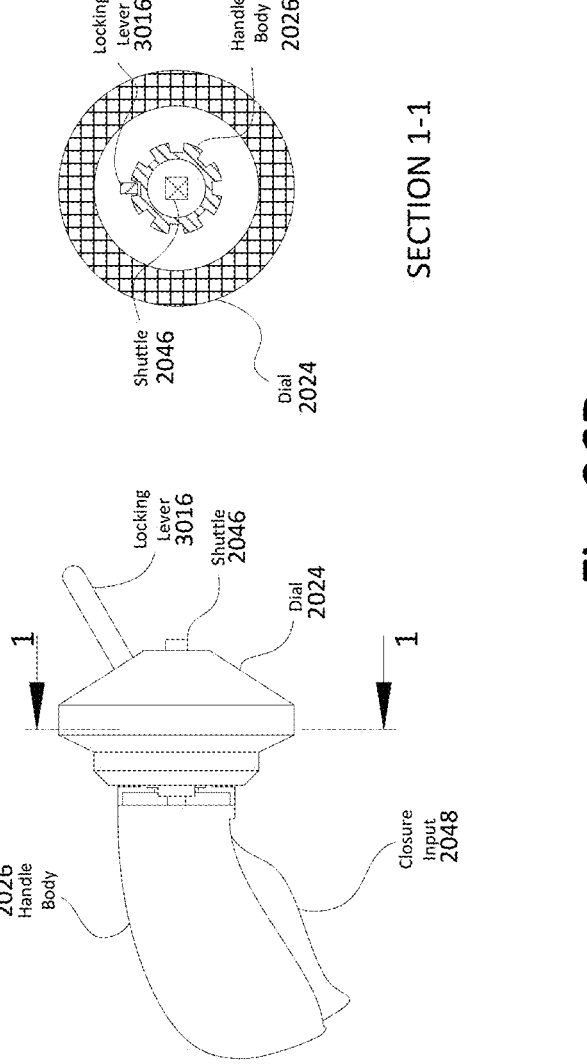

FIG. 36D shows an isolated cross-section of a locking lever 3016 and Handle Body 2026 feature that interfaces with locking lever(s). Once pressed, these levers raise above the Handle Body 2026 such that locking lever(s) can rotate as Dial 2024 rotates about axis 1. When the user releases these levers, the levers sit in a respective slot on the Handle Body 2026 and lock the rotation of Dial 2024 w.r.t. Handle Body 2026 about axis 1. This mechanism provides a discrete rotation of Dial 2024 w.r.t. Handle Body 2026 about axis 1 with pitch being dependent on the pitch of slots on Handle Body 2026 which interface with locking lever(s).

Figure 37A:
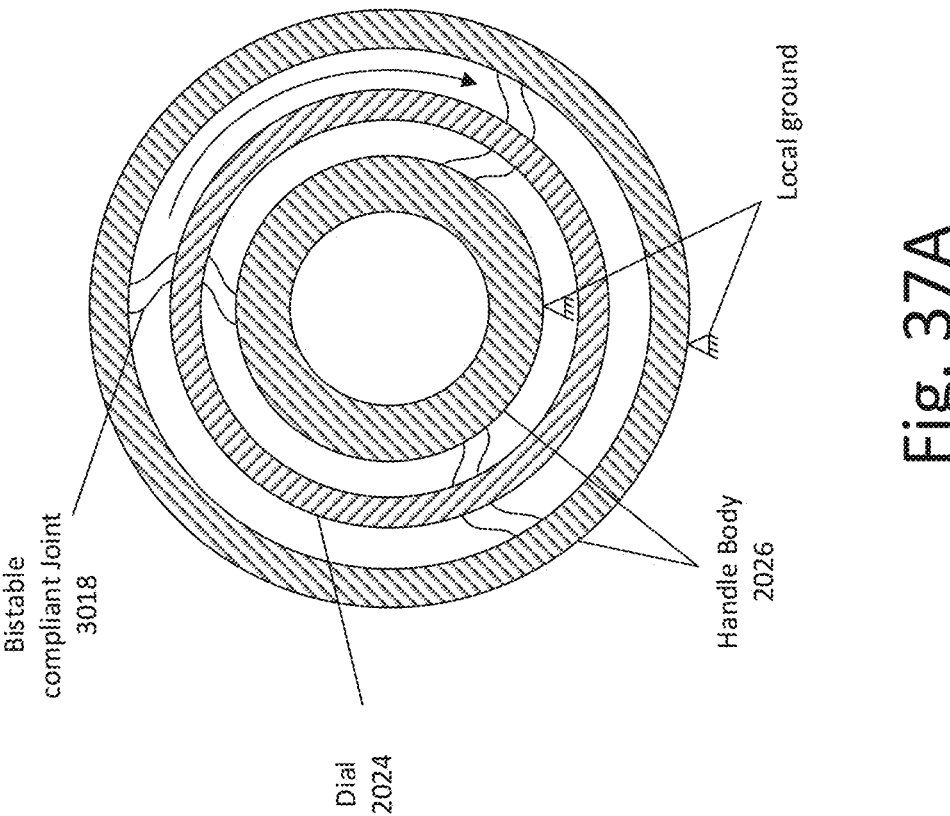
FIGS. 37A-B depict a discrete binary or bistable rotation mechanism (that may be part of a handle assembly) consisting of a dial and a handle body (A); and an illustrative bistable compliant mechanism (B).
Figure 37B:
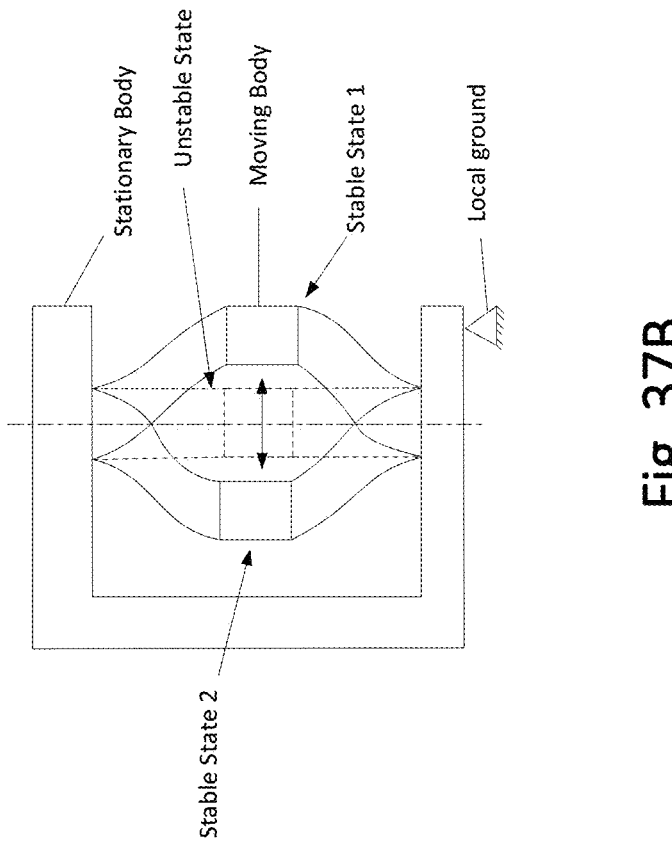

FIG. 37A represents a bistable rotation mechanism embodiment (that may be part of a handle assembly) showing the interface between Handle Body 2026 and Dial 2024 such that the rotation of Dial 2024 w.r.t. Handle Body 2026 about axis 1 is binary in nature. These bodies may be part of a handle assembly 2202 that may map to the constraint map shown in FIGS. 24A-B or FIG. 31. The Dial 2024 can be rotated CW by one discrete angle and Dial 2024 can be rotated CCW by one discrete angle. This is possible due to the presence of a bi-stable compliant mechanism 3018 shown in isolation in FIG. 37B that exists between the Dial 2024 and Handle Body 2026. The bi-stable compliant mechanism 3018 comprises multiple instances of parallel beams connected on one end to the Handle Body and on the other end to the Dial, followed by additional multiple instances of parallel beams attached to Dial on one end and to the Handle Body on the other end. This forms multiple instances of opposing sets of parallel beams between the Handle Body and Dial.

In FIG. 37A, CCW rotation of the Dial 2024 from the given configuration (stable state 1 shown in FIG. 37B for the bi-stable compliant mechanism 3018) will lead to rotation of Dial 2024 by a certain degree. Once the bi-stable compliant mechanism 3018 finds its other unique stable state, it will halt the rotation of the Dial 2024. This brings each of the bi-stable compliant mechanism 3018 to stable state 2, also shown in FIG. 37B. Similarly, rotation of Dial 2024 CW from the new configuration will bring the bi-stable compliant mechanism 3018 back to its original stable configuration, i.e., stable state 1. There may exist one or more such bi-stable compliant mechanisms 3018 between the Dial 2024 and Handle Body 2026. Also, the amount of rotation of Dial 2024 w.r.t. Handle Body 2026 about axis 1 on either side may depend on the length of parallel beams that are part of the bi-stable compliant mechanism 3018.

Figure 38A:
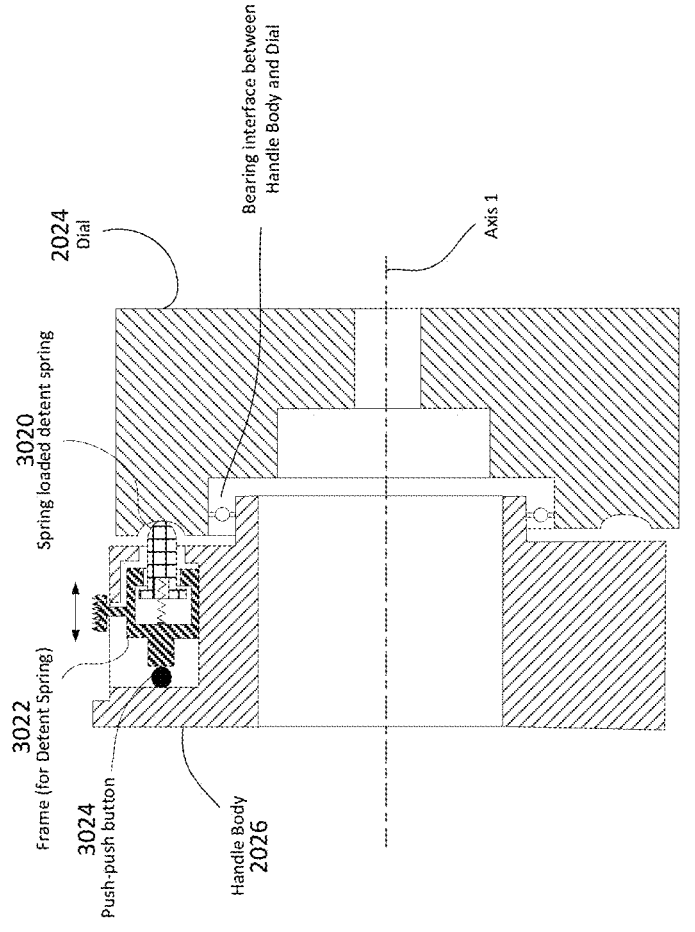
FIGS. 38A-B show a schematic diagram including a handle body, a dial, and a continuous/discrete dial rotation state switch (A); an example of an apparatus including a handle body, a dial, and a continuous/discrete dial rotation state switch (B).

FIG. 38A shows an embodiment which consists of a Handle Body 2026 and Dial 2024. This embodiment may be incorporated in a handle assembly 2202 that maps to constraint map shown in FIGS. 24A-B or FIG. 31. In this embodiment, there exists a detent spring 3020 which is housed in a frame 3022. This detent spring 3020 sits into detent features onto the Dial 2024 which are located around the circumference of the Dial 2024 at a certain pitch. The frame 3022 for detent spring 3020 may be placed on a rail such that it can translate w.r.t. the Handle Body 2026 along direction 1. The frame 3022 may be moved w.r.t. Handle Body 2026 by the user to switch the rotation of Dial 2024 w.r.t. Handle Body 2026 between discrete or continuous states.

In a discrete state, the Dial 2024 can rotate w.r.t. Handle Body 2026 such that it rotates discretely based on the pitch of detent features on the Dial 2024. In a continuous state, the Dial 2024 may rotate freely w.r.t. Handle Body 2026. The frame 3022 may also be locked w.r.t. handle assembly 2022 in the discrete or continuous state using a push-push button 3024. The push-push button 3024 calls for motion of frame 3022 towards the Handle Body 2026 along direction 1 to push the button to lock the frame 3022 in a continuous Dial 2024 rotate state. In order to reset it back to discrete rotation state, it may need another push towards the Handle Body 2026 along direction 1. Instead of a push-push button 3024, there may be other mechanisms such as bi-stable springs to create two states, or rotation push-push button mechanism which is used in many ball-point pens, etc.

Figure 38B:
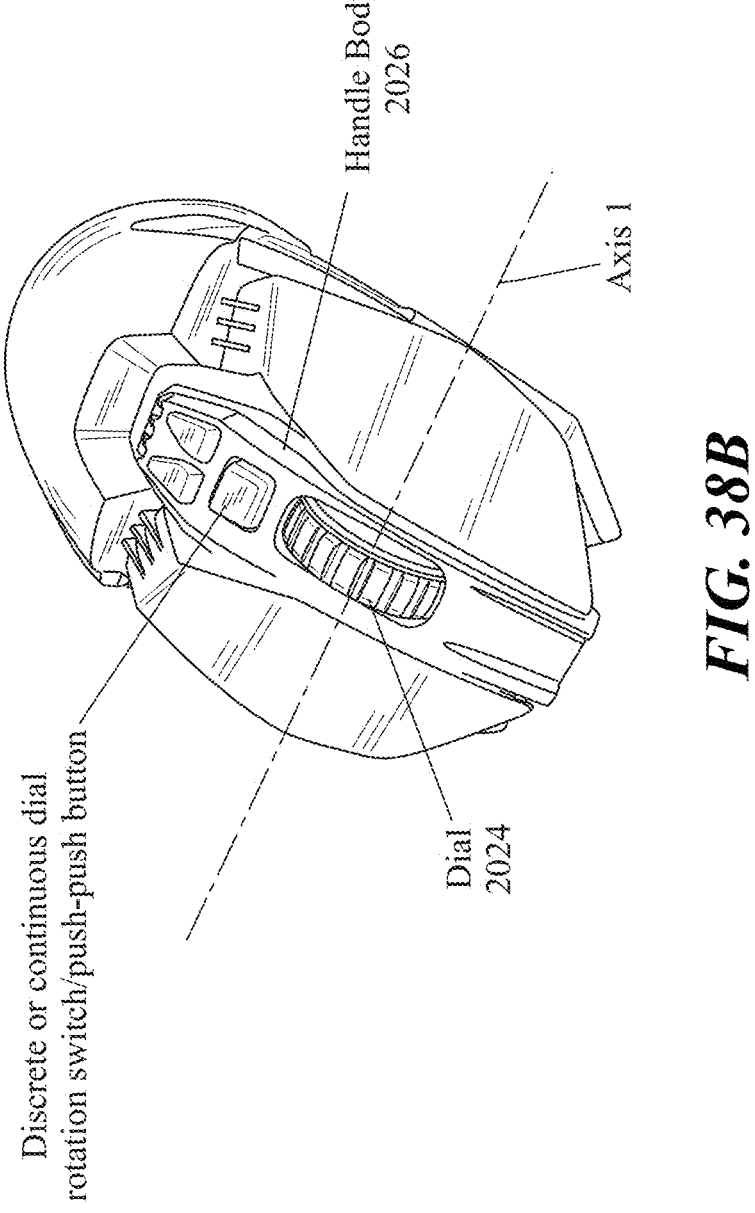

FIG. 38B shows an example of an embodiment similar to one shown in FIG. 38A. Here components of a computer mouse can be considered as Handle Body 2026, Dial 2024 and the switch that helps toggle between discrete and continuous Dial 2024 rotation states. Pressing the button interfaces a pawl or gear to the outer surface of Dial 2024. The outer surface of Dial 2024 has slots or serrations or gear tooth features. This way, rotation of Dial 2024 w.r.t. Handle Body 2026 about axis 1 provides haptic feedback on each specific angle rotation (dependent on the pitch of serrations/slots on the Dial 2024).

Handle Assembly Constraint Map D

Figure 39:
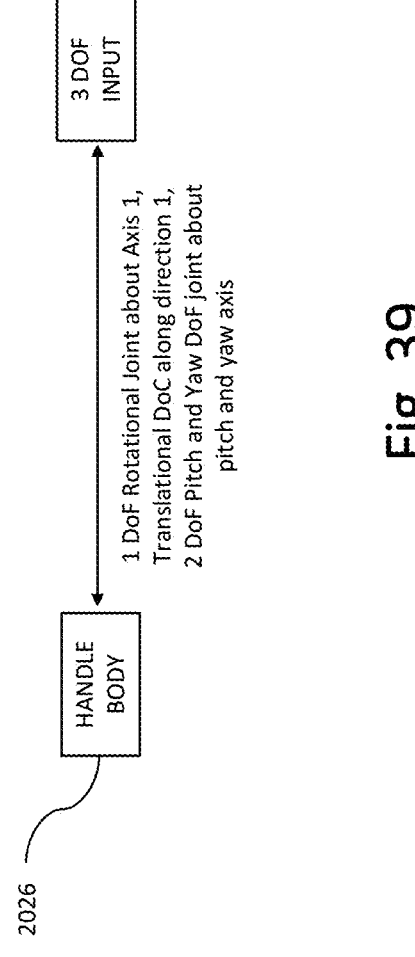
FIG. 39 depicts a constraint map D that includes articulation degrees of freedom between an art-roll input and a handle body.

FIG. 39 shows a constraint map which represents DoFs and DoCs between Handle Body 2026 and "3DOF joint." This "Art-roll Input" may replace Roll Input 2050 and/or Dial 2024 in constraint maps shown in FIGS. 24A-B or FIG. 31 to produce a handle assembly 2022 that includes an articulation input joint along with existing functions, i.e., rotation of Roll Input 2050 leading to rotation of the end-effector and actuation of Closure Input 2048 leading to the closing of Moving Jaw 2012 w.r.t. Fixed Jaw 2014. Here, "Art-roll Input" can be described as an assembly that includes two components, namely "Roll Input" (described above) and "Articulation Dial." Articulation Dial has a 2-DoF joint w.r.t. either Roll Input 2050 or Handle Body 2026 that produces pitch and yaw motion by rotation about pitch and yaw axes respectively. This 2-DoF joint/mechanism is termed as an articulation input mechanism.

This handle assembly 2022 may be part of an apparatus which includes an elongated tool shaft 2011 and EE assembly 2010 at the distal end of the tool shaft 2011. There may also exist an articulation output joint 2020 between tool shaft 2011 and EE assembly 2010. Articulation input mechanism maybe a serial or parallel kinematic mechanism which takes pitch and yaw rotation as inputs and may transmit to output articulation joint 2020 present between tool shaft 2011 and EE assembly 2010 producing pitch and yaw motion output motion of end-effector respectively.

Handle Assembly Embodiments—Mapping to Constraint Map D

Figure 40:
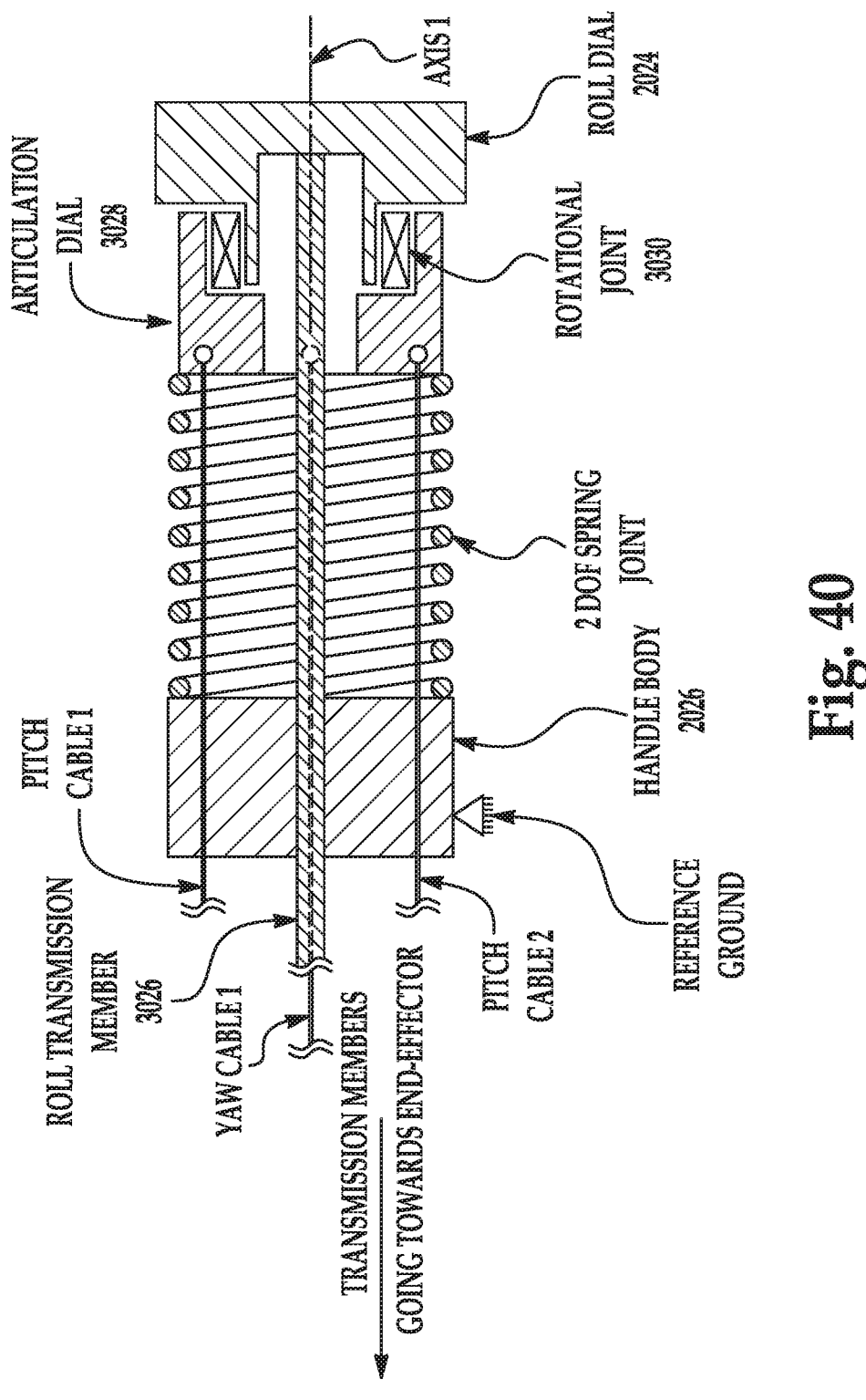
FIG. 40 depicts an embodiment showing a serial input joint between bodies "art-roll input" and a "handle body."
Figure 41:
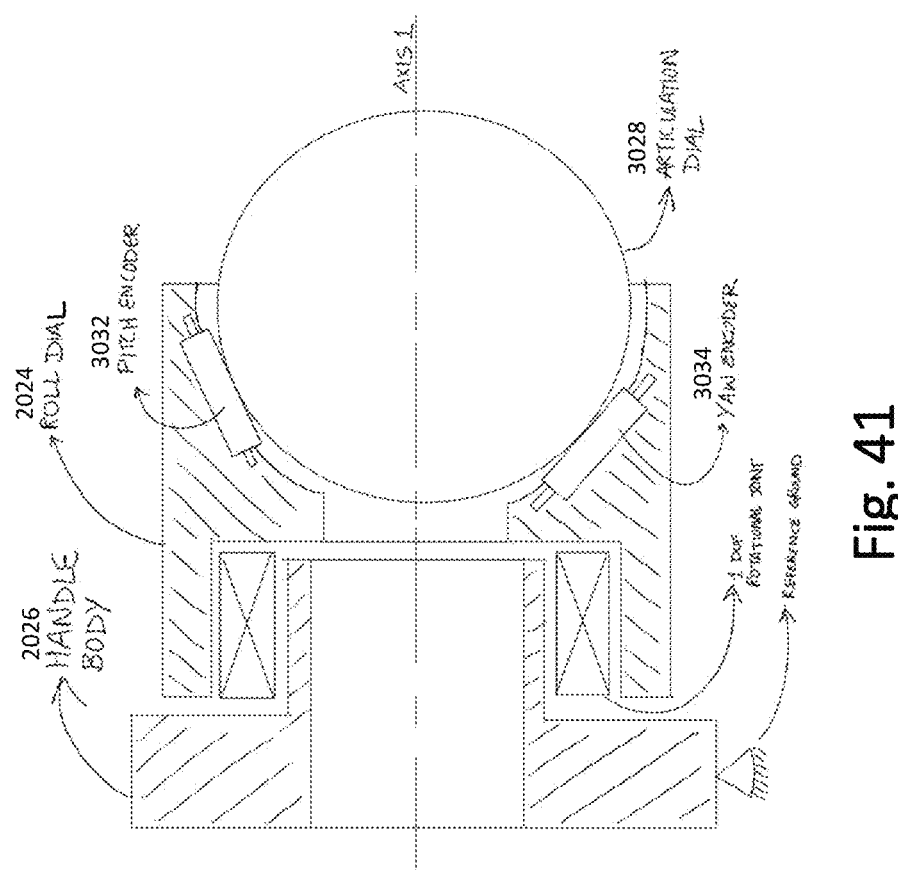
FIG. 41 depicts an embodiment showing a ball-based art-roll input along with encoders receiving articulation input.
Figure 42:
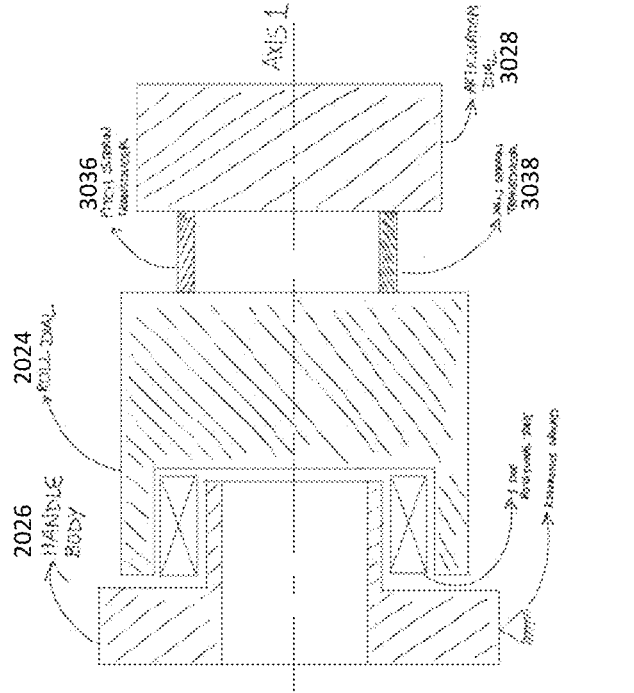
FIG. 42 depicts an embodiment showing a transducer-based articulation input joint between an art-roll input and a handle body.

FIG. 40 through FIG. 42 show a handle assembly 2022, particularly only components namely Handle Body 2026 and Art-roll Input. Some of these figures may also contain a roll transmission member 3026 which transmit roll motion between the Roll Input 2050 and the EE assembly 2010 to produce rotation. Some of these figures may also contain an articulation transmission member which transmits articulation motion (pitch and yaw motion) from articulation input mechanism to articulation output mechanism. Also, "Roll Input" is present in its simplest form as Dial 2024 in these embodiments. Terms, namely, "Roll Input", "Dial", and "roll Dial" may be used interchangeably in the description.

In FIG. 40, there exists a 2-DoF pitch and yaw rotational joint between Articulation Dial 3028 and Handle Body 2026. Also, there exists a 1-DoF rotational joint 3030 between Roll Dial 2024 and Articulation Dial 3028. There exist pitch and yaw motion transmission members which are rigidly mounted to Articulation Dial 3028 such that they capture pitch and yaw motion respectively. These members are referred to in FIG. 40 as cables. These cables may be flexible wires made from nitinol, Kevlar, braided stainless steel/tungsten assembly, or flexible polymers, or a combination of these materials. Each cable or a pair of cables may transmit pitch motion (or yaw motion) due to respective pitch motion (or yaw motion) of Articulation Dial 3028 w.r.t. Handle Body 2026. Moving Articulation Dial 3028 to produce pitch motion produces a pull force on a pitch cable.

Similarly, moving Articulation Dial 3028 to produce yaw motion produces a pull force on a yaw cable. Combining these motions to produce a compound motion consisting of pitch and yaw motion of Articulation Dial 3028 produces pull on both pitch and yaw cables.

There may exist an apparatus consisting of a tool frame, an elongated tool shaft rigidly attached to tool frame and an EE assembly at the distal end of the tool shaft. There may exist a 2-DoF output articulation joint between the tool shaft and EE assembly. The 2-DoF articulation output joint is connected to a 2-DoF articulation input joint via pitch and yaw transmission members. In this arrangement, pitch and yaw cables connect to the output articulation joint and may be routed through the tool frame and/or tool shaft. Also, EE assembly may rotate w.r.t. reference ground or tool shaft. In this arrangement, the roll Dial is rigidly attached to the roll transmission member such that rotation of roll Dial may lead to rotation of EE assembly about tool axis via roll transmission member. The 2-DoF spring joint may be constructed using helical spring, flexible coil spring, or flexible polymer assembly. It may be formed by a combination of these materials.

FIG. 41 represents a handle assembly 2022 consisting of Handle Body 2026, Roll Dial 2024, and Articulation Dial 3028. Here, Handle Body 2026 serves as the reference ground and Roll Dial 2024 has 1 rotational DoF w.r.t. Handle Body 2026 about axis 1. There exists a 2 DoF articulation joint between Articulation Dial 3028 and Roll Dial 2024 such that the pitch and yaw motion of Articulation Dial 3028 w.r.t. Roll Dial 2024 is encoded by pitch and yaw encoders 3032, 3034 respectively. Pitch and yaw encoders 3032, 3034 rotate about pitch and yaw axes respectively. Articulation Dial 3028 is represented as a spherical ball that eventually rotates two rollers, namely pitch and yaw rollers. These rollers are here described as "encoders." The pitch and yaw rotation data encoded by the respective encoders 3032, 3034 may be transmitted to 2-DoF output articulation joint between tool shaft 2011 and end-effector. Further, the rotation of Roll Dial 2024 w.r.t. Handle Body 2026 about axis 1 may either be encoded or transmitted mechanically leading to rotation of the end-effector. Mechanical transmission of rotation of Roll Dial 2024 may occur via roll transmission member that is rigidly mounted to the Roll Dial 2024.

FIG. 42 represents a handle assembly 2022 consisting of Handle Body 2026, roll Dial 2024, and articulation Dial 3028. Here, Handle Body 2026 serves as the reference ground and roll Dial 2024 has 1 rotational DoF w.r.t. Handle Body 2026 about axis 1. There exists a 2-DoF articulation joint between articulation Dial 3028 and roll Dial 2024 such that the pitch and yaw motions of articulation Dial 3028 w.r.t. the roll Dial 2024 are captured by capturing strain produced in pitch and yaw transducers 3036, 3038 respectively. These transducers 3036, 3038 may be piezoelectric strips/plates or smart memory alloys or other strain transducers. This strain captured by the transducers 3036, 3038 is converted into electric signals which may be transmitted to 2-DoF output articulation joint between tool shaft 2011 and EE assembly 2010. Further, the rotation of roll Dial 2024 w.r.t. Handle Body 2026 about axis 1 may either be encoded or transmitted mechanically leading to rotation of end-effector. Mechanical transmission of rotation of roll Dial 2024 may occur via roll transmission member that is rigidly mounted to the roll Dial 2024.

When a feature or element is herein referred to as being "on" another feature or element, it can be directly on the other feature or element or intervening features, and/or other elements that may also be present. In contrast, when a feature or element is referred to as being "directly on" another feature or element, there are no intervening features or elements present. It will also be understood that when a feature or element is referred to as being "connected", "attached", or "coupled" to another feature or element, it can be directly connected, attached, or coupled to the other feature or element or intervening features or other elements that may be present. In contrast, when a feature or element is referred to as being "directly connected", "directly attached", or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components, or sub-steps.

Although various illustrative embodiments are described above, any of several changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value", and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats, and that this data represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

While embodiments of the invention have been illustrated and described, it is not intended that these embodiments illustrate and describe all possible forms of the invention. It is understood that the features of various implementing embodiments may be combined to form further embodiments of the invention. The words used in the specification are words of description rather than limitation, and it is understood that various changes may be made without departing from the spirit and scope of the invention.

The examples and illustrations included herein show, by way of illustration and not of limitation, specific embodiments in which the subject matter may be practiced. These embodiments consist of bodies that have various types of joints and/or mechanisms namely, prismatic, revolute, cylindrical, etc. between them. These joints and/or mechanisms may consist of discrete elements/bodies/component or these joint/mechanisms may be created by compliant extensions of other bodies and/or assemblies.

What is claimed is:

1. A roll handle assembly, comprising:
a handle body;
a roll body coupled to said handle body, said roll body having a rotational degree of freedom about a roll axis relative to said handle body and being translationally constrained along said roll axis relative to said handle body;
a closure body coupled to said handle body, said closure body having at least one degree of freedom of motion relative to said handle body;
a shuttle body coupled to said roll body and coupled to said closure body, said shuttle body having a translational degree of freedom along said roll axis relative to said roll body and being rotationally constrained about said roll axis relative to said roll body, said shuttle body having a rotational degree of freedom about said roll axis relative to said closure body; and
an articulation input joint residing adjacent said roll body, said articulation input joint having two articulation degrees of freedom relative to said handle body to effect pitch and yaw motions at said articulation input joint relative to said handle body.

2. The roll handle assembly as set forth in claim 1, wherein movement of said closure body about said at least one degree of freedom of motion relative to said handle body effects movement of said shuttle body about said translational degree of freedom along said roll axis relative to said roll body.

3. The roll handle assembly as set forth in claim 1, wherein said at least one degree of freedom of motion of said closure body is a translational degree of freedom along said roll axis relative to said handle body, said closure body being rotationally constrained about said roll axis relative to said handle body.

4. The roll handle assembly as set forth in claim 1, further comprising a closure input and a closure input mechanism, said closure input having at least one degree of freedom of motion relative to said handle body, wherein movement of said closure input about said at least one degree of freedom of motion effects movement of said closure body about said at least one degree of freedom of motion relative to said handle body, said closure input mechanism spanning between said closure body and said closure input, said closure input mechanism transmitting movement of said closure input about said at least one degree of freedom of motion relative to said handle body to movement of said closure body about said at least one degree of freedom of motion relative to said handle body.

5. The roll handle assembly as set forth in claim 1, further comprising a roll input and a roll input mechanism, wherein movement of said roll input effects movement of said roll body about said rotational degree of freedom about said roll axis relative to said handle body, said roll input mechanism spanning between said roll body and said roll input, said roll input mechanism transmitting movement of said roll input to movement of said roll body about said rotational degree of freedom about said roll axis relative to said handle body.

6. The roll handle assembly as set forth in claim 1, further comprising a shaft extending distally from the roll handle assembly, and comprising an end-effector at a distal end of said shaft so that rotation of said roll body about said roll axis relative to said handle body effects rotation of said end-effector relative to said handle body.

7. The roll handle assembly as set forth in claim 6, wherein said end-effector comprises a jaw assembly, opening and closing movements of said jaw assembly are effected by movement of said closure body about said at least one degree of freedom of motion relative to said handle body.

8. The roll handle assembly as set forth in claim 6, wherein said end-effector comprises a jaw assembly, said jaw assembly is coupled to said shuttle body via a jaw closure transmission assembly, opening and closing movements of said jaw assembly are effected by movement of said shuttle body about said translational degree of freedom along said roll axis relative to said roll body.

9. The roll handle assembly as set forth in claim 1, wherein said closure body comprises a trigger, a lever, a button, a push rod, or a mechanism that couples a lever to a push rod.

10. A surgical tool comprising the roll handle assembly as set forth in claim 1.

11. A roll handle assembly, comprising:
a handle assembly comprising:
    a handle body;
    a roll body coupled to said handle body, said roll body having a rotational degree of freedom about a roll axis relative to said handle body and being translationally constrained along said roll axis relative to said handle body; and
    a shuttle body coupled to said roll body, said shuttle body having a translational degree of freedom along said roll axis relative to said roll body and being rotationally constrained about said roll axis relative to said roll body;
a frame; and
an input joint providing a pitch rotation and a yaw rotation between said handle assembly and said frame, wherein said roll body and said frame are connected together via said input joint, said input joint constraining rotation between said roll body and said frame, rotation of said roll body about said roll axis relative to said handle body effects rotation of said frame relative to said handle body.

12. The roll handle assembly as set forth in claim 11, wherein said input joint having a pitch motion path and a yaw motion path, said pitch motion path transmitting a pitch motion of said handle assembly relative to said frame about a pitch axis of rotation, said yaw motion path transmitting a yaw motion of said handle assembly relative to said frame about a yaw axis of rotation, and said input joint is a parallel kinematic input joint with said pitch motion path and said yaw motion path arranged parallel with each other.

13. The roll handle assembly as set forth in claim 12, wherein said pitch axis of rotation and said yaw axis of rotation are situated proximal to said handle assembly.

14. The roll handle assembly as set forth in claim 11, wherein said handle assembly further comprises a closure body coupled to said handle body and having at least one degree of freedom of motion relative to said handle body, said shuttle body coupled to said closure body and having a rotational degree of freedom about said roll axis relative to said closure body.

15. The roll handle assembly as set forth in claim 14, further comprising a shaft extending from said frame, and comprising an end-effector at a distal end of said shaft so that rotation of said roll body about said roll axis relative to said handle body effects rotation of said end-effector relative to said handle body.

16. The roll handle assembly as set forth in claim 15, wherein said end-effector comprises a jaw assembly, opening and closing movements of said jaw assembly are effected by movement of said closure body about said at least one degree of freedom of motion relative to said handle body.

17. The roll handle assembly as set forth in claim 16, wherein said jaw assembly is coupled to said shuttle body via a jaw closure transmission assembly, opening and closing movements of said jaw assembly are effected by movement of said shuttle body about said translational degree of freedom along said roll axis relative to said roll body.

18. The roll handle assembly as set forth in claim 15, further comprising an output joint residing between said shaft and said end-effector, said pitch motion path transmitting pitch motion of said handle assembly relative to said frame to said output joint, and said yaw motion path transmitting yaw motion of said handle assembly relative to said frame to said output joint.

19. The roll handle assembly as set forth in claim 18, wherein said roll body and said frame are connected together via said input joint.

20. The roll handle assembly as set forth in claim 19, wherein said input joint constrains rotation between said roll body and said frame, rotation of said roll body about said roll axis relative to said handle body effects rotation of said frame, said shaft, and said end-effector relative to said handle body for any pitch rotation and yaw rotation of said input joint.

* * * * *